(12) United States Patent
Kawai et al.

(10) Patent No.: US 6,939,928 B1
(45) Date of Patent: Sep. 6, 2005

(54) METALLOCENE COMPOUND, PROCESS FOR PRODUCING METALLOCENE COMPOUND, OLEFIN POLYMERIZATION CATALYST, PROCESS FOR PRODUCING POLYOLEFIN, AND POLYOLEFIN

(75) Inventors: Koji Kawai, Yamaguchi (JP); Masahiro Yamashita, Yamaguchi (JP); Yasushi Tohi, Yamaguchi (JP); Nobuo Kawahara, Yamaguchi (JP); Kenji Michiue, Yamaguchi (JP); Hiromu Kaneyoshi, Yamaguchi (JP); Ryoji Mori, Yamaguchi (JP)

(73) Assignee: Mitsui Chemicals, Inc., Tokyo (JP)

( * ) Notice: Subject to any disclaimer, the term of this patent is extended or adjusted under 35 U.S.C. 154(b) by 132 days.

(21) Appl. No.: 09/857,687

(22) PCT Filed: Oct. 5, 2000

(86) PCT No.: PCT/JP00/06945

§ 371 (c)(1),
(2), (4) Date: Jun. 8, 2001

(87) PCT Pub. No.: WO01/27124

PCT Pub. Date: Apr. 19, 2001

(30) Foreign Application Priority Data

| Oct. 8, 1999 | (JP) | 11/288838 |
|---|---|---|
| Oct. 8, 1999 | (JP) | 11/288839 |
| Oct. 8, 1999 | (JP) | 11/288840 |
| Aug. 21, 2000 | (JP) | 2000/250387 |
| Aug. 21, 2000 | (JP) | 2000/250390 |
| Aug. 21, 2000 | (JP) | 2000/250391 |

(51) Int. Cl.[7] ............... C08F 4/64; C08F 4/642; C08F 4/643
(52) U.S. Cl. .......... 526/160; 526/127; 526/134; 526/170; 526/943; 502/103; 502/117; 502/152; 502/154
(58) Field of Search ............. 526/127, 160, 526/170, 943; 502/103, 117, 152, 154; 556/53

(56) References Cited

U.S. PATENT DOCUMENTS

| 6,184,318 B1 * | 2/2001 | Razavi et al. ........... 526/160 |
| 6,469,188 B1 * | 10/2002 | Miller et al. ........... 556/12 |
| 6,515,086 B1 * | 2/2003 | Razavi ........... 526/160 |

FOREIGN PATENT DOCUMENTS

| EP | 0-503-422 A1 | 9/1992 | C08F/232/08 |
| EP | 0-610-847 | 8/1994 | C08F/232/08 |
| EP | 0-747-406 A1 | 12/1996 | C08F/297/06 |
| EP | 0-848-022 A1 | 6/1998 | C08F/210/16 |
| JP | 05-59077 A | 3/1993 | |
| JP | 10101689 | 4/1998 | C07F/17/00 |
| WO | 0-754-698 A2 | 1/1997 | C07F/17/00 |
| WO | WO 97/36937 | 10/1997 | C08F/4/603 |
| WO | WO 98/02470 | 1/1998 | C08F/10/00 |
| WO | WO 98/54230 | * 12/1998 | |
| WO | WO 99/02569 | 1/1999 | C08F/2/04 |
| WO | WO 99/14219 | * 3/1999 | |

OTHER PUBLICATIONS

U.S. Appl. No. 60/150,083.*

Alt et al., J. Organometallic Chemistry 568 (1998) 87–112.*

Yano et al., Macromol. Chem. Phys. 200 (1999) 1542–1553.*

Angermund, Klaaus et al: "The role of intermediate chain migration in propene polymerization using substituted {iPr(CpFlu)}ZrC12/MAO catalysts" Macromol. Rapid Commun. (Feb. 2000), 21(2), 91–97.

Yano, Akihiro et al: "Ethylene/1–hexene copolymerization with Ph2C(Cp) (Flu) ZrC12 derivatives. Correlation between ligand structure and copolymerization behavior at high temperature" Macromol. Chem. Phys. (1999), 200(6), 1542–1553.

Ruchatz, Dieter et al: "Ethene–Norbornene Copolymerization with Homogeneous Metallocene and Half–Sandwich Catalysts: Kinetics and Relationships between Catalyst Structure and Polymer Structure. 4. Development of Molecular Weights" Macromolecules (1998), 31(15), 4684–4686.

Alt Helmut G. et al: "ansa–Metallocene complexes of type (C13H8–SiR2–C9H6–nR'n)ZrC12 (n=0, 1; R=Me, Ph, alkenyl; R'=alkyl, alkenyl): self–immobilized catalysts for ethylene polymerization" J. Organomet. Chem. (1998), 562(2), 229–253.

(Continued)

*Primary Examiner*—Roberto Rabago
(74) *Attorney, Agent, or Firm*—Burns, Doane, Swecker & Mathis, LLP

(57) ABSTRACT

The metallocene compound according to the invention and the olefin polymerization catalyst containing the compound are intended to produce a catalyst capable of preparing an isotactic polymer with a high polymerization activity. The metallocene compound contains a substituted cyclopentadienyl group and a (substituted) fluorenyl group and has a structure wherein these groups are bridged by a hydrocarbon group or the like. The process for preparing a metallocene compound according to the invention is intended to selectively prepare a specific metallocene compound so as not to produce an isomer, and in this process an intermediate product is synthesized by a specific method. The process for preparing a polyolefin according to the invention is intended to prepare a polyolefin having excellent impact resistance and transparency, and this process comprises homopolymerizing an α-olefin of 3 to 8 carbon atoms or copolymerizing an olefin of 3 to 8 carbon atoms and another α-olefin in the presence of an olefin polymerization catalyst containing the above-mentioned metallocene compound.

14 Claims, 1 Drawing Sheet

OTHER PUBLICATIONS

Alt, Helmut G. et al: "C1–Bridged fluorenylidene–indenylidene complexes of type (C13H8–CR2–C9H6–nR'n)ZrC12 (n=0, 1; R=Me, Ph, butenyl; R'alkyl, alkenyl) as metallocene catalysts for ethylene polymerization" J. Organomet. Chem. (1998), 562(2), 153–181.

Peifer, Bernd et al: "Self–immobilized metallocene catalysts" J. Organomet. Chem. (1988), 553(1–2), 205–220.

Stehling, U.M. et al: " Stereospecific polymerization of functionalized olefins with metallocene catalysts" Polym. Mater. Sci. Eng. (1997), 76, 244–245.

Spaleck, Walter et al: "Stereospecific metallocene catalysts: scope and limits of rotational catalyst design" Macromol. Symp. (1995), 89(Synthetic, Structural and Industrial Aspects 0 Stereopecific Polymerization), 237–247.

Razavi, Abbas et al: "Preparation and crystal structures of the complexes (.eta.5–C5H3Me–CMe2–.eta.5–C13H8)MC12 (M=Zr or Hf): mechanistic aspects of the catalytic formation of a syndiotactic–isotactic stereoblock–type Polypropylene" J. Organomet. Chem. (1995), 497(1–2), 105–111.

Cavallo, Luigi et al: "A possible model for the stereospecificity in the syndiospecific polymerization of propene with group 4a metallocenes" Macromolecules (1991), 24(8), 1784–1790.

* cited by examiner

Fig. 1

Transition metal component

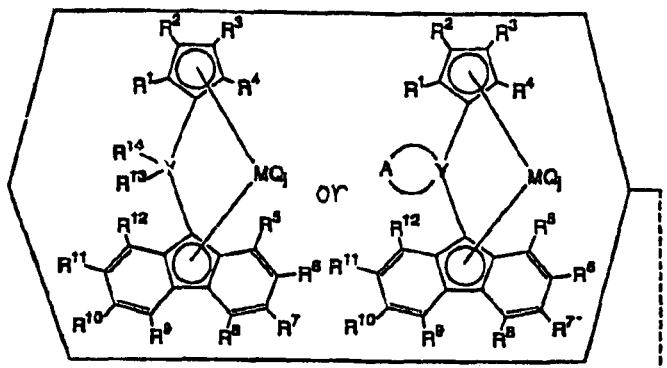

M: metal of Group 4 of the periodic table
$R^3$: hydrocarbon group, silicon-containing hydrocarbon group
$R^1$, $R^2$, $R^4$ – $R^{14}$: hydrogen, hydrocarbon group, silicon-containing hydrocarbon group
Y: carbon or silicon
A: divalent hydrocarbon group
Q: halogen, hydrocarbon group or the like
j: integer of 1 to 4

Organometallic component

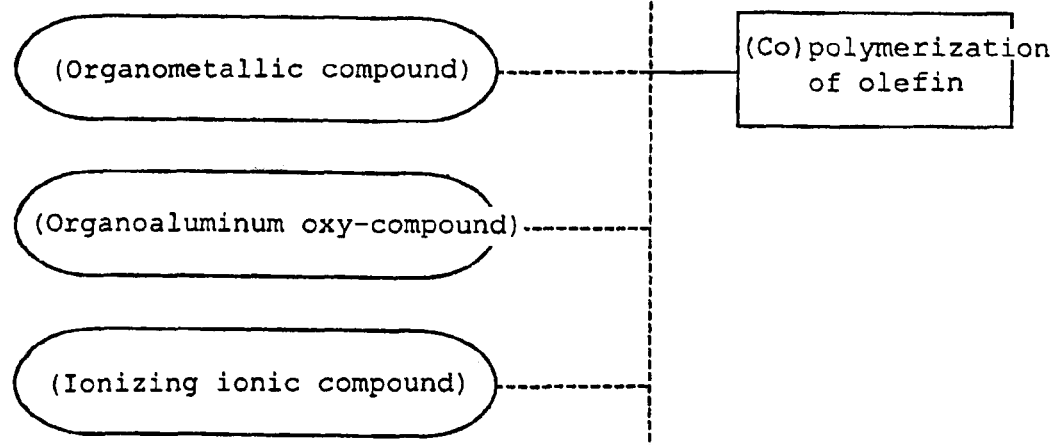

(Organometallic compound) ------- (Co)polymerization of olefin (Organoaluminum oxy-compound) -------

(Ionizing ionic compound) -------

Third component
( Carrier ) -------

METALLOCENE COMPOUND, PROCESS FOR PRODUCING METALLOCENE COMPOUND, OLEFIN POLYMERIZATION CATALYST, PROCESS FOR PRODUCING POLYOLEFIN, AND POLYOLEFIN

TECHNICAL FIELD

The present invention relates to a metallocene compound having a specific structure, a process for preparing the metallocene compound, an olefin polymerization catalyst containing the metallocene compound, a process for preparing a polyolefin using the olefin polymerization catalyst, and a polyolefin.

BACKGROUND ART

The "metallocene compound" is well known as a homogeneous catalyst for olefin polymerization. Since the isotactic polymerization was reported by W. Kaminsky, et al. (Angew. Chem. Int. Ed. Engl., 24, 507 (1985)), there have been made many improvements in the olefin polymerization process using a metallocene compound, particularly a process for stereoregularly polymerizing an α-olefin. As an example of the improvement, a metallocene compound having a C2 symmetric structure wherein some hydrogen atoms of the cyclopentadienyl group in the ligand part are replaced with alkyl groups has been reported (by Yamazaki, et al., Chemistry Letters, 1853 (1989), Japanese Patent Laid-Open Publication No. 268307/1992). As like attempts, further, a large number of attempts to improve the isotactic stereoregularity of an olefin polymer by the use of a metallocene compound having, as a ligand, a bisindenyl derivative having a C2 symmetric structure have been reported (e.g., Angew. Chem. Int. Ed. Engl., 31, 1347 (1992), Organometallics, 13, 954 (1994)).

The metallocene compound of the C2 symmetric structure, however, is usually obtained as a mixture of a racemic modification and a mesoisomer, and only the racemic modification provides an isotactic polymer, while obtainable from the mesoisomer is only an atactic polymer, so that it is necessary to separate the racemic modification and the mesoisomer from each other in order to selectively obtain the isotactic polymer.

On the other hand, J. A. Ewen has found that an α-olefin is polymerized with syndiotactic stereoregularity by the use of a metallocene compound having a Cs symmetric structure wherein the cyclopentadienyl group and the fluorenyl group are bridged by dimethylmethylene (J. Am. Chem. Soc., 110, 6255 (1988)). To improve the metallocene compound, an attempt to introduce tert-butyl groups at the 2-position and the 7-position of the fluorenyl group and thereby further control the syndiotactic stereoregularity has been made (Japanese Patent Laid-Open Publication No. 69394/1992).

In addition, an attempt to synthesize an isotactic polymer by the use of a metallocene compound having a C1 symmetric structure that is different from the C2 symmetric and the Cs symmetric structures has been reported (see, for example, Japanese Patent Laid-Open Publications No. 193796/1991 and No. 122718/1994, EP 0881236).

The polymerization activities of these metallocene compounds, however, are still insufficient, and hence development of metallocene compounds having excellent polymerization activities and olefin polymerization catalysts containing such metallocene compounds has been desired.

The metallocene compounds having Cs and C1 symmetric structures have an advantage in that the structural isomers such as a mesoisomer and a racemic modification are not produced, differently from the metallocene compound having a C2 symmetric structure.

Of the above metallocene compounds, the metallocene compound of the C1 symmetric structure, however, has a problem in that an unnecessary isomer wherein the substituent group is attached at a position different from the intended proper position is produced depending upon the preparation process. When such an isomer is used as, for example, an olefin polymerization catalyst, unfavorable results such as production of an atactic polymer as a by-product are often brought about. Hence, development of a process for selectively preparing a metallocene compound in which such an unnecessary isomer is not included has been desired.

DISCLOSURE OF THE INVENTION

The metallocene compound according to the invention is represented by the following formula (1) or (2):

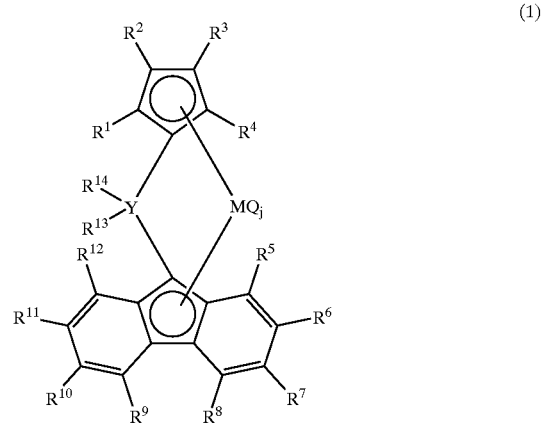

(1)

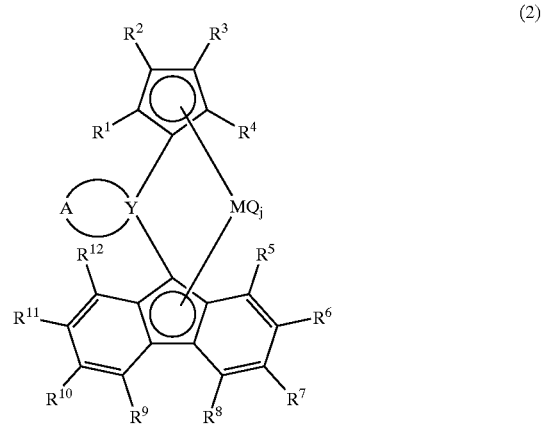

(2)

wherein $R^3$ is selected from a hydrocarbon group and a silicon-containing hydrocarbon group; $R^1$, $R^2$, $R^4$, $R^5$, $R^6$, $R^7$, $R^8$, $R^9$, $R^{10}$, $R^{11}$, $R^{12}$, $R^{13}$ and $R^{14}$ may be the same or different and are each selected from a hydrogen atom, a hydrocarbon group and a silicon-containing hydrocarbon group; of the groups indicated by $R^1$ to $R^{12}$, neighboring groups may be bonded to form a ring; in case of the formula (1), a group selected from $R^1$, $R^4$, $R^5$ and $R^{12}$ may be bonded to $R^{13}$ or $R^{14}$ to form a ring; A is a divalent hydrocarbon group of 2 to 20 carbon atoms which may contain an unsaturated bond and/or an aromatic ring; A may contain two or more cyclic structures including a ring formed by A in cooperation with Y; Y is a carbon atom or a silicon atom; M is a metal selected from Group 4 of the periodic table; j is an integer of 1 to 4; Q is selected from a halogen atom, a hydrocarbon group, an anionic ligand and a neutral ligand capable of coordination by a lone pair; and when j is 2 or greater, each Q may be the same or different.

Another embodiment of the metallocene compound of the invention is represented by the following formula (1a) or (2a):

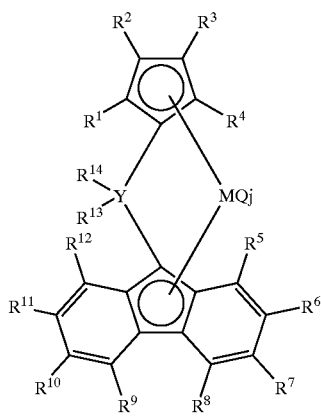

(1a)

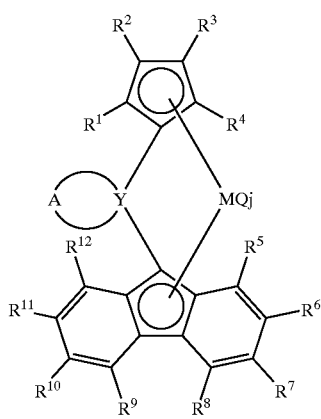

(2a)

wherein $R^3$ is selected from a hydrocarbon group and a silicon-containing hydrocarbon group; $R^1$, $R^2$, $R^4$, $R^5$, $R^6$, $R^7$, $R^8$, $R^9$, $R^{10}$, $R^{11}$, $R^{12}$, $R^{13}$ and $R^{14}$ may be the same or different and are each selected from a hydrogen atom, a hydrocarbon group and a silicon-containing hydrocarbon group; in case of a compound of the formula (1a), when $R^3$ is a tert-butyl group or a trimethylsilyl group and when $R^{13}$ and $R^{14}$ are methyl groups or phenyl groups at the same time, $R^6$ and $R^{11}$ are not hydrogen atoms at the same time; of the groups indicated by $R^1$ to $R^{12}$, neighboring groups may be bonded to form a ring; in case of the formula (1a), a group selected from $R^1$, $R^4$, $R^5$ and $R^{12}$ may be bonded to $R^{13}$ or $R^{14}$ to form a ring; A is a divalent hydrocarbon group of 2 to 20 carbon atoms which may contain an unsaturated bond and/or an aromatic ring; A may contain two or more cyclic structures including a ring formed by A in cooperation with Y; Y is a carbon atom or a silicon atom; M is a metal selected from Group 4 of the periodic table; j is an integer of 1 to 4; Q is selected from a halogen atom, a hydrocarbon group, an anionic ligand and a neutral ligand capable of coordination by a lone pair; and when j is 2 or greater, each Q may be the same or different.

A further embodiment of the metallocene compound of the invention is represented by the following formula (1b) or (2b):

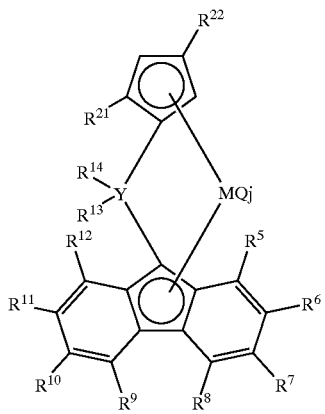

(1b)

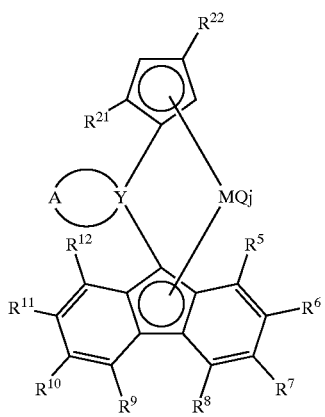

(2b)

wherein $R^{21}$ and $R^{22}$ may be the same or different and are each selected from a hydrocarbon group and a silicon-containing hydrocarbon group; $R^5$, $R^6$, $R^7$, $R^8$, $R^9$, $R^{10}$, $R^{11}$, $R^{12}$, $R^{13}$ and $R^{14}$ may be the same or different and are each selected from a hydrogen atom, a hydrocarbon group and a silicon-containing hydrocarbon group; of the groups indicated by $R^5$ to $R^{12}$, neighboring groups may be bonded to form a ring; A is a divalent hydrocarbon group of 2 to 20 carbon atoms which may contain an unsaturated bond and/or an aromatic ring; A may contain two or more cyclic structures including a ring formed by A in cooperation with Y; M is a metal selected from Group 4 of the periodic table; Y is a carbon atom or a silicon atom; j is an integer of 1 to 4; Q is selected from a halogen atom, a hydrocarbon group, an anionic ligand and a neutral ligand capable of coordination by a lone pair; and when j is 2 or greater, each Q may be the same or different.

The process for preparing a metallocene compound according to the invention comprises selectively preparing a metallocene compound represented by the above formula (1b) or (2b) so as not to include an isomeric compound represented by the following formula (3b), (4b), (5b) or (6b):

(3b)
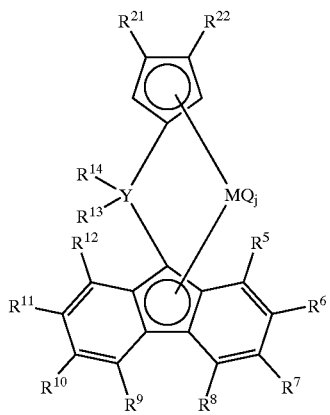

(6b)
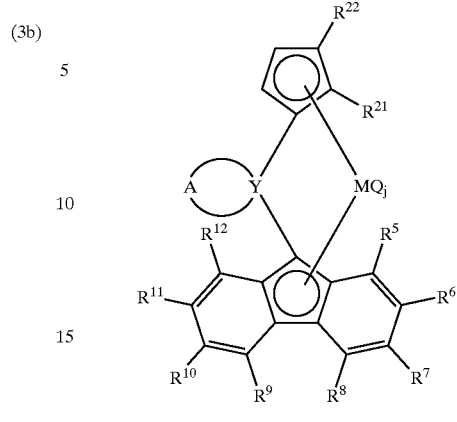

wherein $R^{21}$, $R^{22}$, $R^5$ to $R^{14}$, A, M, Y, Q and j have the same meanings as those of $R^{21}$, $R^{22}$, $R^5$ to $R^{14}$, A, M, Y, Q and j in the formula (1b) or (2b), respectively.

In the present invention, it is preferable that a ligand precursor represented by the following formula (7b) or (8b) is selectively prepared so as not to include an isomeric compound represented by the following formula (9b), (10b), (11b) or (12b) and the resulting ligand precursor is used as a material to selectively prepare the metallocene compound represented by the formula (1b) or (2b);

(4b)
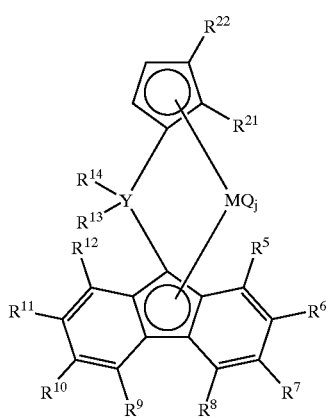

(7b)
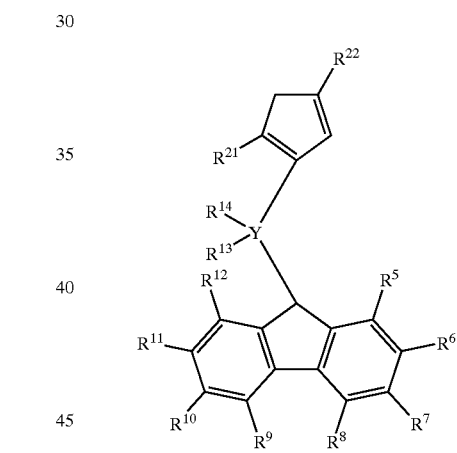

(5b)
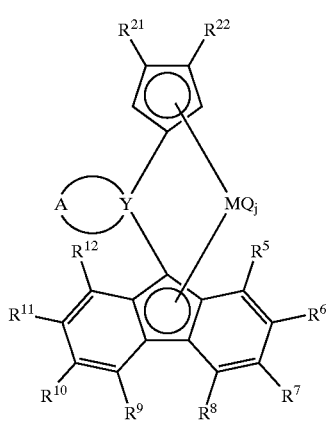

(8b)
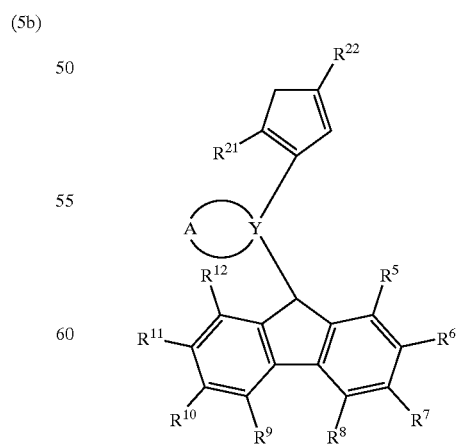

wherein $R^{21}$ $R^{22}$, $R^5$ to $R^{14}$, A and Y have the same meanings as those of $R^{21}$ $R^{22}$, $R^5$ to $R^{14}$, A and Y in the formula (1b) or (2b), respectively; and the cyclopentadienyl group may be another isomer different in only the position of a double bond in the cyclopentadienyl ring or a mixture thereof;

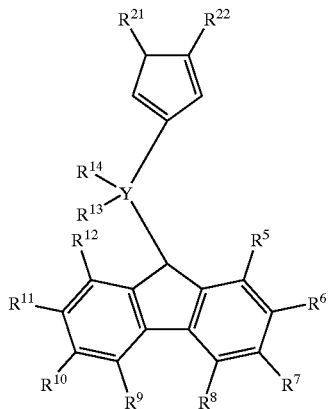
(9b)

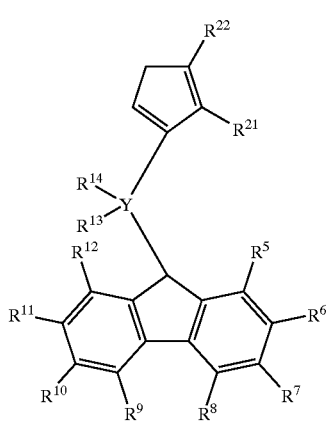
(10b)

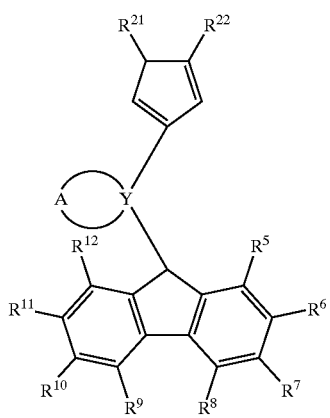
(11b)

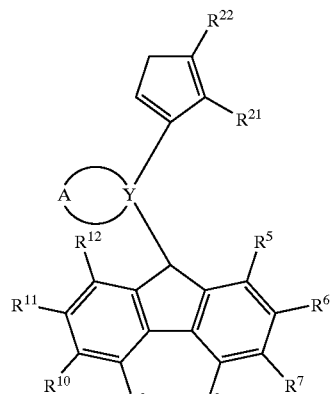
(12b)

wherein $R^{21}$, $R^{22}$, $R^5$ to $R^{14}$, A and Y have the same meanings as those of $R^{21}$, $R^{22}$, $R^5$ to $R^{14}$, A and Y in the formula (1b) or (2b), respectively; and the cyclopentadienyl group may be another isomer different in only the position of a double bond in the cyclopentadienyl ring or a mixture thereof.

In the present invention, further, it is preferable that a precursor compound represented by the following formula (13b) or (14b) is selectively prepared so as not to include an isomeric compound represented by the following formula (15b), (16b), (17b) or (18b) and the resulting precursor compound is used as a material to selectively prepare the ligand precursor represented by the formula (7b) or (8b);

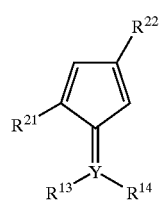
(13b)

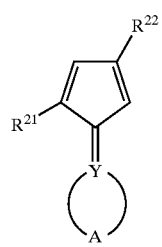
(14b)

wherein $R^{21}$, $R^{22}$, $R^{13}$, $R^{14}$, Y and A have the same meanings as those of $R^{21}$, $R^{22}$, $R^{13}$, $R^{14}$, Y and A in the formula (1b) or (2b), respectively;

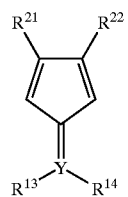
(15b)

-continued

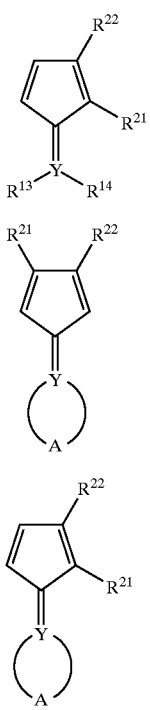

(16b)

(17b)

(18b)

wherein $R^{21}$, $R^{22}$, $R^{13}$, $R^{14}$, Y and A have the same meanings as those of $R^{21}$, $R^{22}$, $R^{13}$, $R^{14}$, Y and A in the formula (1b) or (2b), respectively.

In the present invention, furthermore, it is preferable that cyclopentadiene represented by the following formula (19b) is selectively prepared so as not to include an isomeric compound represented by the following formula (20b) and the resulting cyclopentadiene is used as a material to selectively prepare the precursor compound represented by the formula (13b) or (14b);

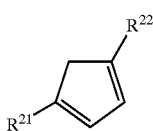

(19b)

wherein $R^{21}$ and $R^{22}$ have the same meanings as those of $R^{21}$ and $R^{22}$ in the formula (1b) or (2b), respectively; and the cyclopentadienyl group may be another isomer different in only the position of a double bond in the cyclopentadienyl ring or a mixture thereof;

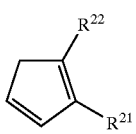

(20b)

wherein $R^{21}$ and $R^{22}$ have the same meanings as those of $R^{21}$ and $R^{22}$ in the formula (1b) or (2b), respectively; and the cyclopentadienyl group may be another isomer different in only the position of a double bond in the cyclopentadienyl ring or a mixture thereof.

The olefin polymerization catalyst according to the invention comprises any one of the above-mentioned metallocene compounds.

The olefin polymerization catalyst of the invention may be an olefin polymerization catalyst comprising:
(A) any one of the above-mentioned metallocene compounds, and (B) at least one compound selected from:
(B-1) an organometallic compound,
(B-2) an organoaluminum oxy-compound, and
(B-3) a compound which reacts with the metallocene compound (A) to form an ion pair.

The olefin polymerization catalyst of the invention may be an olefin polymerization catalyst comprising the above-mentioned olefin polymerization catalyst and (C) a particle carrier.

The process for preparing a polyolefin according to the invention comprises polymerizing or copolymerizing an olefin in the presence of any one of the above-mentioned olefin polymerization catalysts.

In the present invention, it is preferable that the metallocene compound (A) is a metallocene compound represented by the formula (1) or (2) and at least 2 kinds of olefins are copolymerized. It is also preferable that the metallocene compound (A) is a metallocene compound represented by the formula (1a) or (2a) and a single olefin is polymerized.

The polyolefin according to the invention comprises recurring units ($U_1$) derived from one α-olefin selected from α-olefins of 3 to 8 carbon atoms in amounts of 50 to 100% by mol and recurring units ($U_2$) other than the recurring units ($U_1$), said recurring units ($U_2$) being derived from at least one olefin selected from α-olefins of 2 to 20 carbon atoms, in amounts of 50 to 0% by mol, and has the following properties:
(i) the proportion of 2,1-insertion and the proportion of 1,3-insertion are each not more than 0.2%,
(ii) the molecular weight distribution (Mw/Mn) as determined by gel permeation chromatography is in the range of 1 to 3, and
(iii) the quantity of a decane-soluble component is not more than 2% by weight.

The polyolefin preferably comprises recurring units derived from propylene in amounts of 50 to 99.5% by mol and recurring units derived from at least one olefin selected from α-olefins of 2 to 20 carbon atoms other than propylene in amounts of 50 to 0.5% by mol.

Another embodiment of the polyolefin of the invention is a homopolymer of one α-olefin selected from α-olefins of 3 to 8 carbon atoms and has the following properties:
(i) the pentad isotacticity as determined from $^{13}$C-NMR spectrum measurement is not less than 85%,
(ii) the proportion of 2,1-insertion and the proportion of 1,3-insertion are each not more than 0.2%,
(iii) the MFR is in the range of 0.01 to 1000 g/10 min,
(iv) the molecular weight distribution (Mw/Mn) as determined by gel permeation chromatography is in the range of 1 to 3,
(v) the quantity of a decane-soluble component is not more than 2% by weight, and
(vi) the melting point (Tm) as measured by a differential scanning calorimeter is not lower than 140° C.

The polyolefin is preferably a homopolymer of propylene.

A further embodiment of the polyolefin of the invention is a polyolefin comprising recurring units ($U_1$) derived from one α-olefin selected from α-olefins of 3 to 8 carbon atoms in amounts of 95 to 99.5% by mol and recurring units ($U_2$) other than the recurring units ($U_1$), said recurring units ($U_2$) being derived from at least one olefin selected from α-olefins of 2 to 20 carbon atoms, in amounts of 5 to 0.05% by mol, and has the following properties:

(i) the pentad isotacticity as determined from $^{13}$C-NMR spectrum measurement is not less than 80%, (ii) the proportion of 2,1-insertion and the proportion of 1,3-insertion are each not more than 0.2%, (iii) the MFR is in the range of 0.01 to 1000 g/10 min, (iv) the molecular weight distribution (Mw/Mn) as determined by gel permeation chromatography is in the range of 1 to 3, (v) the quantity of a decane-soluble component is not more than 2% by weight, and (vi) the melting point (Tm) as measured by a differential scanning calorimeter is not higher than 145° C.

The polyolefin preferably comprises recurring units derived from propylene in amounts of 95 to 99.5% by mol and recurring units derived from at least one olefin selected from α-olefins of 2 to 20 carbon atoms other than propylene in amounts of 5 to 0.5% by mol.

BRIEF DESCRIPTION OF THE DRAWING

FIG. 1 is a view to explain an embodiment of a process for preparing the olefin polymerization catalyst according to the present invention.

BEST MODE FOR CARRYING OUT THE INVENTION

The metallocene compound, the process for preparing the metallocene compound, the olefin polymerization catalyst, the process for preparing a polyolefin, and the polyolefin according to the invention are described in detail hereinafter.

Metallocene Compound

The metallocene compound according to the invention is represented by the following formula (1) or (2).

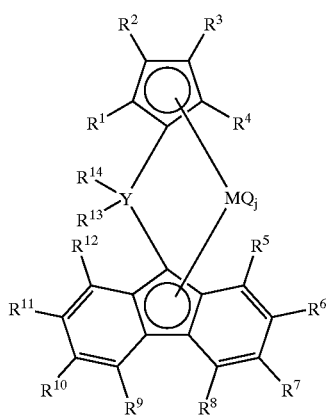

(1)

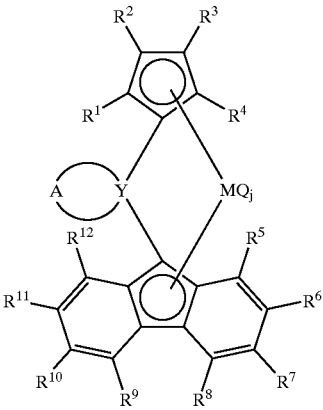

(2)

In the formula (1) or (2), $R^3$ is selected from a hydrocarbon group and a silicon-containing hydrocarbon group.

The hydrocarbon group preferably is, for example, an alkyl group of 1 to 20 carbon atoms, an arylalkyl group of 7 to 20 carbon atoms, an aryl group of 6 to 20 carbon atoms or an alkylaryl group of 7 to 20 carbon atoms. $R^3$ may be a cyclic hydrocarbon group containing a heteroatom (e.g., sulfur or oxygen), such as thienyl or furyl.

Specific examples of such groups include methyl, ethyl, n-propyl, isopropyl, 2-methylpropyl, 1,1-dimethylpropyl, 2,2-dimethylpropyl, 1,1-diethylpropyl, 1-ethyl-1-methylpropyl, 1,1,2,2-tetramethylpropyl, sec-butyl, tert-butyl, 1,1-dimethylbutyl, 1,1,3-trimethylbutyl, neopentyl, cyclohexylmethyl, cyclohexyl, 1-methyl-1-cyclohexyl, 1-adamantyl, 2-adamantyl, 2-methyl-2-adamantyl, menthyl, norbornyl, benzyl, 2-phenylethyl, 1-tetrahydronaphthyl, 1-methyl-1-tetrahydronaphthyl, phenyl, naphthyl and tolyl.

The silicon-containing hydrocarbon group is preferably an alkylsilyl or arylsilyl group having 1 to 4 silicon atoms and 3 to 20 carbon atoms.

Specific examples of such groups include trimethylsilyl, tert-butyldimethylsilyl and triphenylsilyl.

$R^3$ is preferably a sterically bulky substituent group, more preferably a substituent group of 4 or more carbon atoms.

In the formula (1) or (2), $R^1$, $R^2$, $R^4$, $R^5$, $R^6$, $R^7$, $R^8$, $R^9$, $R^{10}$, $R^{11}$, $R^{12}$, $R^{13}$ and $R^{14}$ may be the same or different and are each selected from a hydrogen atom, a hydrocarbon group and a silicon-containing hydrocarbon group. Preferred examples of the hydrocarbon groups and the silicon-containing hydrocarbon groups include the same ones as described above.

The neighboring substituent groups of $R^1$ to $R^4$ on the cyclopentadienyl ring may be bonded to form a ring. Examples of such substituted cyclopentadienyl groups include indenyl, 2-methylindenyl, tetrahydroindenyl, 2-methyltetrahydroindenyl and 2,4,4-trimethyltetrahydroindenyl.

The neighboring substituent groups of $R^5$ to $R^{12}$ on the fluorene ring may be bonded to form a ring. Examples of such substituted fluorenyl groups include benzofluorenyl, dibenzofluorenyl, octahydrodibenzofluorenyl and octamethyloctahydrodibenzofluorenyl.

The substituent groups of $R^5$ to $R^{12}$ on the fluorene ring are preferred to be bilaterally symmetric from the viewpoint of ease of synthesis. That is, $R^5$ and $R^{12}$, $R^6$ and $R^{11}$, $R^7$ and $R^{10}$, and $R^8$ and $R^9$ are preferred to be the same groups, and unsubstituted fluorene, 3,6-di-substituted fluorene, 2,7-disubstituted fluorene or 2,3,6,7-tetra-substituted fluorene is more preferred. The 3-position, 6-position, 2-position and 7-position of the fluorene ring correspond to $R^7$, $R^{10}$, $R^6$ and $R^{11}$, respectively.

In the formula (1) or (2), Y is a carbon atom or a silicon atom.

In the metallocene compound represented by the formula (1), $R^{13}$ and $R^{14}$ are bonded to Y and become a bridge part to form a substituted methylene group or a substituted silylene group. Preferred examples thereof include methylene, dimethylmethylene, diethylmethylene, diisopropylmethylene, methyl-tert-butylmethylene, di-tert-butylmethylene, dicyclohexylmethylene, methylcyclohexylmethylene, methylphenylmethylene, diphenylmethylene, methylnaphthylmethylene, dinaphthylmethylene, dimethylsilylene, diisopropylsilylene, methyl-tert-butylsilylene, dicyclohexylsilylene, methylcyclohexylsilylene, methylphenylsilylene, diphenylsilylene, methylnaphthylsilylene and dinaphthylsilylene.

In the metallocene compound represented by the formula (1), a substituent group selected from $R^1$, $R^4$, $R^5$ and $R^{12}$ may be bonded to $R^{13}$ or $R^{14}$ of the bridge part to form a ring. An example of such structure wherein $R^1$ and $R^{14}$ are bonded to each other to form a ring is given below. In the metallocene compound represented by the following formula (Ic), the bridge part and the cyclopentadienyl group are united to form tetrahydropentalene skeleton, while in the metallocene compound represented by the following formula (1d), the bridge part and the cyclopentadienyl group are united to form tetrahydroindenyl skeleton. Likewise, the bridge part and the fluorenyl group may be bonded to form a ring.

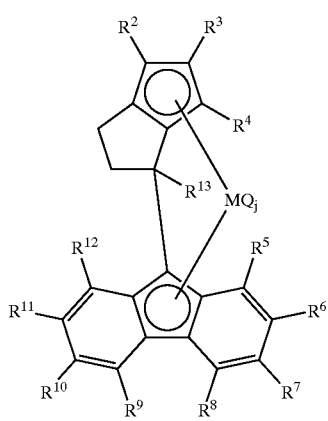

(1c)

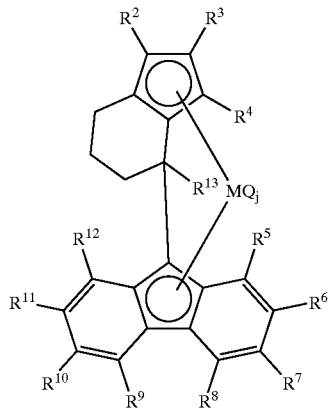

(1d)

In the metallocene compound represented by the formula (2), A is a divalent hydrocarbon group of 2 to 20 carbon atoms which may contain an unsaturated bond and/or an aromatic ring, and Y is bonded to A to form a cycloalkylidene group, a cyclomethylenesilylene group or the like.

A may contain two or more cyclic structures including a ring formed by A in cooperation with Y. Preferred examples thereof include cyclopropylidene, cyclobutylidene, cyclopentylidene, cyclohexylidene, cycloheptylidene, bicyclo[3,3,1]nonylidene, norbornylidene, adamantylidene, tetrahydronaphthylidene, dihydroindanylidene, cyclodimethylenesilylene, cyclotrimethylenesilylene, cyclotetramethylenesilylene, cyclopentamethylenesilylene, cyclohexamethylenesilylene and cycloheptamethylenesilylene.

In the formula (1) or (2), M is a metal selected from Group 4 of the periodic table and is specifically titanium, zirconium or hafnium.

In the formula (1) or (2), j is an integer of 1 to 4.

In the formula (1) or (2), Q is selected from a halogen atom, a hydrocarbon group of 1 to 20 carbon atoms, an anionic ligand and a neutral ligand capable of coordination by a lone pair. When j is 2 or greater, each Q may be the same or different.

Examples of the halogen atoms include fluorine, chlorine, bromine and iodine. Examples of the hydrocarbon groups include the same ones as previously described.

Examples of the anionic ligands include alkoxy groups, such as methoxy, tert-butoxy and phenoxy; carboxylate groups, such as acetate and benzoate; and sulfonate groups, such as mesylate and tosylate.

Examples of the neutral ligands capable of coordination by a lone pair include organophosphorus compounds, such as trimethylphosphine, triethylphosphine, triphenylphosphine and diphenylmethylphosphine; and ethers, such as tetrahydrofuran, diethyl ether, dioxane and 1,2-dimethoxyethane.

At least one of Q is preferably a halogen atom or an alkyl group.

Examples of the metallocene compounds represented by the formula (1) or (2) according to the invention are given below.

The ligand structure excluding MQj (metal part) in the metallocene compound is divided into three parts of Cp (cyclopentadienyl ring part), Bridge (bridge part) and Flu (fluorenyl ring part), and specific examples of these partial structures and specific examples of ligand structures formed by combination of these partial structures are described first.

Examples of Cp a1
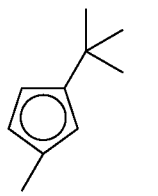

a2
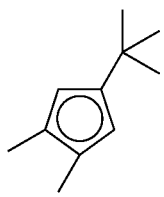

a3
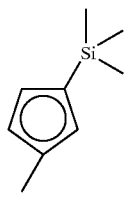

a4
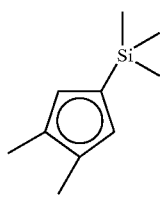

a5
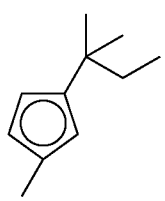

a6
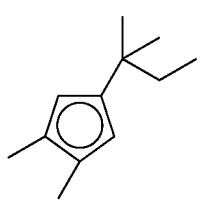

a7
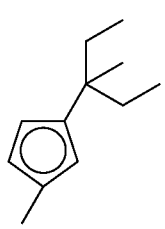

-continued a8
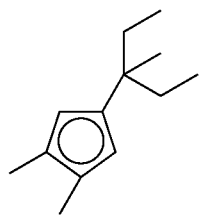

a9
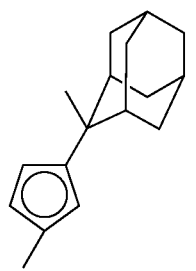

a10
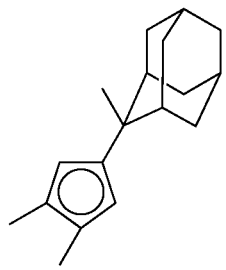

a11
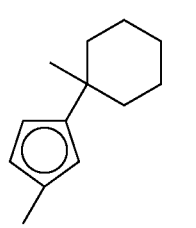

a12
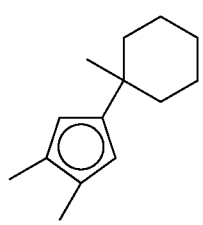

a13
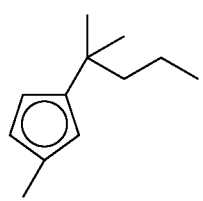

a14
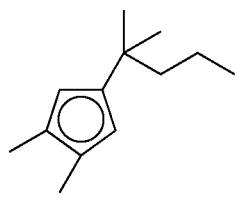

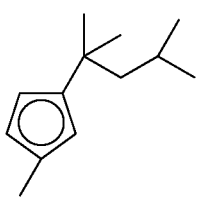
a15
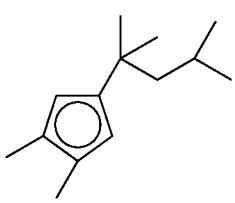
a16
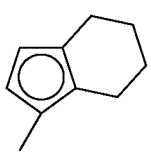
a17
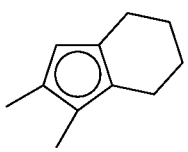
a18
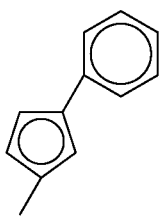
a19
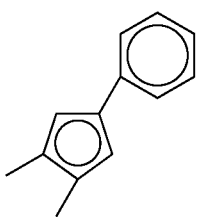
a20
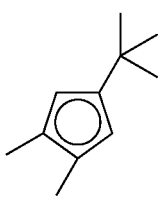
a21
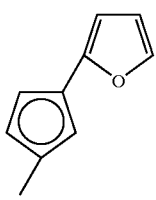
a22
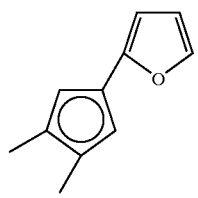
a23
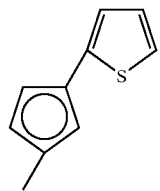
a24
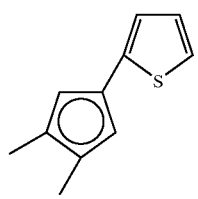
a25
Examples of Bridge
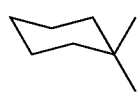
b1
b2
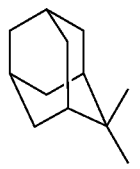
b3
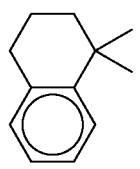
b4
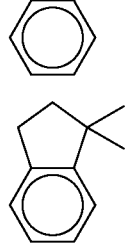
b5
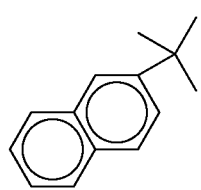
b6

-continued
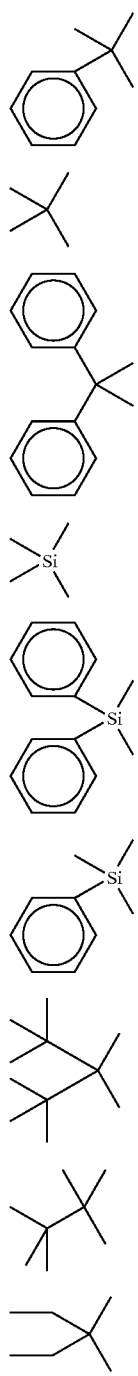
Examples of Flu
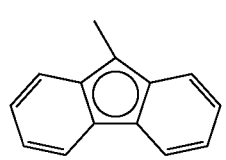
c1
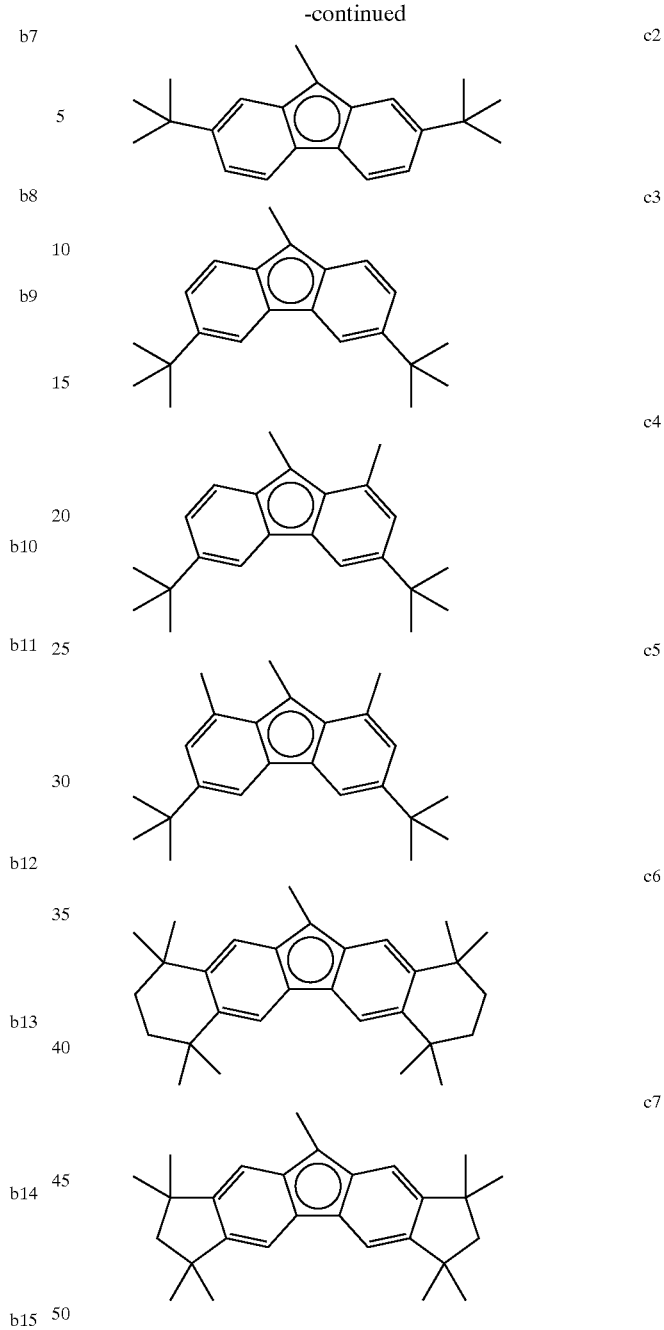
Examples of the ligand structures are described in the following table.
| No. | Cp | Bridge | Flu |
|---|---|---|---|
| 1 | a 1 | b 1 | c 1 |
| 2 | a 2 | b 1 | c 1 |
| 3 | a 3 | b 1 | c 1 |
| 4 | a 4 | b 1 | c 1 |
| 5 | a 5 | b 1 | c 1 |
| 6 | a 6 | b 1 | c 1 |
| 7 | a 7 | b 1 | c 1 |
| 8 | a 8 | b 1 | c 1 |
| 9 | a 9 | b 1 | c 1 |
| 10 | a 10 | b 1 | c 1 |

|     |       |        |     |
| --- | ----- | ------ | --- |
| No. | Cp    | Bridge | Flu |
| 11  | a 11  | b 1    | c 1 |
| 12  | a 12  | b 1    | c 1 |
| 13  | a 13  | b 1    | c 1 |
| 14  | a 14  | b 1    | c 1 |
| 15  | a 15  | b 1    | c 1 |
| 16  | a 16  | b 1    | c 1 |
| 17  | a 17  | b 1    | c 1 |
| 18  | a 18  | b 1    | c 1 |
| 19  | a 19  | b 1    | c 1 |
| 20  | a 20  | b 1    | c 1 |
| 21  | a 21  | b 1    | c 1 |
| 22  | a 22  | b 1    | c 1 |
| 23  | a 23  | b 1    | c 1 |
| 24  | a 24  | b 1    | c 1 |
| 25  | a 25  | b 1    | c 1 |
| 26  | a 1   | b 2    | c 1 |
| 27  | a 2   | b 2    | c 1 |
| 28  | a 3   | b 2    | c 1 |
| 29  | a 4   | b 2    | c 1 |
| 30  | a 5   | b 2    | c 1 |
| 31  | a 6   | b 2    | c 1 |
| 32  | a 7   | b 2    | c 1 |
| 33  | a 8   | b 2    | c 1 |
| 34  | a 9   | b 2    | c 1 |
| 35  | a 10  | b 2    | c 1 |
| 36  | a 11  | b 2    | c 1 |
| 37  | a 12  | b 2    | c 1 |
| 38  | a 13  | b 2    | c 1 |
| 39  | a 14  | b 2    | c 1 |
| 40  | a 15  | b 2    | c 1 |
| 41  | a 16  | b 2    | c 1 |
| 42  | a 17  | b 2    | c 1 |
| 43  | a 18  | b 2    | c 1 |
| 44  | a 19  | b 2    | c 1 |
| 45  | a 20  | b 2    | c 1 |
| 46  | a 21  | b 2    | c 1 |
| 47  | a 22  | b 2    | c 1 |
| 48  | a 23  | b 2    | c 1 |
| 49  | a 24  | b 2    | c 1 |
| 50  | a 25  | b 2    | c 1 |
| 51  | a 1   | b 3    | c 1 |
| 52  | a 2   | b 3    | c 1 |
| 53  | a 3   | b 3    | c 1 |
| 54  | a 4   | b 3    | c 1 |
| 55  | a 5   | b 3    | c 1 |
| 56  | a 6   | b 3    | c 1 |
| 57  | a 7   | b 3    | c 1 |
| 58  | a 8   | b 3    | c 1 |
| 59  | a 9   | b 3    | c 1 |
| 60  | a 10  | b 3    | c 1 |
| 61  | a 11  | b 3    | c 1 |
| 62  | a 12  | b 3    | c 1 |
| 63  | a 13  | b 3    | c 1 |
| 64  | a 14  | b 3    | c 1 |
| 65  | a 15  | b 3    | c 1 |
| 66  | a 16  | b 3    | c 1 |
| 67  | a 17  | b 3    | c 1 |
| 68  | a 18  | b 3    | c 1 |
| 69  | a 19  | b 3    | c 1 |
| 70  | a 20  | b 3    | c 1 |
| 71  | a 21  | b 3    | c 1 |
| 72  | a 22  | b 3    | c 1 |
| 73  | a 23  | b 3    | c 1 |
| 74  | a 24  | b 3    | c 1 |
| 75  | a 25  | b 3    | c 1 |
| 76  | a 1   | b 4    | c 1 |
| 77  | a 2   | b 4    | c 1 |
| 78  | a 3   | b 4    | c 1 |
| 79  | a 4   | b 4    | c 1 |
| 80  | a 5   | b 4    | c 1 |
| 81  | a 6   | b 4    | c 1 |
| 82  | a 7   | b 4    | c 1 |
| 83  | a 8   | b 4    | c 1 |
| 84  | a 9   | b 4    | c 1 |
| 85  | a 10  | b 4    | c 1 |
| 86  | a 11  | b 4    | c 1 |
| 87  | a 12  | b 4    | c 1 |
| 88  | a 13  | b 4    | c 1 |
| 89  | a 14  | b 4    | c 1 |
| 90  | a 15  | b 4    | c 1 |
| 91  | a 16  | b 4    | c 1 |
| 92  | a 17  | b 4    | c 1 |
| 93  | a 18  | b 4    | c 1 |
| 94  | a 19  | b 4    | c 1 |
| 95  | a 20  | b 4    | c 1 |
| 96  | a 21  | b 4    | c 1 |
| 97  | a 22  | b 4    | c 1 |
| 98  | a 23  | b 4    | c 1 |
| 99  | a 24  | b 4    | c 1 |
| 100 | a 25  | b 4    | c 1 |
| 101 | a 1   | b 5    | c 1 |
| 102 | a 2   | b 5    | c 1 |
| 103 | a 3   | b 5    | c 1 |
| 104 | a 4   | b 5    | c 1 |
| 105 | a 5   | b 5    | c 1 |
| 106 | a 6   | b 5    | c 1 |
| 107 | a 7   | b 5    | c 1 |
| 108 | a 8   | b 5    | c 1 |
| 109 | a 9   | b 5    | c 1 |
| 110 | a 10  | b 5    | c 1 |
| 111 | a 11  | b 5    | c 1 |
| 112 | a 12  | b 5    | c 1 |
| 113 | a 13  | b 5    | c 1 |
| 114 | a 14  | b 5    | c 1 |
| 115 | a 15  | b 5    | c 1 |
| 116 | a 16  | b 5    | c 1 |
| 117 | a 17  | b 5    | c 1 |
| 118 | a 18  | b 5    | c 1 |
| 119 | a 19  | b 5    | c 1 |
| 120 | a 20  | b 5    | c 1 |
| 121 | a 21  | b 5    | c 1 |
| 122 | a 22  | b 5    | c 1 |
| 123 | a 23  | b 5    | c 1 |
| 124 | a 24  | b 5    | c 1 |
| 125 | a 25  | b 5    | c 1 |
| 126 | a 1   | b 6    | c 1 |
| 127 | a 2   | b 6    | c 1 |
| 128 | a 3   | b 6    | c 1 |
| 129 | a 4   | b 6    | c 1 |
| 130 | a 5   | b 6    | c 1 |
| 131 | a 6   | b 6    | c 1 |
| 132 | a 7   | b 6    | c 1 |
| 133 | a 8   | b 6    | c 1 |
| 134 | a 9   | b 6    | c 1 |
| 135 | a 10  | b 6    | c 1 |
| 136 | a 11  | b 6    | c 1 |
| 137 | a 12  | b 6    | c 1 |
| 138 | a 13  | b 6    | c 1 |
| 139 | a 14  | b 6    | c 1 |
| 140 | a 15  | b 6    | c 1 |
| 141 | a 16  | b 6    | c 1 |
| 142 | a 17  | b 6    | c 1 |
| 143 | a 18  | b 6    | c 1 |
| 144 | a 19  | b 6    | c 1 |
| 145 | a 20  | b 6    | c 1 |
| 146 | a 21  | b 6    | c 1 |
| 147 | a 22  | b 6    | c 1 |
| 148 | a 23  | b 6    | c 1 |
| 149 | a 24  | b 6    | c 1 |
| 150 | a 25  | b 6    | c 1 |
| 151 | a 1   | b 7    | c 1 |
| 152 | a 2   | b 7    | c 1 |
| 153 | a 3   | b 7    | c 1 |
| 154 | a 4   | b 7    | c 1 |
| 155 | a 5   | b 7    | c 1 |
| 156 | a 6   | b 7    | c 1 |
| 157 | a 7   | b 7    | c 1 |
| 158 | a 8   | b 7    | c 1 |
| 159 | a 9   | b 7    | c 1 |
| 160 | a 10  | b 7    | c 1 |
| 161 | a 11  | b 7    | c 1 |
| 162 | a 12  | b 7    | c 1 |
| 163 | a 13  | b 7    | c 1 |
| 164 | a 14  | b 7    | c 1 |

-continued

| No. | Cp | Bridge | Flu |
|---|---|---|---|
| 165 | a 15 | b 7 | c 1 |
| 166 | a 16 | b 7 | c 1 |
| 167 | a 17 | b 7 | c 1 |
| 168 | a 18 | b 7 | c 1 |
| 169 | a 19 | b 7 | c 1 |
| 170 | a 20 | b 7 | c 1 |
| 171 | a 21 | b 7 | c 1 |
| 172 | a 22 | b 7 | c 1 |
| 173 | a 23 | b 7 | c 1 |
| 174 | a 24 | b 7 | c 1 |
| 175 | a 25 | b 7 | c 1 |
| 176 | a 1 | b 8 | c 1 |
| 177 | a 2 | b 8 | c 1 |
| 178 | a 3 | b 8 | c 1 |
| 179 | a 4 | b 8 | c 1 |
| 180 | a 5 | b 8 | c 1 |
| 181 | a 6 | b 8 | c 1 |
| 182 | a 7 | b 8 | c 1 |
| 183 | a 8 | b 8 | c 1 |
| 184 | a 9 | b 8 | c 1 |
| 185 | a 10 | b 8 | c 1 |
| 186 | a 11 | b 8 | c 1 |
| 187 | a 12 | b 8 | c 1 |
| 188 | a 13 | b 8 | c 1 |
| 189 | a 14 | b 8 | c 1 |
| 190 | a 15 | b 8 | c 1 |
| 191 | a 16 | b 8 | c 1 |
| 192 | a 17 | b 8 | c 1 |
| 193 | a 18 | b 8 | c 1 |
| 194 | a 19 | b 8 | c 1 |
| 195 | a 20 | b 8 | c 1 |
| 196 | a 21 | b 8 | c 1 |
| 197 | a 22 | b 8 | c 1 |
| 198 | a 23 | b 8 | c 1 |
| 199 | a 24 | b 8 | c 1 |
| 200 | a 25 | b 8 | c 1 |
| 201 | a 1 | b 9 | c 1 |
| 202 | a 2 | b 9 | c 1 |
| 203 | a 3 | b 9 | c 1 |
| 204 | a 4 | b 9 | c 1 |
| 205 | a 5 | b 9 | c 1 |
| 206 | a 6 | b 9 | c 1 |
| 207 | a 7 | b 9 | c 1 |
| 208 | a 8 | b 9 | c 1 |
| 209 | a 9 | b 9 | c 1 |
| 210 | a 10 | b 9 | c 1 |
| 211 | a 11 | b 9 | c 1 |
| 212 | a 12 | b 9 | c 1 |
| 213 | a 13 | b 9 | c 1 |
| 214 | a 14 | b 9 | c 1 |
| 215 | a 15 | b 9 | c 1 |
| 216 | a 16 | b 9 | c 1 |
| 217 | a 17 | b 9 | c 1 |
| 218 | a 18 | b 9 | c 1 |
| 219 | a 19 | b 9 | c 1 |
| 220 | a 20 | b 9 | c 1 |
| 221 | a 21 | b 9 | c 1 |
| 222 | a 22 | b 9 | c 1 |
| 223 | a 23 | b 9 | c 1 |
| 224 | a 24 | b 9 | c 1 |
| 225 | a 25 | b 9 | c 1 |
| 226 | a 1 | b 10 | c 1 |
| 227 | a 2 | b 10 | c 1 |
| 228 | a 3 | b 10 | c 1 |
| 229 | a 4 | b 10 | c 1 |
| 230 | a 5 | b 10 | c 1 |
| 231 | a 6 | b 10 | c 1 |
| 232 | a 7 | b 10 | c 1 |
| 233 | a 8 | b 10 | c 1 |
| 234 | a 9 | b 10 | c 1 |
| 235 | a 10 | b 10 | c 1 |
| 236 | a 11 | b 10 | c 1 |
| 237 | a 12 | b 10 | c 1 |
| 238 | a 13 | b 10 | c 1 |
| 239 | a 14 | b 10 | c 1 |
| 240 | a 15 | b 10 | c 1 |
| 241 | a 16 | b 10 | c 1 |
| 242 | a 17 | b 10 | c 1 |
| 243 | a 18 | b 10 | c 1 |
| 244 | a 19 | b 10 | c 1 |
| 245 | a 20 | b 10 | c 1 |
| 246 | a 21 | b 10 | c 1 |
| 247 | a 22 | b 10 | c 1 |
| 248 | a 23 | b 10 | c 1 |
| 249 | a 24 | b 10 | c 1 |
| 250 | a 25 | b 10 | c 1 |
| 251 | a 1 | b 11 | c 1 |
| 252 | a 2 | b 11 | c 1 |
| 253 | a 3 | b 11 | c 1 |
| 254 | a 4 | b 11 | c 1 |
| 255 | a 5 | b 11 | c 1 |
| 256 | a 6 | b 11 | c 1 |
| 257 | a 7 | b 11 | c 1 |
| 258 | a 8 | b 11 | c 1 |
| 259 | a 9 | b 11 | c 1 |
| 260 | a 10 | b 11 | c 1 |
| 261 | a 11 | b 11 | c 1 |
| 262 | a 12 | b 11 | c 1 |
| 263 | a 13 | b 11 | c 1 |
| 264 | a 14 | b 11 | c 1 |
| 265 | a 15 | b 11 | c 1 |
| 266 | a 16 | b 11 | c 1 |
| 267 | a 17 | b 11 | c 1 |
| 268 | a 18 | b 11 | c 1 |
| 269 | a 19 | b 11 | c 1 |
| 270 | a 20 | b 11 | c 1 |
| 271 | a 21 | b 11 | c 1 |
| 272 | a 22 | b 11 | c 1 |
| 273 | a 23 | b 11 | c 1 |
| 274 | a 24 | b 11 | c 1 |
| 275 | a 25 | b 11 | c 1 |
| 276 | a 1 | b 12 | c 1 |
| 277 | a 2 | b 12 | c 1 |
| 278 | a 3 | b 12 | c 1 |
| 279 | a 4 | b 12 | c 1 |
| 280 | a 5 | b 12 | c 1 |
| 281 | a 6 | b 12 | c 1 |
| 282 | a 7 | b 12 | c 1 |
| 283 | a 8 | b 12 | c 1 |
| 284 | a 9 | b 12 | c 1 |
| 285 | a 10 | b 12 | c 1 |
| 286 | a 11 | b 12 | c 1 |
| 287 | a 12 | b 12 | c 1 |
| 288 | a 13 | b 12 | c 1 |
| 289 | a 14 | b 12 | c 1 |
| 290 | a 15 | b 12 | c 1 |
| 291 | a 16 | b 12 | c 1 |
| 292 | a 17 | b 12 | c 1 |
| 293 | a 18 | b 12 | c 1 |
| 294 | a 19 | b 12 | c 1 |
| 295 | a 20 | b 12 | c 1 |
| 296 | a 21 | b 12 | c 1 |
| 297 | a 22 | b 12 | c 1 |
| 298 | a 23 | b 12 | c 1 |
| 299 | a 24 | b 12 | c 1 |
| 300 | a 25 | b 12 | c 1 |
| 301 | a 1 | b 13 | c 1 |
| 302 | a 2 | b 13 | c 1 |
| 303 | a 3 | b 13 | c 1 |
| 304 | a 4 | b 13 | c 1 |
| 305 | a 5 | b 13 | c 1 |
| 306 | a 6 | b 13 | c 1 |
| 307 | a 7 | b 13 | c 1 |
| 308 | a 8 | b 13 | c 1 |
| 309 | a 9 | b 13 | c 1 |
| 310 | a 10 | b 13 | c 1 |
| 311 | a 11 | b 13 | c 1 |
| 312 | a 12 | b 13 | c 1 |
| 313 | a 13 | b 13 | c 1 |
| 314 | a 14 | b 13 | c 1 |
| 315 | a 15 | b 13 | c 1 |
| 316 | a 16 | b 13 | c 1 |
| 317 | a 17 | b 13 | c 1 |
| 318 | a 18 | b 13 | c 1 |

| No. | Cp | Bridge | Flu |
|---|---|---|---|
| 319 | a 19 | b 13 | c 1 |
| 320 | a 20 | b 13 | c 1 |
| 321 | a 21 | b 13 | c 1 |
| 322 | a 22 | b 13 | c 1 |
| 323 | a 23 | b 13 | c 1 |
| 324 | a 24 | b 13 | c 1 |
| 325 | a 25 | b 13 | c 1 |
| 326 | a 1 | b 14 | c 1 |
| 327 | a 2 | b 14 | c 1 |
| 328 | a 3 | b 14 | c 1 |
| 329 | a 4 | b 14 | c 1 |
| 330 | a 5 | b 14 | c 1 |
| 331 | a 6 | b 14 | c 1 |
| 332 | a 7 | b 14 | c 1 |
| 333 | a 8 | b 14 | c 1 |
| 334 | a 9 | b 14 | c 1 |
| 335 | a 10 | b 14 | c 1 |
| 336 | a 11 | b 14 | c 1 |
| 337 | a 12 | b 14 | c 1 |
| 338 | a 13 | b 14 | c 1 |
| 339 | a 14 | b 14 | c 1 |
| 340 | a 15 | b 14 | c 1 |
| 341 | a 16 | b 14 | c 1 |
| 342 | a 17 | b 14 | c 1 |
| 343 | a 18 | b 14 | c 1 |
| 344 | a 19 | b 14 | c 1 |
| 345 | a 20 | b 14 | c 1 |
| 346 | a 21 | b 14 | c 1 |
| 347 | a 22 | b 14 | c 1 |
| 348 | a 23 | b 14 | c 1 |
| 349 | a 24 | b 14 | c 1 |
| 350 | a 25 | b 14 | c 1 |
| 351 | a 1 | b 15 | c 1 |
| 352 | a 2 | b 15 | c 1 |
| 353 | a 3 | b 15 | c 1 |
| 354 | a 4 | b 15 | c 1 |
| 355 | a 5 | b 15 | c 1 |
| 356 | a 6 | b 15 | c 1 |
| 357 | a 7 | b 15 | c 1 |
| 358 | a 8 | b 15 | c 1 |
| 359 | a 9 | b 15 | c 1 |
| 360 | a 10 | b 15 | c 1 |
| 361 | a 11 | b 15 | c 1 |
| 362 | a 12 | b 15 | c 1 |
| 363 | a 13 | b 15 | c 1 |
| 364 | a 14 | b 15 | c 1 |
| 365 | a 15 | b 15 | c 1 |
| 366 | a 16 | b 15 | c 1 |
| 367 | a 17 | b 15 | c 1 |
| 368 | a 18 | b 15 | c 1 |
| 369 | a 19 | b 15 | c 1 |
| 370 | a 20 | b 15 | c 1 |
| 371 | a 21 | b 15 | c 1 |
| 372 | a 22 | b 15 | c 1 |
| 373 | a 23 | b 15 | c 1 |
| 374 | a 24 | b 15 | c 1 |
| 375 | a 25 | b 15 | c 1 |
| 376 | a 1 | b 1 | c 2 |
| 377 | a 2 | b 1 | c 2 |
| 378 | a 3 | b 1 | c 2 |
| 379 | a 4 | b 1 | c 2 |
| 380 | a 5 | b 1 | c 2 |
| 381 | a 6 | b 1 | c 2 |
| 382 | a 7 | b 1 | c 2 |
| 383 | a 8 | b 1 | c 2 |
| 384 | a 9 | b 1 | c 2 |
| 385 | a 10 | b 1 | c 2 |
| 386 | a 11 | b 1 | c 2 |
| 387 | a 12 | b 1 | c 2 |
| 388 | a 13 | b 1 | c 2 |
| 389 | a 14 | b 1 | c 2 |
| 390 | a 15 | b 1 | c 2 |
| 391 | a 16 | b 1 | c 2 |
| 392 | a 17 | b 1 | c 2 |
| 393 | a 18 | b 1 | c 2 |
| 394 | a 19 | b 1 | c 2 |
| 395 | a 20 | b 1 | c 2 |
| 396 | a 21 | b 1 | c 2 |
| 397 | a 22 | b 1 | c 2 |
| 398 | a 23 | b 1 | c 2 |
| 399 | a 24 | b 1 | c 2 |
| 400 | a 25 | b 1 | c 2 |
| 401 | a 1 | b 2 | c 2 |
| 402 | a 2 | b 2 | c 2 |
| 403 | a 3 | b 2 | c 2 |
| 404 | a 4 | b 2 | c 2 |
| 405 | a 5 | b 2 | c 2 |
| 406 | a 6 | b 2 | c 2 |
| 407 | a 7 | b 2 | c 2 |
| 408 | a 8 | b 2 | c 2 |
| 409 | a 9 | b 2 | c 2 |
| 410 | a 10 | b 2 | c 2 |
| 411 | a 11 | b 2 | c 2 |
| 412 | a 12 | b 2 | c 2 |
| 413 | a 13 | b 2 | c 2 |
| 414 | a 14 | b 2 | c 2 |
| 415 | a 15 | b 2 | c 2 |
| 416 | a 16 | b 2 | c 2 |
| 417 | a 17 | b 2 | c 2 |
| 418 | a 18 | b 2 | c 2 |
| 419 | a 19 | b 2 | c 2 |
| 420 | a 20 | b 2 | c 2 |
| 421 | a 21 | b 2 | c 2 |
| 422 | a 22 | b 2 | c 2 |
| 423 | a 23 | b 2 | c 2 |
| 424 | a 24 | b 2 | c 2 |
| 425 | a 25 | b 2 | c 2 |
| 426 | a 1 | b 3 | c 2 |
| 427 | a 2 | b 3 | c 2 |
| 428 | a 3 | b 3 | c 2 |
| 429 | a 4 | b 3 | c 2 |
| 430 | a 5 | b 3 | c 2 |
| 431 | a 6 | b 3 | c 2 |
| 432 | a 7 | b 3 | c 2 |
| 433 | a 8 | b 3 | c 2 |
| 434 | a 9 | b 3 | c 2 |
| 435 | a 10 | b 3 | c 2 |
| 436 | a 11 | b 3 | c 2 |
| 437 | a 12 | b 3 | c 2 |
| 438 | a 13 | b 3 | c 2 |
| 439 | a 14 | b 3 | c 2 |
| 440 | a 15 | b 3 | c 2 |
| 441 | a 16 | b 3 | c 2 |
| 442 | a 17 | b 3 | c 2 |
| 443 | a 18 | b 3 | c 2 |
| 444 | a 19 | b 3 | c 2 |
| 445 | a 20 | b 3 | c 2 |
| 446 | a 21 | b 3 | c 2 |
| 447 | a 22 | b 3 | c 2 |
| 448 | a 23 | b 3 | c 2 |
| 449 | a 24 | b 3 | c 2 |
| 450 | a 25 | b 3 | c 2 |
| 451 | a 1 | b 4 | c 2 |
| 452 | a 2 | b 4 | c 2 |
| 453 | a 3 | b 4 | c 2 |
| 454 | a 4 | b 4 | c 2 |
| 455 | a 5 | b 4 | c 2 |
| 456 | a 6 | b 4 | c 2 |
| 457 | a 7 | b 4 | c 2 |
| 458 | a 8 | b 4 | c 2 |
| 459 | a 9 | b 4 | c 2 |
| 460 | a 10 | b 4 | c 2 |
| 461 | a 11 | b 4 | c 2 |
| 462 | a 12 | b 4 | c 2 |
| 463 | a 13 | b 4 | c 2 |
| 464 | a 14 | b 4 | c 2 |
| 465 | a 15 | b 4 | c 2 |
| 466 | a 16 | b 4 | c 2 |
| 467 | a 17 | b 4 | c 2 |
| 468 | a 18 | b 4 | c 2 |
| 469 | a 19 | b 4 | c 2 |
| 470 | a 20 | b 4 | c 2 |
| 471 | a 21 | b 4 | c 2 |
| 472 | a 22 | b 4 | c 2 |

-continued

| No. | Cp | Bridge | Flu |
|---|---|---|---|
| 473 | a 23 | b 4 | c 2 |
| 474 | a 24 | b 4 | c 2 |
| 475 | a 25 | b 4 | c 2 |
| 476 | a 1 | b 5 | c 2 |
| 477 | a 2 | b 5 | c 2 |
| 478 | a 3 | b 5 | c 2 |
| 479 | a 4 | b 5 | c 2 |
| 480 | a 5 | b 5 | c 2 |
| 481 | a 6 | b 5 | c 2 |
| 482 | a 7 | b 5 | c 2 |
| 483 | a 8 | b 5 | c 2 |
| 484 | a 9 | b 5 | c 2 |
| 485 | a 10 | b 5 | c 2 |
| 486 | a 11 | b 5 | c 2 |
| 487 | a 12 | b 5 | c 2 |
| 488 | a 13 | b 5 | c 2 |
| 489 | a 14 | b 5 | c 2 |
| 490 | a 15 | b 5 | c 2 |
| 491 | a 16 | b 5 | c 2 |
| 492 | a 17 | b 5 | c 2 |
| 493 | a 18 | b 5 | c 2 |
| 494 | a 19 | b 5 | c 2 |
| 495 | a 20 | b 5 | c 2 |
| 496 | a 21 | b 5 | c 2 |
| 497 | a 22 | b 5 | c 2 |
| 498 | a 23 | b 5 | c 2 |
| 499 | a 24 | b 5 | c 2 |
| 500 | a 25 | b 5 | c 2 |
| 501 | a 1 | b 6 | c 2 |
| 502 | a 2 | b 6 | c 2 |
| 503 | a 3 | b 6 | c 2 |
| 504 | a 4 | b 6 | c 2 |
| 505 | a 5 | b 6 | c 2 |
| 506 | a 6 | b 6 | c 2 |
| 507 | a 7 | b 6 | c 2 |
| 508 | a 8 | b 6 | c 2 |
| 509 | a 9 | b 6 | c 2 |
| 510 | a 10 | b 6 | c 2 |
| 511 | a 11 | b 6 | c 2 |
| 512 | a 12 | b 6 | c 2 |
| 513 | a 13 | b 6 | c 2 |
| 514 | a 14 | b 6 | c 2 |
| 515 | a 15 | b 6 | c 2 |
| 516 | a 16 | b 6 | c 2 |
| 517 | a 17 | b 6 | c 2 |
| 518 | a 18 | b 6 | c 2 |
| 519 | a 19 | b 6 | c 2 |
| 520 | a 20 | b 6 | c 2 |
| 521 | a 21 | b 6 | c 2 |
| 522 | a 22 | b 6 | c 2 |
| 523 | a 23 | b 6 | c 2 |
| 524 | a 24 | b 6 | c 2 |
| 525 | a 25 | b 6 | c 2 |
| 526 | a 1 | b 7 | c 2 |
| 527 | a 2 | b 7 | c 2 |
| 528 | a 3 | b 7 | c 2 |
| 529 | a 4 | b 7 | c 2 |
| 530 | a 5 | b 7 | c 2 |
| 531 | a 6 | b 7 | c 2 |
| 532 | a 7 | b 7 | c 2 |
| 533 | a 8 | b 7 | c 2 |
| 534 | a 9 | b 7 | c 2 |
| 535 | a 10 | b 7 | c 2 |
| 536 | a 11 | b 7 | c 2 |
| 537 | a 12 | b 7 | c 2 |
| 538 | a 13 | b 7 | c 2 |
| 539 | a 14 | b 7 | c 2 |
| 540 | a 15 | b 7 | c 2 |
| 541 | a 16 | b 7 | c 2 |
| 542 | a 17 | b 7 | c 2 |
| 543 | a 18 | b 7 | c 2 |
| 544 | a 19 | b 7 | c 2 |
| 545 | a 20 | b 7 | c 2 |
| 546 | a 21 | b 7 | c 2 |
| 547 | a 22 | b 7 | c 2 |
| 548 | a 23 | b 7 | c 2 |
| 549 | a 24 | b 7 | c 2 |
| 550 | a 25 | b 7 | c 2 |
| 551 | a 1 | b 8 | c 2 |
| 552 | a 2 | b 8 | c 2 |
| 553 | a 3 | b 8 | c 2 |
| 554 | a 4 | b 8 | c 2 |
| 555 | a 5 | b 8 | c 2 |
| 556 | a 6 | b 8 | c 2 |
| 557 | a 7 | b 8 | c 2 |
| 558 | a 8 | b 8 | c 2 |
| 559 | a 9 | b 8 | c 2 |
| 560 | a 10 | b 8 | c 2 |
| 561 | a 11 | b 8 | c 2 |
| 562 | a 12 | b 8 | c 2 |
| 563 | a 13 | b 8 | c 2 |
| 564 | a 14 | b 8 | c 2 |
| 565 | a 15 | b 8 | c 2 |
| 566 | a 16 | b 8 | c 2 |
| 567 | a 17 | b 8 | c 2 |
| 568 | a 18 | b 8 | c 2 |
| 569 | a 19 | b 8 | c 2 |
| 570 | a 20 | b 8 | c 2 |
| 571 | a 21 | b 8 | c 2 |
| 572 | a 22 | b 8 | c 2 |
| 573 | a 23 | b 8 | c 2 |
| 574 | a 24 | b 8 | c 2 |
| 575 | a 25 | b 8 | c 2 |
| 576 | a 1 | b 9 | c 2 |
| 577 | a 2 | b 9 | c 2 |
| 578 | a 3 | b 9 | c 2 |
| 579 | a 4 | b 9 | c 2 |
| 580 | a 5 | b 9 | c 2 |
| 581 | a 6 | b 9 | c 2 |
| 582 | a 7 | b 9 | c 2 |
| 583 | a 8 | b 9 | c 2 |
| 584 | a 9 | b 9 | c 2 |
| 585 | a 10 | b 9 | c 2 |
| 586 | a 11 | b 9 | c 2 |
| 587 | a 12 | b 9 | c 2 |
| 588 | a 13 | b 9 | c 2 |
| 589 | a 14 | b 9 | c 2 |
| 590 | a 15 | b 9 | c 2 |
| 591 | a 16 | b 9 | c 2 |
| 592 | a 17 | b 9 | c 2 |
| 593 | a 18 | b 9 | c 2 |
| 594 | a 19 | b 9 | c 2 |
| 595 | a 20 | b 9 | c 2 |
| 596 | a 21 | b 9 | c 2 |
| 597 | a 22 | b 9 | c 2 |
| 598 | a 23 | b 9 | c 2 |
| 599 | a 24 | b 9 | c 2 |
| 600 | a 25 | b 9 | c 2 |
| 601 | a 1 | b 10 | c 2 |
| 602 | a 2 | b 10 | c 2 |
| 603 | a 3 | b 10 | c 2 |
| 604 | a 4 | b 10 | c 2 |
| 605 | a 5 | b 10 | c 2 |
| 606 | a 6 | b 10 | c 2 |
| 607 | a 7 | b 10 | c 2 |
| 608 | a 8 | b 10 | c 2 |
| 609 | a 9 | b 10 | c 2 |
| 610 | a 10 | b 10 | c 2 |
| 611 | a 11 | b 10 | c 2 |
| 612 | a 12 | b 10 | c 2 |
| 613 | a 13 | b 10 | c 2 |
| 614 | a 14 | b 10 | c 2 |
| 615 | a 15 | b 10 | c 2 |
| 616 | a 16 | b 10 | c 2 |
| 617 | a 17 | b 10 | c 2 |
| 618 | a 18 | b 10 | c 2 |
| 619 | a 19 | b 10 | c 2 |
| 620 | a 20 | b 10 | c 2 |
| 621 | a 21 | b 10 | c 2 |
| 622 | a 22 | b 10 | c 2 |
| 623 | a 23 | b 10 | c 2 |
| 624 | a 24 | b 10 | c 2 |
| 625 | a 25 | b 10 | c 2 |
| 626 | a 1 | b 11 | c 2 |

-continued

| No. | Cp | Bridge | Flu |
|---|---|---|---|
| 627 | a 2 | b 11 | c 2 |
| 628 | a 3 | b 11 | c 2 |
| 629 | a 4 | b 11 | c 2 |
| 630 | a 5 | b 11 | c 2 |
| 631 | a 6 | b 11 | c 2 |
| 632 | a 7 | b 11 | c 2 |
| 633 | a 8 | b 11 | c 2 |
| 634 | a 9 | b 11 | c 2 |
| 635 | a 10 | b 11 | c 2 |
| 636 | a 11 | b 11 | c 2 |
| 637 | a 12 | b 11 | c 2 |
| 638 | a 13 | b 11 | c 2 |
| 639 | a 14 | b 11 | c 2 |
| 640 | a 15 | b 11 | c 2 |
| 641 | a 16 | b 11 | c 2 |
| 642 | a 17 | b 11 | c 2 |
| 643 | a 18 | b 11 | c 2 |
| 644 | a 19 | b 11 | c 2 |
| 645 | a 20 | b 11 | c 2 |
| 646 | a 21 | b 11 | c 2 |
| 647 | a 22 | b 11 | c 2 |
| 648 | a 23 | b 11 | c 2 |
| 649 | a 24 | b 11 | c 2 |
| 650 | a 25 | b 11 | c 2 |
| 651 | a 1 | b 12 | c 2 |
| 652 | a 2 | b 12 | c 2 |
| 653 | a 3 | b 12 | c 2 |
| 654 | a 4 | b 12 | c 2 |
| 655 | a 5 | b 12 | c 2 |
| 656 | a 6 | b 12 | c 2 |
| 657 | a 7 | b 12 | c 2 |
| 658 | a 8 | b 12 | c 2 |
| 659 | a 9 | b 12 | c 2 |
| 660 | a 10 | b 12 | c 2 |
| 661 | a 11 | b 12 | c 2 |
| 662 | a 12 | b 12 | c 2 |
| 663 | a 13 | b 12 | c 2 |
| 664 | a 14 | b 12 | c 2 |
| 665 | a 15 | b 12 | c 2 |
| 666 | a 16 | b 12 | c 2 |
| 667 | a 17 | b 12 | c 2 |
| 668 | a 18 | b 12 | c 2 |
| 669 | a 19 | b 12 | c 2 |
| 670 | a 20 | b 12 | c 2 |
| 671 | a 21 | b 12 | c 2 |
| 672 | a 22 | b 12 | c 2 |
| 673 | a 23 | b 12 | c 2 |
| 674 | a 24 | b 12 | c 2 |
| 675 | a 25 | b 12 | c 2 |
| 676 | a 1 | b 13 | c 2 |
| 677 | a 2 | b 13 | c 2 |
| 678 | a 3 | b 13 | c 2 |
| 679 | a 4 | b 13 | c 2 |
| 680 | a 5 | b 13 | c 2 |
| 681 | a 6 | b 13 | c 2 |
| 682 | a 7 | b 13 | c 2 |
| 683 | a 8 | b 13 | c 2 |
| 684 | a 9 | b 13 | c 2 |
| 685 | a 10 | b 13 | c 2 |
| 686 | a 11 | b 13 | c 2 |
| 687 | a 12 | b 13 | c 2 |
| 688 | a 13 | b 13 | c 2 |
| 689 | a 14 | b 13 | c 2 |
| 690 | a 15 | b 13 | c 2 |
| 691 | a 16 | b 13 | c 2 |
| 692 | a 17 | b 13 | c 2 |
| 693 | a 18 | b 13 | c 2 |
| 694 | a 19 | b 13 | c 2 |
| 695 | a 20 | b 13 | c 2 |
| 696 | a 21 | b 13 | c 2 |
| 697 | a 22 | b 13 | c 2 |
| 698 | a 23 | b 13 | c 2 |
| 699 | a 24 | b 13 | c 2 |
| 700 | a 25 | b 13 | c 2 |
| 701 | a 1 | b 14 | c 2 |
| 702 | a 2 | b 14 | c 2 |
| 703 | a 3 | b 14 | c 2 |
| 704 | a 4 | b 14 | c 2 |
| 705 | a 5 | b 14 | c 2 |
| 706 | a 6 | b 14 | c 2 |
| 707 | a 7 | b 14 | c 2 |
| 708 | a 8 | b 14 | c 2 |
| 709 | a 9 | b 14 | c 2 |
| 710 | a 10 | b 14 | c 2 |
| 711 | a 11 | b 14 | c 2 |
| 712 | a 12 | b 14 | c 2 |
| 713 | a 13 | b 14 | c 2 |
| 714 | a 14 | b 14 | c 2 |
| 715 | a 15 | b 14 | c 2 |
| 716 | a 16 | b 14 | c 2 |
| 717 | a 17 | b 14 | c 2 |
| 718 | a 18 | b 14 | c 2 |
| 719 | a 19 | b 14 | c 2 |
| 720 | a 20 | b 14 | c 2 |
| 721 | a 21 | b 14 | c 2 |
| 722 | a 22 | b 14 | c 2 |
| 723 | a 23 | b 14 | c 2 |
| 724 | a 24 | b 14 | c 2 |
| 725 | a 25 | b 14 | c 2 |
| 726 | a 1 | b 15 | c 2 |
| 727 | a 2 | b 15 | c 2 |
| 728 | a 3 | b 15 | c 2 |
| 729 | a 4 | b 15 | c 2 |
| 730 | a 5 | b 15 | c 2 |
| 731 | a 6 | b 15 | c 2 |
| 732 | a 7 | b 15 | c 2 |
| 733 | a 8 | b 15 | c 2 |
| 734 | a 9 | b 15 | c 2 |
| 735 | a 10 | b 15 | c 2 |
| 736 | a 11 | b 15 | c 2 |
| 737 | a 12 | b 15 | c 2 |
| 738 | a 13 | b 15 | c 2 |
| 739 | a 14 | b 15 | c 2 |
| 740 | a 15 | b 15 | c 2 |
| 741 | a 16 | b 15 | c 2 |
| 742 | a 17 | b 15 | c 2 |
| 743 | a 18 | b 15 | c 2 |
| 744 | a 19 | b 15 | c 2 |
| 745 | a 20 | b 15 | c 2 |
| 746 | a 21 | b 15 | c 2 |
| 747 | a 22 | b 15 | c 2 |
| 748 | a 23 | b 15 | c 2 |
| 749 | a 24 | b 15 | c 2 |
| 750 | a 25 | b 15 | c 2 |
| 751 | a 1 | b 1 | c 3 |
| 752 | a 2 | b 1 | c 3 |
| 753 | a 3 | b 1 | c 3 |
| 754 | a 4 | b 1 | c 3 |
| 755 | a 5 | b 1 | c 3 |
| 756 | a 6 | b 1 | c 3 |
| 757 | a 7 | b 1 | c 3 |
| 758 | a 8 | b 1 | c 3 |
| 759 | a 9 | b 1 | c 3 |
| 760 | a 10 | b 1 | c 3 |
| 761 | a 11 | b 1 | c 3 |
| 762 | a 12 | b 1 | c 3 |
| 763 | a 13 | b 1 | c 3 |
| 764 | a 14 | b 1 | c 3 |
| 765 | a 15 | b 1 | c 3 |
| 766 | a 16 | b 1 | c 3 |
| 767 | a 17 | b 1 | c 3 |
| 768 | a 18 | b 1 | c 3 |
| 769 | a 19 | b 1 | c 3 |
| 770 | a 20 | b 1 | c 3 |
| 771 | a 21 | b 1 | c 3 |
| 772 | a 22 | b 1 | c 3 |
| 773 | a 23 | b 1 | c 3 |
| 774 | a 24 | b 1 | c 3 |
| 775 | a 25 | b 1 | c 3 |
| 776 | a 1 | b 2 | c 3 |
| 777 | a 2 | b 2 | c 3 |
| 778 | a 3 | b 2 | c 3 |
| 779 | a 4 | b 2 | c 3 |
| 780 | a 5 | b 2 | c 3 |

| No. | Cp | Bridge | Flu |
|---|---|---|---|
| 781 | a 6 | b 2 | c 3 |
| 782 | a 7 | b 2 | c 3 |
| 783 | a 8 | b 2 | c 3 |
| 784 | a 9 | b 2 | c 3 |
| 785 | a 10 | b 2 | c 3 |
| 786 | a 11 | b 2 | c 3 |
| 787 | a 12 | b 2 | c 3 |
| 788 | a 13 | b 2 | c 3 |
| 789 | a 14 | b 2 | c 3 |
| 790 | a 15 | b 2 | c 3 |
| 791 | a 16 | b 2 | c 3 |
| 792 | a 17 | b 2 | c 3 |
| 793 | a 18 | b 2 | c 3 |
| 794 | a 19 | b 2 | c 3 |
| 795 | a 20 | b 2 | c 3 |
| 796 | a 21 | b 2 | c 3 |
| 797 | a 22 | b 2 | c 3 |
| 798 | a 23 | b 2 | c 3 |
| 799 | a 24 | b 2 | c 3 |
| 800 | a 25 | b 2 | c 3 |
| 801 | a 1 | b 3 | c 3 |
| 802 | a 2 | b 3 | c 3 |
| 803 | a 3 | b 3 | c 3 |
| 804 | a 4 | b 3 | c 3 |
| 805 | a 5 | b 3 | c 3 |
| 806 | a 6 | b 3 | c 3 |
| 807 | a 7 | b 3 | c 3 |
| 808 | a 8 | b 3 | c 3 |
| 809 | a 9 | b 3 | c 3 |
| 810 | a 10 | b 3 | c 3 |
| 811 | a 11 | b 3 | c 3 |
| 812 | a 12 | b 3 | c 3 |
| 813 | a 13 | b 3 | c 3 |
| 814 | a 14 | b 3 | c 3 |
| 815 | a 15 | b 3 | c 3 |
| 816 | a 16 | b 3 | c 3 |
| 817 | a 17 | b 3 | c 3 |
| 818 | a 18 | b 3 | c 3 |
| 819 | a 19 | b 3 | c 3 |
| 820 | a 20 | b 3 | c 3 |
| 821 | a 21 | b 3 | c 3 |
| 822 | a 22 | b 3 | c 3 |
| 823 | a 23 | b 3 | c 3 |
| 824 | a 24 | b 3 | c 3 |
| 825 | a 25 | b 3 | c 3 |
| 826 | a 1 | b 4 | c 3 |
| 827 | a 2 | b 4 | c 3 |
| 828 | a 3 | b 4 | c 3 |
| 829 | a 4 | b 4 | c 3 |
| 830 | a 5 | b 4 | c 3 |
| 831 | a 6 | b 4 | c 3 |
| 832 | a 7 | b 4 | c 3 |
| 833 | a 8 | b 4 | c 3 |
| 834 | a 9 | b 4 | c 3 |
| 835 | a 10 | b 4 | c 3 |
| 836 | a 11 | b 4 | c 3 |
| 837 | a 12 | b 4 | c 3 |
| 838 | a 13 | b 4 | c 3 |
| 839 | a 14 | b 4 | c 3 |
| 840 | a 15 | b 4 | c 3 |
| 841 | a 16 | b 4 | c 3 |
| 842 | a 17 | b 4 | c 3 |
| 843 | a 18 | b 4 | c 3 |
| 844 | a 19 | b 4 | c 3 |
| 845 | a 20 | b 4 | c 3 |
| 846 | a 21 | b 4 | c 3 |
| 847 | a 22 | b 4 | c 3 |
| 848 | a 23 | b 4 | c 3 |
| 849 | a 24 | b 4 | c 3 |
| 850 | a 25 | b 4 | c 3 |
| 851 | a 1 | b 5 | c 3 |
| 852 | a 2 | b 5 | c 3 |
| 853 | a 3 | b 5 | c 3 |
| 854 | a 4 | b 5 | c 3 |
| 855 | a 5 | b 5 | c 3 |
| 856 | a 6 | b 5 | c 3 |
| 857 | a 7 | b 5 | c 3 |
| 858 | a 8 | b 5 | c 3 |
| 859 | a 9 | b 5 | c 3 |
| 860 | a 10 | b 5 | c 3 |
| 861 | a 11 | b 5 | c 3 |
| 862 | a 12 | b 5 | c 3 |
| 863 | a 13 | b 5 | c 3 |
| 864 | a 14 | b 5 | c 3 |
| 865 | a 15 | b 5 | c 3 |
| 866 | a 16 | b 5 | c 3 |
| 867 | a 17 | b 5 | c 3 |
| 868 | a 18 | b 5 | c 3 |
| 869 | a 19 | b 5 | c 3 |
| 870 | a 20 | b 5 | c 3 |
| 871 | a 21 | b 5 | c 3 |
| 872 | a 22 | b 5 | c 3 |
| 873 | a 23 | b 5 | c 3 |
| 874 | a 24 | b 5 | c 3 |
| 875 | a 25 | b 5 | c 3 |
| 876 | a 1 | b 6 | c 3 |
| 877 | a 2 | b 6 | c 3 |
| 878 | a 3 | b 6 | c 3 |
| 879 | a 4 | b 6 | c 3 |
| 880 | a 5 | b 6 | c 3 |
| 881 | a 6 | b 6 | c 3 |
| 882 | a 7 | b 6 | c 3 |
| 883 | a 8 | b 6 | c 3 |
| 884 | a 9 | b 6 | c 3 |
| 885 | a 10 | b 6 | c 3 |
| 886 | a 11 | b 6 | c 3 |
| 887 | a 12 | b 6 | c 3 |
| 888 | a 13 | b 6 | c 3 |
| 889 | a 14 | b 6 | c 3 |
| 890 | a 15 | b 6 | c 3 |
| 891 | a 16 | b 6 | c 3 |
| 892 | a 17 | b 6 | c 3 |
| 893 | a 18 | b 6 | c 3 |
| 894 | a 19 | b 6 | c 3 |
| 895 | a 20 | b 6 | c 3 |
| 896 | a 21 | b 6 | c 3 |
| 897 | a 22 | b 6 | c 3 |
| 898 | a 23 | b 6 | c 3 |
| 899 | a 24 | b 6 | c 3 |
| 900 | a 25 | b 6 | c 3 |
| 901 | a 1 | b 7 | c 3 |
| 902 | a 2 | b 7 | c 3 |
| 903 | a 3 | b 7 | c 3 |
| 904 | a 4 | b 7 | c 3 |
| 905 | a 5 | b 7 | c 3 |
| 906 | a 6 | b 7 | c 3 |
| 907 | a 7 | b 7 | c 3 |
| 908 | a 8 | b 7 | c 3 |
| 909 | a 9 | b 7 | c 3 |
| 910 | a 10 | b 7 | c 3 |
| 911 | a 11 | b 7 | c 3 |
| 912 | a 12 | b 7 | c 3 |
| 913 | a 13 | b 7 | c 3 |
| 914 | a 14 | b 7 | c 3 |
| 915 | a 15 | b 7 | c 3 |
| 916 | a 16 | b 7 | c 3 |
| 917 | a 17 | b 7 | c 3 |
| 918 | a 18 | b 7 | c 3 |
| 919 | a 19 | b 7 | c 3 |
| 920 | a 20 | b 7 | c 3 |
| 921 | a 21 | b 7 | c 3 |
| 922 | a 22 | b 7 | c 3 |
| 923 | a 23 | b 7 | c 3 |
| 924 | a 24 | b 7 | c 3 |
| 925 | a 25 | b 7 | c 3 |
| 926 | a 1 | b 8 | c 3 |
| 927 | a 2 | b 8 | c 3 |
| 928 | a 3 | b 8 | c 3 |
| 929 | a 4 | b 8 | c 3 |
| 930 | a 5 | b 8 | c 3 |
| 931 | a 6 | b 8 | c 3 |
| 932 | a 7 | b 8 | c 3 |
| 933 | a 8 | b 8 | c 3 |
| 934 | a 9 | b 8 | c 3 |

| No. | Cp | Bridge | Flu |
|---|---|---|---|
| 935 | a 10 | b 8 | c 3 |
| 936 | a 11 | b 8 | c 3 |
| 937 | a 12 | b 8 | c 3 |
| 938 | a 13 | b 8 | c 3 |
| 939 | a 14 | b 8 | c 3 |
| 940 | a 15 | b 8 | c 3 |
| 941 | a 16 | b 8 | c 3 |
| 942 | a 17 | b 8 | c 3 |
| 943 | a 18 | b 8 | c 3 |
| 944 | a 19 | b 8 | c 3 |
| 945 | a 20 | b 8 | c 3 |
| 946 | a 21 | b 8 | c 3 |
| 947 | a 22 | b 8 | c 3 |
| 948 | a 23 | b 8 | c 3 |
| 949 | a 24 | b 8 | c 3 |
| 950 | a 25 | b 8 | c 3 |
| 951 | a 1 | b 9 | c 3 |
| 952 | a 2 | b 9 | c 3 |
| 953 | a 3 | b 9 | c 3 |
| 954 | a 4 | b 9 | c 3 |
| 955 | a 5 | b 9 | c 3 |
| 956 | a 6 | b 9 | c 3 |
| 957 | a 7 | b 9 | c 3 |
| 958 | a 8 | b 9 | c 3 |
| 959 | a 9 | b 9 | c 3 |
| 960 | a 10 | b 9 | c 3 |
| 961 | a 11 | b 9 | c 3 |
| 962 | a 12 | b 9 | c 3 |
| 963 | a 13 | b 9 | c 3 |
| 964 | a 14 | b 9 | c 3 |
| 965 | a 15 | b 9 | c 3 |
| 966 | a 16 | b 9 | c 3 |
| 967 | a 17 | b 9 | c 3 |
| 968 | a 18 | b 9 | c 3 |
| 969 | a 19 | b 9 | c 3 |
| 970 | a 20 | b 9 | c 3 |
| 971 | a 21 | b 9 | c 3 |
| 972 | a 22 | b 9 | c 3 |
| 973 | a 23 | b 9 | c 3 |
| 974 | a 24 | b 9 | c 3 |
| 975 | a 25 | b 9 | c 3 |
| 976 | a 1 | b 10 | c 3 |
| 977 | a 2 | b 10 | c 3 |
| 978 | a 3 | b 10 | c 3 |
| 979 | a 4 | b 10 | c 3 |
| 980 | a 5 | b 10 | c 3 |
| 981 | a 6 | b 10 | c 3 |
| 982 | a 7 | b 10 | c 3 |
| 983 | a 8 | b 10 | c 3 |
| 984 | a 9 | b 10 | c 3 |
| 985 | a 10 | b 10 | c 3 |
| 986 | a 11 | b 10 | c 3 |
| 987 | a 12 | b 10 | c 3 |
| 988 | a 13 | b 10 | c 3 |
| 989 | a 14 | b 10 | c 3 |
| 990 | a 15 | b 10 | c 3 |
| 991 | a 16 | b 10 | c 3 |
| 992 | a 17 | b 10 | c 3 |
| 993 | a 18 | b 10 | c 3 |
| 994 | a 19 | b 10 | c 3 |
| 995 | a 20 | b 10 | c 3 |
| 996 | a 21 | b 10 | c 3 |
| 997 | a 22 | b 10 | c 3 |
| 998 | a 23 | b 10 | c 3 |
| 999 | a 24 | b 10 | c 3 |
| 1000 | a 25 | b 10 | c 3 |
| 1001 | a 1 | b 11 | c 3 |
| 1002 | a 2 | b 11 | c 3 |
| 1003 | a 3 | b 11 | c 3 |
| 1004 | a 4 | b 11 | c 3 |
| 1005 | a 5 | b 11 | c 3 |
| 1006 | a 6 | b 11 | c 3 |
| 1007 | a 7 | b 11 | c 3 |
| 1008 | a 8 | b 11 | c 3 |
| 1009 | a 9 | b 11 | c 3 |
| 1010 | a 10 | b 11 | c 3 |
| 1011 | a 11 | b 11 | c 3 |
| 1012 | a 12 | b 11 | c 3 |
| 1013 | a 13 | b 11 | c 3 |
| 1014 | a 14 | b 11 | c 3 |
| 1015 | a 15 | b 11 | c 3 |
| 1016 | a 16 | b 11 | c 3 |
| 1017 | a 17 | b 11 | c 3 |
| 1018 | a 18 | b 11 | c 3 |
| 1019 | a 19 | b 11 | c 3 |
| 1020 | a 20 | b 11 | c 3 |
| 1021 | a 21 | b 11 | c 3 |
| 1022 | a 22 | b 11 | c 3 |
| 1023 | a 23 | b 11 | c 3 |
| 1024 | a 24 | b 11 | c 3 |
| 1025 | a 25 | b 11 | c 3 |
| 1026 | a 1 | b 12 | c 3 |
| 1027 | a 2 | b 12 | c 3 |
| 1028 | a 3 | b 12 | c 3 |
| 1029 | a 4 | b 12 | c 3 |
| 1030 | a 5 | b 12 | c 3 |
| 1031 | a 6 | b 12 | c 3 |
| 1032 | a 7 | b 12 | c 3 |
| 1033 | a 8 | b 12 | c 3 |
| 1034 | a 9 | b 12 | c 3 |
| 1035 | a 10 | b 12 | c 3 |
| 1036 | a 11 | b 12 | c 3 |
| 1037 | a 12 | b 12 | c 3 |
| 1038 | a 13 | b 12 | c 3 |
| 1039 | a 14 | b 12 | c 3 |
| 1040 | a 15 | b 12 | c 3 |
| 1041 | a 16 | b 12 | c 3 |
| 1042 | a 17 | b 12 | c 3 |
| 1043 | a 18 | b 12 | c 3 |
| 1044 | a 19 | b 12 | c 3 |
| 1045 | a 20 | b 12 | c 3 |
| 1046 | a 21 | b 12 | c 3 |
| 1047 | a 22 | b 12 | c 3 |
| 1048 | a 23 | b 12 | c 3 |
| 1049 | a 24 | b 12 | c 3 |
| 1050 | a 25 | b 12 | c 3 |
| 1051 | a 1 | b 13 | c 3 |
| 1052 | a 2 | b 13 | c 3 |
| 1053 | a 3 | b 13 | c 3 |
| 1054 | a 4 | b 13 | c 3 |
| 1055 | a 5 | b 13 | c 3 |
| 1056 | a 6 | b 13 | c 3 |
| 1057 | a 7 | b 13 | c 3 |
| 1058 | a 8 | b 13 | c 3 |
| 1059 | a 9 | b 13 | c 3 |
| 1060 | a 10 | b 13 | c 3 |
| 1061 | a 11 | b 13 | c 3 |
| 1062 | a 12 | b 13 | c 3 |
| 1063 | a 13 | b 13 | c 3 |
| 1064 | a 14 | b 13 | c 3 |
| 1065 | a 15 | b 13 | c 3 |
| 1066 | a 16 | b 13 | c 3 |
| 1067 | a 17 | b 13 | c 3 |
| 1068 | a 18 | b 13 | c 3 |
| 1069 | a 19 | b 13 | c 3 |
| 1070 | a 20 | b 13 | c 3 |
| 1071 | a 21 | b 13 | c 3 |
| 1072 | a 22 | b 13 | c 3 |
| 1073 | a 23 | b 13 | c 3 |
| 1074 | a 24 | b 13 | c 3 |
| 1075 | a 25 | b 13 | c 3 |
| 1076 | a 1 | b 14 | c 3 |
| 1077 | a 2 | b 14 | c 3 |
| 1078 | a 3 | b 14 | c 3 |
| 1079 | a 4 | b 14 | c 3 |
| 1080 | a 5 | b 14 | c 3 |
| 1081 | a 6 | b 14 | c 3 |
| 1082 | a 7 | b 14 | c 3 |
| 1083 | a 8 | b 14 | c 3 |
| 1084 | a 9 | b 14 | c 3 |
| 1085 | a 10 | b 14 | c 3 |
| 1086 | a 11 | b 14 | c 3 |
| 1087 | a 12 | b 14 | c 3 |
| 1088 | a 13 | b 14 | c 3 |

| No. | Cp | Bridge | Flu |
|---|---|---|---|
| 1089 | a 14 | b 14 | c 3 |
| 1090 | a 15 | b 14 | c 3 |
| 1091 | a 16 | b 14 | c 3 |
| 1092 | a 17 | b 14 | c 3 |
| 1093 | a 18 | b 14 | c 3 |
| 1094 | a 19 | b 14 | c 3 |
| 1095 | a 20 | b 14 | c 3 |
| 1096 | a 21 | b 14 | c 3 |
| 1097 | a 22 | b 14 | c 3 |
| 1098 | a 23 | b 14 | c 3 |
| 1099 | a 24 | b 14 | c 3 |
| 1100 | a 25 | b 14 | c 3 |
| 1101 | a 1 | b 15 | c 3 |
| 1102 | a 2 | b 15 | c 3 |
| 1103 | a 3 | b 15 | c 3 |
| 1104 | a 4 | b 15 | c 3 |
| 1105 | a 5 | b 15 | c 3 |
| 1106 | a 6 | b 15 | c 3 |
| 1107 | a 7 | b 15 | c 3 |
| 1108 | a 8 | b 15 | c 3 |
| 1109 | a 9 | b 15 | c 3 |
| 1110 | a 10 | b 15 | c 3 |
| 1111 | a 11 | b 15 | c 3 |
| 1112 | a 12 | b 15 | c 3 |
| 1113 | a 13 | b 15 | c 3 |
| 1114 | a 14 | b 15 | c 3 |
| 1115 | a 15 | b 15 | c 3 |
| 1116 | a 16 | b 15 | c 3 |
| 1117 | a 17 | b 15 | c 3 |
| 1118 | a 18 | b 15 | c 3 |
| 1119 | a 19 | b 15 | c 3 |
| 1120 | a 20 | b 15 | c 3 |
| 1121 | a 21 | b 15 | c 3 |
| 1122 | a 22 | b 15 | c 3 |
| 1123 | a 23 | b 15 | c 3 |
| 1124 | a 24 | b 15 | c 3 |
| 1125 | a 25 | b 15 | c 3 |
| 1126 | a 1 | b 1 | c 4 |
| 1127 | a 2 | b 1 | c 4 |
| 1128 | a 3 | b 1 | c 4 |
| 1129 | a 4 | b 1 | c 4 |
| 1130 | a 5 | b 1 | c 4 |
| 1131 | a 6 | b 1 | c 4 |
| 1132 | a 7 | b 1 | c 4 |
| 1133 | a 8 | b 1 | c 4 |
| 1134 | a 9 | b 1 | c 4 |
| 1135 | a 10 | b 1 | c 4 |
| 1136 | a 11 | b 1 | c 4 |
| 1137 | a 12 | b 1 | c 4 |
| 1138 | a 13 | b 1 | c 4 |
| 1139 | a 14 | b 1 | c 4 |
| 1140 | a 15 | b 1 | c 4 |
| 1141 | a 16 | b 1 | c 4 |
| 1142 | a 17 | b 1 | c 4 |
| 1143 | a 18 | b 1 | c 4 |
| 1144 | a 19 | b 1 | c 4 |
| 1145 | a 20 | b 1 | c 4 |
| 1146 | a 21 | b 1 | c 4 |
| 1147 | a 22 | b 1 | c 4 |
| 1148 | a 23 | b 1 | c 4 |
| 1149 | a 24 | b 1 | c 4 |
| 1150 | a 25 | b 1 | c 4 |
| 1151 | a 1 | b 2 | c 4 |
| 1152 | a 2 | b 2 | c 4 |
| 1153 | a 3 | b 2 | c 4 |
| 1154 | a 4 | b 2 | c 4 |
| 1155 | a 5 | b 2 | c 4 |
| 1156 | a 6 | b 2 | c 4 |
| 1157 | a 7 | b 2 | c 4 |
| 1158 | a 8 | b 2 | c 4 |
| 1159 | a 9 | b 2 | c 4 |
| 1160 | a 10 | b 2 | c 4 |
| 1161 | a 11 | b 2 | c 4 |
| 1162 | a 12 | b 2 | c 4 |
| 1163 | a 13 | b 2 | c 4 |
| 1164 | a 14 | b 2 | c 4 |
| 1165 | a 15 | b 2 | c 4 |
| 1166 | a 16 | b 2 | c 4 |
| 1167 | a 17 | b 2 | c 4 |
| 1168 | a 18 | b 2 | c 4 |
| 1169 | a 19 | b 2 | c 4 |
| 1170 | a 20 | b 2 | c 4 |
| 1171 | a 21 | b 2 | c 4 |
| 1172 | a 22 | b 2 | c 4 |
| 1173 | a 23 | b 2 | c 4 |
| 1174 | a 24 | b 2 | c 4 |
| 1175 | a 25 | b 2 | c 4 |
| 1176 | a 1 | b 3 | c 4 |
| 1177 | a 2 | b 3 | c 4 |
| 1178 | a 3 | b 3 | c 4 |
| 1179 | a 4 | b 3 | c 4 |
| 1180 | a 5 | b 3 | c 4 |
| 1181 | a 6 | b 3 | c 4 |
| 1182 | a 7 | b 3 | c 4 |
| 1183 | a 8 | b 3 | c 4 |
| 1184 | a 9 | b 3 | c 4 |
| 1185 | a 10 | b 3 | c 4 |
| 1186 | a 11 | b 3 | c 4 |
| 1187 | a 12 | b 3 | c 4 |
| 1188 | a 13 | b 3 | c 4 |
| 1189 | a 14 | b 3 | c 4 |
| 1190 | a 15 | b 3 | c 4 |
| 1191 | a 16 | b 3 | c 4 |
| 1192 | a 17 | b 3 | c 4 |
| 1193 | a 18 | b 3 | c 4 |
| 1194 | a 19 | b 3 | c 4 |
| 1195 | a 20 | b 3 | c 4 |
| 1196 | a 21 | b 3 | c 4 |
| 1197 | a 22 | b 3 | c 4 |
| 1198 | a 23 | b 3 | c 4 |
| 1199 | a 24 | b 3 | c 4 |
| 1200 | a 25 | b 3 | c 4 |
| 1201 | a 1 | b 4 | c 4 |
| 1202 | a 2 | b 4 | c 4 |
| 1203 | a 3 | b 4 | c 4 |
| 1204 | a 4 | b 4 | c 4 |
| 1205 | a 5 | b 4 | c 4 |
| 1206 | a 6 | b 4 | c 4 |
| 1207 | a 7 | b 4 | c 4 |
| 1208 | a 8 | b 4 | c 4 |
| 1209 | a 9 | b 4 | c 4 |
| 1210 | a 10 | b 4 | c 4 |
| 1211 | a 11 | b 4 | c 4 |
| 1212 | a 12 | b 4 | c 4 |
| 1213 | a 13 | b 4 | c 4 |
| 1214 | a 14 | b 4 | c 4 |
| 1215 | a 15 | b 4 | c 4 |
| 1216 | a 16 | b 4 | c 4 |
| 1217 | a 17 | b 4 | c 4 |
| 1218 | a 18 | b 4 | c 4 |
| 1219 | a 19 | b 4 | c 4 |
| 1220 | a 20 | b 4 | c 4 |
| 1221 | a 21 | b 4 | c 4 |
| 1222 | a 22 | b 4 | c 4 |
| 1223 | a 23 | b 4 | c 4 |
| 1224 | a 24 | b 4 | c 4 |
| 1225 | a 25 | b 4 | c 4 |
| 1226 | a 1 | b 5 | c 4 |
| 1227 | a 2 | b 5 | c 4 |
| 1228 | a 3 | b 5 | c 4 |
| 1229 | a 4 | b 5 | c 4 |
| 1230 | a 5 | b 5 | c 4 |
| 1231 | a 6 | b 5 | c 4 |
| 1232 | a 7 | b 5 | c 4 |
| 1233 | a 8 | b 5 | c 4 |
| 1234 | a 9 | b 5 | c 4 |
| 1235 | a 10 | b 5 | c 4 |
| 1236 | a 11 | b 5 | c 4 |
| 1237 | a 12 | b 5 | c 4 |
| 1238 | a 13 | b 5 | c 4 |
| 1239 | a 14 | b 5 | c 4 |
| 1240 | a 15 | b 5 | c 4 |
| 1241 | a 16 | b 5 | c 4 |
| 1242 | a 17 | b 5 | c 4 |

| No. | Cp | Bridge | Flu |
| --- | --- | --- | --- |
| 1243 | a 18 | b 5 | c 4 |
| 1244 | a 19 | b 5 | c 4 |
| 1245 | a 20 | b 5 | c 4 |
| 1246 | a 21 | b 5 | c 4 |
| 1247 | a 22 | b 5 | c 4 |
| 1248 | a 23 | b 5 | c 4 |
| 1249 | a 24 | b 5 | c 4 |
| 1250 | a 25 | b 5 | c 4 |
| 1251 | a 1 | b 6 | c 4 |
| 1252 | a 2 | b 6 | c 4 |
| 1253 | a 3 | b 6 | c 4 |
| 1254 | a 4 | b 6 | c 4 |
| 1255 | a 5 | b 6 | c 4 |
| 1256 | a 6 | b 6 | c 4 |
| 1257 | a 7 | b 6 | c 4 |
| 1258 | a 8 | b 6 | c 4 |
| 1259 | a 9 | b 6 | c 4 |
| 1260 | a 10 | b 6 | c 4 |
| 1261 | a 11 | b 6 | c 4 |
| 1262 | a 12 | b 6 | c 4 |
| 1263 | a 13 | b 6 | c 4 |
| 1264 | a 14 | b 6 | c 4 |
| 1265 | a 15 | b 6 | c 4 |
| 1266 | a 16 | b 6 | c 4 |
| 1267 | a 17 | b 6 | c 4 |
| 1268 | a 18 | b 6 | c 4 |
| 1269 | a 19 | b 6 | c 4 |
| 1270 | a 20 | b 6 | c 4 |
| 1271 | a 21 | b 6 | c 4 |
| 1272 | a 22 | b 6 | c 4 |
| 1273 | a 23 | b 6 | c 4 |
| 1274 | a 24 | b 6 | c 4 |
| 1275 | a 25 | b 6 | c 4 |
| 1276 | a 1 | b 7 | c 4 |
| 1277 | a 2 | b 7 | c 4 |
| 1278 | a 3 | b 7 | c 4 |
| 1279 | a 4 | b 7 | c 4 |
| 1280 | a 5 | b 7 | c 4 |
| 1281 | a 6 | b 7 | c 4 |
| 1282 | a 7 | b 7 | c 4 |
| 1283 | a 8 | b 7 | c 4 |
| 1284 | a 9 | b 7 | c 4 |
| 1285 | a 10 | b 7 | c 4 |
| 1286 | a 11 | b 7 | c 4 |
| 1287 | a 12 | b 7 | c 4 |
| 1288 | a 13 | b 7 | c 4 |
| 1289 | a 14 | b 7 | c 4 |
| 1290 | a 15 | b 7 | c 4 |
| 1291 | a 16 | b 7 | c 4 |
| 1292 | a 17 | b 7 | c 4 |
| 1293 | a 18 | b 7 | c 4 |
| 1294 | a 19 | b 7 | c 4 |
| 1295 | a 20 | b 7 | c 4 |
| 1296 | a 21 | b 7 | c 4 |
| 1297 | a 22 | b 7 | c 4 |
| 1298 | a 23 | b 7 | c 4 |
| 1299 | a 24 | b 7 | c 4 |
| 1300 | a 25 | b 7 | c 4 |
| 1301 | a 1 | b 8 | c 4 |
| 1302 | a 2 | b 8 | c 4 |
| 1303 | a 3 | b 8 | c 4 |
| 1304 | a 4 | b 8 | c 4 |
| 1305 | a 5 | b 8 | c 4 |
| 1306 | a 6 | b 8 | c 4 |
| 1307 | a 7 | b 8 | c 4 |
| 1308 | a 8 | b 8 | c 4 |
| 1309 | a 9 | b 8 | c 4 |
| 1310 | a 10 | b 8 | c 4 |
| 1311 | a 11 | b 8 | c 4 |
| 1312 | a 12 | b 8 | c 4 |
| 1313 | a 13 | b 8 | c 4 |
| 1314 | a 14 | b 8 | c 4 |
| 1315 | a 15 | b 8 | c 4 |
| 1316 | a 16 | b 8 | c 4 |
| 1317 | a 17 | b 8 | c 4 |
| 1318 | a 18 | b 8 | c 4 |
| 1319 | a 19 | b 8 | c 4 |
| 1320 | a 20 | b 8 | c 4 |
| 1321 | a 21 | b 8 | c 4 |
| 1322 | a 22 | b 8 | c 4 |
| 1323 | a 23 | b 8 | c 4 |
| 1324 | a 24 | b 8 | c 4 |
| 1325 | a 25 | b 8 | c 4 |
| 1326 | a 1 | b 9 | c 4 |
| 1327 | a 2 | b 9 | c 4 |
| 1328 | a 3 | b 9 | c 4 |
| 1329 | a 4 | b 9 | c 4 |
| 1330 | a 5 | b 9 | c 4 |
| 1331 | a 6 | b 9 | c 4 |
| 1332 | a 7 | b 9 | c 4 |
| 1333 | a 8 | b 9 | c 4 |
| 1334 | a 9 | b 9 | c 4 |
| 1335 | a 10 | b 9 | c 4 |
| 1336 | a 11 | b 9 | c 4 |
| 1337 | a 12 | b 9 | c 4 |
| 1338 | a 13 | b 9 | c 4 |
| 1339 | a 14 | b 9 | c 4 |
| 1340 | a 15 | b 9 | c 4 |
| 1341 | a 16 | b 9 | c 4 |
| 1342 | a 17 | b 9 | c 4 |
| 1343 | a 18 | b 9 | c 4 |
| 1344 | a 19 | b 9 | c 4 |
| 1345 | a 20 | b 9 | c 4 |
| 1346 | a 21 | b 9 | c 4 |
| 1347 | a 22 | b 9 | c 4 |
| 1348 | a 23 | b 9 | c 4 |
| 1349 | a 24 | b 9 | c 4 |
| 1350 | a 25 | b 9 | c 4 |
| 1351 | a 1 | b 10 | c 4 |
| 1352 | a 2 | b 10 | c 4 |
| 1353 | a 3 | b 10 | c 4 |
| 1354 | a 4 | b 10 | c 4 |
| 1355 | a 5 | b 10 | c 4 |
| 1356 | a 6 | b 10 | c 4 |
| 1357 | a 7 | b 10 | c 4 |
| 1358 | a 8 | b 10 | c 4 |
| 1359 | a 9 | b 10 | c 4 |
| 1360 | a 10 | b 10 | c 4 |
| 1361 | a 11 | b 10 | c 4 |
| 1362 | a 12 | b 10 | c 4 |
| 1363 | a 13 | b 10 | c 4 |
| 1364 | a 14 | b 10 | c 4 |
| 1365 | a 15 | b 10 | c 4 |
| 1366 | a 16 | b 10 | c 4 |
| 1367 | a 17 | b 10 | c 4 |
| 1368 | a 18 | b 10 | c 4 |
| 1369 | a 19 | b 10 | c 4 |
| 1370 | a 20 | b 10 | c 4 |
| 1371 | a 21 | b 10 | c 4 |
| 1372 | a 22 | b 10 | c 4 |
| 1373 | a 23 | b 10 | c 4 |
| 1374 | a 24 | b 10 | c 4 |
| 1375 | a 25 | b 10 | c 4 |
| 1376 | a 1 | b 11 | c 4 |
| 1377 | a 2 | b 11 | c 4 |
| 1378 | a 3 | b 11 | c 4 |
| 1379 | a 4 | b 11 | c 4 |
| 1380 | a 5 | b 11 | c 4 |
| 1381 | a 6 | b 11 | c 4 |
| 1382 | a 7 | b 11 | c 4 |
| 1383 | a 8 | b 11 | c 4 |
| 1384 | a 9 | b 11 | c 4 |
| 1385 | a 10 | b 11 | c 4 |
| 1386 | a 11 | b 11 | c 4 |
| 1387 | a 12 | b 11 | c 4 |
| 1388 | a 13 | b 11 | c 4 |
| 1389 | a 14 | b 11 | c 4 |
| 1390 | a 15 | b 11 | c 4 |
| 1391 | a 16 | b 11 | c 4 |
| 1392 | a 17 | b 11 | c 4 |
| 1393 | a 18 | b 11 | c 4 |
| 1394 | a 19 | b 11 | c 4 |
| 1395 | a 20 | b 11 | c 4 |
| 1396 | a 21 | b 11 | c 4 |

-continued

| No. | Cp | Bridge | Flu |
|---|---|---|---|
| 1397 | a 22 | b 11 | c 4 |
| 1398 | a 23 | b 11 | c 4 |
| 1399 | a 24 | b 11 | c 4 |
| 1400 | a 25 | b 11 | c 4 |
| 1401 | a 1 | b 12 | c 4 |
| 1402 | a 2 | b 12 | c 4 |
| 1403 | a 3 | b 12 | c 4 |
| 1404 | a 4 | b 12 | c 4 |
| 1405 | a 5 | b 12 | c 4 |
| 1406 | a 6 | b 12 | c 4 |
| 1407 | a 7 | b 12 | c 4 |
| 1408 | a 8 | b 12 | c 4 |
| 1409 | a 9 | b 12 | c 4 |
| 1410 | a 10 | b 12 | c 4 |
| 1411 | a 11 | b 12 | c 4 |
| 1412 | a 12 | b 12 | c 4 |
| 1413 | a 13 | b 12 | c 4 |
| 1414 | a 14 | b 12 | c 4 |
| 1415 | a 15 | b 12 | c 4 |
| 1416 | a 16 | b 12 | c 4 |
| 1417 | a 17 | b 12 | c 4 |
| 1418 | a 18 | b 12 | c 4 |
| 1419 | a 19 | b 12 | c 4 |
| 1420 | a 20 | b 12 | c 4 |
| 1421 | a 21 | b 12 | c 4 |
| 1422 | a 22 | b 12 | c 4 |
| 1423 | a 23 | b 12 | c 4 |
| 1424 | a 24 | b 12 | c 4 |
| 1425 | a 25 | b 12 | c 4 |
| 1426 | a 1 | b 13 | c 4 |
| 1427 | a 2 | b 13 | c 4 |
| 1428 | a 3 | b 13 | c 4 |
| 1429 | a 4 | b 13 | c 4 |
| 1430 | a 5 | b 13 | c 4 |
| 1431 | a 6 | b 13 | c 4 |
| 1432 | a 7 | b 13 | c 4 |
| 1433 | a 8 | b 13 | c 4 |
| 1434 | a 9 | b 13 | c 4 |
| 1435 | a 10 | b 13 | c 4 |
| 1436 | a 11 | b 13 | c 4 |
| 1437 | a 12 | b 13 | c 4 |
| 1438 | a 13 | b 13 | c 4 |
| 1439 | a 14 | b 13 | c 4 |
| 1440 | a 15 | b 13 | c 4 |
| 1441 | a 16 | b 13 | c 4 |
| 1442 | a 17 | b 13 | c 4 |
| 1443 | a 18 | b 13 | c 4 |
| 1444 | a 19 | b 13 | c 4 |
| 1445 | a 20 | b 13 | c 4 |
| 1446 | a 21 | b 13 | c 4 |
| 1447 | a 22 | b 13 | c 4 |
| 1448 | a 23 | b 13 | c 4 |
| 1449 | a 24 | b 13 | c 4 |
| 1450 | a 25 | b 13 | c 4 |
| 1451 | a 1 | b 14 | c 4 |
| 1452 | a 2 | b 14 | c 4 |
| 1453 | a 3 | b 14 | c 4 |
| 1454 | a 4 | b 14 | c 4 |
| 1455 | a 5 | b 14 | c 4 |
| 1456 | a 6 | b 14 | c 4 |
| 1457 | a 7 | b 14 | c 4 |
| 1458 | a 8 | b 14 | c 4 |
| 1459 | a 9 | b 14 | c 4 |
| 1460 | a 10 | b 14 | c 4 |
| 1461 | a 11 | b 14 | c 4 |
| 1462 | a 12 | b 14 | c 4 |
| 1463 | a 13 | b 14 | c 4 |
| 1464 | a 14 | b 14 | c 4 |
| 1465 | a 15 | b 14 | c 4 |
| 1466 | a 16 | b 14 | c 4 |
| 1467 | a 17 | b 14 | c 4 |
| 1468 | a 18 | b 14 | c 4 |
| 1469 | a 19 | b 14 | c 4 |
| 1470 | a 20 | b 14 | c 4 |
| 1471 | a 21 | b 14 | c 4 |
| 1472 | a 22 | b 14 | c 4 |
| 1473 | a 23 | b 14 | c 4 |
| 1474 | a 24 | b 14 | c 4 |
| 1475 | a 25 | b 14 | c 4 |
| 1476 | a 1 | b 15 | c 4 |
| 1477 | a 2 | b 15 | c 4 |
| 1478 | a 3 | b 15 | c 4 |
| 1479 | a 4 | b 15 | c 4 |
| 1480 | a 5 | b 15 | c 4 |
| 1481 | a 6 | b 15 | c 4 |
| 1482 | a 7 | b 15 | c 4 |
| 1483 | a 8 | b 15 | c 4 |
| 1484 | a 9 | b 15 | c 4 |
| 1485 | a 10 | b 15 | c 4 |
| 1486 | a 11 | b 15 | c 4 |
| 1487 | a 12 | b 15 | c 4 |
| 1488 | a 13 | b 15 | c 4 |
| 1489 | a 14 | b 15 | c 4 |
| 1490 | a 15 | b 15 | c 4 |
| 1491 | a 16 | b 15 | c 4 |
| 1492 | a 17 | b 15 | c 4 |
| 1493 | a 18 | b 15 | c 4 |
| 1494 | a 19 | b 15 | c 4 |
| 1495 | a 20 | b 15 | c 4 |
| 1496 | a 21 | b 15 | c 4 |
| 1497 | a 22 | b 15 | c 4 |
| 1498 | a 23 | b 15 | c 4 |
| 1499 | a 24 | b 15 | c 4 |
| 1500 | a 25 | b 15 | c 4 |
| 1501 | a 1 | b 1 | c 5 |
| 1502 | a 2 | b 1 | c 5 |
| 1503 | a 3 | b 1 | c 5 |
| 1504 | a 4 | b 1 | c 5 |
| 1505 | a 5 | b 1 | c 5 |
| 1506 | a 6 | b 1 | c 5 |
| 1507 | a 7 | b 1 | c 5 |
| 1508 | a 8 | b 1 | c 5 |
| 1509 | a 9 | b 1 | c 5 |
| 1510 | a 10 | b 1 | c 5 |
| 1511 | a 11 | b 1 | c 5 |
| 1512 | a 12 | b 1 | c 5 |
| 1513 | a 13 | b 1 | c 5 |
| 1514 | a 14 | b 1 | c 5 |
| 1515 | a 15 | b 1 | c 5 |
| 1516 | a 16 | b 1 | c 5 |
| 1517 | a 17 | b 1 | c 5 |
| 1518 | a 18 | b 1 | c 5 |
| 1519 | a 19 | b 1 | c 5 |
| 1520 | a 20 | b 1 | c 5 |
| 1521 | a 21 | b 1 | c 5 |
| 1522 | a 22 | b 1 | c 5 |
| 1523 | a 23 | b 1 | c 5 |
| 1524 | a 24 | b 1 | c 5 |
| 1525 | a 25 | b 1 | c 5 |
| 1526 | a 1 | b 2 | c 5 |
| 1527 | a 2 | b 2 | c 5 |
| 1528 | a 3 | b 2 | c 5 |
| 1529 | a 4 | b 2 | c 5 |
| 1530 | a 5 | b 2 | c 5 |
| 1531 | a 6 | b 2 | c 5 |
| 1532 | a 7 | b 2 | c 5 |
| 1533 | a 8 | b 2 | c 5 |
| 1534 | a 9 | b 2 | c 5 |
| 1535 | a 10 | b 2 | c 5 |
| 1536 | a 11 | b 2 | c 5 |
| 1537 | a 12 | b 2 | c 5 |
| 1538 | a 13 | b 2 | c 5 |
| 1539 | a 14 | b 2 | c 5 |
| 1540 | a 15 | b 2 | c 5 |
| 1541 | a 16 | b 2 | c 5 |
| 1542 | a 17 | b 2 | c 5 |
| 1543 | a 18 | b 2 | c 5 |
| 1544 | a 19 | b 2 | c 5 |
| 1545 | a 20 | b 2 | c 5 |
| 1546 | a 21 | b 2 | c 5 |
| 1547 | a 22 | b 2 | c 5 |
| 1548 | a 23 | b 2 | c 5 |
| 1549 | a 24 | b 2 | c 5 |
| 1550 | a 25 | b 2 | c 5 |

| No. | Cp | Bridge | Flu |
|---|---|---|---|
| 1551 | a 1 | b 3 | c 5 |
| 1552 | a 2 | b 3 | c 5 |
| 1553 | a 3 | b 3 | c 5 |
| 1554 | a 4 | b 3 | c 5 |
| 1555 | a 5 | b 3 | c 5 |
| 1556 | a 6 | b 3 | c 5 |
| 1557 | a 7 | b 3 | c 5 |
| 1558 | a 8 | b 3 | c 5 |
| 1559 | a 9 | b 3 | c 5 |
| 1560 | a 10 | b 3 | c 5 |
| 1561 | a 11 | b 3 | c 5 |
| 1562 | a 12 | b 3 | c 5 |
| 1563 | a 13 | b 3 | c 5 |
| 1564 | a 14 | b 3 | c 5 |
| 1565 | a 15 | b 3 | c 5 |
| 1566 | a 16 | b 3 | c 5 |
| 1567 | a 17 | b 3 | c 5 |
| 1568 | a 18 | b 3 | c 5 |
| 1569 | a 19 | b 3 | c 5 |
| 1570 | a 20 | b 3 | c 5 |
| 1571 | a 21 | b 3 | c 5 |
| 1572 | a 22 | b 3 | c 5 |
| 1573 | a 23 | b 3 | c 5 |
| 1574 | a 24 | b 3 | c 5 |
| 1575 | a 25 | b 3 | c 5 |
| 1576 | a 1 | b 4 | c 5 |
| 1577 | a 2 | b 4 | c 5 |
| 1578 | a 3 | b 4 | c 5 |
| 1579 | a 4 | b 4 | c 5 |
| 1580 | a 5 | b 4 | c 5 |
| 1581 | a 6 | b 4 | c 5 |
| 1582 | a 7 | b 4 | c 5 |
| 1583 | a 8 | b 4 | c 5 |
| 1584 | a 9 | b 4 | c 5 |
| 1585 | a 10 | b 4 | c 5 |
| 1586 | a 11 | b 4 | c 5 |
| 1587 | a 12 | b 4 | c 5 |
| 1588 | a 13 | b 4 | c 5 |
| 1589 | a 14 | b 4 | c 5 |
| 1590 | a 15 | b 4 | c 5 |
| 1591 | a 16 | b 4 | c 5 |
| 1592 | a 17 | b 4 | c 5 |
| 1593 | a 18 | b 4 | c 5 |
| 1594 | a 19 | b 4 | c 5 |
| 1595 | a 20 | b 4 | c 5 |
| 1596 | a 21 | b 4 | c 5 |
| 1597 | a 22 | b 4 | c 5 |
| 1598 | a 23 | b 4 | c 5 |
| 1599 | a 24 | b 4 | c 5 |
| 1600 | a 25 | b 4 | c 5 |
| 1601 | a 1 | b 5 | c 5 |
| 1602 | a 2 | b 5 | c 5 |
| 1603 | a 3 | b 5 | c 5 |
| 1604 | a 4 | b 5 | c 5 |
| 1605 | a 5 | b 5 | c 5 |
| 1606 | a 6 | b 5 | c 5 |
| 1607 | a 7 | b 5 | c 5 |
| 1608 | a 8 | b 5 | c 5 |
| 1609 | a 9 | b 5 | c 5 |
| 1610 | a 10 | b 5 | c 5 |
| 1611 | a 11 | b 5 | c 5 |
| 1612 | a 12 | b 5 | c 5 |
| 1613 | a 13 | b 5 | c 5 |
| 1614 | a 14 | b 5 | c 5 |
| 1615 | a 15 | b 5 | c 5 |
| 1616 | a 16 | b 5 | c 5 |
| 1617 | a 17 | b 5 | c 5 |
| 1618 | a 18 | b 5 | c 5 |
| 1619 | a 19 | b 5 | c 5 |
| 1620 | a 20 | b 5 | c 5 |
| 1621 | a 21 | b 5 | c 5 |
| 1622 | a 22 | b 5 | c 5 |
| 1623 | a 23 | b 5 | c 5 |
| 1624 | a 24 | b 5 | c 5 |
| 1625 | a 25 | b 5 | c 5 |
| 1626 | a 1 | b 6 | c 5 |
| 1627 | a 2 | b 6 | c 5 |
| 1628 | a 3 | b 6 | c 5 |
| 1629 | a 4 | b 6 | c 5 |
| 1630 | a 5 | b 6 | c 5 |
| 1631 | a 6 | b 6 | c 5 |
| 1632 | a 7 | b 6 | c 5 |
| 1633 | a 8 | b 6 | c 5 |
| 1634 | a 9 | b 6 | c 5 |
| 1635 | a 10 | b 6 | c 5 |
| 1636 | a 11 | b 6 | c 5 |
| 1637 | a 12 | b 6 | c 5 |
| 1638 | a 13 | b 6 | c 5 |
| 1639 | a 14 | b 6 | c 5 |
| 1640 | a 15 | b 6 | c 5 |
| 1641 | a 16 | b 6 | c 5 |
| 1642 | a 17 | b 6 | c 5 |
| 1643 | a 18 | b 6 | c 5 |
| 1644 | a 19 | b 6 | c 5 |
| 1645 | a 20 | b 6 | c 5 |
| 1646 | a 21 | b 6 | c 5 |
| 1647 | a 22 | b 6 | c 5 |
| 1648 | a 23 | b 6 | c 5 |
| 1649 | a 24 | b 6 | c 5 |
| 1650 | a 25 | b 6 | c 5 |
| 1651 | a 1 | b 7 | c 5 |
| 1652 | a 2 | b 7 | c 5 |
| 1653 | a 3 | b 7 | c 5 |
| 1654 | a 4 | b 7 | c 5 |
| 1655 | a 5 | b 7 | c 5 |
| 1656 | a 6 | b 7 | c 5 |
| 1657 | a 7 | b 7 | c 5 |
| 1658 | a 8 | b 7 | c 5 |
| 1659 | a 9 | b 7 | c 5 |
| 1660 | a 10 | b 7 | c 5 |
| 1661 | a 11 | b 7 | c 5 |
| 1662 | a 12 | b 7 | c 5 |
| 1663 | a 13 | b 7 | c 5 |
| 1664 | a 14 | b 7 | c 5 |
| 1665 | a 15 | b 7 | c 5 |
| 1666 | a 16 | b 7 | c 5 |
| 1667 | a 17 | b 7 | c 5 |
| 1668 | a 18 | b 7 | c 5 |
| 1669 | a 19 | b 7 | c 5 |
| 1670 | a 20 | b 7 | c 5 |
| 1671 | a 21 | b 7 | c 5 |
| 1672 | a 22 | b 7 | c 5 |
| 1673 | a 23 | b 7 | c 5 |
| 1674 | a 24 | b 7 | c 5 |
| 1675 | a 25 | b 7 | c 5 |
| 1676 | a 1 | b 8 | c 5 |
| 1677 | a 2 | b 8 | c 5 |
| 1678 | a 3 | b 8 | c 5 |
| 1679 | a 4 | b 8 | c 5 |
| 1680 | a 5 | b 8 | c 5 |
| 1681 | a 6 | b 8 | c 5 |
| 1682 | a 7 | b 8 | c 5 |
| 1683 | a 8 | b 8 | c 5 |
| 1684 | a 9 | b 8 | c 5 |
| 1685 | a 10 | b 8 | c 5 |
| 1686 | a 11 | b 8 | c 5 |
| 1687 | a 12 | b 8 | c 5 |
| 1688 | a 13 | b 8 | c 5 |
| 1689 | a 14 | b 8 | c 5 |
| 1690 | a 15 | b 8 | c 5 |
| 1691 | a 16 | b 8 | c 5 |
| 1692 | a 17 | b 8 | c 5 |
| 1693 | a 18 | b 8 | c 5 |
| 1694 | a 19 | b 8 | c 5 |
| 1695 | a 20 | b 8 | c 5 |
| 1696 | a 21 | b 8 | c 5 |
| 1697 | a 22 | b 8 | c 5 |
| 1698 | a 23 | b 8 | c 5 |
| 1699 | a 24 | b 8 | c 5 |
| 1700 | a 25 | b 8 | c 5 |
| 1701 | a 1 | b 9 | c 5 |
| 1702 | a 2 | b 9 | c 5 |
| 1703 | a 3 | b 9 | c 5 |
| 1704 | a 4 | b 9 | c 5 |

-continued

| No. | Cp | Bridge | Flu |
|---|---|---|---|
| 1705 | a 5 | b 9 | c 5 |
| 1706 | a 6 | b 9 | c 5 |
| 1707 | a 7 | b 9 | c 5 |
| 1708 | a 8 | b 9 | c 5 |
| 1709 | a 9 | b 9 | c 5 |
| 1710 | a 10 | b 9 | c 5 |
| 1711 | a 11 | b 9 | c 5 |
| 1712 | a 12 | b 9 | c 5 |
| 1713 | a 13 | b 9 | c 5 |
| 1714 | a 14 | b 9 | c 5 |
| 1715 | a 15 | b 9 | c 5 |
| 1716 | a 16 | b 9 | c 5 |
| 1717 | a 17 | b 9 | c 5 |
| 1718 | a 18 | b 9 | c 5 |
| 1719 | a 19 | b 9 | c 5 |
| 1720 | a 20 | b 9 | c 5 |
| 1721 | a 21 | b 9 | c 5 |
| 1722 | a 22 | b 9 | c 5 |
| 1723 | a 23 | b 9 | c 5 |
| 1724 | a 24 | b 9 | c 5 |
| 1725 | a 25 | b 9 | c 5 |
| 1726 | a 1 | b 10 | c 5 |
| 1727 | a 2 | b 10 | c 5 |
| 1728 | a 3 | b 10 | c 5 |
| 1729 | a 4 | b 10 | c 5 |
| 1730 | a 5 | b 10 | c 5 |
| 1731 | a 6 | b 10 | c 5 |
| 1732 | a 7 | b 10 | c 5 |
| 1733 | a 8 | b 10 | c 5 |
| 1734 | a 9 | b 10 | c 5 |
| 1735 | a 10 | b 10 | c 5 |
| 1736 | a 11 | b 10 | c 5 |
| 1737 | a 12 | b 10 | c 5 |
| 1738 | a 13 | b 10 | c 5 |
| 1739 | a 14 | b 10 | c 5 |
| 1740 | a 15 | b 10 | c 5 |
| 1741 | a 16 | b 10 | c 5 |
| 1742 | a 17 | b 10 | c 5 |
| 1743 | a 18 | b 10 | c 5 |
| 1744 | a 19 | b 10 | c 5 |
| 1745 | a 20 | b 10 | c 5 |
| 1746 | a 21 | b 10 | c 5 |
| 1747 | a 22 | b 10 | c 5 |
| 1748 | a 23 | b 10 | c 5 |
| 1749 | a 24 | b 10 | c 5 |
| 1750 | a 25 | b 10 | c 5 |
| 1751 | a 1 | b 11 | c 5 |
| 1752 | a 2 | b 11 | c 5 |
| 1753 | a 3 | b 11 | c 5 |
| 1754 | a 4 | b 11 | c 5 |
| 1755 | a 5 | b 11 | c 5 |
| 1756 | a 6 | b 11 | c 5 |
| 1757 | a 7 | b 11 | c 5 |
| 1758 | a 8 | b 11 | c 5 |
| 1759 | a 9 | b 11 | c 5 |
| 1760 | a 10 | b 11 | c 5 |
| 1761 | a 11 | b 11 | c 5 |
| 1762 | a 12 | b 11 | c 5 |
| 1763 | a 13 | b 11 | c 5 |
| 1764 | a 14 | b 11 | c 5 |
| 1765 | a 15 | b 11 | c 5 |
| 1766 | a 16 | b 11 | c 5 |
| 1767 | a 17 | b 11 | c 5 |
| 1768 | a 18 | b 11 | c 5 |
| 1769 | a 19 | b 11 | c 5 |
| 1770 | a 20 | b 11 | c 5 |
| 1771 | a 21 | b 11 | c 5 |
| 1772 | a 22 | b 11 | c 5 |
| 1773 | a 23 | b 11 | c 5 |
| 1774 | a 24 | b 11 | c 5 |
| 1775 | a 25 | b 11 | c 5 |
| 1776 | a 1 | b 12 | c 5 |
| 1777 | a 2 | b 12 | c 5 |
| 1778 | a 3 | b 12 | c 5 |
| 1779 | a 4 | b 12 | c 5 |
| 1780 | a 5 | b 12 | c 5 |
| 1781 | a 6 | b 12 | c 5 |

-continued

| No. | Cp | Bridge | Flu |
|---|---|---|---|
| 1782 | a 7 | b 12 | c 5 |
| 1783 | a 8 | b 12 | c 5 |
| 1784 | a 9 | b 12 | c 5 |
| 1785 | a 10 | b 12 | c 5 |
| 1786 | a 11 | b 12 | c 5 |
| 1787 | a 12 | b 12 | c 5 |
| 1788 | a 13 | b 12 | c 5 |
| 1789 | a 14 | b 12 | c 5 |
| 1790 | a 15 | b 12 | c 5 |
| 1791 | a 16 | b 12 | c 5 |
| 1792 | a 17 | b 12 | c 5 |
| 1793 | a 18 | b 12 | c 5 |
| 1794 | a 19 | b 12 | c 5 |
| 1795 | a 20 | b 12 | c 5 |
| 1796 | a 21 | b 12 | c 5 |
| 1797 | a 22 | b 12 | c 5 |
| 1798 | a 23 | b 12 | c 5 |
| 1799 | a 24 | b 12 | c 5 |
| 1800 | a 25 | b 12 | c 5 |
| 1801 | a 1 | b 13 | c 5 |
| 1802 | a 2 | b 13 | c 5 |
| 1803 | a 3 | b 13 | c 5 |
| 1804 | a 4 | b 13 | c 5 |
| 1805 | a 5 | b 13 | c 5 |
| 1806 | a 6 | b 13 | c 5 |
| 1807 | a 7 | b 13 | c 5 |
| 1808 | a 8 | b 13 | c 5 |
| 1809 | a 9 | b 13 | c 5 |
| 1810 | a 10 | b 13 | c 5 |
| 1811 | a 11 | b 13 | c 5 |
| 1812 | a 12 | b 13 | c 5 |
| 1813 | a 13 | b 13 | c 5 |
| 1814 | a 14 | b 13 | c 5 |
| 1815 | a 15 | b 13 | c 5 |
| 1816 | a 16 | b 13 | c 5 |
| 1817 | a 17 | b 13 | c 5 |
| 1818 | a 18 | b 13 | c 5 |
| 1819 | a 19 | b 13 | c 5 |
| 1820 | a 20 | b 13 | c 5 |
| 1821 | a 21 | b 13 | c 5 |
| 1822 | a 22 | b 13 | c 5 |
| 1823 | a 23 | b 13 | c 5 |
| 1824 | a 24 | b 13 | c 5 |
| 1825 | a 25 | b 13 | c 5 |
| 1826 | a 1 | b 14 | c 5 |
| 1827 | a 2 | b 14 | c 5 |
| 1828 | a 3 | b 14 | c 5 |
| 1829 | a 4 | b 14 | c 5 |
| 1830 | a 5 | b 14 | c 5 |
| 1831 | a 6 | b 14 | c 5 |
| 1832 | a 7 | b 14 | c 5 |
| 1833 | a 8 | b 14 | c 5 |
| 1834 | a 9 | b 14 | c 5 |
| 1835 | a 10 | b 14 | c 5 |
| 1836 | a 11 | b 14 | c 5 |
| 1837 | a 12 | b 14 | c 5 |
| 1838 | a 13 | b 14 | c 5 |
| 1839 | a 14 | b 14 | c 5 |
| 1840 | a 15 | b 14 | c 5 |
| 1841 | a 16 | b 14 | c 5 |
| 1842 | a 17 | b 14 | c 5 |
| 1843 | a 18 | b 14 | c 5 |
| 1844 | a 19 | b 14 | c 5 |
| 1845 | a 20 | b 14 | c 5 |
| 1846 | a 21 | b 14 | c 5 |
| 1847 | a 22 | b 14 | c 5 |
| 1848 | a 23 | b 14 | c 5 |
| 1849 | a 24 | b 14 | c 5 |
| 1850 | a 25 | b 14 | c 5 |
| 1851 | a 1 | b 15 | c 5 |
| 1852 | a 2 | b 15 | c 5 |
| 1853 | a 3 | b 15 | c 5 |
| 1854 | a 4 | b 15 | c 5 |
| 1855 | a 5 | b 15 | c 5 |
| 1856 | a 6 | b 15 | c 5 |
| 1857 | a 7 | b 15 | c 5 |
| 1858 | a 8 | b 15 | c 5 |

| No. | Cp | Bridge | Flu |
|---|---|---|---|
| 1859 | a 9 | b 15 | c 5 |
| 1860 | a 10 | b 15 | c 5 |
| 1861 | a 11 | b 15 | c 5 |
| 1862 | a 12 | b 15 | c 5 |
| 1863 | a 13 | b 15 | c 5 |
| 1864 | a 14 | b 15 | c 5 |
| 1865 | a 15 | b 15 | c 5 |
| 1866 | a 16 | b 15 | c 5 |
| 1867 | a 17 | b 15 | c 5 |
| 1868 | a 18 | b 15 | c 5 |
| 1869 | a 19 | b 15 | c 5 |
| 1870 | a 20 | b 15 | c 5 |
| 1871 | a 21 | b 15 | c 5 |
| 1872 | a 22 | b 15 | c 5 |
| 1873 | a 23 | b 15 | c 5 |
| 1874 | a 24 | b 15 | c 5 |
| 1875 | a 25 | b 15 | c 5 |
| 1876 | a 1 | b 1 | c 6 |
| 1877 | a 2 | b 1 | c 6 |
| 1878 | a 3 | b 1 | c 6 |
| 1879 | a 4 | b 1 | c 6 |
| 1880 | a 5 | b 1 | c 6 |
| 1881 | a 6 | b 1 | c 6 |
| 1882 | a 7 | b 1 | c 6 |
| 1883 | a 8 | b 1 | c 6 |
| 1884 | a 9 | b 1 | c 6 |
| 1885 | a 10 | b 1 | c 6 |
| 1886 | a 11 | b 1 | c 6 |
| 1887 | a 12 | b 1 | c 6 |
| 1888 | a 13 | b 1 | c 6 |
| 1889 | a 14 | b 1 | c 6 |
| 1890 | a 15 | b 1 | c 6 |
| 1891 | a 16 | b 1 | c 6 |
| 1892 | a 17 | b 1 | c 6 |
| 1893 | a 18 | b 1 | c 6 |
| 1894 | a 19 | b 1 | c 6 |
| 1895 | a 20 | b 1 | c 6 |
| 1896 | a 21 | b 1 | c 6 |
| 1897 | a 22 | b 1 | c 6 |
| 1898 | a 23 | b 1 | c 6 |
| 1899 | a 24 | b 1 | c 6 |
| 1900 | a 25 | b 1 | c 6 |
| 1901 | a 1 | b 2 | c 6 |
| 1902 | a 2 | b 2 | c 6 |
| 1903 | a 3 | b 2 | c 6 |
| 1904 | a 4 | b 2 | c 6 |
| 1905 | a 5 | b 2 | c 6 |
| 1906 | a 6 | b 2 | c 6 |
| 1907 | a 7 | b 2 | c 6 |
| 1908 | a 8 | b 2 | c 6 |
| 1909 | a 9 | b 2 | c 6 |
| 1910 | a 10 | b 2 | c 6 |
| 1911 | a 11 | b 2 | c 6 |
| 1912 | a 12 | b 2 | c 6 |
| 1913 | a 13 | b 2 | c 6 |
| 1914 | a 14 | b 2 | c 6 |
| 1915 | a 15 | b 2 | c 6 |
| 1916 | a 16 | b 2 | c 6 |
| 1917 | a 17 | b 2 | c 6 |
| 1918 | a 18 | b 2 | c 6 |
| 1919 | a 19 | b 2 | c 6 |
| 1920 | a 20 | b 2 | c 6 |
| 1921 | a 21 | b 2 | c 6 |
| 1922 | a 22 | b 2 | c 6 |
| 1923 | a 23 | b 2 | c 6 |
| 1924 | a 24 | b 2 | c 6 |
| 1925 | a 25 | b 2 | c 6 |
| 1926 | a 1 | b 3 | c 6 |
| 1927 | a 2 | b 3 | c 6 |
| 1928 | a 3 | b 3 | c 6 |
| 1929 | a 4 | b 3 | c 6 |
| 1930 | a 5 | b 3 | c 6 |
| 1931 | a 6 | b 3 | c 6 |
| 1932 | a 7 | b 3 | c 6 |
| 1933 | a 8 | b 3 | c 6 |
| 1934 | a 9 | b 3 | c 6 |
| 1935 | a 10 | b 3 | c 6 |
| 1936 | a 11 | b 3 | c 6 |
| 1937 | a 12 | b 3 | c 6 |
| 1938 | a 13 | b 3 | c 6 |
| 1939 | a 14 | b 3 | c 6 |
| 1940 | a 15 | b 3 | c 6 |
| 1941 | a 16 | b 3 | c 6 |
| 1942 | a 17 | b 3 | c 6 |
| 1943 | a 18 | b 3 | c 6 |
| 1944 | a 19 | b 3 | c 6 |
| 1945 | a 20 | b 3 | c 6 |
| 1946 | a 21 | b 3 | c 6 |
| 1947 | a 22 | b 3 | c 6 |
| 1948 | a 23 | b 3 | c 6 |
| 1949 | a 24 | b 3 | c 6 |
| 1950 | a 25 | b 3 | c 6 |
| 1951 | a 1 | b 4 | c 6 |
| 1952 | a 2 | b 4 | c 6 |
| 1953 | a 3 | b 4 | c 6 |
| 1954 | a 4 | b 4 | c 6 |
| 1955 | a 5 | b 4 | c 6 |
| 1956 | a 6 | b 4 | c 6 |
| 1957 | a 7 | b 4 | c 6 |
| 1958 | a 8 | b 4 | c 6 |
| 1959 | a 9 | b 4 | c 6 |
| 1960 | a 10 | b 4 | c 6 |
| 1961 | a 11 | b 4 | c 6 |
| 1962 | a 12 | b 4 | c 6 |
| 1963 | a 13 | b 4 | c 6 |
| 1964 | a 14 | b 4 | c 6 |
| 1965 | a 15 | b 4 | c 6 |
| 1966 | a 16 | b 4 | c 6 |
| 1967 | a 17 | b 4 | c 6 |
| 1968 | a 18 | b 4 | c 6 |
| 1969 | a 19 | b 4 | c 6 |
| 1970 | a 20 | b 4 | c 6 |
| 1971 | a 21 | b 4 | c 6 |
| 1972 | a 22 | b 4 | c 6 |
| 1973 | a 23 | b 4 | c 6 |
| 1974 | a 24 | b 4 | c 6 |
| 1975 | a 25 | b 4 | c 6 |
| 1976 | a 1 | b 5 | c 6 |
| 1977 | a 2 | b 5 | c 6 |
| 1978 | a 3 | b 5 | c 6 |
| 1979 | a 4 | b 5 | c 6 |
| 1980 | a 5 | b 5 | c 6 |
| 1981 | a 6 | b 5 | c 6 |
| 1982 | a 7 | b 5 | c 6 |
| 1983 | a 8 | b 5 | c 6 |
| 1984 | a 9 | b 5 | c 6 |
| 1985 | a 10 | b 5 | c 6 |
| 1986 | a 11 | b 5 | c 6 |
| 1987 | a 12 | b 5 | c 6 |
| 1988 | a 13 | b 5 | c 6 |
| 1989 | a 14 | b 5 | c 6 |
| 1990 | a 15 | b 5 | c 6 |
| 1991 | a 16 | b 5 | c 6 |
| 1992 | a 17 | b 5 | c 6 |
| 1993 | a 18 | b 5 | c 6 |
| 1994 | a 19 | b 5 | c 6 |
| 1995 | a 20 | b 5 | c 6 |
| 1996 | a 21 | b 5 | c 6 |
| 1997 | a 22 | b 5 | c 6 |
| 1998 | a 23 | b 5 | c 6 |
| 1999 | a 24 | b 5 | c 6 |
| 2000 | a 25 | b 5 | c 6 |
| 2001 | a 1 | b 6 | c 6 |
| 2002 | a 2 | b 6 | c 6 |
| 2003 | a 3 | b 6 | c 6 |
| 2004 | a 4 | b 6 | c 6 |
| 2005 | a 5 | b 6 | c 6 |
| 2006 | a 6 | b 6 | c 6 |
| 2007 | a 7 | b 6 | c 6 |
| 2008 | a 8 | b 6 | c 6 |
| 2009 | a 9 | b 6 | c 6 |
| 2010 | a 10 | b 6 | c 6 |
| 2011 | a 11 | b 6 | c 6 |
| 2012 | a 12 | b 6 | c 6 |

| No. | Cp | Bridge | Flu |
|---|---|---|---|
| 2013 | a 13 | b 6 | c 6 |
| 2014 | a 14 | b 6 | c 6 |
| 2015 | a 15 | b 6 | c 6 |
| 2016 | a 16 | b 6 | c 6 |
| 2017 | a 17 | b 6 | c 6 |
| 2018 | a 18 | b 6 | c 6 |
| 2019 | a 19 | b 6 | c 6 |
| 2020 | a 20 | b 6 | c 6 |
| 2021 | a 21 | b 6 | c 6 |
| 2022 | a 22 | b 6 | c 6 |
| 2023 | a 23 | b 6 | c 6 |
| 2024 | a 24 | b 6 | c 6 |
| 2025 | a 25 | b 6 | c 6 |
| 2026 | a 1 | b 7 | c 6 |
| 2027 | a 2 | b 7 | c 6 |
| 2028 | a 3 | b 7 | c 6 |
| 2029 | a 4 | b 7 | c 6 |
| 2030 | a 5 | b 7 | c 6 |
| 2031 | a 6 | b 7 | c 6 |
| 2032 | a 7 | b 7 | c 6 |
| 2033 | a 8 | b 7 | c 6 |
| 2034 | a 9 | b 7 | c 6 |
| 2035 | a 10 | b 7 | c 6 |
| 2036 | a 11 | b 7 | c 6 |
| 2037 | a 12 | b 7 | c 6 |
| 2038 | a 13 | b 7 | c 6 |
| 2039 | a 14 | b 7 | c 6 |
| 2040 | a 15 | b 7 | c 6 |
| 2041 | a 16 | b 7 | c 6 |
| 2042 | a 17 | b 7 | c 6 |
| 2043 | a 18 | b 7 | c 6 |
| 2044 | a 19 | b 7 | c 6 |
| 2045 | a 20 | b 7 | c 6 |
| 2046 | a 21 | b 7 | c 6 |
| 2047 | a 22 | b 7 | c 6 |
| 2048 | a 23 | b 7 | c 6 |
| 2049 | a 24 | b 7 | c 6 |
| 2050 | a 25 | b 7 | c 6 |
| 2051 | a 1 | b 8 | c 6 |
| 2052 | a 2 | b 8 | c 6 |
| 2053 | a 3 | b 8 | c 6 |
| 2054 | a 4 | b 8 | c 6 |
| 2055 | a 5 | b 8 | c 6 |
| 2056 | a 6 | b 8 | c 6 |
| 2057 | a 7 | b 8 | c 6 |
| 2058 | a 8 | b 8 | c 6 |
| 2059 | a 9 | b 8 | c 6 |
| 2060 | a 10 | b 8 | c 6 |
| 2061 | a 11 | b 8 | c 6 |
| 2062 | a 12 | b 8 | c 6 |
| 2063 | a 13 | b 8 | c 6 |
| 2064 | a 14 | b 8 | c 6 |
| 2065 | a 15 | b 8 | c 6 |
| 2066 | a 16 | b 8 | c 6 |
| 2067 | a 17 | b 8 | c 6 |
| 2068 | a 18 | b 8 | c 6 |
| 2069 | a 19 | b 8 | c 6 |
| 2070 | a 20 | b 8 | c 6 |
| 2071 | a 21 | b 8 | c 6 |
| 2072 | a 22 | b 8 | c 6 |
| 2073 | a 23 | b 8 | c 6 |
| 2074 | a 24 | b 8 | c 6 |
| 2075 | a 25 | b 8 | c 6 |
| 2076 | a 1 | b 9 | c 6 |
| 2077 | a 2 | b 9 | c 6 |
| 2078 | a 3 | b 9 | c 6 |
| 2079 | a 4 | b 9 | c 6 |
| 2080 | a 5 | b 9 | c 6 |
| 2081 | a 6 | b 9 | c 6 |
| 2082 | a 7 | b 9 | c 6 |
| 2083 | a 8 | b 9 | c 6 |
| 2084 | a 9 | b 9 | c 6 |
| 2085 | a 10 | b 9 | c 6 |
| 2086 | a 11 | b 9 | c 6 |
| 2087 | a 12 | b 9 | c 6 |
| 2088 | a 13 | b 9 | c 6 |
| 2089 | a 14 | b 9 | c 6 |
| 2090 | a 15 | b 9 | c 6 |
| 2091 | a 16 | b 9 | c 6 |
| 2092 | a 17 | b 9 | c 6 |
| 2093 | a 18 | b 9 | c 6 |
| 2094 | a 19 | b 9 | c 6 |
| 2095 | a 20 | b 9 | c 6 |
| 2096 | a 21 | b 9 | c 6 |
| 2097 | a 22 | b 9 | c 6 |
| 2098 | a 23 | b 9 | c 6 |
| 2099 | a 24 | b 9 | c 6 |
| 2100 | a 25 | b 9 | c 6 |
| 2101 | a 1 | b 10 | c 6 |
| 2102 | a 2 | b 10 | c 6 |
| 2103 | a 3 | b 10 | c 6 |
| 2104 | a 4 | b 10 | c 6 |
| 2105 | a 5 | b 10 | c 6 |
| 2106 | a 6 | b 10 | c 6 |
| 2107 | a 7 | b 10 | c 6 |
| 2108 | a 8 | b 10 | c 6 |
| 2109 | a 9 | b 10 | c 6 |
| 2110 | a 10 | b 10 | c 6 |
| 2111 | a 11 | b 10 | c 6 |
| 2112 | a 12 | b 10 | c 6 |
| 2113 | a 13 | b 10 | c 6 |
| 2114 | a 14 | b 10 | c 6 |
| 2115 | a 15 | b 10 | c 6 |
| 2116 | a 16 | b 10 | c 6 |
| 2117 | a 17 | b 10 | c 6 |
| 2118 | a 18 | b 10 | c 6 |
| 2119 | a 19 | b 10 | c 6 |
| 2120 | a 20 | b 10 | c 6 |
| 2121 | a 21 | b 10 | c 6 |
| 2122 | a 22 | b 10 | c 6 |
| 2123 | a 23 | b 10 | c 6 |
| 2124 | a 24 | b 10 | c 6 |
| 2125 | a 25 | b 10 | c 6 |
| 2126 | a 1 | b 11 | c 6 |
| 2127 | a 2 | b 11 | c 6 |
| 2128 | a 3 | b 11 | c 6 |
| 2129 | a 4 | b 11 | c 6 |
| 2130 | a 5 | b 11 | c 6 |
| 2131 | a 6 | b 11 | c 6 |
| 2132 | a 7 | b 11 | c 6 |
| 2133 | a 8 | b 11 | c 6 |
| 2134 | a 9 | b 11 | c 6 |
| 2135 | a 10 | b 11 | c 6 |
| 2136 | a 11 | b 11 | c 6 |
| 2137 | a 12 | b 11 | c 6 |
| 2138 | a 13 | b 11 | c 6 |
| 2139 | a 14 | b 11 | c 6 |
| 2140 | a 15 | b 11 | c 6 |
| 2141 | a 16 | b 11 | c 6 |
| 2142 | a 17 | b 11 | c 6 |
| 2143 | a 18 | b 11 | c 6 |
| 2144 | a 19 | b 11 | c 6 |
| 2145 | a 20 | b 11 | c 6 |
| 2146 | a 21 | b 11 | c 6 |
| 2147 | a 22 | b 11 | c 6 |
| 2148 | a 23 | b 11 | c 6 |
| 2149 | a 24 | b 11 | c 6 |
| 2150 | a 25 | b 11 | c 6 |
| 2151 | a 1 | b 12 | c 6 |
| 2152 | a 2 | b 12 | c 6 |
| 2153 | a 3 | b 12 | c 6 |
| 2154 | a 4 | b 12 | c 6 |
| 2155 | a 5 | b 12 | c 6 |
| 2156 | a 6 | b 12 | c 6 |
| 2157 | a 7 | b 12 | c 6 |
| 2158 | a 8 | b 12 | c 6 |
| 2159 | a 9 | b 12 | c 6 |
| 2160 | a 10 | b 12 | c 6 |
| 2161 | a 11 | b 12 | c 6 |
| 2162 | a 12 | b 12 | c 6 |
| 2163 | a 13 | b 12 | c 6 |
| 2164 | a 14 | b 12 | c 6 |
| 2165 | a 15 | b 12 | c 6 |
| 2166 | a 16 | b 12 | c 6 |

-continued

| No. | Cp | Bridge | Flu |
|---|---|---|---|
| 2167 | a 17 | b 12 | c 6 |
| 2168 | a 18 | b 12 | c 6 |
| 2169 | a 19 | b 12 | c 6 |
| 2170 | a 20 | b 12 | c 6 |
| 2171 | a 21 | b 12 | c 6 |
| 2172 | a 22 | b 12 | c 6 |
| 2173 | a 23 | b 12 | c 6 |
| 2174 | a 24 | b 12 | c 6 |
| 2175 | a 25 | b 12 | c 6 |
| 2176 | a 1 | b 13 | c 6 |
| 2177 | a 2 | b 13 | c 6 |
| 2178 | a 3 | b 13 | c 6 |
| 2179 | a 4 | b 13 | c 6 |
| 2180 | a 5 | b 13 | c 6 |
| 2181 | a 6 | b 13 | c 6 |
| 2182 | a 7 | b 13 | c 6 |
| 2183 | a 8 | b 13 | c 6 |
| 2184 | a 9 | b 13 | c 6 |
| 2185 | a 10 | b 13 | c 6 |
| 2186 | a 11 | b 13 | c 6 |
| 2187 | a 12 | b 13 | c 6 |
| 2188 | a 13 | b 13 | c 6 |
| 2189 | a 14 | b 13 | c 6 |
| 2190 | a 15 | b 13 | c 6 |
| 2191 | a 16 | b 13 | c 6 |
| 2192 | a 17 | b 13 | c 6 |
| 2193 | a 18 | b 13 | c 6 |
| 2194 | a 19 | b 13 | c 6 |
| 2195 | a 20 | b 13 | c 6 |
| 2196 | a 21 | b 13 | c 6 |
| 2197 | a 22 | b 13 | c 6 |
| 2198 | a 23 | b 13 | c 6 |
| 2199 | a 24 | b 13 | c 6 |
| 2200 | a 25 | b 13 | c 6 |
| 2201 | a 1 | b 14 | c 6 |
| 2202 | a 2 | b 14 | c 6 |
| 2203 | a 3 | b 14 | c 6 |
| 2204 | a 4 | b 14 | c 6 |
| 2205 | a 5 | b 14 | c 6 |
| 2206 | a 6 | b 14 | c 6 |
| 2207 | a 7 | b 14 | c 6 |
| 2208 | a 8 | b 14 | c 6 |
| 2209 | a 9 | b 14 | c 6 |
| 2210 | a 10 | b 14 | c 6 |
| 2211 | a 11 | b 14 | c 6 |
| 2212 | a 12 | b 14 | c 6 |
| 2213 | a 13 | b 14 | c 6 |
| 2214 | a 14 | b 14 | c 6 |
| 2215 | a 15 | b 14 | c 6 |
| 2216 | a 16 | b 14 | c 6 |
| 2217 | a 17 | b 14 | c 6 |
| 2218 | a 18 | b 14 | c 6 |
| 2219 | a 19 | b 14 | c 6 |
| 2220 | a 20 | b 14 | c 6 |
| 2221 | a 21 | b 14 | c 6 |
| 2222 | a 22 | b 14 | c 6 |
| 2223 | a 23 | b 14 | c 6 |
| 2224 | a 24 | b 14 | c 6 |
| 2225 | a 25 | b 14 | c 6 |
| 2226 | a 1 | b 15 | c 6 |
| 2227 | a 2 | b 15 | c 6 |
| 2228 | a 3 | b 15 | c 6 |
| 2229 | a 4 | b 15 | c 6 |
| 2230 | a 5 | b 15 | c 6 |
| 2231 | a 6 | b 15 | c 6 |
| 2232 | a 7 | b 15 | c 6 |
| 2233 | a 8 | b 15 | c 6 |
| 2234 | a 9 | b 15 | c 6 |
| 2235 | a 10 | b 15 | c 6 |
| 2236 | a 11 | b 15 | c 6 |
| 2237 | a 12 | b 15 | c 6 |
| 2238 | a 13 | b 15 | c 6 |
| 2239 | a 14 | b 15 | c 6 |
| 2240 | a 15 | b 15 | c 6 |
| 2241 | a 16 | b 15 | c 6 |
| 2242 | a 17 | b 15 | c 6 |
| 2243 | a 18 | b 15 | c 6 |
| 2244 | a 19 | b 15 | c 6 |
| 2245 | a 20 | b 15 | c 6 |
| 2246 | a 21 | b 15 | c 6 |
| 2247 | a 22 | b 15 | c 6 |
| 2248 | a 23 | b 15 | c 6 |
| 2249 | a 24 | b 15 | c 6 |
| 2250 | a 25 | b 15 | c 6 |
| 2251 | a 1 | b 1 | c 7 |
| 2252 | a 2 | b 1 | c 7 |
| 2253 | a 3 | b 1 | c 7 |
| 2254 | a 4 | b 1 | c 7 |
| 2255 | a 5 | b 1 | c 7 |
| 2256 | a 6 | b 1 | c 7 |
| 2257 | a 7 | b 1 | c 7 |
| 2258 | a 8 | b 1 | c 7 |
| 2259 | a 9 | b 1 | c 7 |
| 2260 | a 10 | b 1 | c 7 |
| 2261 | a 11 | b 1 | c 7 |
| 2262 | a 12 | b 1 | c 7 |
| 2263 | a 13 | b 1 | c 7 |
| 2264 | a 14 | b 1 | c 7 |
| 2265 | a 15 | b 1 | c 7 |
| 2266 | a 16 | b 1 | c 7 |
| 2267 | a 17 | b 1 | c 7 |
| 2268 | a 18 | b 1 | c 7 |
| 2269 | a 19 | b 1 | c 7 |
| 2270 | a 20 | b 1 | c 7 |
| 2271 | a 21 | b 1 | c 7 |
| 2272 | a 22 | b 1 | c 7 |
| 2273 | a 23 | b 1 | c 7 |
| 2274 | a 24 | b 1 | c 7 |
| 2275 | a 25 | b 1 | c 7 |
| 2276 | a 1 | b 2 | c 7 |
| 2277 | a 2 | b 2 | c 7 |
| 2278 | a 3 | b 2 | c 7 |
| 2279 | a 4 | b 2 | c 7 |
| 2280 | a 5 | b 2 | c 7 |
| 2281 | a 6 | b 2 | c 7 |
| 2282 | a 7 | b 2 | c 7 |
| 2283 | a 8 | b 2 | c 7 |
| 2284 | a 9 | b 2 | c 7 |
| 2285 | a 10 | b 2 | c 7 |
| 2286 | a 11 | b 2 | c 7 |
| 2287 | a 12 | b 2 | c 7 |
| 2288 | a 13 | b 2 | c 7 |
| 2289 | a 14 | b 2 | c 7 |
| 2290 | a 15 | b 2 | c 7 |
| 2291 | a 16 | b 2 | c 7 |
| 2292 | a 17 | b 2 | c 7 |
| 2293 | a 18 | b 2 | c 7 |
| 2294 | a 19 | b 2 | c 7 |
| 2295 | a 20 | b 2 | c 7 |
| 2296 | a 21 | b 2 | c 7 |
| 2297 | a 22 | b 2 | c 7 |
| 2298 | a 23 | b 2 | c 7 |
| 2299 | a 24 | b 2 | c 7 |
| 2300 | a 25 | b 2 | c 7 |
| 2301 | a 1 | b 3 | c 7 |
| 2302 | a 2 | b 3 | c 7 |
| 2303 | a 3 | b 3 | c 7 |
| 2304 | a 4 | b 3 | c 7 |
| 2305 | a 5 | b 3 | c 7 |
| 2306 | a 6 | b 3 | c 7 |
| 2307 | a 7 | b 3 | c 7 |
| 2308 | a 8 | b 3 | c 7 |
| 2309 | a 9 | b 3 | c 7 |
| 2310 | a 10 | b 3 | c 7 |
| 2311 | a 11 | b 3 | c 7 |
| 2312 | a 12 | b 3 | c 7 |
| 2313 | a 13 | b 3 | c 7 |
| 2314 | a 14 | b 3 | c 7 |
| 2315 | a 15 | b 3 | c 7 |
| 2316 | a 16 | b 3 | c 7 |
| 2317 | a 17 | b 3 | c 7 |
| 2318 | a 18 | b 3 | c 7 |
| 2319 | a 19 | b 3 | c 7 |
| 2320 | a 20 | b 3 | c 7 |

| No. | Cp | Bridge | Flu |
|---|---|---|---|
| 2321 | a 21 | b 3 | c 7 |
| 2322 | a 22 | b 3 | c 7 |
| 2323 | a 23 | b 3 | c 7 |
| 2324 | a 24 | b 3 | c 7 |
| 2325 | a 25 | b 3 | c 7 |
| 2326 | a 1 | b 4 | c 7 |
| 2327 | a 2 | b 4 | c 7 |
| 2328 | a 3 | b 4 | c 7 |
| 2329 | a 4 | b 4 | c 7 |
| 2330 | a 5 | b 4 | c 7 |
| 2331 | a 6 | b 4 | c 7 |
| 2332 | a 7 | b 4 | c 7 |
| 2333 | a 8 | b 4 | c 7 |
| 2334 | a 9 | b 4 | c 7 |
| 2335 | a 10 | b 4 | c 7 |
| 2336 | a 11 | b 4 | c 7 |
| 2337 | a 12 | b 4 | c 7 |
| 2338 | a 13 | b 4 | c 7 |
| 2339 | a 14 | b 4 | c 7 |
| 2340 | a 15 | b 4 | c 7 |
| 2341 | a 16 | b 4 | c 7 |
| 2342 | a 17 | b 4 | c 7 |
| 2343 | a 18 | b 4 | c 7 |
| 2344 | a 19 | b 4 | c 7 |
| 2345 | a 20 | b 4 | c 7 |
| 2346 | a 21 | b 4 | c 7 |
| 2347 | a 22 | b 4 | c 7 |
| 2348 | a 23 | b 4 | c 7 |
| 2349 | a 24 | b 4 | c 7 |
| 2350 | a 25 | b 4 | c 7 |
| 2351 | a 1 | b 5 | c 7 |
| 2352 | a 2 | b 5 | c 7 |
| 2353 | a 3 | b 5 | c 7 |
| 2354 | a 4 | b 5 | c 7 |
| 2355 | a 5 | b 5 | c 7 |
| 2356 | a 6 | b 5 | c 7 |
| 2357 | a 7 | b 5 | c 7 |
| 2358 | a 8 | b 5 | c 7 |
| 2359 | a 9 | b 5 | c 7 |
| 2360 | a 10 | b 5 | c 7 |
| 2361 | a 11 | b 5 | c 7 |
| 2362 | a 12 | b 5 | c 7 |
| 2363 | a 13 | b 5 | c 7 |
| 2364 | a 14 | b 5 | c 7 |
| 2365 | a 15 | b 5 | c 7 |
| 2366 | a 16 | b 5 | c 7 |
| 2367 | a 17 | b 5 | c 7 |
| 2368 | a 18 | b 5 | c 7 |
| 2369 | a 19 | b 5 | c 7 |
| 2370 | a 20 | b 5 | c 7 |
| 2371 | a 21 | b 5 | c 7 |
| 2372 | a 22 | b 5 | c 7 |
| 2373 | a 23 | b 5 | c 7 |
| 2374 | a 24 | b 5 | c 7 |
| 2375 | a 25 | b 5 | c 7 |
| 2376 | a 1 | b 6 | c 7 |
| 2377 | a 2 | b 6 | c 7 |
| 2378 | a 3 | b 6 | c 7 |
| 2379 | a 4 | b 6 | c 7 |
| 2380 | a 5 | b 6 | c 7 |
| 2381 | a 6 | b 6 | c 7 |
| 2382 | a 7 | b 6 | c 7 |
| 2383 | a 8 | b 6 | c 7 |
| 2384 | a 9 | b 6 | c 7 |
| 2385 | a 10 | b 6 | c 7 |
| 2386 | a 11 | b 6 | c 7 |
| 2387 | a 12 | b 6 | c 7 |
| 2388 | a 13 | b 6 | c 7 |
| 2389 | a 14 | b 6 | c 7 |
| 2390 | a 15 | b 6 | c 7 |
| 2391 | a 16 | b 6 | c 7 |
| 2392 | a 17 | b 6 | c 7 |
| 2393 | a 18 | b 6 | c 7 |
| 2394 | a 19 | b 6 | c 7 |
| 2395 | a 20 | b 6 | c 7 |
| 2396 | a 21 | b 6 | c 7 |
| 2397 | a 22 | b 6 | c 7 |
| 2398 | a 23 | b 6 | c 7 |
| 2399 | a 24 | b 6 | c 7 |
| 2400 | a 25 | b 6 | c 7 |
| 2401 | a 1 | b 7 | c 7 |
| 2402 | a 2 | b 7 | c 7 |
| 2403 | a 3 | b 7 | c 7 |
| 2404 | a 4 | b 7 | c 7 |
| 2405 | a 5 | b 7 | c 7 |
| 2406 | a 6 | b 7 | c 7 |
| 2407 | a 7 | b 7 | c 7 |
| 2408 | a 8 | b 7 | c 7 |
| 2409 | a 9 | b 7 | c 7 |
| 2410 | a 10 | b 7 | c 7 |
| 2411 | a 11 | b 7 | c 7 |
| 2412 | a 12 | b 7 | c 7 |
| 2413 | a 13 | b 7 | c 7 |
| 2414 | a 14 | b 7 | c 7 |
| 2415 | a 15 | b 7 | c 7 |
| 2416 | a 16 | b 7 | c 7 |
| 2417 | a 17 | b 7 | c 7 |
| 2418 | a 18 | b 7 | c 7 |
| 2419 | a 19 | b 7 | c 7 |
| 2420 | a 20 | b 7 | c 7 |
| 2421 | a 21 | b 7 | c 7 |
| 2422 | a 22 | b 7 | c 7 |
| 2423 | a 23 | b 7 | c 7 |
| 2424 | a 24 | b 7 | c 7 |
| 2425 | a 25 | b 7 | c 7 |
| 2426 | a 1 | b 8 | c 7 |
| 2427 | a 2 | b 8 | c 7 |
| 2428 | a 3 | b 8 | c 7 |
| 2429 | a 4 | b 8 | c 7 |
| 2430 | a 5 | b 8 | c 7 |
| 2431 | a 6 | b 8 | c 7 |
| 2432 | a 7 | b 8 | c 7 |
| 2433 | a 8 | b 8 | c 7 |
| 2434 | a 9 | b 8 | c 7 |
| 2435 | a 10 | b 8 | c 7 |
| 2436 | a 11 | b 8 | c 7 |
| 2437 | a 12 | b 8 | c 7 |
| 2438 | a 13 | b 8 | c 7 |
| 2439 | a 14 | b 8 | c 7 |
| 2440 | a 15 | b 8 | c 7 |
| 2441 | a 16 | b 8 | c 7 |
| 2442 | a 17 | b 8 | c 7 |
| 2443 | a 18 | b 8 | c 7 |
| 2444 | a 19 | b 8 | c 7 |
| 2445 | a 20 | b 8 | c 7 |
| 2446 | a 21 | b 8 | c 7 |
| 2447 | a 22 | b 8 | c 7 |
| 2448 | a 23 | b 8 | c 7 |
| 2449 | a 24 | b 8 | c 7 |
| 2450 | a 25 | b 8 | c 7 |
| 2451 | a 1 | b 9 | c 7 |
| 2452 | a 2 | b 9 | c 7 |
| 2453 | a 3 | b 9 | c 7 |
| 2454 | a 4 | b 9 | c 7 |
| 2455 | a 5 | b 9 | c 7 |
| 2456 | a 6 | b 9 | c 7 |
| 2457 | a 7 | b 9 | c 7 |
| 2458 | a 8 | b 9 | c 7 |
| 2459 | a 9 | b 9 | c 7 |
| 2460 | a 10 | b 9 | c 7 |
| 2461 | a 11 | b 9 | c 7 |
| 2462 | a 12 | b 9 | c 7 |
| 2463 | a 13 | b 9 | c 7 |
| 2464 | a 14 | b 9 | c 7 |
| 2465 | a 15 | b 9 | c 7 |
| 2466 | a 16 | b 9 | c 7 |
| 2467 | a 17 | b 9 | c 7 |
| 2468 | a 18 | b 9 | c 7 |
| 2469 | a 19 | b 9 | c 7 |
| 2470 | a 20 | b 9 | c 7 |
| 2471 | a 21 | b 9 | c 7 |
| 2472 | a 22 | b 9 | c 7 |
| 2473 | a 23 | b 9 | c 7 |
| 2474 | a 24 | b 9 | c 7 |

| No. | Cp | Bridge | Flu |
|---|---|---|---|
| 2475 | a 25 | b 9 | c 7 |
| 2476 | a 1 | b 10 | c 7 |
| 2477 | a 2 | b 10 | c 7 |
| 2478 | a 3 | b 10 | c 7 |
| 2479 | a 4 | b 10 | c 7 |
| 2480 | a 5 | b 10 | c 7 |
| 2481 | a 6 | b 10 | c 7 |
| 2482 | a 7 | b 10 | c 7 |
| 2483 | a 8 | b 10 | c 7 |
| 2484 | a 9 | b 10 | c 7 |
| 2485 | a 10 | b 10 | c 7 |
| 2486 | a 11 | b 10 | c 7 |
| 2487 | a 12 | b 10 | c 7 |
| 2488 | a 13 | b 10 | c 7 |
| 2489 | a 14 | b 10 | c 7 |
| 2490 | a 15 | b 10 | c 7 |
| 2491 | a 16 | b 10 | c 7 |
| 2492 | a 17 | b 10 | c 7 |
| 2493 | a 18 | b 10 | c 7 |
| 2494 | a 19 | b 10 | c 7 |
| 2495 | a 20 | b 10 | c 7 |
| 2496 | a 21 | b 10 | c 7 |
| 2497 | a 22 | b 10 | c 7 |
| 2498 | a 23 | b 10 | c 7 |
| 2499 | a 24 | b 10 | c 7 |
| 2500 | a 25 | b 10 | c 7 |
| 2501 | a 1 | b 11 | c 7 |
| 2502 | a 2 | b 11 | c 7 |
| 2503 | a 3 | b 11 | c 7 |
| 2504 | a 4 | b 11 | c 7 |
| 2505 | a 5 | b 11 | c 7 |
| 2506 | a 6 | b 11 | c 7 |
| 2507 | a 7 | b 11 | c 7 |
| 2508 | a 8 | b 11 | c 7 |
| 2509 | a 9 | b 11 | c 7 |
| 2510 | a 10 | b 11 | c 7 |
| 2511 | a 11 | b 11 | c 7 |
| 2512 | a 12 | b 11 | c 7 |
| 2513 | a 13 | b 11 | c 7 |
| 2514 | a 14 | b 11 | c 7 |
| 2515 | a 15 | b 11 | c 7 |
| 2516 | a 16 | b 11 | c 7 |
| 2517 | a 17 | b 11 | c 7 |
| 2518 | a 18 | b 11 | c 7 |
| 2519 | a 19 | b 11 | c 7 |
| 2520 | a 20 | b 11 | c 7 |
| 2521 | a 21 | b 11 | c 7 |
| 2522 | a 22 | b 11 | c 7 |
| 2523 | a 23 | b 11 | c 7 |
| 2524 | a 24 | b 11 | c 7 |
| 2525 | a 25 | b 11 | c 7 |
| 2526 | a 1 | b 12 | c 7 |
| 2527 | a 2 | b 12 | c 7 |
| 2528 | a 3 | b 12 | c 7 |
| 2529 | a 4 | b 12 | c 7 |
| 2530 | a 5 | b 12 | c 7 |
| 2531 | a 6 | b 12 | c 7 |
| 2532 | a 7 | b 12 | c 7 |
| 2533 | a 8 | b 12 | c 7 |
| 2534 | a 9 | b 12 | c 7 |
| 2535 | a 10 | b 12 | c 7 |
| 2536 | a 11 | b 12 | c 7 |
| 2537 | a 12 | b 12 | c 7 |
| 2538 | a 13 | b 12 | c 7 |
| 2539 | a 14 | b 12 | c 7 |
| 2540 | a 15 | b 12 | c 7 |
| 2541 | a 16 | b 12 | c 7 |
| 2542 | a 17 | b 12 | c 7 |
| 2543 | a 18 | b 12 | c 7 |
| 2544 | a 19 | b 12 | c 7 |
| 2545 | a 20 | b 12 | c 7 |
| 2546 | a 21 | b 12 | c 7 |
| 2547 | a 22 | b 12 | c 7 |
| 2548 | a 23 | b 12 | c 7 |
| 2549 | a 24 | b 12 | c 7 |
| 2550 | a 25 | b 12 | c 7 |
| 2551 | a 1 | b 13 | c 7 |
| 2552 | a 2 | b 13 | c 7 |
| 2553 | a 3 | b 13 | c 7 |
| 2554 | a 4 | b 13 | c 7 |
| 2555 | a 5 | b 13 | c 7 |
| 2556 | a 6 | b 13 | c 7 |
| 2557 | a 7 | b 13 | c 7 |
| 2558 | a 8 | b 13 | c 7 |
| 2559 | a 9 | b 13 | c 7 |
| 2560 | a 10 | b 13 | c 7 |
| 2561 | a 11 | b 13 | c 7 |
| 2562 | a 12 | b 13 | c 7 |
| 2563 | a 13 | b 13 | c 7 |
| 2564 | a 14 | b 13 | c 7 |
| 2565 | a 15 | b 13 | c 7 |
| 2566 | a 16 | b 13 | c 7 |
| 2567 | a 17 | b 13 | c 7 |
| 2568 | a 18 | b 13 | c 7 |
| 2569 | a 19 | b 13 | c 7 |
| 2570 | a 20 | b 13 | c 7 |
| 2571 | a 21 | b 13 | c 7 |
| 2572 | a 22 | b 13 | c 7 |
| 2573 | a 23 | b 13 | c 7 |
| 2574 | a 24 | b 13 | c 7 |
| 2575 | a 25 | b 13 | c 7 |
| 2576 | a 1 | b 14 | c 7 |
| 2577 | a 2 | b 14 | c 7 |
| 2578 | a 3 | b 14 | c 7 |
| 2579 | a 4 | b 14 | c 7 |
| 2580 | a 5 | b 14 | c 7 |
| 2581 | a 6 | b 14 | c 7 |
| 2582 | a 7 | b 14 | c 7 |
| 2583 | a 8 | b 14 | c 7 |
| 2584 | a 9 | b 14 | c 7 |
| 2585 | a 10 | b 14 | c 7 |
| 2586 | a 11 | b 14 | c 7 |
| 2587 | a 12 | b 14 | c 7 |
| 2588 | a 13 | b 14 | c 7 |
| 2589 | a 14 | b 14 | c 7 |
| 2590 | a 15 | b 14 | c 7 |
| 2591 | a 16 | b 14 | c 7 |
| 2592 | a 17 | b 14 | c 7 |
| 2593 | a 18 | b 14 | c 7 |
| 2594 | a 19 | b 14 | c 7 |
| 2595 | a 20 | b 14 | c 7 |
| 2596 | a 21 | b 14 | c 7 |
| 2597 | a 22 | b 14 | c 7 |
| 2598 | a 23 | b 14 | c 7 |
| 2599 | a 24 | b 14 | c 7 |
| 2600 | a 25 | b 14 | c 7 |
| 2601 | a 1 | b 15 | c 7 |
| 2602 | a 2 | b 15 | c 7 |
| 2603 | a 3 | b 15 | c 7 |
| 2604 | a 4 | b 15 | c 7 |
| 2605 | a 5 | b 15 | c 7 |
| 2606 | a 6 | b 15 | c 7 |
| 2607 | a 7 | b 15 | c 7 |
| 2608 | a 8 | b 15 | c 7 |
| 2609 | a 9 | b 15 | c 7 |
| 2610 | a 10 | b 15 | c 7 |
| 2611 | a 11 | b 15 | c 7 |
| 2612 | a 12 | b 15 | c 7 |
| 2613 | a 13 | b 15 | c 7 |
| 2614 | a 14 | b 15 | c 7 |
| 2615 | a 15 | b 15 | c 7 |
| 2616 | a 16 | b 15 | c 7 |
| 2617 | a 17 | b 15 | c 7 |
| 2618 | a 18 | b 15 | c 7 |
| 2619 | a 19 | b 15 | c 7 |
| 2620 | a 20 | b 15 | c 7 |
| 2621 | a 21 | b 15 | c 7 |
| 2622 | a 22 | b 15 | c 7 |
| 2623 | a 23 | b 15 | c 7 |
| 2624 | a 24 | b 15 | c 7 |
| 2625 | a 25 | b 15 | c 7 |

According to the above table, the ligand structure of No. 752 means a combination of a2-b1-c3, so that when the metal part MQj is ZrCl₂, the following metallocene compound is exemplified.

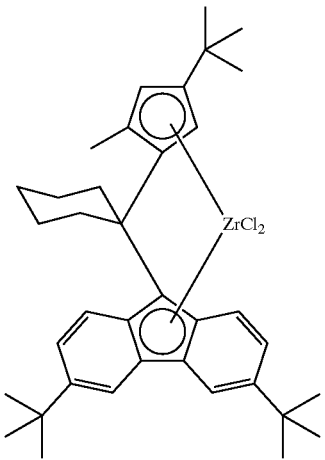

Specific examples of MQj include ZrCl₂, ZrBr₂, ZrMe₂, Zr(OTs)₂, Zr(OMs)₂, Zr(OTf)₂, TiCl₂, TiBr₂, TiMe₂, Ti(OTs)₂, Ti(OMs)₂, Ti(OTf)₂, HfCl₂, HfBr₂, HfMe₂, Hf(OTs)₂, Hf(OMs)₂ and Hf(OTf)₂, wherein Ts indicates a p-toluenesulfonyl group, Ms indicates a methanesulfonyl group, and Tf indicates a trifluoromethanesulfonyl group.

Examples of the metallocene compounds wherein the substituent group on the Cp ring and the substituent group on the bridge part are bonded to form a ring include the following compounds.

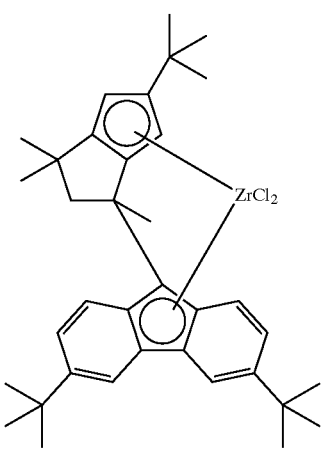

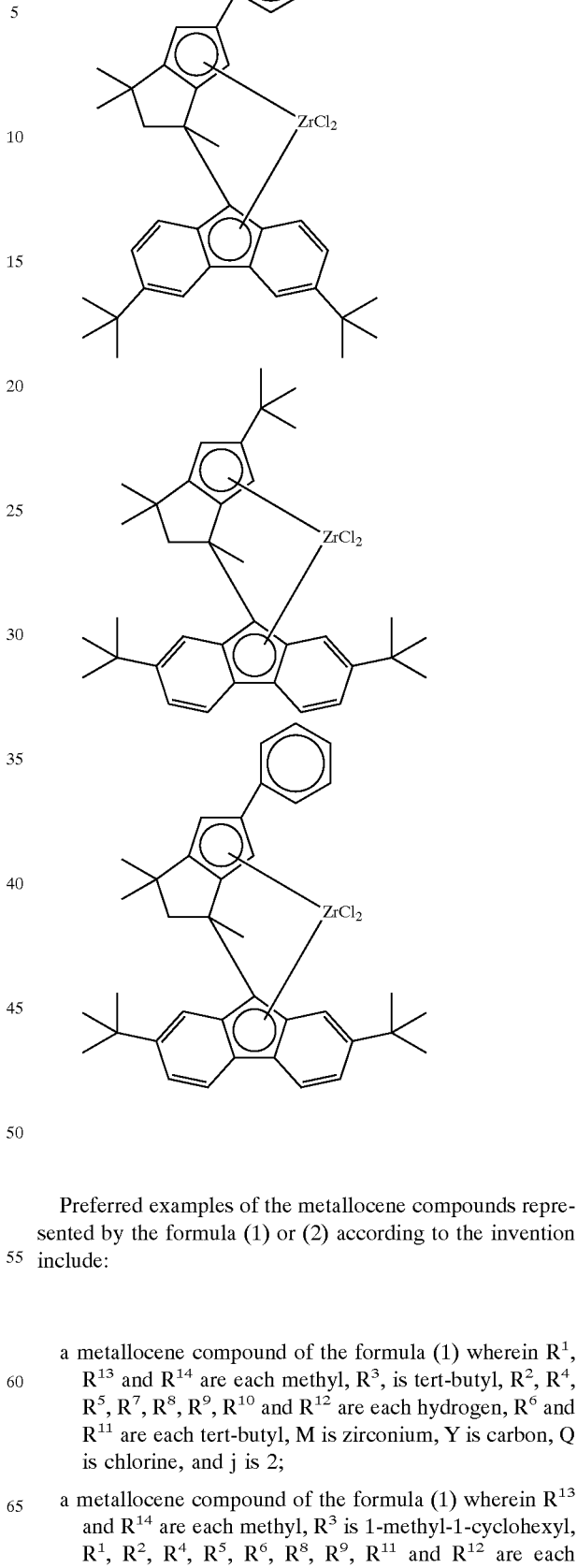

Preferred examples of the metallocene compounds represented by the formula (1) or (2) according to the invention include:

a metallocene compound of the formula (1) wherein $R^1$, $R^{13}$ and $R^{14}$ are each methyl, $R^3$, is tert-butyl, $R^2$, $R^4$, $R^5$, $R^7$, $R^8$, $R^9$, $R^{10}$ and $R^{12}$ are each hydrogen, $R^6$ and $R^{11}$ are each tert-butyl, M is zirconium, Y is carbon, Q is chlorine, and j is 2;

a metallocene compound of the formula (1) wherein $R^{13}$ and $R^{14}$ are each methyl, $R^3$ is 1-methyl-1-cyclohexyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (1) wherein $R^{13}$ and $R^{14}$ are each methyl, $R^3$ is tert-butyl, $R^1$, $R^2$, $R^4$, $R^5$, $R^8$, $R^9$ and $R^{12}$ are each hydrogen, $R^6$ and $R^7$ are bonded to form —(C(CH$_3$)$_2$CH$_2$CH$_2$C(CH$_3$)$_2$)- and thereby form a ring, $R^{10}$ and $R^{11}$ are bonded to form —(C(CH$_3$)$_2$CH$_2$CH$_2$C(CH$_3$)$_2$)— and thereby form a ring, M is zirconium, Y is carbon, Q is chlorine, and j is 2;

a metallocene compound of the formula (1) wherein $R^{13}$ and $R^{14}$ are each methyl, $R^3$ is trimethylsilyl, $R^1$, $R^2$, $R^4$, $R^5$, $R^8$, $R^9$ and $R^{12}$ are each hydrogen, $R^6$ and $R^7$ are bonded to form —(C(CH$_3$)$_2$CH$_2$CH$_2$C(CH$_3$)$_2$)- and thereby form a ring, $R^{10}$ and $R^{11}$ are bonded to form—(C(CH$_3$)$_2$CH$_2$CH$_2$C(CH$_3$)$_2$)- and thereby form a ring, M is zirconium, Y is carbon, Q is chlorine, and j is 2;

a metallocene compound of the formula (1) wherein $R^{13}$ and $R^{14}$ are each methyl, $R^3$ is 1,1-dimethylpropyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (1) wherein $R^{13}$ and $R^{14}$ are each methyl, $R^3$ is 1-ethyl-1-methylpropyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (1) wherein $R^{13}$ and $R^{14}$ are each methyl, $R^3$ is 1,1,3-trimethylbutyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (1) wherein $R^{13}$ and $R^{14}$ are each methyl, $R^3$ is 1,1-dimethylbutyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (1) wherein $R^{13}$ and $R^{14}$ are each methyl, $R^3$ is tert-butyl, $R^1$, $R^2$, $R^4$, $R^5$, $R^7$, $R^8$, $R^9$, $R^{10}$ and $R^{12}$ are each hydrogen, $R^6$ and $R^{11}$ are each tert-butyl, M is zirconium, Y is carbon, Q is chlorine, and j is 2;

a metallocene compound of the formula (1) wherein $R^3$, $R^{13}$ and $R^{14}$ are each phenyl, $R^1$, $R^2$, $R^4$, $R^5$, $R^8$, $R^9$ and $R^{12}$ are each hydrogen, $R^6$ and $R^7$ are bonded to form—(C(CH$_3$)$_2$CH$_2$CH$_2$C(CH$_3$)$_2$)- and thereby form a ring, $R^{10}$ and $R^{11}$ are bonded to form —(C(CH$_3$)$_2$CH$_2$CH$_2$C(CH$_3$)$_2$)- and thereby form a ring, M is zirconium, Y is carbon, Q is chlorine, and j is 2;

a metallocene compound of the formula (1) wherein $R^3$ is trimethylsilyl, $R^{13}$ and $R^{14}$ are each phenyl, $R^1$, $R^2$, $R^4$, $R^5$, $R^8$, $R^9$ and $R^{12}$ are each hydrogen, $R^6$ and $R^7$ are bonded to form—(C(CH$_3$)$_2$CH$_2$CH$_2$C(CH$_3$)$_2$)- and thereby form a ring, $R^{10}$ and $R^{11}$ are bonded to form —(C(CH$_3$)$_2$CH$_2$CH$_2$C(CH$_3$)$_2$)- and thereby form a ring, M is zirconium, Y is carbon, Q is chlorine, and j is 2;

a metallocene compound of the formula (1) wherein $R^{13}$ is methyl, $R^{14}$ is phenyl, $R^3$ is tert-butyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (1) wherein $R^{13}$ and $R^{14}$ are each ethyl, $R^3$ is tert-butyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (2) wherein $R^1$ is methyl, $R^3$ is tert-butyl, $R^2$, $R^4$, $R^5$, $R^6$, $R^7$, $R^8$, $R^9$, $R^{10}$, $R^{11}$ and $R^{12}$ are each hydrogen, M is zirconium, Y is carbon, Q is chlorine, j is 2, and A is —(CH$_2$)$_5$—;

a metallocene compound of the formula (2) wherein $R^1$ is methyl, $R^3$ is tert-butyl, $R^2$, $R^4$, $R^5$, $R^6$, $R^8$, $R^9$, $R^{11}$ and $R^{12}$ are each hydrogen, $R^7$ and $R^{10}$ are each ter-t-butyl, M is zirconium, Y is carbon, Q is chlorine, j is 2, and A is —(CH$_2$)$_5$—;

a metallocene compound of the formula (2) wherein $R^3$ is trimethylsilyl, $R^1$, $R^2$, $R^4$, $R^5$, $R^7$, $R^8$, $R^9$, $R^{10}$ and $R^{12}$ are each hydrogen, $R^6$ and $R^{11}$ are each tert-butyl, M is zirconium, Y is carbon, Q is chlorine, j is 2, and A is —(CH$_2$)$_5$—;

a metallocene compound of the formula (2) wherein $R^3$ is trimethylsilyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, j is 2, and A is—(CH2)$_5$—;

a metallocene compound of the formula (2) wherein $R^3$ is tert-butyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, j is 2, and A is —(CH2)$_4$—;

a metallocene compound of the formula (2) wherein $R^3$ is 1,1-dimethylpropyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, j is 2, and A is —(CF$_2$)$_5$—;

a metallocene compound of the formula (2) wherein $R^3$ is tert-butyl, $R^1$, $R^2$, $R^4$, $R^5$, $R^8$, $R^9$ and $R^{12}$ are each hydrogen, $R^6$ and $R^7$ are bonded to form —(C(CH$_3$)$_2$CH$_2$CH$_2$C(CH$_3$)$_2$)- and thereby form a ring, $R^{10}$ and $R^{11}$ are bonded to form—(C(CH$_3$)$_2$CH$_2$CH$_2$C(CH$_3$)$_2$)- and thereby form a ring, M is zirconium, Y is carbon, Q is chlorine, j is 2, and A is —(CH$_2$)$_4$—;

a metallocene compound of the formula (1) wherein $R^1$, $R^{13}$ and $R^{14}$ are each methyl, $R^3$ is tert-butyl, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (1) wherein $R^{13}$ and $R^{14}$ are each methyl, $R^3$ is tert-butyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (1) wherein $R^1$, $R^{13}$ and $R^{14}$ are each methyl, $R^3$ is tert-butyl, $R^2$, $R^4$ $R^5$, $R^6$, $R^7$, $R^8$, $R^9$, $R^{10}$, $R^{11}$ and $R^{12}$ are each hydrogen, M is zirconium, Y is carbon, Q is chlorine, and j is 2;

a metallocene compound of the formula (1) wherein $R^{13}$ and $R^{14}$ are each methyl, $R^3$ is trimethylsilyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2; and a metallocene compound of the formula (1) wherein $R^{13}$ and $R^{14}$ are each phenyl, $R^3$ is trimethylsilyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2.

There is no specific limitation on the process for preparing the metallocene compound represented by the formula (1) or (2), and the compound can be prepared by, for example, the below-described process.

First, the ligand precursor (5) used as starting material for preparing the metallocene compound represented by the formula (1) can be prepared through the following step (A) or (B).
[A]
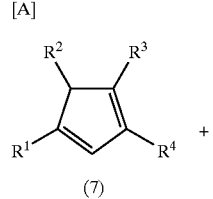
(7)
+
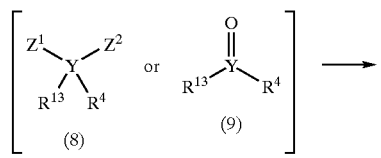
(8)    (9)
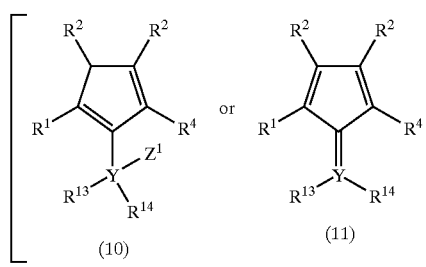
(10)    (11)
→ +
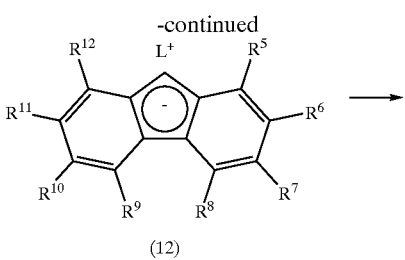
(12)
→
(5)
[B]
(12) + (8) or (9) →
(13) or (14) → + (15) →

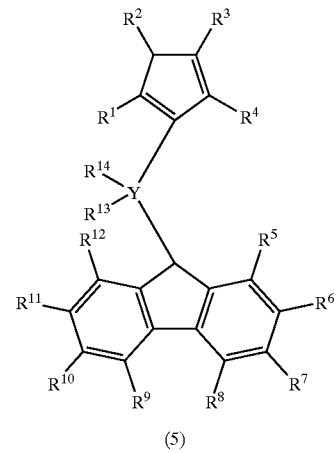

(5)

In the compounds shown in the above steps (A) and (B), $R^1$ to $R^{14}$ and Y have the same meanings as those of $R^1$ to $R^{14}$ and Y in the formula (1), respectively, L is an alkali metal, and $Z^1$ and $Z^2$ may be the same or different and are each a halogen or an anionic ligand.

With regard to the cyclopentadiene (7), the precursor compound (10) and the ligand precursor (5), presence of isomers different in only the position of a double bond in the cyclopentadienyl ring can be thought, but only one example is shown. Each of them may be another isomer different in only the position of a double bond in the cyclopentadienyl ring or a mixture thereof.

The ligand precursor (6) used as starting material for preparing the metallocene compound represented by the formula (2) can be prepared through the following step (C) or (D).

-continued

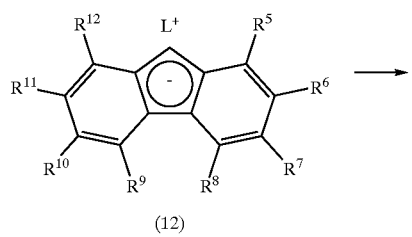

(12)

[C]

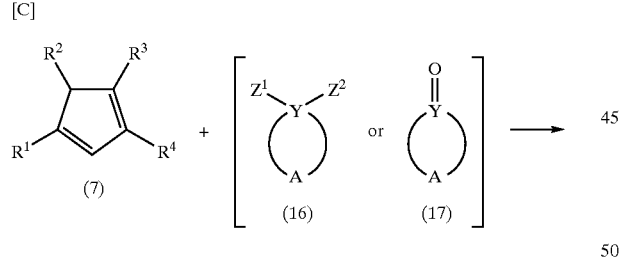

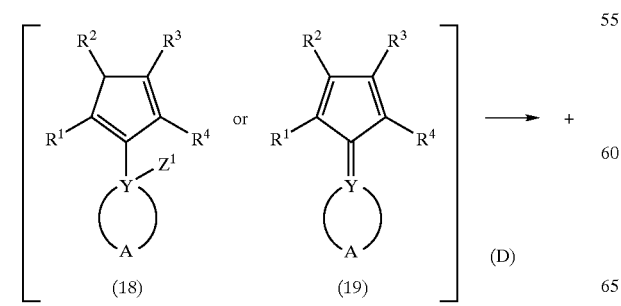

(D)

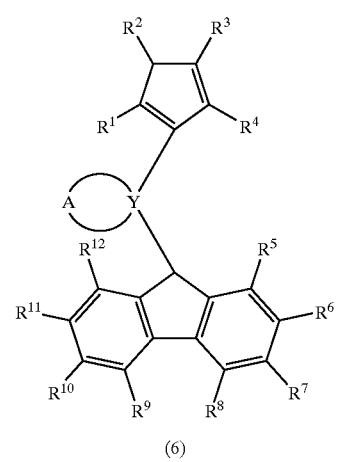

(6)

[D]

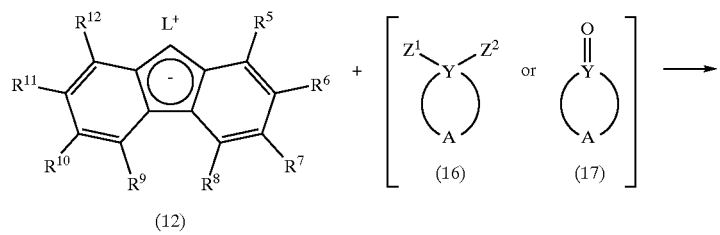

(12) (16) (17)

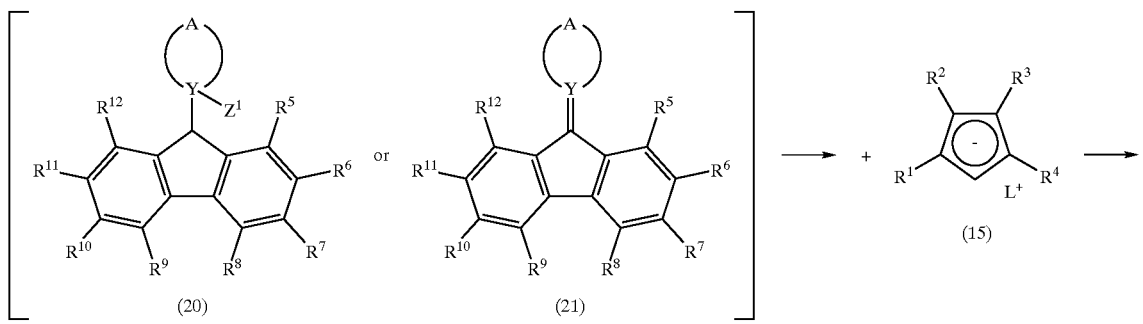

(20) (21) (15)

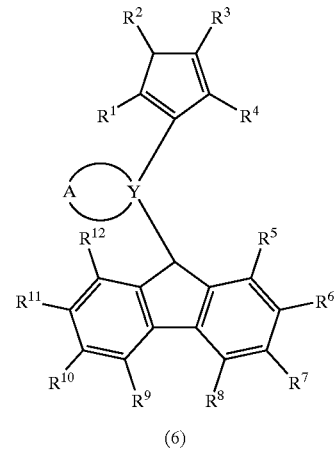

(6)

In the compounds shown in the above steps (C) and (D), $R^1$ to $R^{14}$, Y and A have the same meanings as those of $R^1$ to $R^{14}$, Y and A in the formula (2), respectively, L is an alkali metal, and $Z^1$ and $Z^2$ may be the same or different and are each a halogen or an anionic ligand.

With regard to the cyclopentadiene (7), the precursor compound (18) and the ligand precursor (6), presence of isomers different in only the position of a double bond in the cyclopentadienyl ring can be thought, but only one example is shown. Each of them may be another isomer different in only the position of a double bond in the cyclopentadienyl ring or a mixture thereof.

The cyclopentadiene (7) that is a precursor common to the metallocene compounds represented by the formulas (1) and (2) can be prepared through, for example, the following step (E) or (F).

[E]

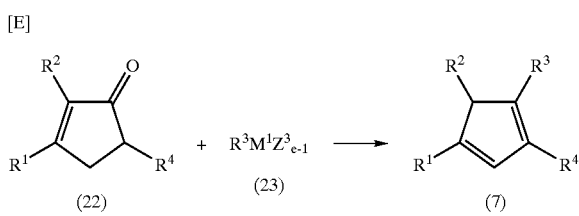

(22) (23) (7)

In the compounds shown in the step (E), $R^1$, $R^2$, $R^3$ and $R^4$ have the same meanings as those of $R^1$, $R^2$, $R^3$ and $R^4$ in the formula (1) or (2), respectively, $M^1$ is an alkali metal or an alkaline earth metal, $Z^3$ is the same as $R^3$ or is a halogen or an anionic ligand, and e is a valence of $M^1$.

[F]

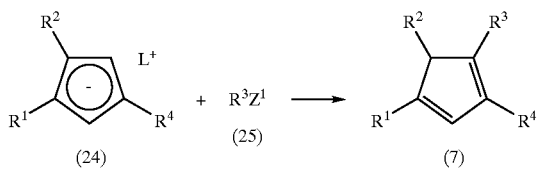

In the compounds shown in the step (F), $R^1$, $R^2$, $R^3$ and $R^4$ have the same meanings as those of $R^1$, $R^2$, $R^3$ and $R^4$ in the formula (1) or (2), respectively, L is an alkali metal, and $Z^1$ is a halogen or an anionic ligand.

When $R^3$ is a substituent group represented by $CR^{15}R^{16}R^{17}$, the cyclopentadiene (7) can be prepared also through the following step (G).

[G]

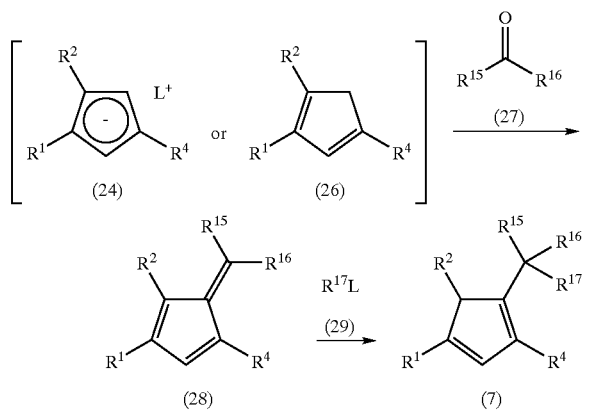

In the step (G), $R^1$, $R^2$ and $R^4$ have the same meanings as those of $R^1$, $R^2$ and $R^4$ in the formula (1) or (2), respectively, $R^{15}$, $R^{16}$ and $R^{17}$ are each selected from a hydrogen atom, a hydrocarbon group and a silicon-containing hydrocarbon group and may be the same or different, and L is an alkali metal.

In the steps (E) to (G), though, examples of methods to introduce the substituent group $R^3$ are shown, the substituent groups $R^1$, $R^2$ and $R^4$ can also be introduced similarly to those methods.

The alkali metal used for the reactions in the steps (A) to (G) is lithium, sodium or potassium, and the alkaline earth metal is magnesium or calcium. The halogen is fluorine, chlorine, bromine or iodine. Examples of the anionic ligands include alkoxy groups, such as methoxy, tert-butoxy and phenoxy; carboxylate groups, such as acetate and benzoate; and sulfonate groups, such as mesylate and tosylate.

Next, an example of the process for preparing a metallocene compound from the ligand precursor represented by the formula (5) or (6) is described.

In the first place, the ligand precursor represented by the formula (5) or (6) that is obtained by the reaction of the step (A), (B), (C) or (D) is brought into contact with an alkali metal, an alkali metal hydride or an organic alkali metal in an organic solvent at a reaction temperature of −80 to 200° C. to prepare a di-alkali metal salt.

Examples of the organic solvents used for the above reaction include aliphatic hydrocarbons, such as pentane, hexane, heptane, cyclohexane and decalin; aromatic hydrocarbons, such as benzene, toluene and xylene; ethers, such as THF (tetrahydrofuran), diethyl ether, dioxane and 1,2-dimethoxyethane; and halogenated hydrocarbons, such as dichloromethane and chloroform.

Examples of the alkali metals used for the reaction include lithium, sodium and potassium. Examples of the alkali metal hydrides include sodium hydride and potassium hydride. Examples of the organic alkali metals include methyllithium, butyllithium and phenyllithium.

In the next place, the di-alkali metal salt is allowed to react, in an organic solvent, with a compound represented by the following formula (30):

wherein M is a metal selected from Group 4 of the periodic table, each Z may be the same or different and is selected from a halogen, an anionic ligand and a neutral ligand capable of coordination by a lone pair, and k is an integer of 3 to 6.

Thus, the metallocene compound represented by the formula (i) or (2) can be synthesized.

Preferred examples of the compounds represented by the formula (30) include trivalent or tetravalent titanium fluoride, chloride, bromide or iodide; tetravalent zirconium fluoride, chloride, bromide or iodide; tetravalent hafnium fluoride, chloride, bromide or iodide; and complexes of these compounds with ethers such as THF, diethyl ether, dioxane and 1,2-dimethoxyethane.

Examples of the organic solvents used include the same ones as previously described.

The reaction of the di-alkali metal salt with the compound represented by the formula (30) is preferably an equimolar reaction, and can be carried out in the aforesaid organic solvent at a reaction temperature of −80 to 200° C.

The metallocene compound obtained by the reaction can be isolated and purified by, for example, extraction, recrystallization or sublimation.

Next, the metallocene compound represented by the formula (1a) or (2a) is described.

Another embodiment of the metallocene compound of the invention is represented by the following formula (1a) or (2a).

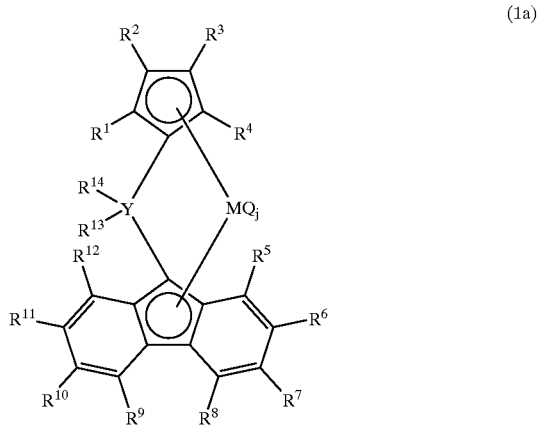

-continued

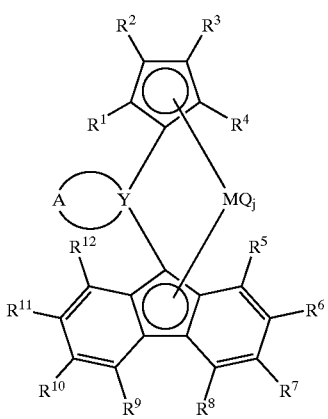
(2a)

In the formula (1a) or (2a), $R^3$ has the same meaning as that of $R^3$ in the formula (1) or (2); $R^1$, $R^2$, and $R^4$ to $R^{14}$ have the same meanings as those of $R^1$, $R^2$, and $R^4$ to $R^{14}$ in the formula (1) or (2), respectively; and A, Y, M, Q and j have the same meanings as those of A, Y, M, Q and j in the formula (1) or (2), respectively. In case of the compound of the formula (1a) wherein $R^3$ is tert-butyl or trimethylsilyl and $R^{13}$ and $R^{14}$ are methyl groups or phenyl groups at the same time, $R^6$ and $R^{11}$ are not hydrogen atoms at the same time.

$R^3$ is preferably a sterically bulky substituent group, more preferably a substituent group of 4 or more carbon atoms.

Examples of the metallocene compounds represented by the formula (1a) or (2a) according to the invention are given below.

Examples of the ligand structure excluding MQj (metal part) in the metallocene compound are described first. Examples of Cp (cyclopentadienyl ring part), Bridge (bridge part) and Flu (fluorenyl ring part) are the same as those previously described with respect to the metallocene compound represented by the formula (1) or (2).

| No. | Cp | Bridge | Flu |
|---|---|---|---|
| 1 | a 1 | b1 | c1 |
| 2 | a 2 | b1 | c1 |
| 3 | a 3 | b1 | c1 |
| 4 | a 4 | b1 | c1 |
| 5 | a 5 | b1 | c1 |
| 6 | a 6 | b1 | c1 |
| 7 | a 7 | b1 | c1 |
| 8 | a 8 | b1 | c1 |
| 9 | a 9 | b1 | c1 |
| 10 | a10 | b1 | c1 |
| 11 | a11 | b1 | c1 |
| 12 | a12 | b1 | c1 |
| 13 | a13 | b1 | c1 |
| 14 | a14 | b1 | c1 |
| 15 | a15 | b1 | c1 |
| 16 | a16 | b1 | c1 |
| 17 | a17 | b1 | c1 |
| 18 | a18 | b1 | c1 |
| 19 | a19 | b1 | c1 |
| 20 | a20 | b1 | c1 |
| 21 | a21 | b1 | c1 |
| 22 | a22 | b1 | c1 |
| 23 | a23 | b1 | c1 |
| 24 | a24 | b1 | c1 |
| 25 | a25 | b1 | c1 |
| 26 | a 1 | b2 | c1 |
| 27 | a 2 | b2 | c1 |
| 28 | a 3 | b2 | c1 |
| 29 | a 4 | b2 | c1 |
| 30 | a 5 | b2 | c1 |
| 31 | a 6 | b2 | c1 |
| 32 | a 7 | b2 | c1 |
| 33 | a 8 | b2 | c1 |
| 34 | a 9 | b2 | c1 |
| 35 | a10 | b2 | c1 |
| 36 | a11 | b2 | c1 |
| 37 | a12 | b2 | c1 |
| 38 | a13 | b2 | c1 |
| 39 | a14 | b2 | c1 |
| 40 | a15 | b2 | c1 |
| 41 | a16 | b2 | c1 |
| 42 | a17 | b2 | c1 |
| 43 | a18 | b2 | c1 |
| 44 | a19 | b2 | c1 |
| 45 | a20 | b2 | c1 |
| 46 | a21 | b2 | c1 |
| 47 | a22 | b2 | c1 |
| 48 | a23 | b2 | c1 |
| 49 | a24 | b2 | c1 |
| 50 | a25 | b2 | c1 |
| 51 | a 1 | b3 | c1 |
| 52 | a 2 | b3 | c1 |
| 53 | a 3 | b3 | c1 |
| 54 | a 4 | b3 | c1 |
| 55 | a 5 | b3 | c1 |
| 56 | a 6 | b3 | c1 |
| 57 | a 7 | b3 | c1 |
| 58 | a 8 | b3 | c1 |
| 59 | a 9 | b3 | c1 |
| 60 | a10 | b3 | c1 |
| 61 | a11 | b3 | c1 |
| 62 | a12 | b3 | c1 |
| 63 | a13 | b3 | c1 |
| 64 | a14 | b3 | c1 |
| 65 | a15 | b3 | c1 |
| 66 | a16 | b3 | c1 |
| 67 | a17 | b3 | c1 |
| 68 | a18 | b3 | c1 |
| 69 | a19 | b3 | c1 |
| 70 | a20 | b3 | c1 |
| 71 | a21 | b3 | c1 |
| 72 | a22 | b3 | c1 |
| 73 | a23 | b3 | c1 |
| 74 | a24 | b3 | c1 |
| 75 | a25 | b3 | c1 |
| 76 | a 1 | b4 | c1 |
| 77 | a 2 | b4 | c1 |
| 78 | a 3 | b4 | c1 |
| 79 | a 4 | b4 | c1 |
| 80 | a 5 | b4 | c1 |
| 81 | a 6 | b4 | c1 |
| 82 | a 7 | b4 | c1 |
| 83 | a 8 | b4 | c1 |
| 84 | a 9 | b4 | c1 |
| 85 | a10 | b4 | c1 |
| 86 | a11 | b4 | c1 |
| 87 | a12 | b4 | c1 |
| 88 | a13 | b4 | c1 |
| 89 | a14 | b4 | c1 |
| 90 | a15 | b4 | c1 |
| 91 | a16 | b4 | c1 |
| 92 | a17 | b4 | c1 |
| 93 | a18 | b4 | c1 |
| 94 | a19 | b4 | c1 |
| 95 | a20 | b4 | c1 |
| 96 | a21 | b4 | c1 |
| 97 | a22 | b4 | c1 |
| 98 | a23 | b4 | c1 |
| 99 | a24 | b4 | c1 |
| 100 | a25 | b4 | c1 |
| 101 | a 1 | b5 | c1 |
| 102 | a 2 | b5 | c1 |
| 103 | a 3 | b5 | c1 |
| 104 | a 4 | b5 | c1 |

-continued

| No. | Cp | Bridge | Flu |
|---|---|---|---|
| 105 | a 5 | b5 | c1 |
| 106 | a 6 | b5 | c1 |
| 107 | a 7 | b5 | c1 |
| 108 | a 8 | b5 | c1 |
| 109 | a 9 | b5 | c1 |
| 110 | a10 | b5 | c1 |
| 111 | a11 | b5 | c1 |
| 112 | a12 | b5 | c1 |
| 113 | a13 | b5 | c1 |
| 114 | a14 | b5 | c1 |
| 115 | a15 | b5 | c1 |
| 116 | a16 | b5 | c1 |
| 117 | a17 | b5 | c1 |
| 118 | a18 | b5 | c1 |
| 119 | a19 | b5 | c1 |
| 120 | a20 | b5 | c1 |
| 121 | a21 | b5 | c1 |
| 122 | a22 | b5 | c1 |
| 123 | a23 | b5 | c1 |
| 124 | a24 | b5 | c1 |
| 125 | a25 | b5 | c1 |
| 126 | a 1 | b6 | c1 |
| 127 | a 2 | b6 | c1 |
| 128 | a 3 | b6 | c1 |
| 129 | a 4 | b6 | c1 |
| 130 | a 5 | b6 | c1 |
| 131 | a 6 | b6 | c1 |
| 132 | a 7 | b6 | c1 |
| 133 | a 8 | b6 | c1 |
| 134 | a 9 | b6 | c1 |
| 135 | a10 | b6 | c1 |
| 136 | a11 | b6 | c1 |
| 137 | a12 | b6 | c1 |
| 138 | a13 | b6 | c1 |
| 139 | a14 | b6 | c1 |
| 140 | a15 | b6 | c1 |
| 141 | a16 | b6 | c1 |
| 142 | a17 | b6 | c1 |
| 143 | a18 | b6 | c1 |
| 144 | a19 | b6 | c1 |
| 145 | a20 | b6 | c1 |
| 146 | a21 | b6 | c1 |
| 147 | a22 | b6 | c1 |
| 148 | a23 | b6 | c1 |
| 149 | a24 | b6 | c1 |
| 150 | a25 | b6 | c1 |
| 151 | a 1 | b7 | c1 |
| 152 | a 2 | b7 | c1 |
| 153 | a 3 | b7 | c1 |
| 154 | a 4 | b7 | c1 |
| 155 | a 5 | b7 | c1 |
| 156 | a 6 | b7 | c1 |
| 157 | a 7 | b7 | c1 |
| 158 | a 8 | b7 | c1 |
| 159 | a 9 | b7 | c1 |
| 160 | a10 | b7 | c1 |
| 161 | a11 | b7 | c1 |
| 162 | a12 | b7 | c1 |
| 163 | a13 | b7 | c1 |
| 164 | a14 | b7 | c1 |
| 165 | a15 | b7 | c1 |
| 166 | a16 | b7 | c1 |
| 167 | a17 | b7 | c1 |
| 168 | a18 | b7 | c1 |
| 169 | a19 | b7 | c1 |
| 170 | a20 | b7 | c1 |
| 171 | a21 | b7 | c1 |
| 172 | a22 | b7 | c1 |
| 173 | a23 | b7 | c1 |
| 174 | a24 | b7 | c1 |
| 175 | a25 | b7 | c1 |
| 176 | a 5 | b8 | c1 |
| 177 | a 6 | b8 | c1 |
| 178 | a 7 | b8 | c1 |
| 179 | a 8 | b8 | c1 |
| 180 | a 9 | b8 | c1 |
| 181 | a10 | b8 | c1 |
| 182 | a11 | b 8 | c1 |
| 183 | a12 | b 8 | c1 |
| 184 | a13 | b 8 | c1 |
| 185 | a14 | b 8 | c1 |
| 186 | a15 | b 8 | c1 |
| 187 | a16 | b 8 | c1 |
| 188 | a17 | b 8 | c1 |
| 189 | a18 | b 8 | c1 |
| 190 | a19 | b 8 | c1 |
| 191 | a20 | b 8 | c1 |
| 192 | a21 | b 8 | c1 |
| 193 | a22 | b 8 | c1 |
| 194 | a23 | b 8 | c1 |
| 195 | a24 | b 8 | c1 |
| 196 | a25 | b 8 | c1 |
| 197 | a 5 | b 9 | c1 |
| 198 | a 6 | b 9 | c1 |
| 199 | a 7 | b 9 | c1 |
| 200 | a 8 | b 9 | c1 |
| 201 | a 9 | b 9 | c1 |
| 202 | a10 | b 9 | c1 |
| 203 | a11 | b 9 | c1 |
| 204 | a12 | b 9 | c1 |
| 205 | a13 | b 9 | c1 |
| 206 | a14 | b 9 | c1 |
| 207 | a15 | b 9 | c1 |
| 208 | a16 | b 9 | c1 |
| 209 | a17 | b 9 | c1 |
| 210 | a18 | b 9 | c1 |
| 211 | a19 | b 9 | c1 |
| 212 | a20 | b 9 | c1 |
| 213 | a21 | b 9 | c1 |
| 214 | a22 | b 9 | c1 |
| 215 | a23 | b 9 | c1 |
| 216 | a24 | b 9 | c1 |
| 217 | a25 | b 9 | c1 |
| 218 | a 5 | b10 | c1 |
| 219 | a 6 | b10 | c1 |
| 220 | a 7 | b10 | c1 |
| 221 | a 8 | b10 | c1 |
| 222 | a 9 | b10 | c1 |
| 223 | a10 | b10 | c1 |
| 224 | a11 | b10 | c1 |
| 225 | a12 | b10 | c1 |
| 226 | a13 | b10 | c1 |
| 227 | a14 | b10 | c1 |
| 228 | a15 | b10 | c1 |
| 229 | a16 | b10 | c1 |
| 230 | a17 | b10 | c1 |
| 231 | a18 | b10 | c1 |
| 232 | a19 | b10 | c1 |
| 233 | a20 | b10 | c1 |
| 234 | a21 | b10 | c1 |
| 235 | a22 | b10 | c1 |
| 236 | a23 | b10 | c1 |
| 237 | a24 | b10 | c1 |
| 238 | a25 | b10 | c1 |
| 239 | a 5 | b11 | c1 |
| 240 | a 6 | b11 | c1 |
| 241 | a 7 | b11 | c1 |
| 242 | a 8 | b11 | c1 |
| 243 | a 9 | b11 | c1 |
| 244 | a10 | b11 | c1 |
| 245 | a11 | b11 | c1 |
| 246 | a12 | b11 | c1 |
| 247 | a13 | b11 | c1 |
| 248 | a14 | b11 | c1 |
| 249 | a15 | b11 | c1 |
| 250 | a16 | b11 | c1 |
| 251 | a17 | b11 | c1 |
| 252 | a18 | b11 | c1 |
| 253 | a19 | b11 | c1 |
| 254 | a20 | b11 | c1 |
| 255 | a21 | b11 | c1 |
| 256 | a22 | b11 | c1 |
| 257 | a23 | b11 | c1 |
| 258 | a24 | b11 | c1 |

-continued

| No. | Cp | Bridge | Flu |
|---|---|---|---|
| 259 | a25 | b11 | c1 |
| 260 | a 1 | b12 | c1 |
| 261 | a 2 | b12 | c1 |
| 262 | a 3 | b12 | c1 |
| 263 | a 4 | b12 | c1 |
| 264 | a 5 | b12 | c1 |
| 265 | a 6 | b12 | c1 |
| 266 | a 7 | b12 | c1 |
| 267 | a 8 | b12 | c1 |
| 268 | a 9 | b12 | c1 |
| 269 | a10 | b12 | c1 |
| 270 | a11 | b12 | c1 |
| 271 | a12 | b12 | c1 |
| 272 | a13 | b12 | c1 |
| 273 | a14 | b12 | c1 |
| 274 | a15 | b12 | c1 |
| 275 | a16 | b12 | c1 |
| 276 | a17 | b12 | c1 |
| 277 | a18 | b12 | c1 |
| 278 | a19 | b12 | c1 |
| 279 | a20 | b12 | c1 |
| 280 | a21 | b12 | c1 |
| 281 | a22 | b12 | c1 |
| 282 | a23 | b12 | c1 |
| 283 | a24 | b12 | c1 |
| 284 | a25 | b12 | c1 |
| 285 | a 1 | b13 | c1 |
| 286 | a 2 | b13 | c1 |
| 287 | a 3 | b13 | c1 |
| 288 | a 4 | b13 | c1 |
| 289 | a 5 | b13 | c1 |
| 290 | a 6 | b13 | c1 |
| 291 | a 7 | b13 | c1 |
| 292 | a 8 | b13 | c1 |
| 293 | a 9 | b13 | c1 |
| 294 | a10 | b13 | c1 |
| 295 | a11 | b13 | c1 |
| 296 | a12 | b13 | c1 |
| 297 | a13 | b13 | c1 |
| 298 | a14 | b13 | c1 |
| 299 | a15 | b13 | c1 |
| 300 | a16 | b13 | c1 |
| 301 | a17 | b13 | c1 |
| 302 | a18 | b13 | c1 |
| 303 | a19 | b13 | c1 |
| 304 | a20 | b13 | c1 |
| 305 | a21 | b13 | c1 |
| 306 | a22 | b13 | c1 |
| 307 | a23 | b13 | c1 |
| 308 | a24 | b13 | c1 |
| 309 | a25 | b13 | c1 |
| 310 | a 1 | b14 | c1 |
| 311 | a 2 | b14 | c1 |
| 312 | a 3 | b14 | c1 |
| 313 | a 4 | b14 | c1 |
| 314 | a 5 | b14 | c1 |
| 315 | a 6 | b14 | c1 |
| 316 | a 7 | b14 | c1 |
| 317 | a 8 | b14 | c1 |
| 318 | a 9 | b14 | c1 |
| 319 | a10 | b14 | c1 |
| 320 | a11 | b14 | c1 |
| 321 | a12 | b14 | c1 |
| 322 | a13 | b14 | c1 |
| 323 | a14 | b14 | c1 |
| 324 | a15 | b14 | c1 |
| 325 | a16 | b14 | c1 |
| 326 | a17 | b14 | c1 |
| 327 | a18 | b14 | c1 |
| 328 | a19 | b14 | c1 |
| 329 | a20 | b14 | c1 |
| 330 | a21 | b14 | c1 |
| 331 | a22 | b14 | c1 |
| 332 | a23 | b14 | c1 |
| 333 | a24 | b14 | c1 |
| 334 | a25 | b14 | c1 |
| 335 | a 1 | b15 | c1 |
| 336 | a 2 | b15 | c1 |
| 337 | a 3 | b15 | c1 |
| 338 | a 4 | b15 | c1 |
| 339 | a 5 | b15 | c1 |
| 340 | a 6 | b15 | c1 |
| 341 | a 7 | b15 | c1 |
| 342 | a 8 | b15 | c1 |
| 343 | a 9 | b15 | c1 |
| 344 | a10 | b15 | c1 |
| 345 | a11 | b15 | c1 |
| 346 | a12 | b15 | c1 |
| 347 | a13 | b15 | c1 |
| 348 | a14 | b15 | c1 |
| 349 | a15 | b15 | c1 |
| 350 | a16 | b15 | c1 |
| 351 | a17 | b15 | c1 |
| 352 | a18 | b15 | c1 |
| 353 | a19 | b15 | c1 |
| 354 | a20 | b15 | c1 |
| 355 | a21 | b15 | c1 |
| 356 | a22 | b15 | c1 |
| 357 | a23 | b15 | c1 |
| 358 | a24 | b15 | c1 |
| 359 | a25 | b15 | c1 |
| 360 | a 1 | b 1 | c2 |
| 361 | a 2 | b 1 | c2 |
| 362 | a 3 | b 1 | c2 |
| 363 | a 4 | b 1 | c2 |
| 364 | a 5 | b 1 | c2 |
| 365 | a 6 | b 1 | c2 |
| 366 | a 7 | b 1 | c2 |
| 367 | a 8 | b 1 | c2 |
| 368 | a 9 | b 1 | c2 |
| 369 | a10 | b 1 | c2 |
| 370 | a11 | b 1 | c2 |
| 371 | a12 | b 1 | c2 |
| 372 | a13 | b 1 | c2 |
| 373 | a14 | b 1 | c2 |
| 374 | a15 | b 1 | c2 |
| 375 | a16 | b 1 | c2 |
| 376 | a17 | b 1 | c2 |
| 377 | a18 | b 1 | c2 |
| 378 | a19 | b 1 | c2 |
| 379 | a20 | b 1 | c2 |
| 380 | a21 | b 1 | c2 |
| 381 | a22 | b 1 | c2 |
| 382 | a23 | b 1 | c2 |
| 383 | a24 | b 1 | c2 |
| 384 | a25 | b 1 | c2 |
| 385 | a 1 | b 2 | c2 |
| 386 | a 2 | b 2 | c2 |
| 387 | a 3 | b 2 | c2 |
| 388 | a 4 | b 2 | c2 |
| 389 | a 5 | b 2 | c2 |
| 390 | a 6 | b 2 | c2 |
| 391 | a 7 | b 2 | c2 |
| 392 | a 8 | b 2 | c2 |
| 393 | a 9 | b 2 | c2 |
| 394 | a10 | b 2 | c2 |
| 395 | a11 | b 2 | c2 |
| 396 | a12 | b 2 | c2 |
| 397 | a13 | b 2 | c2 |
| 398 | a14 | b 2 | c2 |
| 399 | a15 | b 2 | c2 |
| 400 | a16 | b 2 | c2 |
| 401 | a17 | b 2 | c2 |
| 402 | a18 | b 2 | c2 |
| 403 | a19 | b 2 | c2 |
| 404 | a20 | b 2 | c2 |
| 405 | a21 | b 2 | c2 |
| 406 | a22 | b 2 | c2 |
| 407 | a23 | b 2 | c2 |
| 408 | a24 | b 2 | c2 |
| 409 | a25 | b 2 | c2 |
| 410 | a 1 | b 3 | c2 |
| 411 | a 2 | b 3 | c2 |
| 412 | a 3 | b 3 | c2 |

-continued

| No. | Cp | Bridge | Flu |
|---|---|---|---|
| 413 | a 4 | b3 | c2 |
| 414 | a 5 | b3 | c2 |
| 415 | a 6 | b3 | c2 |
| 416 | a 7 | b3 | c2 |
| 417 | a 8 | b3 | c2 |
| 418 | a 9 | b3 | c2 |
| 419 | a10 | b3 | c2 |
| 420 | a11 | b3 | c2 |
| 421 | a12 | b3 | c2 |
| 422 | a13 | b3 | c2 |
| 423 | a14 | b3 | c2 |
| 424 | a15 | b3 | c2 |
| 425 | a16 | b3 | c2 |
| 426 | a17 | b3 | c2 |
| 427 | a18 | b3 | c2 |
| 428 | a19 | b3 | c2 |
| 429 | a20 | b3 | c2 |
| 430 | a21 | b3 | c2 |
| 431 | a22 | b3 | c2 |
| 432 | a23 | b3 | c2 |
| 433 | a24 | b3 | c2 |
| 434 | a25 | b3 | c2 |
| 435 | a 1 | b4 | c2 |
| 436 | a 2 | b4 | c2 |
| 437 | a 3 | b4 | c2 |
| 438 | a 4 | b4 | c2 |
| 439 | a 5 | b4 | c2 |
| 440 | a 6 | b4 | c2 |
| 441 | a 7 | b4 | c2 |
| 442 | a 8 | b4 | c2 |
| 443 | a 9 | b4 | c2 |
| 444 | a10 | b4 | c2 |
| 445 | a11 | b4 | c2 |
| 446 | a12 | b4 | c2 |
| 447 | a13 | b4 | c2 |
| 448 | a14 | b4 | c2 |
| 449 | a15 | b4 | c2 |
| 450 | a16 | b4 | c2 |
| 451 | a17 | b4 | c2 |
| 452 | a18 | b4 | c2 |
| 453 | a19 | b4 | c2 |
| 454 | a20 | b4 | c2 |
| 455 | a21 | b4 | c2 |
| 456 | a22 | b4 | c2 |
| 457 | a23 | b4 | c2 |
| 458 | a24 | b4 | c2 |
| 459 | a25 | b4 | c2 |
| 460 | a 1 | b5 | c2 |
| 461 | a 2 | b5 | c2 |
| 462 | a 3 | b5 | c2 |
| 463 | a 4 | b5 | c2 |
| 464 | a 5 | b5 | c2 |
| 465 | a 6 | b5 | c2 |
| 466 | a 7 | b5 | c2 |
| 467 | a 8 | b5 | c2 |
| 468 | a 9 | b5 | c2 |
| 469 | a10 | b5 | c2 |
| 470 | a11 | b5 | c2 |
| 471 | a12 | b5 | c2 |
| 472 | a13 | b5 | c2 |
| 473 | a14 | b5 | c2 |
| 474 | a15 | b5 | c2 |
| 475 | a16 | b5 | c2 |
| 476 | a17 | b5 | c2 |
| 477 | a18 | b5 | c2 |
| 478 | a19 | b5 | c2 |
| 479 | a20 | b5 | c2 |
| 480 | a21 | b5 | c2 |
| 481 | a22 | b5 | c2 |
| 482 | a23 | b5 | c2 |
| 483 | a24 | b5 | c2 |
| 484 | a25 | b5 | c2 |
| 485 | a 1 | b6 | c2 |
| 486 | a 2 | b6 | c2 |
| 487 | a 3 | b6 | c2 |
| 488 | a 4 | b6 | c2 |
| 489 | a 5 | b6 | c2 |

-continued

| No. | Cp | Bridge | Flu |
|---|---|---|---|
| 490 | a 6 | b6 | c2 |
| 491 | a 7 | b6 | c2 |
| 492 | a 8 | b6 | c2 |
| 493 | a 9 | b6 | c2 |
| 494 | a10 | b6 | c2 |
| 495 | a11 | b6 | c2 |
| 496 | a12 | b6 | c2 |
| 497 | a13 | b6 | c2 |
| 498 | a14 | b6 | c2 |
| 499 | a15 | b6 | c2 |
| 500 | a16 | b6 | c2 |
| 501 | a17 | b6 | c2 |
| 502 | a18 | b6 | c2 |
| 503 | a19 | b6 | c2 |
| 504 | a20 | b6 | c2 |
| 505 | a21 | b6 | c2 |
| 506 | a22 | b6 | c2 |
| 507 | a23 | b6 | c2 |
| 508 | a24 | b6 | c2 |
| 509 | a25 | b6 | c2 |
| 510 | a 1 | b7 | c2 |
| 511 | a 2 | b7 | c2 |
| 512 | a 3 | b7 | c2 |
| 513 | a 4 | b7 | c2 |
| 514 | a 5 | b7 | c2 |
| 515 | a 6 | b7 | c2 |
| 516 | a 7 | b7 | c2 |
| 517 | a 8 | b7 | c2 |
| 518 | a 9 | b7 | c2 |
| 519 | a10 | b7 | c2 |
| 520 | a11 | b7 | c2 |
| 521 | a12 | b7 | c2 |
| 522 | a13 | b7 | c2 |
| 523 | a14 | b7 | c2 |
| 524 | a15 | b7 | c2 |
| 525 | a16 | b7 | c2 |
| 526 | a17 | b7 | c2 |
| 527 | a18 | b7 | c2 |
| 528 | a19 | b7 | c2 |
| 529 | a20 | b7 | c2 |
| 530 | a21 | b7 | c2 |
| 531 | a22 | b7 | c2 |
| 532 | a23 | b7 | c2 |
| 533 | a24 | b7 | c2 |
| 534 | a25 | b7 | c2 |
| 535 | a 1 | b8 | c2 |
| 536 | a 2 | b8 | c2 |
| 537 | a 3 | b8 | c2 |
| 538 | a 4 | b8 | c2 |
| 539 | a 5 | b8 | c2 |
| 540 | a 6 | b8 | c2 |
| 541 | a 7 | b8 | c2 |
| 542 | a 8 | b8 | c2 |
| 543 | a 9 | b8 | c2 |
| 544 | a10 | b8 | c2 |
| 545 | a11 | b8 | c2 |
| 546 | a12 | b8 | c2 |
| 547 | a13 | b8 | c2 |
| 548 | a14 | b8 | c2 |
| 549 | a15 | b8 | c2 |
| 550 | a16 | b8 | c2 |
| 551 | a17 | b8 | c2 |
| 552 | a18 | b8 | c2 |
| 553 | a19 | b8 | c2 |
| 554 | a20 | b8 | c2 |
| 555 | a21 | b8 | c2 |
| 556 | a22 | b8 | c2 |
| 557 | a23 | b8 | c2 |
| 558 | a24 | b8 | c2 |
| 559 | a25 | b8 | c2 |
| 560 | a 1 | b9 | c2 |
| 561 | a 2 | b9 | c2 |
| 562 | a 3 | b9 | c2 |
| 563 | a 4 | b9 | c2 |
| 564 | a 5 | b9 | c2 |
| 565 | a 6 | b9 | c2 |
| 566 | a 7 | b9 | c2 |

-continued

| No. | Cp | Bridge | Flu |
|---|---|---|---|
| 567 | a 8 | b 9 | c2 |
| 568 | a 9 | b 9 | c2 |
| 569 | a10 | b 9 | c2 |
| 570 | a11 | b 9 | c2 |
| 571 | a12 | b 9 | c2 |
| 572 | a13 | b 9 | c2 |
| 573 | a14 | b 9 | c2 |
| 574 | a15 | b 9 | c2 |
| 575 | a16 | b 9 | c2 |
| 576 | a17 | b 9 | c2 |
| 577 | a18 | b 9 | c2 |
| 578 | a19 | b 9 | c2 |
| 579 | a20 | b 9 | c2 |
| 580 | a21 | b 9 | c2 |
| 581 | a22 | b 9 | c2 |
| 582 | a23 | b 9 | c2 |
| 583 | a24 | b 9 | c2 |
| 584 | a25 | b 9 | c2 |
| 585 | a 1 | b10 | c2 |
| 586 | a 2 | b10 | c2 |
| 587 | a 3 | b10 | c2 |
| 588 | a 4 | b10 | c2 |
| 589 | a 5 | b10 | c2 |
| 590 | a 6 | b10 | c2 |
| 591 | a 7 | b10 | c2 |
| 592 | a 8 | b10 | c2 |
| 593 | a 9 | b10 | c2 |
| 594 | a10 | b10 | c2 |
| 595 | a11 | b10 | c2 |
| 596 | a12 | b10 | c2 |
| 597 | a13 | b10 | c2 |
| 598 | a14 | b10 | c2 |
| 599 | a15 | b10 | c2 |
| 600 | a16 | b10 | c2 |
| 601 | a17 | b10 | c2 |
| 602 | a18 | b10 | c2 |
| 603 | a19 | b10 | c2 |
| 604 | a20 | b10 | c2 |
| 605 | a21 | b10 | c2 |
| 606 | a22 | b10 | c2 |
| 607 | a23 | b10 | c2 |
| 608 | a24 | b10 | c2 |
| 609 | a25 | b10 | c2 |
| 610 | a 1 | b11 | c2 |
| 611 | a 2 | b11 | c2 |
| 612 | a 3 | b11 | c2 |
| 613 | a 4 | b11 | c2 |
| 614 | a 5 | b11 | c2 |
| 615 | a 6 | b11 | c2 |
| 616 | a 7 | b11 | c2 |
| 617 | a 8 | b11 | c2 |
| 618 | a 9 | b11 | c2 |
| 619 | a10 | b11 | c2 |
| 620 | a11 | b11 | c2 |
| 621 | a12 | b11 | c2 |
| 622 | a13 | b11 | c2 |
| 623 | a14 | b11 | c2 |
| 624 | a15 | b11 | c2 |
| 625 | a16 | b11 | c2 |
| 626 | a17 | b11 | c2 |
| 627 | a18 | b11 | c2 |
| 628 | a19 | b11 | c2 |
| 629 | a20 | b11 | c2 |
| 630 | a21 | b11 | c2 |
| 631 | a22 | b11 | c2 |
| 632 | a23 | b11 | c2 |
| 633 | a24 | b11 | c2 |
| 634 | a25 | b11 | c2 |
| 635 | a 1 | b12 | c2 |
| 636 | a 2 | b12 | c2 |
| 637 | a 3 | b12 | c2 |
| 638 | a 4 | b12 | c2 |
| 639 | a 5 | b12 | c2 |
| 640 | a 6 | b12 | c2 |
| 641 | a 7 | b12 | c2 |
| 642 | a 8 | b12 | c2 |
| 643 | a 9 | b12 | c2 |

-continued

| No. | Cp | Bridge | Flu |
|---|---|---|---|
| 644 | a10 | b12 | c2 |
| 645 | a11 | b12 | c2 |
| 646 | a12 | b12 | c2 |
| 647 | a13 | b12 | c2 |
| 648 | a14 | b12 | c2 |
| 649 | a15 | b12 | c2 |
| 650 | a16 | b12 | c2 |
| 651 | a17 | b12 | c2 |
| 652 | a18 | b12 | c2 |
| 653 | a19 | b12 | c2 |
| 654 | a20 | b12 | c2 |
| 655 | a21 | b12 | c2 |
| 656 | a22 | b12 | c2 |
| 657 | a23 | b12 | c2 |
| 658 | a24 | b12 | c2 |
| 659 | a25 | b12 | c2 |
| 660 | a 1 | b13 | c2 |
| 661 | a 2 | b13 | c2 |
| 662 | a 3 | b13 | c2 |
| 663 | a 4 | b13 | c2 |
| 664 | a 5 | b13 | c2 |
| 665 | a 6 | b13 | c2 |
| 666 | a 7 | b13 | c2 |
| 667 | a 8 | b13 | c2 |
| 668 | a 9 | b13 | c2 |
| 669 | a10 | b13 | c2 |
| 670 | a11 | b13 | c2 |
| 671 | a12 | b13 | c2 |
| 672 | a13 | b13 | c2 |
| 673 | a14 | b13 | c2 |
| 674 | a15 | b13 | c2 |
| 675 | a16 | b13 | c2 |
| 676 | a17 | b13 | c2 |
| 677 | a18 | b13 | c2 |
| 678 | a19 | b13 | c2 |
| 679 | a20 | b13 | c2 |
| 680 | a21 | b13 | c2 |
| 681 | a22 | b13 | c2 |
| 682 | a23 | b13 | c2 |
| 683 | a24 | b13 | c2 |
| 684 | a25 | b13 | c2 |
| 685 | a 1 | b14 | c2 |
| 686 | a 2 | b14 | c2 |
| 687 | a 3 | b14 | c2 |
| 688 | a 4 | b14 | c2 |
| 689 | a 5 | b14 | c2 |
| 690 | a 6 | b14 | c2 |
| 691 | a 7 | b14 | c2 |
| 692 | a 8 | b14 | c2 |
| 693 | a 9 | b14 | c2 |
| 694 | a10 | b14 | c2 |
| 695 | a11 | b14 | c2 |
| 696 | a12 | b14 | c2 |
| 697 | a13 | b14 | c2 |
| 698 | a14 | b14 | c2 |
| 699 | a15 | b14 | c2 |
| 700 | a16 | b14 | c2 |
| 701 | a17 | b14 | c2 |
| 702 | a18 | b14 | c2 |
| 703 | a19 | b14 | c2 |
| 704 | a20 | b14 | c2 |
| 705 | a21 | b14 | c2 |
| 706 | a22 | b14 | c2 |
| 707 | a23 | b14 | c2 |
| 708 | a24 | b14 | c2 |
| 709 | a25 | b14 | c2 |
| 710 | a 1 | b15 | c2 |
| 711 | a 2 | b15 | c2 |
| 712 | a 3 | b15 | c2 |
| 713 | a 4 | b15 | c2 |
| 714 | a 5 | b15 | c2 |
| 715 | a 6 | b15 | c2 |
| 716 | a 7 | b15 | c2 |
| 717 | a 8 | b15 | c2 |
| 718 | a 9 | b15 | c2 |
| 719 | a10 | b15 | c2 |
| 720 | a11 | b15 | c2 |

| No. | Cp | Bridge | Flu |
|---|---|---|---|
| 721 | a12 | b15 | c2 |
| 722 | a13 | b15 | c2 |
| 723 | a14 | b15 | c2 |
| 724 | a15 | b15 | c2 |
| 725 | a16 | b15 | c2 |
| 726 | a17 | b15 | c2 |
| 727 | a18 | b15 | c2 |
| 728 | a19 | b15 | c2 |
| 729 | a20 | b15 | c2 |
| 730 | a21 | b15 | c2 |
| 731 | a22 | b15 | c2 |
| 732 | a23 | b15 | c2 |
| 733 | a24 | b15 | c2 |
| 734 | a25 | b15 | c2 |
| 735 | a 1 | b 1 | c3 |
| 736 | a 2 | b 1 | c3 |
| 737 | a 3 | b 1 | c3 |
| 738 | a 4 | b 1 | c3 |
| 739 | a 5 | b 1 | c3 |
| 740 | a 6 | b 1 | c3 |
| 741 | a 7 | b 1 | c3 |
| 742 | a 8 | b 1 | c3 |
| 743 | a 9 | b 1 | c3 |
| 744 | a10 | b 1 | c3 |
| 745 | a11 | b 1 | c3 |
| 746 | a12 | b 1 | c3 |
| 747 | a13 | b 1 | c3 |
| 748 | a14 | b 1 | c3 |
| 749 | a15 | b 1 | c3 |
| 750 | a16 | b 1 | c3 |
| 751 | a17 | b 1 | c3 |
| 752 | a18 | b 1 | c3 |
| 753 | a19 | b 1 | c3 |
| 754 | a20 | b 1 | c3 |
| 755 | a21 | b 1 | c3 |
| 756 | a22 | b 1 | c3 |
| 757 | a23 | b 1 | c3 |
| 758 | a24 | b 1 | c3 |
| 759 | a25 | b 1 | c3 |
| 760 | a 1 | b 2 | c3 |
| 761 | a 2 | b 2 | c3 |
| 762 | a 3 | b 2 | c3 |
| 763 | a 4 | b 2 | c3 |
| 764 | a 5 | b 2 | c3 |
| 765 | a 6 | b 2 | c3 |
| 766 | a 7 | b 2 | c3 |
| 767 | a 8 | b 2 | c3 |
| 768 | a 9 | b 2 | c3 |
| 769 | a10 | b 2 | c3 |
| 770 | a11 | b 2 | c3 |
| 771 | a12 | b 2 | c3 |
| 772 | a13 | b 2 | c3 |
| 773 | a14 | b 2 | c3 |
| 774 | a15 | b 2 | c3 |
| 775 | a16 | b 2 | c3 |
| 776 | a17 | b 2 | c3 |
| 777 | a18 | b 2 | c3 |
| 778 | a19 | b 2 | c3 |
| 779 | a20 | b 2 | c3 |
| 780 | a21 | b 2 | c3 |
| 781 | a22 | b 2 | c3 |
| 782 | a23 | b 2 | c3 |
| 783 | a24 | b 2 | c3 |
| 784 | a25 | b 2 | c3 |
| 785 | a 1 | b 3 | c3 |
| 786 | a 2 | b 3 | c3 |
| 787 | a 3 | b 3 | c3 |
| 788 | a 4 | b 3 | c3 |
| 789 | a 5 | b 3 | c3 |
| 790 | a 6 | b 3 | c3 |
| 791 | a 7 | b 3 | c3 |
| 792 | a 8 | b 3 | c3 |
| 793 | a 9 | b 3 | c3 |
| 794 | a10 | b 3 | c3 |
| 795 | a11 | b 3 | c3 |
| 796 | a12 | b 3 | c3 |
| 797 | a13 | b 3 | c3 |
| 798 | a14 | b3 | c3 |
| 799 | a15 | b3 | c3 |
| 800 | a16 | b3 | c3 |
| 801 | a17 | b3 | c3 |
| 802 | a18 | b3 | c3 |
| 803 | a19 | b3 | c3 |
| 804 | a20 | b3 | c3 |
| 805 | a21 | b3 | c3 |
| 806 | a22 | b3 | c3 |
| 807 | a23 | b3 | c3 |
| 808 | a24 | b3 | c3 |
| 809 | a25 | b3 | c3 |
| 810 | a 1 | b4 | c3 |
| 811 | a 2 | b4 | c3 |
| 812 | a 3 | b4 | c3 |
| 813 | a 4 | b4 | c3 |
| 814 | a 5 | b4 | c3 |
| 815 | a 6 | b4 | c3 |
| 816 | a 7 | b4 | c3 |
| 817 | a 8 | b4 | c3 |
| 818 | a 9 | b4 | c3 |
| 819 | a10 | b4 | c3 |
| 820 | a11 | b4 | c3 |
| 821 | a12 | b4 | c3 |
| 822 | a13 | b4 | c3 |
| 823 | a14 | b4 | c3 |
| 824 | a15 | b4 | c3 |
| 825 | a16 | b4 | c3 |
| 826 | a17 | b4 | c3 |
| 827 | a18 | b4 | c3 |
| 828 | a19 | b4 | c3 |
| 829 | a20 | b4 | c3 |
| 830 | a21 | b4 | c3 |
| 831 | a22 | b4 | c3 |
| 832 | a23 | b4 | c3 |
| 833 | a24 | b4 | c3 |
| 834 | a25 | b4 | c3 |
| 835 | a 1 | b5 | c3 |
| 836 | a 2 | b5 | c3 |
| 837 | a 3 | b5 | c3 |
| 838 | a 4 | b5 | c3 |
| 839 | a 5 | b5 | c3 |
| 840 | a 6 | b5 | c3 |
| 841 | a 7 | b5 | c3 |
| 842 | a 8 | b5 | c3 |
| 843 | a 9 | b5 | c3 |
| 844 | a10 | b5 | c3 |
| 845 | a11 | b5 | c3 |
| 846 | a12 | b5 | c3 |
| 847 | a13 | b5 | c3 |
| 848 | a14 | b5 | c3 |
| 849 | a15 | b5 | c3 |
| 850 | a16 | b5 | c3 |
| 851 | a17 | b5 | c3 |
| 852 | a18 | b5 | c3 |
| 853 | a19 | b5 | c3 |
| 854 | a20 | b5 | c3 |
| 855 | a21 | b5 | c3 |
| 856 | a22 | b5 | c3 |
| 857 | a23 | b5 | c3 |
| 858 | a24 | b5 | c3 |
| 859 | a25 | b5 | c3 |
| 860 | a 1 | b6 | c3 |
| 861 | a 2 | b6 | c3 |
| 862 | a 3 | b6 | c3 |
| 863 | a 4 | b6 | c3 |
| 864 | a 5 | b6 | c3 |
| 865 | a 6 | b6 | c3 |
| 866 | a 7 | b6 | c3 |
| 867 | a 8 | b6 | c3 |
| 868 | a 9 | b6 | c3 |
| 869 | a10 | b6 | c3 |
| 870 | a11 | b6 | c3 |
| 871 | a12 | b6 | c3 |
| 872 | a13 | b6 | c3 |
| 873 | a14 | b6 | c3 |
| 874 | a15 | b6 | c3 |

| No. | Cp | Bridge | Flu |
|---|---|---|---|
| 875 | a16 | b6 | c3 |
| 876 | a17 | b6 | c3 |
| 877 | a18 | b6 | c3 |
| 878 | a19 | b6 | c3 |
| 879 | a20 | b6 | c3 |
| 880 | a21 | b6 | c3 |
| 881 | a22 | b6 | c3 |
| 882 | a23 | b6 | c3 |
| 883 | a24 | b6 | c3 |
| 884 | a25 | b6 | c3 |
| 885 | a 1 | b7 | c3 |
| 886 | a 2 | b7 | c3 |
| 887 | a 3 | b7 | c3 |
| 888 | a 4 | b7 | c3 |
| 889 | a 5 | b7 | c3 |
| 890 | a 6 | b7 | c3 |
| 891 | a 7 | b7 | c3 |
| 892 | a 8 | b7 | c3 |
| 893 | a 9 | b7 | c3 |
| 894 | a10 | b7 | c3 |
| 895 | a11 | b7 | c3 |
| 896 | a12 | b7 | c3 |
| 897 | a13 | b7 | c3 |
| 898 | a14 | b7 | c3 |
| 899 | a15 | b7 | c3 |
| 900 | a16 | b7 | c3 |
| 901 | a17 | b7 | c3 |
| 902 | a18 | b7 | c3 |
| 903 | a19 | b7 | c3 |
| 904 | a20 | b7 | c3 |
| 905 | a21 | b7 | c3 |
| 906 | a22 | b7 | c3 |
| 907 | a23 | b7 | c3 |
| 908 | a24 | b7 | c3 |
| 909 | a25 | b7 | c3 |
| 910 | a 5 | b8 | c3 |
| 911 | a 6 | b8 | c3 |
| 912 | a 7 | b8 | c3 |
| 913 | a 8 | b8 | c3 |
| 914 | a 9 | b8 | c3 |
| 915 | a10 | b8 | c3 |
| 916 | a11 | b8 | c3 |
| 917 | a12 | b8 | c3 |
| 918 | a13 | b8 | c3 |
| 919 | a14 | b8 | c3 |
| 920 | a15 | b8 | c3 |
| 921 | a16 | b8 | c3 |
| 922 | a17 | b8 | c3 |
| 923 | a18 | b8 | c3 |
| 924 | a19 | b8 | c3 |
| 925 | a20 | b8 | c3 |
| 926 | a21 | b8 | c3 |
| 927 | a22 | b8 | c3 |
| 928 | a23 | b8 | c3 |
| 929 | a24 | b8 | c3 |
| 930 | a25 | b8 | c3 |
| 931 | a 5 | b9 | c3 |
| 932 | a 6 | b9 | c3 |
| 933 | a 7 | b9 | c3 |
| 934 | a 8 | b9 | c3 |
| 935 | a 9 | b9 | c3 |
| 936 | a10 | b9 | c3 |
| 937 | a11 | b9 | c3 |
| 938 | a12 | b9 | c3 |
| 939 | a13 | b9 | c3 |
| 940 | a14 | b9 | c3 |
| 941 | a15 | b9 | c3 |
| 942 | a16 | b9 | c3 |
| 943 | a17 | b9 | c3 |
| 944 | a18 | b9 | c3 |
| 945 | a19 | b9 | c3 |
| 946 | a20 | b9 | c3 |
| 947 | a21 | b9 | c3 |
| 948 | a22 | b9 | c3 |
| 949 | a23 | b9 | c3 |
| 950 | a24 | b9 | c3 |
| 951 | a25 | b9 | c3 |
| 952 | a 5 | b10 | c3 |
| 953 | a 6 | b10 | c3 |
| 954 | a 7 | b10 | c3 |
| 955 | a 8 | b10 | c3 |
| 956 | a 9 | b10 | c3 |
| 957 | a10 | b10 | c3 |
| 958 | a11 | b10 | c3 |
| 959 | a12 | b10 | c3 |
| 960 | a13 | b10 | c3 |
| 961 | a14 | b10 | c3 |
| 962 | a15 | b10 | c3 |
| 963 | a16 | b10 | c3 |
| 964 | a17 | b10 | c3 |
| 965 | a18 | b10 | c3 |
| 966 | a19 | b10 | c3 |
| 967 | a20 | b10 | c3 |
| 968 | a21 | b10 | c3 |
| 969 | a22 | b10 | c3 |
| 970 | a23 | b10 | c3 |
| 971 | a24 | b10 | c3 |
| 972 | a25 | b10 | c3 |
| 973 | a 5 | b11 | c3 |
| 974 | a 6 | b11 | c3 |
| 975 | a 7 | b11 | c3 |
| 976 | a 8 | b11 | c3 |
| 977 | a 9 | b11 | c3 |
| 978 | a10 | b11 | c3 |
| 979 | a11 | b11 | c3 |
| 980 | a12 | b11 | c3 |
| 981 | a13 | b11 | c3 |
| 982 | a14 | b11 | c3 |
| 983 | a15 | b11 | c3 |
| 984 | a16 | b11 | c3 |
| 985 | a17 | b11 | c3 |
| 986 | a18 | b11 | c3 |
| 987 | a19 | b11 | c3 |
| 988 | a20 | b11 | c3 |
| 989 | a21 | b11 | c3 |
| 990 | a22 | b11 | c3 |
| 991 | a23 | b11 | c3 |
| 992 | a24 | b11 | c3 |
| 993 | a25 | b11 | c3 |
| 994 | a 1 | b12 | c3 |
| 995 | a 2 | b12 | c3 |
| 996 | a 3 | b12 | c3 |
| 997 | a 4 | b12 | c3 |
| 998 | a 5 | b12 | c3 |
| 999 | a 6 | b12 | c3 |
| 1000 | a 7 | b12 | c3 |
| 1001 | a 8 | b12 | c3 |
| 1002 | a 9 | b12 | c3 |
| 1003 | a10 | b12 | c3 |
| 1004 | a11 | b12 | c3 |
| 1005 | a12 | b12 | c3 |
| 1006 | a13 | b12 | c3 |
| 1007 | a14 | b12 | c3 |
| 1008 | a15 | b12 | c3 |
| 1009 | a16 | b12 | c3 |
| 1010 | a17 | b12 | c3 |
| 1011 | a18 | b12 | c3 |
| 1012 | a19 | b12 | c3 |
| 1013 | a20 | b12 | c3 |
| 1014 | a21 | b12 | c3 |
| 1015 | a22 | b12 | c3 |
| 1016 | a23 | b12 | c3 |
| 1017 | a24 | b12 | c3 |
| 1018 | a25 | b12 | c3 |
| 1019 | a 1 | b13 | c3 |
| 1020 | a 2 | b13 | c3 |
| 1021 | a 3 | b13 | c3 |
| 1022 | a 4 | b13 | c3 |
| 1023 | a 5 | b13 | c3 |
| 1024 | a 6 | b13 | c3 |
| 1025 | a 7 | b13 | c3 |
| 1026 | a 8 | b13 | c3 |
| 1027 | a 9 | b13 | c3 |
| 1028 | a10 | b13 | c3 |

-continued

| No. | Cp | Bridge | Flu |
|---|---|---|---|
| 1029 | a11 | b13 | c3 |
| 1030 | a12 | b13 | c3 |
| 1031 | a13 | b13 | c3 |
| 1032 | a14 | b13 | c3 |
| 1033 | a15 | b13 | c3 |
| 1034 | a16 | b13 | c3 |
| 1035 | a17 | b13 | c3 |
| 1036 | a18 | b13 | c3 |
| 1037 | a19 | b13 | c3 |
| 1038 | a20 | b13 | c3 |
| 1039 | a21 | b13 | c3 |
| 1040 | a22 | b13 | c3 |
| 1041 | a23 | b13 | c3 |
| 1042 | a24 | b13 | c3 |
| 1043 | a25 | b13 | c3 |
| 1044 | a 1 | b14 | c3 |
| 1045 | a 2 | b14 | c3 |
| 1046 | a 3 | b14 | c3 |
| 1047 | a 4 | b14 | c3 |
| 1048 | a 5 | b14 | c3 |
| 1049 | a 6 | b14 | c3 |
| 1050 | a 7 | b14 | c3 |
| 1051 | a 8 | b14 | c3 |
| 1052 | a 9 | b14 | c3 |
| 1053 | a10 | b14 | c3 |
| 1054 | a11 | b14 | c3 |
| 1055 | a12 | b14 | c3 |
| 1056 | a13 | b14 | c3 |
| 1057 | a14 | b14 | c3 |
| 1058 | a15 | b14 | c3 |
| 1059 | a16 | b14 | c3 |
| 1060 | a17 | b14 | c3 |
| 1061 | a18 | b14 | c3 |
| 1062 | a19 | b14 | c3 |
| 1063 | a20 | b14 | c3 |
| 1064 | a21 | b14 | c3 |
| 1065 | a22 | b14 | c3 |
| 1066 | a23 | b14 | c3 |
| 1067 | a24 | b14 | c3 |
| 1068 | a25 | b14 | c3 |
| 1069 | a 1 | b15 | c3 |
| 1070 | a 2 | b15 | c3 |
| 1071 | a 3 | b15 | c3 |
| 1072 | a 4 | b15 | c3 |
| 1073 | a 5 | b15 | c3 |
| 1074 | a 6 | b15 | c3 |
| 1075 | a 7 | b15 | c3 |
| 1076 | a 8 | b15 | c3 |
| 1077 | a 9 | b15 | c3 |
| 1078 | a10 | b15 | c3 |
| 1079 | a11 | b15 | c3 |
| 1080 | a12 | b15 | c3 |
| 1081 | a13 | b15 | c3 |
| 1082 | a14 | b15 | c3 |
| 1083 | a15 | b15 | c3 |
| 1084 | a16 | b15 | c3 |
| 1085 | a17 | b15 | c3 |
| 1086 | a18 | b15 | c3 |
| 1087 | a19 | b15 | c3 |
| 1088 | a20 | b15 | c3 |
| 1089 | a21 | b15 | c3 |
| 1090 | a22 | b15 | c3 |
| 1091 | a23 | b15 | c3 |
| 1092 | a24 | b15 | c3 |
| 1093 | a25 | b15 | c3 |
| 1094 | a 1 | b 1 | c4 |
| 1095 | a 2 | b 1 | c4 |
| 1096 | a 3 | b 1 | c4 |
| 1097 | a 4 | b 1 | c4 |
| 1098 | a 5 | b 1 | c4 |
| 1099 | a 6 | b 1 | c4 |
| 1100 | a 7 | b 1 | c4 |
| 1101 | a 8 | b 1 | c4 |
| 1102 | a 9 | b 1 | c4 |
| 1103 | a10 | b 1 | c4 |
| 1104 | a11 | b 1 | c4 |
| 1105 | a12 | b 1 | c4 |

-continued

| No. | Cp | Bridge | Flu |
|---|---|---|---|
| 1106 | a13 | b1 | c4 |
| 1107 | a14 | b1 | c4 |
| 1108 | a15 | b1 | c4 |
| 1109 | a16 | b1 | c4 |
| 1110 | a17 | b1 | c4 |
| 1111 | a18 | b1 | c4 |
| 1112 | a19 | b1 | c4 |
| 1113 | a20 | b1 | c4 |
| 1114 | a21 | b1 | c4 |
| 1115 | a22 | b1 | c4 |
| 1116 | a23 | b1 | c4 |
| 1117 | a24 | b1 | c4 |
| 1118 | a25 | b1 | c4 |
| 1119 | a 1 | b2 | c4 |
| 1120 | a 2 | b2 | c4 |
| 1121 | a 3 | b2 | c4 |
| 1122 | a 4 | b2 | c4 |
| 1123 | a 5 | b2 | c4 |
| 1124 | a 6 | b2 | c4 |
| 1125 | a 7 | b2 | c4 |
| 1126 | a 8 | b2 | c4 |
| 1127 | a 9 | b2 | c4 |
| 1128 | a10 | b2 | c4 |
| 1129 | a11 | b2 | c4 |
| 1130 | a12 | b2 | c4 |
| 1131 | a13 | b2 | c4 |
| 1132 | a14 | b2 | c4 |
| 1133 | a15 | b2 | c4 |
| 1134 | a16 | b2 | c4 |
| 1135 | a17 | b2 | c4 |
| 1136 | a18 | b2 | c4 |
| 1137 | a19 | b2 | c4 |
| 1138 | a20 | b2 | c4 |
| 1139 | a21 | b2 | c4 |
| 1140 | a22 | b2 | c4 |
| 1141 | a23 | b2 | c4 |
| 1142 | a24 | b2 | c4 |
| 1143 | a25 | b2 | c4 |
| 1144 | a 1 | b3 | c4 |
| 1145 | a 2 | b3 | c4 |
| 1146 | a 3 | b3 | c4 |
| 1147 | a 4 | b3 | c4 |
| 1148 | a 5 | b3 | c4 |
| 1149 | a 6 | b3 | c4 |
| 1150 | a 7 | b3 | c4 |
| 1151 | a 8 | b3 | c4 |
| 1152 | a 9 | b3 | c4 |
| 1153 | a10 | b3 | c4 |
| 1154 | a11 | b3 | c4 |
| 1155 | a12 | b3 | c4 |
| 1156 | a13 | b3 | c4 |
| 1157 | a14 | b3 | c4 |
| 1158 | a15 | b3 | c4 |
| 1159 | a16 | b3 | c4 |
| 1160 | a17 | b3 | c4 |
| 1161 | a18 | b3 | c4 |
| 1162 | a19 | b3 | c4 |
| 1163 | a20 | b3 | c4 |
| 1164 | a21 | b3 | c4 |
| 1165 | a22 | b3 | c4 |
| 1166 | a23 | b3 | c4 |
| 1167 | a24 | b3 | c4 |
| 1168 | a25 | b3 | c4 |
| 1169 | a 1 | b4 | c4 |
| 1170 | a 2 | b4 | c4 |
| 1171 | a 3 | b4 | c4 |
| 1172 | a 4 | b4 | c4 |
| 1173 | a 5 | b4 | c4 |
| 1174 | a 6 | b4 | c4 |
| 1175 | a 7 | b4 | c4 |
| 1176 | a 8 | b4 | c4 |
| 1177 | a 9 | b4 | c4 |
| 1178 | a10 | b4 | c4 |
| 1179 | a11 | b4 | c4 |
| 1180 | a12 | b4 | c4 |
| 1181 | a13 | b4 | c4 |
| 1182 | a14 | b4 | c4 |

| No. | Cp | Bridge | Flu | | No. | Cp | Bridge | Flu |
|---|---|---|---|---|---|---|---|---|
| 1183 | a15 | b4 | c4 | | 1260 | a17 | b 7 | c4 |
| 1184 | a16 | b4 | c4 | | 1261 | a18 | b 7 | c4 |
| 1185 | a17 | b4 | c4 | | 1262 | a19 | b 7 | c4 |
| 1186 | a18 | b4 | c4 | | 1263 | a20 | b 7 | c4 |
| 1187 | a19 | b4 | c4 | | 1264 | a21 | b 7 | c4 |
| 1188 | a20 | b4 | c4 | | 1265 | a22 | b 7 | c4 |
| 1189 | a21 | b4 | c4 | | 1266 | a23 | b 7 | c4 |
| 1190 | a22 | b4 | c4 | | 1267 | a24 | b 7 | c4 |
| 1191 | a23 | b4 | c4 | | 1268 | a25 | b 7 | c4 |
| 1192 | a24 | b4 | c4 | | 1269 | a 5 | b 8 | c4 |
| 1193 | a25 | b4 | c4 | | 1270 | a 6 | b 8 | c4 |
| 1194 | a 1 | b5 | c4 | | 1271 | a 7 | b 8 | c4 |
| 1195 | a 2 | b5 | c4 | | 1272 | a 8 | b 8 | c4 |
| 1196 | a 3 | b5 | c4 | | 1273 | a 9 | b 8 | c4 |
| 1197 | a 4 | b5 | c4 | | 1274 | a10 | b 8 | c4 |
| 1198 | a 5 | b5 | c4 | | 1275 | a11 | b 8 | c4 |
| 1199 | a 6 | b5 | c4 | | 1276 | a12 | b 8 | c4 |
| 1200 | a 7 | b5 | c4 | | 1277 | a13 | b 8 | c4 |
| 1201 | a 8 | b5 | c4 | | 1278 | a14 | b 8 | c4 |
| 1202 | a 9 | b5 | c4 | | 1279 | a15 | b 8 | c4 |
| 1203 | a10 | b5 | c4 | | 1280 | a16 | b 8 | c4 |
| 1204 | a11 | b5 | c4 | | 1281 | a17 | b 8 | c4 |
| 1205 | a12 | b5 | c4 | | 1282 | a18 | b 8 | c4 |
| 1206 | a13 | b5 | c4 | | 1283 | a19 | b 8 | c4 |
| 1207 | a14 | b5 | c4 | | 1284 | a20 | b 8 | c4 |
| 1208 | a15 | b5 | c4 | | 1285 | a21 | b 8 | c4 |
| 1209 | a16 | b5 | c4 | | 1286 | a22 | b 8 | c4 |
| 1210 | a17 | b5 | c4 | | 1287 | a23 | b 8 | c4 |
| 1211 | a18 | b5 | c4 | | 1288 | a24 | b 8 | c4 |
| 1212 | a19 | b5 | c4 | | 1289 | a25 | b 8 | c4 |
| 1213 | a20 | b5 | c4 | | 1290 | a 5 | b 9 | c4 |
| 1214 | a21 | b5 | c4 | | 1291 | a 6 | b 9 | c4 |
| 1215 | a22 | b5 | c4 | | 1292 | a 7 | b 9 | c4 |
| 1216 | a23 | b5 | c4 | | 1293 | a 8 | b 9 | c4 |
| 1217 | a24 | b5 | c4 | | 1294 | a 9 | b 9 | c4 |
| 1218 | a25 | b5 | c4 | | 1295 | a10 | b 9 | c4 |
| 1219 | a 1 | b6 | c4 | | 1296 | a11 | b 9 | c4 |
| 1220 | a 2 | b6 | c4 | | 1297 | a12 | b 9 | c4 |
| 1221 | a 3 | b6 | c4 | | 1298 | a13 | b 9 | c4 |
| 1222 | a 4 | b6 | c4 | | 1299 | a14 | b 9 | c4 |
| 1223 | a 5 | b6 | c4 | | 1300 | a15 | b 9 | c4 |
| 1224 | a 6 | b6 | c4 | | 1301 | a16 | b 9 | c4 |
| 1225 | a 7 | b6 | c4 | | 1302 | a17 | b 9 | c4 |
| 1226 | a 8 | b6 | c4 | | 1303 | a18 | b 9 | c4 |
| 1227 | a 9 | b6 | c4 | | 1304 | a19 | b 9 | c4 |
| 1228 | a10 | b6 | c4 | | 1305 | a20 | b 9 | c4 |
| 1229 | a11 | b6 | c4 | | 1306 | a21 | b 9 | c4 |
| 1230 | a12 | b6 | c4 | | 1307 | a22 | b 9 | c4 |
| 1231 | a13 | b6 | c4 | | 1308 | a23 | b 9 | c4 |
| 1232 | a14 | b6 | c4 | | 1309 | a24 | b 9 | c4 |
| 1233 | a15 | b6 | c4 | | 1310 | a25 | b 9 | c4 |
| 1234 | a16 | b6 | c4 | | 1311 | a 5 | b10 | c4 |
| 1235 | a17 | b6 | c4 | | 1312 | a 6 | b10 | c4 |
| 1236 | a18 | b6 | c4 | | 1313 | a 7 | b10 | c4 |
| 1237 | a19 | b6 | c4 | | 1314 | a 8 | b10 | c4 |
| 1238 | a20 | b6 | c4 | | 1315 | a 9 | b10 | c4 |
| 1239 | a21 | b6 | c4 | | 1316 | a10 | b10 | c4 |
| 1240 | a22 | b6 | c4 | | 1317 | a11 | b10 | c4 |
| 1241 | a23 | b6 | c4 | | 1318 | a12 | b10 | c4 |
| 1242 | a24 | b6 | c4 | | 1319 | a13 | b10 | c4 |
| 1243 | a25 | b6 | c4 | | 1320 | a14 | b10 | c4 |
| 1244 | a 1 | b7 | c4 | | 1321 | a15 | b10 | c4 |
| 1245 | a 2 | b7 | c4 | | 1322 | a16 | b10 | c4 |
| 1246 | a 3 | b7 | c4 | | 1323 | a17 | b10 | c4 |
| 1247 | a 4 | b7 | c4 | | 1324 | a18 | b10 | c4 |
| 1248 | a 5 | b7 | c4 | | 1325 | a19 | b10 | c4 |
| 1249 | a 6 | b7 | c4 | | 1326 | a20 | b10 | c4 |
| 1250 | a 7 | b7 | c4 | | 1327 | a21 | b10 | c4 |
| 1251 | a 8 | b7 | c4 | | 1328 | a22 | b10 | c4 |
| 1252 | a 9 | b7 | c4 | | 1329 | a23 | b10 | c4 |
| 1253 | a10 | b7 | c4 | | 1330 | a24 | b10 | c4 |
| 1254 | a11 | b7 | c4 | | 1331 | a25 | b10 | c4 |
| 1255 | a12 | b7 | c4 | | 1332 | a 5 | b11 | c4 |
| 1256 | a13 | b7 | c4 | | 1333 | a 6 | b11 | c4 |
| 1257 | a14 | b7 | c4 | | 1334 | a 7 | b11 | c4 |
| 1258 | a15 | b7 | c4 | | 1335 | a 8 | b11 | c4 |
| 1259 | a16 | b7 | c4 | | 1336 | a 9 | b11 | c4 |

| No. | Cp | Bridge | Flu |
|---|---|---|---|
| 1337 | a10 | b11 | c4 |
| 1338 | a11 | b11 | c4 |
| 1339 | a12 | b11 | c4 |
| 1340 | a13 | b11 | c4 |
| 1341 | a14 | b11 | c4 |
| 1342 | a15 | b11 | c4 |
| 1343 | a16 | b11 | c4 |
| 1344 | a17 | b11 | c4 |
| 1345 | a18 | b11 | c4 |
| 1346 | a19 | b11 | c4 |
| 1347 | a20 | b11 | c4 |
| 1348 | a21 | b11 | c4 |
| 1349 | a22 | b11 | c4 |
| 1350 | a23 | b11 | c4 |
| 1351 | a24 | b11 | c4 |
| 1352 | a25 | b11 | c4 |
| 1353 | a 1 | b12 | c4 |
| 1354 | a 2 | b12 | c4 |
| 1355 | a 3 | b12 | c4 |
| 1356 | a 4 | b12 | c4 |
| 1357 | a 5 | b12 | c4 |
| 1358 | a 8 | b12 | c4 |
| 1359 | a 7 | b12 | c4 |
| 1360 | a 8 | b12 | c4 |
| 1361 | a 9 | b12 | c4 |
| 1362 | a10 | b12 | c4 |
| 1363 | a11 | b12 | c4 |
| 1364 | a12 | b12 | c4 |
| 1365 | a13 | b12 | c4 |
| 1366 | a14 | b12 | c4 |
| 1367 | a15 | b12 | c4 |
| 1368 | a16 | b12 | c4 |
| 1369 | a17 | b12 | c4 |
| 1370 | a18 | b12 | c4 |
| 1371 | a19 | b12 | c4 |
| 1372 | a20 | b12 | c4 |
| 1373 | a21 | b12 | c4 |
| 1374 | a22 | b12 | c4 |
| 1375 | a23 | b12 | c4 |
| 1376 | a24 | b12 | c4 |
| 1377 | a25 | b12 | c4 |
| 1378 | a 1 | b13 | c4 |
| 1379 | a 2 | b13 | c4 |
| 1380 | a 3 | b13 | c4 |
| 1381 | a 4 | b13 | c4 |
| 1382 | a 5 | b13 | c4 |
| 1383 | a 6 | b13 | c4 |
| 1384 | a 7 | b13 | c4 |
| 1385 | a 8 | b13 | c4 |
| 1386 | a 9 | b13 | c4 |
| 1387 | a10 | b13 | c4 |
| 1388 | a11 | b13 | c4 |
| 1389 | a12 | b13 | c4 |
| 1390 | a13 | b13 | c4 |
| 1391 | a14 | b13 | c4 |
| 1392 | a15 | b13 | c4 |
| 1393 | a16 | b13 | c4 |
| 1394 | a17 | b13 | c4 |
| 1395 | a18 | b13 | c4 |
| 1396 | a19 | b13 | c4 |
| 1397 | a20 | b13 | c4 |
| 1398 | a21 | b13 | c4 |
| 1399 | a22 | b13 | c4 |
| 1400 | a23 | b13 | c4 |
| 1401 | a24 | b13 | c4 |
| 1402 | a25 | b13 | c4 |
| 1403 | a 1 | b14 | c4 |
| 1404 | a 2 | b14 | c4 |
| 1405 | a 3 | b14 | c4 |
| 1406 | a 4 | b14 | c4 |
| 1407 | a 5 | b14 | c4 |
| 1408 | a 6 | b14 | c4 |
| 1409 | a 7 | b14 | c4 |
| 1410 | a 8 | b14 | c4 |
| 1411 | a 9 | b14 | c4 |
| 1412 | a10 | b14 | c4 |
| 1413 | a11 | b14 | c4 |
| 1414 | a12 | b14 | c4 |
| 1415 | a13 | b14 | c4 |
| 1416 | a14 | b14 | c4 |
| 1417 | a15 | b14 | c4 |
| 1418 | a16 | b14 | c4 |
| 1419 | a17 | b14 | c4 |
| 1420 | a18 | b14 | c4 |
| 1421 | a19 | b14 | c4 |
| 1422 | a20 | b14 | c4 |
| 1423 | a21 | b14 | c4 |
| 1424 | a22 | b14 | c4 |
| 1425 | a23 | b14 | c4 |
| 1426 | a24 | b14 | c4 |
| 1427 | a25 | b14 | c4 |
| 1428 | a 1 | b15 | c4 |
| 1429 | a 2 | b15 | c4 |
| 1430 | a 3 | b15 | c4 |
| 1431 | a 4 | b15 | c4 |
| 1432 | a 5 | b15 | c4 |
| 1433 | a 6 | b15 | c4 |
| 1434 | a 7 | b15 | c4 |
| 1435 | a 8 | b15 | c4 |
| 1436 | a 9 | b15 | c4 |
| 1437 | a10 | b15 | c4 |
| 1438 | a11 | b15 | c4 |
| 1439 | a12 | b15 | c4 |
| 1440 | a13 | b15 | c4 |
| 1441 | a14 | b15 | c4 |
| 1442 | a15 | b15 | c4 |
| 1443 | a16 | b15 | c4 |
| 1444 | a17 | b15 | c4 |
| 1445 | a18 | b15 | c4 |
| 1446 | a19 | b15 | c4 |
| 1447 | a20 | b15 | c4 |
| 1448 | a21 | b15 | c4 |
| 1449 | a22 | b15 | c4 |
| 1450 | a23 | b15 | c4 |
| 1451 | a24 | b15 | c4 |
| 1452 | a25 | b15 | c4 |
| 1453 | a 1 | b 1 | c5 |
| 1454 | a 2 | b 1 | c5 |
| 1455 | a 3 | b 1 | c5 |
| 1456 | a 4 | b 1 | c5 |
| 1457 | a 5 | b 1 | c5 |
| 1458 | a 6 | b 1 | c5 |
| 1459 | a 7 | b 1 | c5 |
| 1460 | a 8 | b 1 | c5 |
| 1461 | a 9 | b 1 | c5 |
| 1462 | a10 | b 1 | c5 |
| 1464 | a12 | b 1 | c5 |
| 1465 | a13 | b 1 | c5 |
| 1466 | a14 | b 1 | c5 |
| 1467 | a15 | b 1 | c5 |
| 1468 | a16 | b 1 | c5 |
| 1469 | a17 | b 1 | c5 |
| 1470 | a18 | b 1 | c5 |
| 1471 | a19 | b 1 | c5 |
| 1472 | a20 | b 1 | c5 |
| 1473 | a21 | b 1 | c5 |
| 1474 | a22 | b 1 | c5 |
| 1475 | a23 | b 1 | c5 |
| 1476 | a24 | b 1 | c5 |
| 1477 | a25 | b 1 | c5 |
| 1478 | a 1 | b 2 | c5 |
| 1479 | a 2 | b 2 | c5 |
| 1480 | a 3 | b 2 | c5 |
| 1481 | a 4 | b 2 | c5 |
| 1482 | a 5 | b 2 | c5 |
| 1483 | a 6 | b 2 | c5 |
| 1484 | a 7 | b 2 | c5 |
| 1485 | a 5 | b 2 | c5 |
| 1486 | a 9 | b 2 | c5 |
| 1487 | a10 | b 2 | c5 |
| 1488 | a11 | b 2 | c5 |
| 1489 | a12 | b 2 | c5 |
| 1490 | a13 | b 2 | c5 |
| 1491 | a14 | b 2 | c5 |

| No. | Cp | Bridge | Flu | No. | Cp | Bridge | Flu |
|---|---|---|---|---|---|---|---|
| 1492 | a15 | b2 | c5 | 1569 | a17 | b5 | c5 |
| 1493 | a16 | b2 | c5 | 1570 | a18 | b5 | c5 |
| 1494 | a17 | b2 | c5 | 1571 | a19 | b5 | c5 |
| 1495 | a18 | b2 | c5 | 1572 | a20 | b5 | c5 |
| 1496 | a19 | b2 | c5 | 1573 | a21 | b5 | c5 |
| 1497 | a20 | b2 | c5 | 1574 | a22 | b5 | c5 |
| 1498 | a21 | b2 | c5 | 1575 | a23 | b5 | c5 |
| 1499 | a22 | b2 | c5 | 1576 | a24 | b5 | c5 |
| 1500 | a23 | b2 | c5 | 1577 | a25 | b5 | c5 |
| 1501 | a24 | b2 | c5 | 1578 | a 1 | b6 | c5 |
| 1502 | a25 | b2 | c5 | 1579 | a 2 | b6 | c5 |
| 1503 | a 1 | b3 | c5 | 1580 | a 3 | b6 | c5 |
| 1504 | a 2 | b3 | c5 | 1581 | a 4 | b6 | c5 |
| 1505 | a 3 | b3 | c5 | 1582 | a 5 | b6 | c5 |
| 1506 | a 4 | b3 | c5 | 1583 | a 6 | b6 | c5 |
| 1507 | a 5 | b3 | c5 | 1584 | a 7 | b6 | c5 |
| 1508 | a 6 | b3 | c5 | 1585 | a 8 | b6 | c5 |
| 1509 | a 7 | b3 | c5 | 1586 | a 9 | b6 | c5 |
| 1510 | a 8 | b3 | c5 | 1587 | a10 | b6 | c5 |
| 1511 | a 9 | b3 | c5 | 1588 | a11 | b6 | c5 |
| 1512 | a10 | b3 | c5 | 1589 | a12 | b6 | c5 |
| 1513 | a11 | b3 | c5 | 1590 | a13 | b6 | c5 |
| 1514 | a12 | b3 | c5 | 1591 | a14 | b6 | c5 |
| 1515 | a13 | b3 | c5 | 1592 | a15 | b6 | c5 |
| 1516 | a14 | b3 | c5 | 1593 | a16 | b6 | c5 |
| 1517 | a15 | b3 | c5 | 1594 | a17 | b6 | c5 |
| 1518 | a16 | b3 | c5 | 1595 | a18 | b6 | c5 |
| 1519 | a17 | b3 | c5 | 1596 | a19 | b6 | c5 |
| 1520 | a18 | b3 | c5 | 1597 | a20 | b6 | c5 |
| 1521 | a19 | b3 | c5 | 1598 | a21 | b6 | c5 |
| 1522 | a20 | b3 | c5 | 1599 | a22 | b6 | c5 |
| 1523 | a21 | b3 | c5 | 1600 | a23 | b6 | c5 |
| 1524 | a22 | b3 | c5 | 1601 | a24 | b6 | c5 |
| 1525 | a23 | b3 | c5 | 1602 | a25 | b6 | c5 |
| 1526 | a24 | b3 | c5 | 1603 | a 1 | b7 | c5 |
| 1527 | a25 | b3 | c5 | 1604 | a 2 | b7 | c5 |
| 1528 | a 1 | b4 | c5 | 1605 | a 3 | b7 | c5 |
| 1529 | a 2 | b4 | c5 | 1606 | a 4 | b7 | c5 |
| 1530 | a 3 | b4 | c5 | 1607 | a 5 | b7 | c5 |
| 1531 | a 4 | b4 | c5 | 1608 | a 6 | b7 | c5 |
| 1532 | a 5 | b4 | c5 | 1609 | a 7 | b7 | c5 |
| 1533 | a 6 | b4 | c5 | 1610 | a 6 | b7 | c5 |
| 1534 | a 7 | b4 | c5 | 1611 | a 9 | b7 | c5 |
| 1535 | a 8 | b4 | c5 | 1612 | a10 | b7 | c5 |
| 1536 | a 9 | b4 | c5 | 1613 | a11 | b7 | c5 |
| 1537 | a10 | b4 | c5 | 1614 | a12 | b7 | c5 |
| 1538 | a11 | b4 | c5 | 1615 | a13 | b7 | c5 |
| 1539 | a12 | b4 | c5 | 1616 | a14 | b7 | c5 |
| 1540 | a13 | b4 | c5 | 1617 | a15 | b7 | c5 |
| 1541 | a14 | b4 | c5 | 1618 | a16 | b7 | c5 |
| 1542 | a15 | b4 | c5 | 1619 | a17 | b7 | c5 |
| 1543 | a16 | b4 | c5 | 1620 | a18 | b7 | c5 |
| 1544 | a17 | b4 | c5 | 1621 | a19 | b7 | c5 |
| 1545 | a18 | b4 | c5 | 1622 | a20 | b7 | c5 |
| 1546 | a19 | b4 | c5 | 1623 | a21 | b7 | c5 |
| 1547 | a20 | b4 | c5 | 1624 | a22 | b7 | c5 |
| 1548 | a21 | b4 | c5 | 1625 | a23 | b7 | c5 |
| 1549 | a22 | b4 | c5 | 1626 | a24 | b7 | c5 |
| 1550 | a23 | b4 | c5 | 1627 | a25 | b7 | c5 |
| 1551 | a24 | b4 | c5 | 1628 | a 5 | b8 | c5 |
| 1552 | a25 | b4 | c5 | 1629 | a 6 | b8 | c5 |
| 1553 | a 1 | b5 | c5 | 1630 | a 7 | b8 | c5 |
| 1554 | a 2 | b5 | c5 | 1631 | a 8 | b8 | c5 |
| 1555 | a 3 | b5 | c5 | 1632 | a 9 | b8 | c5 |
| 1556 | a 4 | b5 | c5 | 1633 | a10 | b8 | c5 |
| 1557 | a 5 | b5 | c5 | 1634 | a11 | b8 | c5 |
| 1558 | a 6 | b5 | c5 | 1635 | a12 | b8 | c5 |
| 1559 | a 7 | b5 | c5 | 1636 | a13 | b8 | c5 |
| 1560 | a 8 | b5 | c5 | 1637 | a14 | b8 | c5 |
| 1561 | a 9 | b5 | c5 | 1638 | a15 | b8 | c5 |
| 1562 | a10 | b5 | c5 | 1639 | a16 | b8 | c5 |
| 1563 | a11 | b5 | c5 | 1640 | a17 | b8 | c5 |
| 1564 | a12 | b5 | c5 | 1641 | a18 | b8 | c5 |
| 1565 | a13 | b5 | c5 | 1642 | a19 | b8 | c5 |
| 1566 | a14 | b5 | c5 | 1643 | a20 | b8 | c5 |
| 1567 | a15 | b5 | c5 | 1644 | a21 | b8 | c5 |
| 1568 | a16 | b5 | c5 | 1645 | a22 | b8 | c5 |

| No. | Cp | Bridge | Flu |
|---|---|---|---|
| 1646 | a23 | b 8 | c5 |
| 1647 | a24 | b 8 | c5 |
| 1648 | a25 | b 8 | c5 |
| 1649 | a 5 | b 9 | c5 |
| 1650 | a 6 | b 9 | c5 |
| 1651 | a 7 | b 9 | c5 |
| 1652 | a 6 | b 9 | c5 |
| 1653 | a 9 | b 9 | c5 |
| 1654 | a10 | b 9 | c5 |
| 1655 | a11 | b 9 | c5 |
| 1656 | a12 | b 9 | c5 |
| 1657 | a13 | b 9 | c5 |
| 1658 | a14 | b 9 | c5 |
| 1659 | a15 | b 9 | c5 |
| 1660 | a16 | b 9 | c5 |
| 1661 | a17 | b 9 | c5 |
| 1662 | a18 | b 9 | c5 |
| 1663 | a19 | b 9 | c5 |
| 1664 | a20 | b 9 | c5 |
| 1665 | a21 | b 9 | c5 |
| 1666 | a22 | b 9 | c5 |
| 1667 | a23 | b 9 | c5 |
| 1668 | a24 | b 9 | c5 |
| 1669 | a25 | b 9 | c5 |
| 1670 | a 5 | b10 | c5 |
| 1671 | a 6 | b10 | c5 |
| 1672 | a 7 | b10 | c5 |
| 1673 | a 8 | b10 | c5 |
| 1674 | a 9 | b10 | c5 |
| 1675 | a10 | b10 | c5 |
| 1676 | a11 | b10 | c5 |
| 1677 | a12 | b10 | c5 |
| 1678 | a13 | b10 | c5 |
| 1679 | a14 | b10 | c5 |
| 1680 | a15 | b10 | c5 |
| 1681 | a16 | b10 | c5 |
| 1682 | a17 | b10 | c5 |
| 1683 | a18 | b10 | c5 |
| 1684 | a19 | b10 | c5 |
| 1685 | a20 | b10 | c5 |
| 1686 | a21 | b10 | c5 |
| 1687 | a22 | b10 | c5 |
| 1688 | a23 | b10 | c5 |
| 1689 | a24 | b10 | c5 |
| 1690 | a25 | b10 | c5 |
| 1691 | a 5 | b11 | c5 |
| 1692 | a 6 | b11 | c5 |
| 1693 | a 7 | b11 | c5 |
| 1694 | a 8 | b11 | c5 |
| 1695 | a 9 | b11 | c5 |
| 1696 | a10 | b11 | c5 |
| 1697 | a11 | b11 | c5 |
| 1698 | a12 | b11 | c5 |
| 1699 | a13 | b11 | c5 |
| 1700 | a14 | b11 | c5 |
| 1701 | a15 | b11 | c5 |
| 1702 | a16 | b11 | c5 |
| 1703 | a17 | b11 | c5 |
| 1704 | a18 | b11 | c5 |
| 1705 | a19 | b11 | c5 |
| 1706 | a20 | b11 | c5 |
| 1707 | a21 | b11 | c5 |
| 1708 | a22 | b11 | c5 |
| 1709 | a23 | b11 | c5 |
| 1710 | a24 | b11 | c5 |
| 1711 | a25 | b11 | c5 |
| 1712 | a 1 | b12 | c5 |
| 1713 | a 2 | b12 | c5 |
| 1714 | a 3 | b12 | c5 |
| 1715 | a 4 | b12 | c5 |
| 1716 | a 5 | b12 | c5 |
| 1717 | a 6 | b12 | c5 |
| 1718 | a 7 | b12 | c5 |
| 1719 | a 8 | b12 | c5 |
| 1720 | a 9 | b12 | c5 |
| 1721 | a10 | b12 | c5 |
| 1722 | a11 | b12 | c5 |
| 1723 | a12 | b12 | c5 |
| 1724 | a13 | b12 | c5 |
| 1725 | a14 | b12 | c5 |
| 1726 | a15 | b12 | c5 |
| 1727 | a16 | b12 | c5 |
| 1728 | a17 | b12 | c5 |
| 1729 | a18 | b12 | c5 |
| 1730 | a19 | b12 | c5 |
| 1731 | a20 | b12 | c5 |
| 1732 | a21 | b12 | c5 |
| 1733 | a22 | b12 | c5 |
| 1734 | a23 | b12 | c5 |
| 1735 | a24 | b12 | c5 |
| 1736 | a25 | b12 | c5 |
| 1737 | a 1 | b13 | c5 |
| 1738 | a 2 | b13 | c5 |
| 1739 | a 3 | b13 | c5 |
| 1740 | a 4 | b13 | c5 |
| 1741 | a 5 | b13 | c5 |
| 1742 | a 6 | b13 | c5 |
| 1743 | a 7 | b13 | c5 |
| 1744 | a 8 | b13 | c5 |
| 1745 | a 9 | b13 | c5 |
| 1746 | a10 | b13 | c5 |
| 1747 | a11 | b13 | c5 |
| 1748 | a12 | b13 | c5 |
| 1749 | a13 | b13 | c5 |
| 1750 | a14 | b13 | c5 |
| 1751 | a15 | b13 | c5 |
| 1752 | a16 | b13 | c5 |
| 1753 | a17 | b13 | c5 |
| 1754 | a15 | b13 | c5 |
| 1755 | a19 | b13 | c5 |
| 1756 | a20 | b13 | c5 |
| 1757 | a21 | b13 | c5 |
| 1758 | a22 | b13 | c5 |
| 1759 | a23 | b13 | c5 |
| 1760 | a24 | b13 | c5 |
| 1761 | a25 | b13 | c5 |
| 1762 | a 1 | b14 | c5 |
| 1763 | a 2 | b14 | c5 |
| 1764 | a 3 | b14 | c5 |
| 1765 | a 4 | b14 | c5 |
| 1766 | a 5 | b14 | c5 |
| 1767 | a 6 | b14 | c5 |
| 1768 | a 7 | b14 | c5 |
| 1769 | a 8 | b14 | c5 |
| 1770 | a 9 | b14 | c5 |
| 1771 | a10 | b14 | c5 |
| 1772 | a11 | b14 | c5 |
| 1773 | a12 | b14 | c5 |
| 1774 | a13 | b14 | c5 |
| 1775 | a14 | b14 | c5 |
| 1776 | a15 | b14 | c5 |
| 1777 | a16 | b14 | c5 |
| 1778 | a17 | b14 | c5 |
| 1779 | a18 | b14 | c5 |
| 1780 | a19 | b14 | c5 |
| 1781 | a20 | b14 | c5 |
| 1782 | a21 | b14 | c5 |
| 1783 | a22 | b14 | c5 |
| 1784 | a23 | b14 | c5 |
| 1785 | a24 | b14 | c5 |
| 1786 | a25 | b14 | c5 |
| 1787 | a 1 | b15 | c5 |
| 1788 | a 2 | b15 | c5 |
| 1789 | a 3 | b15 | c5 |
| 1790 | a 4 | b15 | c5 |
| 1791 | a 5 | b15 | c5 |
| 1792 | a 6 | b15 | c5 |
| 1793 | a 7 | b15 | c5 |
| 1794 | a 8 | b15 | c5 |
| 1795 | a 9 | b15 | c5 |
| 1796 | a10 | b15 | c5 |
| 1797 | a11 | b15 | c5 |
| 1798 | a12 | b15 | c5 |
| 1799 | a13 | b15 | c5 |

-continued

| No. | Cp | Bridge | Flu |
|---|---|---|---|
| 1800 | a14 | b15 | c5 |
| 1801 | a15 | b15 | c5 |
| 1802 | a16 | b15 | c5 |
| 1803 | a17 | b15 | c5 |
| 1804 | a18 | b15 | c5 |
| 1805 | a19 | b15 | c5 |
| 1806 | a20 | b15 | c5 |
| 1807 | a21 | b15 | c5 |
| 1808 | a22 | b15 | c5 |
| 1809 | a23 | b15 | c5 |
| 1810 | a24 | b15 | c5 |
| 1811 | a25 | b15 | c5 |
| 1812 | a 1 | b 1 | c6 |
| 1813 | a 2 | b 1 | c6 |
| 1814 | a 3 | b 1 | c6 |
| 1815 | a 4 | b 1 | c6 |
| 1816 | a 5 | b 1 | c6 |
| 1817 | a 6 | b 1 | c6 |
| 1818 | a 7 | b 1 | c6 |
| 1819 | a 8 | b 1 | c6 |
| 1820 | a 9 | b 1 | c6 |
| 1821 | a10 | b 1 | c6 |
| 1822 | a11 | b 1 | c6 |
| 1823 | a12 | b 1 | c6 |
| 1824 | a13 | b 1 | c6 |
| 1825 | a14 | b 1 | c6 |
| 1826 | a15 | b 1 | c6 |
| 1827 | a16 | b 1 | c6 |
| 1828 | a17 | b 1 | c6 |
| 1829 | a18 | b 1 | c6 |
| 1830 | a19 | b 1 | c6 |
| 1831 | a20 | b 1 | c6 |
| 1832 | a21 | b 1 | c6 |
| 1833 | a22 | b 1 | c6 |
| 1834 | a23 | b 1 | c6 |
| 1835 | a24 | b 1 | c6 |
| 1836 | a25 | b 1 | c6 |
| 1837 | a 1 | b 2 | c6 |
| 1838 | a 2 | b 2 | c6 |
| 1839 | a 3 | b 2 | c6 |
| 1840 | a 4 | b 2 | c6 |
| 1841 | a 5 | b 2 | c6 |
| 1842 | a 6 | b 2 | c6 |
| 1843 | a 7 | b 2 | c6 |
| 1844 | a 8 | b 2 | c6 |
| 1845 | a 9 | b 2 | c6 |
| 1846 | a10 | b 2 | c6 |
| 1847 | a11 | b 2 | c6 |
| 1848 | a12 | b 2 | c6 |
| 1849 | a13 | b 2 | c6 |
| 1850 | a14 | b 2 | c6 |
| 1851 | a15 | b 2 | c6 |
| 1852 | a16 | b 2 | c6 |
| 1853 | a17 | b 2 | c6 |
| 1854 | a18 | b 2 | c6 |
| 1855 | a19 | b 2 | c6 |
| 1856 | a20 | b 2 | c6 |
| 1857 | a21 | b 2 | c6 |
| 1858 | a22 | b 2 | c6 |
| 1859 | a23 | b 2 | c6 |
| 1860 | a24 | b 2 | c6 |
| 1861 | a25 | b 2 | c6 |
| 1862 | a 1 | b 3 | c6 |
| 1863 | a 2 | b 3 | c6 |
| 1864 | a 3 | b 3 | c6 |
| 1865 | a 4 | b 3 | c6 |
| 1866 | a 5 | b 3 | c6 |
| 1867 | a 6 | b 3 | c6 |
| 1868 | a 7 | b 3 | c6 |
| 1869 | a 8 | b 3 | c6 |
| 1870 | a 9 | b 3 | c6 |
| 1871 | a10 | b 3 | c6 |
| 1872 | a11 | b 3 | c6 |
| 1873 | a12 | b 3 | c6 |
| 1874 | a13 | b 3 | c6 |
| 1875 | a14 | b 3 | c6 |
| 1876 | a15 | b 3 | c6 |

-continued

| No. | Cp | Bridge | Flu |
|---|---|---|---|
| 1877 | a16 | b3 | c6 |
| 1878 | a17 | b3 | c6 |
| 1879 | a18 | b3 | c6 |
| 1880 | a19 | b3 | c6 |
| 1881 | a20 | b3 | c6 |
| 1882 | a21 | b3 | c6 |
| 1883 | a22 | b3 | c6 |
| 1884 | a23 | b3 | c6 |
| 1885 | a24 | b3 | c6 |
| 1886 | a25 | b3 | c6 |
| 1887 | a 1 | b4 | c6 |
| 1888 | a 2 | b4 | c6 |
| 1889 | a 3 | b4 | c6 |
| 1890 | a 4 | b4 | c6 |
| 1891 | a 5 | b4 | c6 |
| 1892 | a 6 | b4 | c6 |
| 1893 | a 7 | b4 | c6 |
| 1894 | a 8 | b4 | c6 |
| 1895 | a 9 | b4 | c6 |
| 1896 | a10 | b4 | c6 |
| 1897 | a11 | b4 | c6 |
| 1898 | a12 | b4 | c6 |
| 1899 | a13 | b4 | c6 |
| 1900 | a14 | b4 | c6 |
| 1901 | a15 | b4 | c6 |
| 1902 | a16 | b4 | c6 |
| 1903 | a17 | b4 | c6 |
| 1904 | a18 | b4 | c6 |
| 1905 | a19 | b4 | c6 |
| 1906 | a20 | b4 | c6 |
| 1907 | a21 | b4 | c6 |
| 1908 | a22 | b4 | c6 |
| 1909 | a23 | b4 | c6 |
| 1910 | a24 | b4 | c6 |
| 1911 | a25 | b4 | c6 |
| 1912 | a 1 | b5 | c6 |
| 1913 | a 2 | b5 | c6 |
| 1914 | a 3 | b5 | c6 |
| 1915 | a 4 | b5 | c6 |
| 1916 | a 5 | b5 | c6 |
| 1917 | a 6 | b5 | c6 |
| 1918 | a 7 | b5 | c6 |
| 1919 | a 8 | b5 | c6 |
| 1920 | a 9 | b5 | c6 |
| 1921 | a10 | b5 | c6 |
| 1922 | a11 | b5 | c6 |
| 1923 | a12 | b5 | c6 |
| 1924 | a13 | b5 | c6 |
| 1925 | a14 | b5 | c6 |
| 1926 | a15 | b5 | c6 |
| 1927 | a16 | b5 | c6 |
| 1928 | a17 | b5 | c6 |
| 1929 | a18 | b5 | c6 |
| 1930 | a19 | b5 | c6 |
| 1931 | a20 | b5 | c6 |
| 1932 | a21 | b5 | c6 |
| 1933 | a22 | b5 | c6 |
| 1934 | a23 | b5 | c6 |
| 1935 | a24 | b5 | c6 |
| 1936 | a25 | b5 | c6 |
| 1937 | a 1 | b6 | c6 |
| 1938 | a 2 | b6 | c6 |
| 1939 | a 3 | b6 | c6 |
| 1940 | a 4 | b6 | c6 |
| 1941 | a 5 | b6 | c6 |
| 1942 | a 6 | b6 | c6 |
| 1943 | a 7 | b6 | c6 |
| 1944 | a 8 | b6 | c6 |
| 1945 | a 9 | b6 | c6 |
| 1946 | a10 | b6 | c6 |
| 1947 | a11 | b6 | c6 |
| 1948 | a12 | b6 | c6 |
| 1949 | a13 | b6 | c6 |
| 1950 | a14 | b6 | c6 |
| 1951 | a15 | b6 | c6 |
| 1952 | a16 | b6 | c6 |
| 1953 | a17 | b6 | c6 |

-continued

| No. | Cp | Bridge | Flu |
|---|---|---|---|
| 1954 | a18 | b6 | c6 |
| 1955 | a19 | b6 | c6 |
| 1956 | a20 | b6 | c6 |
| 1957 | a21 | b6 | c6 |
| 1958 | a22 | b6 | c6 |
| 1959 | a23 | b6 | c6 |
| 1960 | a24 | b6 | c6 |
| 1961 | a25 | b6 | c6 |
| 1962 | a 1 | b7 | c6 |
| 1963 | a 2 | b7 | c6 |
| 1964 | a 3 | b7 | c6 |
| 1965 | a 4 | b7 | c6 |
| 1966 | a 5 | b7 | c6 |
| 1967 | a 6 | b7 | c6 |
| 1968 | a 7 | b7 | c6 |
| 1969 | a 8 | b7 | c6 |
| 1970 | a 9 | b7 | c6 |
| 1971 | a10 | b7 | c6 |
| 1972 | a11 | b7 | c6 |
| 1973 | a12 | b7 | c6 |
| 1974 | a13 | b7 | c6 |
| 1975 | a14 | b7 | c6 |
| 1976 | a15 | b7 | c6 |
| 1977 | a16 | b7 | c6 |
| 1978 | a17 | b7 | c6 |
| 1979 | a18 | b7 | c6 |
| 1980 | a19 | b7 | c6 |
| 1981 | a20 | b7 | c6 |
| 1982 | a21 | b7 | c6 |
| 1983 | a22 | b7 | c6 |
| 1984 | a23 | b7 | c6 |
| 1985 | a24 | b7 | c6 |
| 1986 | a25 | b7 | c6 |
| 1987 | a 1 | b8 | c6 |
| 1988 | a 2 | b8 | c6 |
| 1989 | a 3 | b8 | c6 |
| 1990 | a 4 | b8 | c6 |
| 1991 | a 5 | b8 | c6 |
| 1992 | a 6 | b8 | c6 |
| 1993 | a 7 | b8 | c6 |
| 1994 | a 8 | b8 | c6 |
| 1995 | a 9 | b8 | c6 |
| 1996 | a10 | b8 | c6 |
| 1997 | a11 | b8 | c6 |
| 1998 | a12 | b8 | c6 |
| 1999 | a13 | b8 | c6 |
| 2000 | a14 | b8 | c6 |
| 2001 | a15 | b8 | c6 |
| 2002 | a16 | b8 | c6 |
| 2003 | a17 | b8 | c6 |
| 2004 | a18 | b8 | c6 |
| 2005 | a19 | b8 | c6 |
| 2006 | a20 | b8 | c6 |
| 2007 | a21 | b8 | c6 |
| 2008 | a22 | b8 | c6 |
| 2009 | a23 | b8 | c6 |
| 2010 | a24 | b8 | c6 |
| 2011 | a25 | b8 | c6 |
| 2012 | a 1 | b9 | c6 |
| 2013 | a 2 | b9 | c6 |
| 2014 | a 3 | b9 | c6 |
| 2015 | a 4 | b9 | c6 |
| 2016 | a 5 | b9 | c6 |
| 2017 | a 6 | b9 | c6 |
| 2018 | a 7 | b9 | c6 |
| 2019 | a 8 | b9 | c6 |
| 2020 | a 9 | b9 | c6 |
| 2021 | a10 | b9 | c6 |
| 2022 | a11 | b9 | c6 |
| 2023 | a12 | b9 | c6 |
| 2024 | a13 | b9 | c6 |
| 2025 | a14 | b9 | c6 |
| 2026 | a15 | b9 | c6 |
| 2027 | a16 | b9 | c6 |
| 2028 | a17 | b9 | c6 |
| 2029 | a18 | b9 | c6 |
| 2030 | a19 | b9 | c6 |
| 2031 | a20 | b 9 | c6 |
| 2032 | a21 | b 9 | c6 |
| 2033 | a22 | b 9 | c6 |
| 2034 | a23 | b 9 | c6 |
| 2035 | a24 | b 9 | c6 |
| 2036 | a25 | b 9 | c6 |
| 2037 | a 1 | b10 | c6 |
| 2038 | a 2 | b10 | c6 |
| 2039 | a 3 | b10 | c6 |
| 2040 | a 4 | b10 | c6 |
| 2041 | a 5 | b10 | c6 |
| 2042 | a 6 | b10 | c6 |
| 2043 | a 7 | b10 | c6 |
| 2044 | a 8 | b10 | c6 |
| 2045 | a 9 | b10 | c6 |
| 2046 | a10 | b10 | c6 |
| 2047 | a11 | b10 | c6 |
| 2048 | a12 | b10 | c6 |
| 2049 | a13 | b10 | c6 |
| 2050 | a14 | b10 | c6 |
| 2051 | a15 | b10 | c6 |
| 2052 | a16 | b10 | c6 |
| 2053 | a17 | b10 | c6 |
| 2054 | a18 | b10 | c6 |
| 2055 | a19 | b10 | c6 |
| 2056 | a20 | b10 | c6 |
| 2057 | a21 | b10 | c6 |
| 2058 | a22 | b10 | c6 |
| 2059 | a23 | b10 | c6 |
| 2060 | a24 | b10 | c6 |
| 2061 | a25 | b10 | c6 |
| 2062 | a 1 | b11 | c6 |
| 2063 | a 2 | b11 | c6 |
| 2064 | a 3 | b11 | c6 |
| 2065 | a 4 | b11 | c6 |
| 2066 | a 5 | b11 | c6 |
| 2067 | a 6 | b11 | c6 |
| 2068 | a 7 | b11 | c6 |
| 2069 | a 8 | b11 | c6 |
| 2070 | a 9 | b11 | c6 |
| 2071 | a10 | b11 | c6 |
| 2072 | a11 | b11 | c6 |
| 2073 | a12 | b11 | c6 |
| 2074 | a13 | b11 | c6 |
| 2075 | a14 | b11 | c6 |
| 2076 | a15 | b11 | c6 |
| 2077 | a16 | b11 | c6 |
| 2078 | a17 | b11 | c6 |
| 2079 | a18 | b11 | c6 |
| 2080 | a19 | b11 | c6 |
| 2081 | a20 | b11 | c6 |
| 2082 | a21 | b11 | c6 |
| 2083 | a22 | b11 | c6 |
| 2084 | a23 | b11 | c6 |
| 2085 | a24 | b11 | c6 |
| 2086 | a25 | b11 | c6 |
| 2087 | a 1 | b12 | c6 |
| 2088 | a 2 | b12 | c6 |
| 2089 | a 3 | b12 | c6 |
| 2090 | a 4 | b12 | c6 |
| 2091 | a 5 | b12 | c6 |
| 2092 | a 6 | b12 | c6 |
| 2093 | a 7 | b12 | c6 |
| 2094 | a 8 | b12 | c6 |
| 2095 | a 9 | b12 | c6 |
| 2096 | a10 | b12 | c6 |
| 2097 | a11 | b12 | c6 |
| 2098 | a12 | b12 | c6 |
| 2099 | a13 | b12 | c6 |
| 2100 | a14 | b12 | c6 |
| 2101 | a15 | b12 | c6 |
| 2102 | a16 | b12 | c6 |
| 2103 | a17 | b12 | c6 |
| 2104 | a18 | b12 | c6 |
| 2105 | a19 | b12 | c6 |
| 2106 | a20 | b12 | c6 |
| 2107 | a21 | b12 | c6 |

| No. | Cp | Bridge | Flu |
|---|---|---|---|
| 2108 | a22 | b12 | c6 |
| 2109 | a23 | b12 | c6 |
| 2110 | a24 | b12 | c6 |
| 2111 | a25 | b12 | c6 |
| 2112 | a 1 | b13 | c6 |
| 2113 | a 2 | b13 | c6 |
| 2114 | a 3 | b13 | c6 |
| 2115 | a 4 | b13 | c6 |
| 2116 | a 5 | b13 | c6 |
| 2117 | a 6 | b13 | c6 |
| 2118 | a 7 | b13 | c6 |
| 2119 | a 8 | b13 | c6 |
| 2120 | a 9 | b13 | c6 |
| 2121 | a10 | b13 | c6 |
| 2122 | a11 | b13 | c6 |
| 2123 | a12 | b13 | c6 |
| 2124 | a13 | b13 | c6 |
| 2125 | a14 | b13 | c6 |
| 2126 | a15 | b13 | c6 |
| 2127 | a16 | b13 | c6 |
| 2128 | a17 | b13 | c6 |
| 2129 | a18 | b13 | c6 |
| 2130 | a19 | b13 | c6 |
| 2131 | a20 | b13 | c6 |
| 2132 | a21 | b13 | c6 |
| 2133 | a22 | b13 | c6 |
| 2134 | a23 | b13 | c6 |
| 2135 | a24 | b13 | c6 |
| 2136 | a25 | b13 | c6 |
| 2137 | a 1 | b14 | c6 |
| 2138 | a 2 | b14 | c6 |
| 2139 | a 3 | b14 | c6 |
| 2140 | a 4 | b14 | c6 |
| 2141 | a 5 | b14 | c6 |
| 2142 | a 6 | b14 | c6 |
| 2143 | a 7 | b14 | c6 |
| 2144 | a 8 | b14 | c6 |
| 2145 | a 9 | b14 | c6 |
| 2146 | a10 | b14 | c6 |
| 2147 | a11 | b14 | c6 |
| 2148 | a12 | b14 | c6 |
| 2149 | a13 | b14 | c6 |
| 2150 | a14 | b14 | c6 |
| 2151 | a15 | b14 | c6 |
| 2152 | a16 | b14 | c6 |
| 2153 | a17 | b14 | c6 |
| 2154 | a18 | b14 | c6 |
| 2155 | a19 | b14 | c6 |
| 2156 | a20 | b14 | c6 |
| 2157 | a21 | b14 | c6 |
| 2158 | a22 | b14 | c6 |
| 2159 | a23 | b14 | c6 |
| 2160 | a24 | b14 | c6 |
| 2161 | a25 | b14 | c6 |
| 2162 | a 1 | b15 | c6 |
| 2163 | a 2 | b15 | c6 |
| 2164 | a 3 | b15 | c6 |
| 2165 | a 4 | b15 | c6 |
| 2166 | a 5 | b15 | c6 |
| 2167 | a 6 | b15 | c6 |
| 2168 | a 7 | b15 | c6 |
| 2169 | a 8 | b15 | c6 |
| 2170 | a 9 | b15 | c6 |
| 2171 | a10 | b15 | c6 |
| 2172 | a11 | b15 | c6 |
| 2173 | a12 | b15 | c6 |
| 2174 | a13 | b15 | c6 |
| 2175 | a14 | b15 | c6 |
| 2176 | a15 | b15 | c6 |
| 2177 | a16 | b15 | c6 |
| 2178 | a17 | b15 | c6 |
| 2179 | a18 | b15 | c6 |
| 2180 | a19 | b15 | c6 |
| 2181 | a20 | b15 | c6 |
| 2182 | a21 | b15 | c6 |
| 2183 | a22 | b15 | c6 |
| 2184 | a23 | b15 | c6 |
| 2185 | a24 | b15 | c6 |
| 2186 | a25 | b15 | c6 |
| 2187 | a 1 | b 1 | c7 |
| 2188 | a 2 | b 1 | c7 |
| 2189 | a 3 | b 1 | c7 |
| 2190 | a 4 | b 1 | c7 |
| 2191 | a 5 | b 1 | c7 |
| 2192 | a 6 | b 1 | c7 |
| 2193 | a 7 | b 1 | c7 |
| 2194 | a 8 | b 1 | c7 |
| 2195 | a 9 | b 1 | c7 |
| 2196 | a10 | b 1 | c7 |
| 2197 | a11 | b 1 | c7 |
| 2198 | a12 | b 1 | c7 |
| 2199 | a13 | b 1 | c7 |
| 2200 | a14 | b 1 | c7 |
| 2201 | a15 | b 1 | c7 |
| 2202 | a16 | b 1 | c7 |
| 2203 | a17 | b 1 | c7 |
| 2204 | a18 | b 1 | c7 |
| 2205 | a19 | b 1 | c7 |
| 2206 | a20 | b 1 | c7 |
| 2207 | a21 | b 1 | c7 |
| 2208 | a22 | b 1 | c7 |
| 2209 | a23 | b 1 | c7 |
| 2210 | a24 | b 1 | c7 |
| 2211 | a25 | b 1 | c7 |
| 2212 | a 1 | b 2 | c7 |
| 2213 | a 2 | b 2 | c7 |
| 2214 | a 3 | b 2 | c7 |
| 2215 | a 4 | b 2 | c7 |
| 2216 | a 5 | b 2 | c7 |
| 2217 | a 6 | b 2 | c7 |
| 2218 | a 7 | b 2 | c7 |
| 2219 | a 8 | b 2 | c7 |
| 2220 | a 9 | b 2 | c7 |
| 2221 | a10 | b 2 | c7 |
| 2222 | a11 | b 2 | c7 |
| 2223 | a12 | b 2 | c7 |
| 2224 | a13 | b 2 | c7 |
| 2225 | a14 | b 2 | c7 |
| 2226 | a15 | b 2 | c7 |
| 2227 | a16 | b 2 | c7 |
| 2228 | a17 | b 2 | c7 |
| 2229 | a18 | b 2 | c7 |
| 2230 | a19 | b 2 | c7 |
| 2231 | a20 | b 2 | c7 |
| 2232 | a21 | b 2 | c7 |
| 2233 | a22 | b 2 | c7 |
| 2234 | a23 | b 2 | c7 |
| 2235 | a24 | b 2 | c7 |
| 2236 | a25 | b 2 | c7 |
| 2237 | a 1 | b 3 | c7 |
| 2238 | a 2 | b 3 | c7 |
| 2239 | a 3 | b 3 | c7 |
| 2240 | a 4 | b 3 | c7 |
| 2241 | a 5 | b 3 | c7 |
| 2242 | a 6 | b 3 | c7 |
| 2243 | a 7 | b 3 | c7 |
| 2244 | a 8 | b 3 | c7 |
| 2245 | a 9 | b 3 | c7 |
| 2246 | a10 | b 3 | c7 |
| 2247 | a11 | b 3 | c7 |
| 2248 | a12 | b 3 | c7 |
| 2249 | a13 | b 3 | c7 |
| 2250 | a14 | b 3 | c7 |
| 2251 | a15 | b 3 | c7 |
| 2252 | a16 | b 3 | c7 |
| 2253 | a17 | b 3 | c7 |
| 2254 | a18 | b 3 | c7 |
| 2255 | a19 | b 3 | c7 |
| 2256 | a20 | b 3 | c7 |
| 2257 | a21 | b 3 | c7 |
| 2258 | a22 | b 3 | c7 |
| 2259 | a23 | b 3 | c7 |
| 2260 | a24 | b 3 | c7 |
| 2261 | a25 | b 3 | c7 |

-continued

| No. | Cp | Bridge | Flu |
|---|---|---|---|
| 2262 | a 1 | b4 | c7 |
| 2263 | a 2 | b4 | c7 |
| 2264 | a 3 | b4 | c7 |
| 2265 | a 4 | b4 | c7 |
| 2266 | a 5 | b4 | c7 |
| 2267 | a 6 | b4 | c7 |
| 2268 | a 7 | b4 | c7 |
| 2269 | a 8 | b4 | c7 |
| 2270 | a 9 | b4 | c7 |
| 2271 | a10 | b4 | c7 |
| 2272 | a11 | b4 | c7 |
| 2273 | a12 | b4 | c7 |
| 2274 | a13 | b4 | c7 |
| 2275 | a14 | b4 | c7 |
| 2276 | a15 | b4 | c7 |
| 2277 | a16 | b4 | c7 |
| 2278 | a17 | b4 | c7 |
| 2279 | a18 | b4 | c7 |
| 2280 | a19 | b4 | c7 |
| 2281 | a20 | b4 | c7 |
| 2282 | a21 | b4 | c7 |
| 2283 | a22 | b4 | c7 |
| 2284 | a23 | b4 | c7 |
| 2285 | a24 | b4 | c7 |
| 2286 | a25 | b4 | c7 |
| 2287 | a 1 | b5 | c7 |
| 2288 | a 2 | b5 | c7 |
| 2289 | a 3 | b5 | c7 |
| 2290 | a 4 | b5 | c7 |
| 2291 | a 5 | b5 | c7 |
| 2292 | a 6 | b5 | c7 |
| 2293 | a 7 | b5 | c7 |
| 2294 | a 8 | b5 | c7 |
| 2295 | a 9 | b5 | c7 |
| 2296 | a10 | b5 | c7 |
| 2297 | a11 | b5 | c7 |
| 2298 | a12 | b5 | c7 |
| 2299 | a13 | b5 | c7 |
| 2300 | a14 | b5 | c7 |
| 2301 | a15 | b5 | c7 |
| 2302 | a16 | b5 | c7 |
| 2303 | a17 | b5 | c7 |
| 2304 | a18 | b5 | c7 |
| 2305 | a19 | b5 | c7 |
| 2306 | a20 | b5 | c7 |
| 2307 | a21 | b5 | c7 |
| 2308 | a22 | b5 | c7 |
| 2309 | a23 | b5 | c7 |
| 2310 | a24 | b5 | c7 |
| 2311 | a25 | b5 | c7 |
| 2312 | a 1 | b6 | c7 |
| 2313 | a 2 | b6 | c7 |
| 2314 | a 3 | b6 | c7 |
| 2315 | a 4 | b6 | c7 |
| 2316 | a 5 | b6 | c7 |
| 2317 | a 6 | b6 | c7 |
| 2318 | a 7 | b6 | c7 |
| 2319 | a 8 | b6 | c7 |
| 2320 | a 9 | b6 | c7 |
| 2321 | a10 | b6 | c7 |
| 2322 | a11 | b6 | c7 |
| 2323 | a12 | b6 | c7 |
| 2324 | a13 | b6 | c7 |
| 2325 | a14 | b6 | c7 |
| 2326 | a15 | b6 | c7 |
| 2327 | a16 | b6 | c7 |
| 2328 | a17 | b6 | c7 |
| 2329 | a18 | b6 | c7 |
| 2330 | a19 | b6 | c7 |
| 2331 | a20 | b6 | c7 |
| 2332 | a21 | b6 | c7 |
| 2333 | a22 | b6 | c7 |
| 2334 | a23 | b6 | c7 |
| 2335 | a24 | b6 | c7 |
| 2336 | a25 | b6 | c7 |
| 2337 | a 1 | b7 | c7 |
| 2338 | a 2 | b7 | c7 |

-continued

| No. | Cp | Bridge | Flu |
|---|---|---|---|
| 2339 | a 3 | b 7 | c7 |
| 2340 | a 4 | b 7 | c7 |
| 2341 | a 5 | b 7 | c7 |
| 2342 | a 6 | b 7 | c7 |
| 2343 | a 7 | b 7 | c7 |
| 2344 | a 8 | b 7 | c7 |
| 2345 | a 9 | b 7 | c7 |
| 2346 | a10 | b 7 | c7 |
| 2347 | a11 | b 7 | c7 |
| 2348 | a12 | b 7 | c7 |
| 2349 | a13 | b 7 | c7 |
| 2350 | a14 | b 7 | c7 |
| 2351 | a15 | b 7 | c7 |
| 2352 | a16 | b 7 | c7 |
| 2353 | a17 | b 7 | c7 |
| 2354 | a18 | b 7 | c7 |
| 2355 | a19 | b 7 | c7 |
| 2356 | a20 | b 7 | c7 |
| 2357 | a21 | b 7 | c7 |
| 2358 | a22 | b 7 | c7 |
| 2359 | a23 | b 7 | c7 |
| 2360 | a24 | b 7 | c7 |
| 2361 | a25 | b 7 | c7 |
| 2362 | a 1 | b 8 | c7 |
| 2363 | a 2 | b 8 | c7 |
| 2364 | a 3 | b 8 | c7 |
| 2365 | a 4 | b 8 | c7 |
| 2366 | a 5 | b 8 | c7 |
| 2367 | a 6 | b 8 | c7 |
| 2368 | a 7 | b 8 | c7 |
| 2369 | a 8 | b 8 | c7 |
| 2370 | a 9 | b 8 | c7 |
| 2371 | a10 | b 8 | c7 |
| 2372 | a11 | b 8 | c7 |
| 2373 | a12 | b 8 | c7 |
| 2374 | a13 | b 8 | c7 |
| 2375 | a14 | b 8 | c7 |
| 2376 | a15 | b 8 | c7 |
| 2377 | a16 | b 8 | c7 |
| 2378 | a17 | b 8 | c7 |
| 2379 | a18 | b 8 | c7 |
| 2380 | a19 | b 8 | c7 |
| 2381 | a20 | b 8 | c7 |
| 2382 | a21 | b 8 | c7 |
| 2383 | a22 | b 8 | c7 |
| 2384 | a23 | b 8 | c7 |
| 2385 | a24 | b 8 | c7 |
| 2386 | a25 | b 8 | c7 |
| 2387 | a 1 | b 9 | c7 |
| 2388 | a 2 | b 9 | c7 |
| 2389 | a 3 | b 9 | c7 |
| 2390 | a 4 | b 9 | c7 |
| 2391 | a 5 | b 9 | c7 |
| 2392 | a 6 | b 9 | c7 |
| 2393 | a 7 | b 9 | c7 |
| 2394 | a 8 | b 9 | c7 |
| 2395 | a 9 | b 9 | c7 |
| 2396 | a10 | b 9 | c7 |
| 2397 | a11 | b 9 | c7 |
| 2398 | a12 | b 9 | c7 |
| 2399 | a13 | b 9 | c7 |
| 2400 | a14 | b 9 | c7 |
| 2401 | a15 | b 9 | c7 |
| 2402 | a16 | b 9 | c7 |
| 2403 | a17 | b 9 | c7 |
| 2404 | a18 | b 9 | c7 |
| 2405 | a19 | b 9 | c7 |
| 2406 | a20 | b 9 | c7 |
| 2407 | a21 | b 9 | c7 |
| 2408 | a22 | b 9 | c7 |
| 2409 | a23 | b 9 | c7 |
| 2410 | a24 | b 9 | c7 |
| 2411 | a25 | b 9 | c7 |
| 2412 | a 1 | b10 | c7 |
| 2413 | a 2 | b10 | c7 |
| 2414 | a 3 | b10 | c7 |
| 2415 | a 4 | b10 | c7 |

-continued

| No. | Cp | Bridge | Flu |
|---|---|---|---|
| 2416 | a 5 | b10 | c7 |
| 2417 | a 6 | b10 | c7 |
| 2418 | a 7 | b10 | c7 |
| 2419 | a 8 | b10 | c7 |
| 2420 | a 9 | b10 | c7 |
| 2421 | a10 | b10 | c7 |
| 2422 | a11 | b10 | c7 |
| 2423 | a12 | b10 | c7 |
| 2424 | a13 | b10 | c7 |
| 2425 | a14 | b10 | c7 |
| 2426 | a15 | b10 | c7 |
| 2427 | a16 | b10 | c7 |
| 2428 | a17 | b10 | c7 |
| 2429 | a18 | b10 | c7 |
| 2430 | a19 | b10 | c7 |
| 2431 | a20 | b10 | c7 |
| 2432 | a21 | b10 | c7 |
| 2433 | a22 | b10 | c7 |
| 2434 | a23 | b10 | c7 |
| 2435 | a24 | b10 | c7 |
| 2436 | a25 | b10 | c7 |
| 2437 | a 1 | b11 | c7 |
| 2438 | a 2 | b11 | c7 |
| 2439 | a 3 | b11 | c7 |
| 2440 | a 4 | b11 | c7 |
| 2441 | a 5 | b11 | c7 |
| 2442 | a 6 | b11 | c7 |
| 2443 | a 7 | b11 | c7 |
| 2444 | a 8 | b11 | c7 |
| 2445 | a 9 | b11 | c7 |
| 2446 | a10 | b11 | c7 |
| 2447 | a11 | b11 | c7 |
| 2448 | a12 | b11 | c7 |
| 2449 | a13 | b11 | c7 |
| 2450 | a14 | b11 | c7 |
| 2451 | a15 | b11 | c7 |
| 2452 | a16 | b11 | c7 |
| 2453 | a17 | b11 | c7 |
| 2454 | a18 | b11 | c7 |
| 2455 | a19 | b11 | c7 |
| 2456 | a20 | b11 | c7 |
| 2457 | a21 | b11 | c7 |
| 2458 | a22 | b11 | c7 |
| 2459 | a23 | b11 | c7 |
| 2460 | a24 | b11 | c7 |
| 2461 | a25 | b11 | c7 |
| 2462 | a 1 | b12 | c7 |
| 2463 | a 2 | b12 | c7 |
| 2464 | a 3 | b12 | c7 |
| 2465 | a 4 | b12 | c7 |
| 2466 | a 5 | b12 | c7 |
| 2467 | a 6 | b12 | c7 |
| 2468 | a 7 | b12 | c7 |
| 2469 | a 8 | b12 | c7 |
| 2470 | a 9 | b12 | c7 |
| 2471 | a10 | b12 | c7 |
| 2472 | a11 | b12 | c7 |
| 2473 | a12 | b12 | c7 |
| 2474 | a13 | b12 | c7 |
| 2475 | a14 | b12 | c7 |
| 2476 | a15 | b12 | c7 |
| 2477 | a16 | b12 | c7 |
| 2478 | a17 | b12 | c7 |
| 2479 | a18 | b12 | c7 |
| 2480 | a19 | b12 | c7 |
| 2481 | a20 | b12 | c7 |
| 2482 | a21 | b12 | c7 |
| 2483 | a22 | b12 | c7 |
| 2484 | a23 | b12 | c7 |
| 2485 | a24 | b12 | c7 |
| 2486 | a25 | b12 | c7 |
| 2487 | a 1 | b13 | c7 |
| 2488 | a 2 | b13 | c7 |
| 2489 | a 3 | b13 | c7 |
| 2490 | a 4 | b13 | c7 |
| 2491 | a 5 | b13 | c7 |
| 2492 | a 6 | b13 | c7 |
| 2493 | a 7 | b13 | c7 |
| 2494 | a 8 | b13 | c7 |
| 2495 | a 9 | b13 | c7 |
| 2496 | a10 | b13 | c7 |
| 2497 | a11 | b13 | c7 |
| 2498 | a12 | b13 | c7 |
| 2499 | a13 | b13 | c7 |
| 2500 | a14 | b13 | c7 |
| 2501 | a15 | b13 | c7 |
| 2502 | a16 | b13 | c7 |
| 2503 | a17 | b13 | c7 |
| 2504 | a18 | b13 | c7 |
| 2505 | a19 | b13 | c7 |
| 2506 | a20 | b13 | c7 |
| 2507 | a21 | b13 | c7 |
| 2508 | a22 | b13 | c7 |
| 2509 | a23 | b13 | c7 |
| 2510 | a24 | b13 | c7 |
| 2511 | a25 | b13 | c7 |
| 2512 | a 1 | b14 | c7 |
| 2513 | a 2 | b14 | c7 |
| 2514 | a 3 | b14 | c7 |
| 2515 | a 4 | b14 | c7 |
| 2516 | a 5 | b14 | c7 |
| 2517 | a 6 | b14 | c7 |
| 2518 | a 7 | b14 | c7 |
| 2519 | a 8 | b14 | c7 |
| 2520 | a 9 | b14 | c7 |
| 2521 | a10 | b14 | c7 |
| 2522 | a11 | b14 | c7 |
| 2523 | a12 | b14 | c7 |
| 2524 | a13 | b14 | c7 |
| 2525 | a14 | b14 | c7 |
| 2526 | a15 | b14 | c7 |
| 2527 | a16 | b14 | c7 |
| 2528 | a17 | b14 | c7 |
| 2529 | a18 | b14 | c7 |
| 2530 | a19 | b14 | c7 |
| 2531 | a20 | b14 | c7 |
| 2532 | a21 | b14 | c7 |
| 2533 | a22 | b14 | c7 |
| 2534 | a23 | b14 | c7 |
| 2535 | a24 | b14 | c7 |
| 2536 | a25 | b14 | c7 |
| 2537 | a 1 | b15 | c7 |
| 2538 | a 2 | b15 | c7 |
| 2539 | a 3 | b15 | c7 |
| 2540 | a 4 | b15 | c7 |
| 2541 | a 5 | b15 | c7 |
| 2542 | a 6 | b15 | c7 |
| 2543 | a 7 | b15 | c7 |
| 2544 | a 8 | b15 | c7 |
| 2545 | a 9 | b15 | c7 |
| 2546 | a10 | b15 | c7 |
| 2547 | a11 | b15 | c7 |
| 2548 | a12 | b15 | c7 |
| 2549 | a13 | b15 | c7 |
| 2550 | a14 | b15 | c7 |
| 2551 | a15 | b15 | c7 |
| 2552 | a16 | b15 | c7 |
| 2553 | a17 | b15 | c7 |
| 2554 | a18 | b15 | c7 |
| 2555 | a19 | b15 | c7 |
| 2556 | a20 | b15 | c7 |
| 2557 | a21 | b15 | c7 |
| 2558 | a22 | b15 | c7 |
| 2559 | a23 | b15 | c7 |
| 2560 | a24 | b15 | c7 |
| 2561 | a25 | b15 | c7 |

According to the above table, the ligand structure of No. 736 means a combination of a2-b1-c3, so that when the metal part MQj is ZrCl2, the following metallocene compound is exemplified.

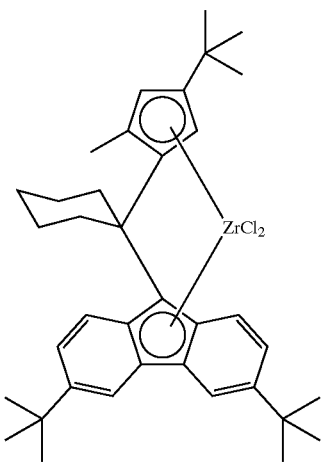

Specific examples of MQj include $ZrCl_2$, $ZrBr_2$, $ZrMe_2$, $Zr(OTs)_2$, $Zr(OMs)_2$, $Zr(OTf)_2$, $TiCl_2$, $TiBr_2$, $TiMe_2$, $Ti(OTs)_2$, $Ti(OMs)_2$, $Ti(OTf)_2$, $HfCl_2$, $HfBr_2$, $HfMe_2$, $Hf(OTs)_2$, $Hf(OMs)_2$ and $Hf(OTf)_2$.

Examples of the metallocene compounds wherein the substituent group on the Cp ring and the substituent group on the bridge part are bonded to form a ring include the following compounds.

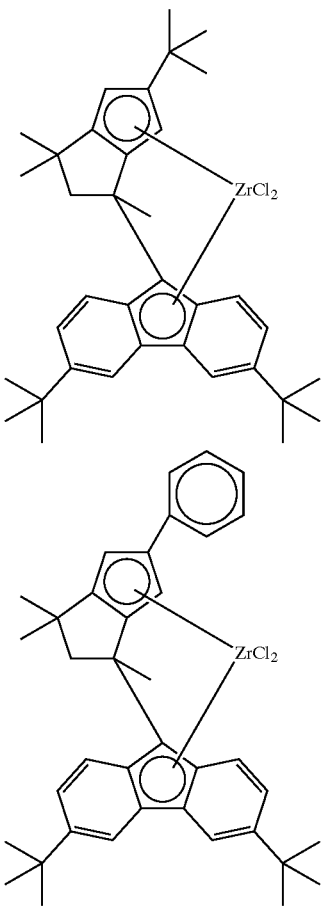

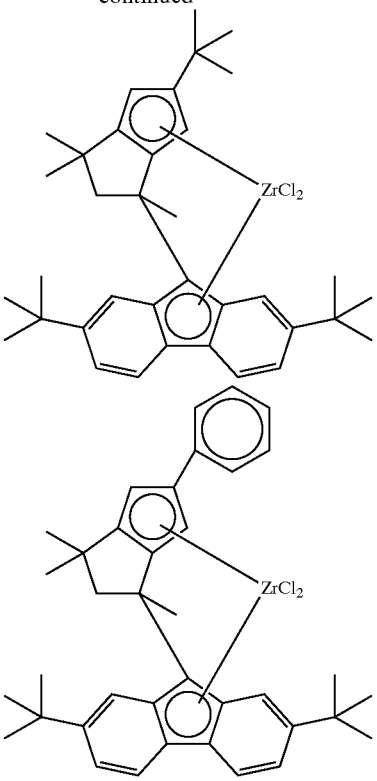

Preferred examples of the metallocene compounds represented by the formula (1a) or (2a) according to the invention include:

a metallocene compound of the formula (1a) wherein $R^1$, $R^{13}$ and $R^{14}$ are each methyl, $R^3$ is tert-butyl, $R^2$, $R^4$, $R^5$, $R^7$, $R^8$, $R^9$, $R^{10}$ and $R^{12}$ are each hydrogen, $R^6$ and $R_{11}$ are each tert-butyl, M is zirconium, Y is carbon, Q is chlorine, and j is 2;

a metallocene compound of the formula (1a) wherein $R^{13}$ and $R^{14}$ are each methyl, $R^3$ is 1-methyl-1-cyclohexyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (1a) wherein $R^{13}$ and $R^{14}$ are each methyl, $R^3$ is tert-butyl, $R^1$, $R^2$, $R^4$, $R^5$, $R^8$, $R^9$ and $R^{12}$ are each hydrogen, $R^6$ and $R^7$ are bonded to form —$(C(CH_3)_2CH_2CH_2C(CH_3)_2)$- and thereby form a ring, $R^{10}$ and $R^{11}$ are bonded to form— $(C(CH_3)_2CH_2CH_2C(CH_3)_2)$- and thereby form a ring, M is zirconium, Y is carbon, Q is chlorine, and j is 2;

a metallocene compound of the formula (1a) wherein $R^{13}$ and $R^{14}$ are each methyl, $R^3$ is trimethylsilyl, $R^1$, $R^2$, $R^4$, $R^5$, $R^8$, $R^9$ and $R^{12}$ are each hydrogen, $R^6$ and $R^7$ are bonded to form —$(C(CH3)_2CH_2CH_2C(CH_3)_2)$- and thereby form a ring, $R^{10}$ and $R^{11}$ are bonded to form —$(C(CH_3)_2CH_2CH_2C(CH_3)_2)$- and thereby form a ring, M is zirconium, Y is carbon, Q is chlorine, and j is 2;

a metallocene compound of the formula (1a) wherein $R^{13}$ and $R^{14}$ are each methyl, $R^3$ is 1,1-dimethylpropyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (1a) wherein $R^{13}$ and $R^{14}$ are each methyl, $R^3$ is 1-ethyl-1-methylpropyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (1a) wherein $R^{13}$ and $R^{14}$ are each methyl, $R^3$ is 1,1,3-trimethylbutyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (1a) wherein $R^{13}$ and $R^{14}$ are each methyl, $R^3$ is 1,1-dimethylbutyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (1a) wherein $R^{13}$ and $R^{14}$ are each methyl, $R^3$ is tert-butyl, $R^1$, $R^2$, $R^4$, $R^5$, $R^7$, $R^8$, $R^9$, $R^{10}$ and $R^{12}$ are each hydrogen, $R^6$ and $R^{11}$ are each tert-butyl, M is zirconium, Y is carbon, Q is chlorine, and j is 2;

a metallocene compound of the formula (1a) wherein $R^3$, $R^{13}$ and $R^{14}$ are each phenyl, $R^1$, $R^2$, $R^4$, $R^5$, $R^8$, $R^9$ and $R^{12}$ are each hydrogen, $R^6$ and $R^7$ are bonded to form—$(C(CH_3)_2CH_2CH_2C(CH_3)_2)$- and thereby form a ring, $R^{10}$ and $R^{11}$ are bonded to form —$(C(CH_3)_2CH_2CH_2C(CH_3)_2)$— and thereby form a ring, M is zirconium, Y is carbon, Q is chlorine, and j is 2;

a metallocene compound of the formula (1a) wherein $R^3$ is trimethylsilyl, $R^{13}$ and $R^{14}$ are each phenyl, $R^1$, $R^2$, $R^4$, $R^5$, $R^8$, $R^9$ and $R^{12}$ are each hydrogen, $R^6$ and $R^7$ are bonded to form —$(C(CH_3)_2CH_2CH_2C(CH_3)_2)$- and thereby form a ring, $R^{10}$ and $R^{11}$ are bonded to form— $(C(CH_3)_2CH_2CH_2C(CH_3)_2)$- and thereby form a ring, M is zirconium, Y is carbon, Q is chlorine, and j is 2;

a metallocene compound of the formula (1a) wherein $R^{13}$ is methyl, $R^{14}$ is phenyl, $R^3$ is tert-butyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (1a) wherein $R^{13}$ and $R^{14}$ are each ethyl, $R^3$ is tert-butyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (2a) wherein $R^1$ is methyl, $R^3$ is tert-butyl, $R^2$, $R^4$, $R^5$, $R^6$, $R^7$, $R^8$, $R^9$, $R^{10}$, $R^{11}$ and $R^{12}$ are each hydrogen, M is zirconium, Y is carbon, Q is chlorine, j is 2, and A is —$(CH2)_5$—;

a metallocene compound of the formula (2a) wherein $R^1$ is methyl, $R^3$ is tert-butyl, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, j is 2, and A is —$(CH_2)_5$—;

a metallocene compound of the formula (2a) wherein $R^3$ is trimethylsilyl, $R^1$, $R^2$, $R^4$, $R^5$, $R^7$, $R^8$, $R^9$, $R^{10}$ and $R^{12}$ are each hydrogen, $R^6$ and $R^{11}$ are each tert-butyl, M is zirconium, Y is carbon, Q is chlorine, j is 2, and A is —$(CH_2)_5$—;

a metallocene compound of the formula (2a) wherein $R^3$ is trimethylsilyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, j is 2, and A is —$(CH_2)_5$—;

a metallocene compound of the formula (2a) wherein $R^3$ is tert-butyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, j is 2, and A is —$(CH_2)_4$—;

a metallocene compound of the formula (2a) wherein $R^3$ is 1,1-dimethylpropyl, $R^1$, $R^2$, $R^4$, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, j is 2, and A is —$(CH_2)_5$—; and a metallocene compound of the formula (2a) wherein $R^3$ is tert-butyl, $R^1$, $R^2$, $R^4$, $R^5$, $R^8$, $R^9$ and $R^{12}$ are each hydrogen, $R^6$ and $R^7$ are bonded to form —$(C(CH_3)_2CH_2CH_2C(CH_3)_2)$- and thereby form a ring, $R^{10}$ and $R^{11}$ are bonded to form —$(C(CH_3)_2CH_2CH_2C(CH_3)_2)$- and thereby form a ring, M is zirconium, Y is carbon, Q is chlorine, j is 2, and A is —$(CH_2)_4$—.

There is no specific limitation on the process for preparing the metallocene compound represented by the formula (1a) or (2a), and the compound can be prepared by, for example, a process similar to the process for preparing the metallocene compound represented by the formula (1) or (2).

Next, the metallocene compound represented by the formula (1b) or (2b) is described.

A further embodiment of the metallocene compound of the invention is represented by the following formula (1b) or (2b).

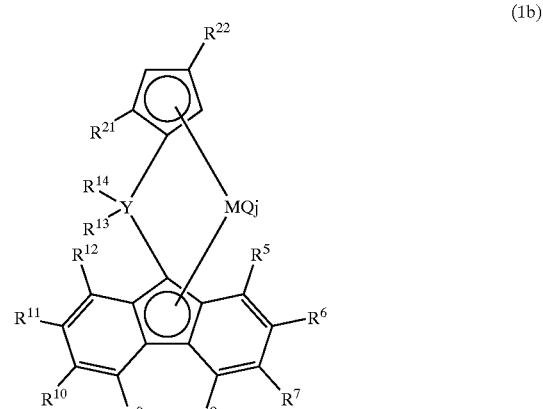

(1b)

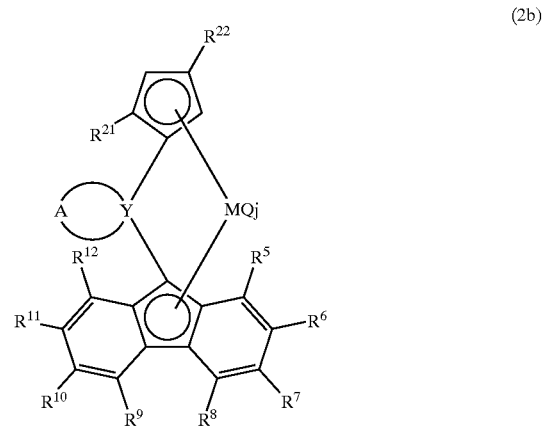

(2b)

In the formula (1b) or (2b), each of $R^{21}$ and $R^{22}$ has the same meaning as that of $R^3$ in the formula (1) or (2); each of $R^5$ to $R^{14}$ has the same meaning as that of $R^1$, $R^2$ or each of $R^4$ to $R^{14}$ in the formula (1) or (2); and A, Y, M, Q and j have the same meanings as those of A, Y, M, Q and j in the formula (1) or (2), respectively.

$R^{22}$ is preferably a sterically bulky substituent group, more preferably a substituent group of 4 or more carbon atoms.

Examples of the metallocene compounds represented by the formula (1b) or (2b) according to the invention are given below.

The ligand structure excluding MQj (metal part) in the metallocene compound is divided into three parts of Cp (cyclopentadienyl ring part), Bridge (bridge part) and Flu (fluorenyl ring part), and specific examples of these partial structures and specific examples of ligand structures formed by combination of these partial structures are described first. Examples of Bridge (bridge part) and Flu (fluorenyl ring part) are the same as those previously described with respect to the metallocene compound represented by the formula (1) or (2).

Examples of Cp a1
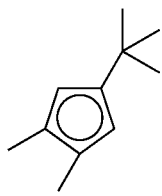

a2
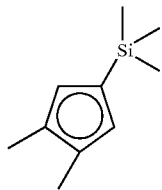

a3
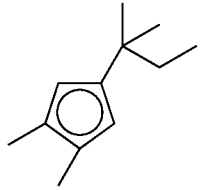

a4
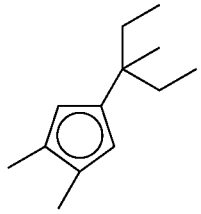

a5
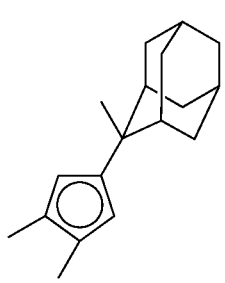

a6
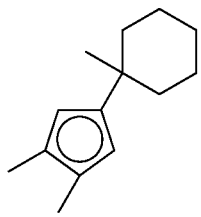

a7
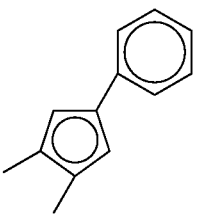

a8
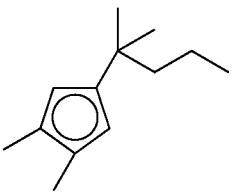

a9
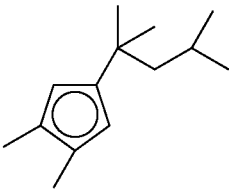

a10
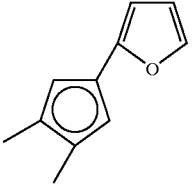

a11
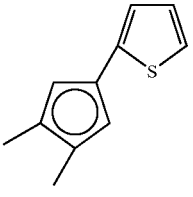

Examples of the ligand structures are described in the following table.

| No. | Cp  | Bridge | Flu |
|-----|-----|--------|-----|
| 1   | a 1 | b1     | c 1 |
| 2   | a 2 | b1     | c 1 |
| 3   | a 3 | b1     | c 1 |
| 4   | a 4 | b1     | c 1 |
| 5   | a 5 | b1     | c 1 |
| 6   | a 6 | b1     | c 1 |
| 7   | a 7 | b1     | c 1 |
| 8   | a 8 | b1     | c 1 |
| 9   | a 9 | b1     | c 1 |
| 10  | a10 | b1     | c 1 |
| 11  | a11 | b1     | c 1 |
| 12  | a 1 | b2     | c 1 |
| 13  | a 2 | b2     | c 1 |
| 14  | a 3 | b2     | c 1 |
| 15  | a 4 | b2     | c 1 |
| 16  | a 5 | b2     | c 1 |
| 17  | a 6 | b2     | c 1 |
| 18  | a 7 | b2     | c 1 |
| 19  | a 8 | b2     | c 1 |
| 20  | a 9 | b2     | c 1 |

-continued

| No. | Cp | Bridge | Flu |
|---|---|---|---|
| 21 | a10 | b2 | c 1 |
| 22 | a11 | b2 | c 1 |
| 23 | a 1 | b3 | c 1 |
| 24 | a 2 | b3 | c 1 |
| 25 | a 3 | b3 | c 1 |
| 26 | a 4 | b3 | c 1 |
| 27 | a 5 | b3 | c 1 |
| 28 | a 6 | b3 | c 1 |
| 29 | a 7 | b3 | c 1 |
| 30 | a 8 | b3 | c 1 |
| 31 | a 9 | b3 | c 1 |
| 32 | a10 | b3 | c 1 |
| 33 | a11 | b3 | c 1 |
| 34 | a 1 | b4 | c 1 |
| 35 | a 2 | b4 | c 1 |
| 36 | a 3 | b4 | c 1 |
| 37 | a 4 | b4 | c 1 |
| 38 | a 5 | b4 | c 1 |
| 39 | a 6 | b4 | c 1 |
| 40 | a 7 | b4 | c 1 |
| 41 | a 8 | b4 | c 1 |
| 42 | a 9 | b4 | c 1 |
| 43 | a10 | b4 | c 1 |
| 44 | a11 | b4 | c 1 |
| 45 | a 1 | b5 | c 1 |
| 46 | a 2 | b5 | c 1 |
| 47 | a 3 | b5 | c 1 |
| 48 | a 4 | b5 | c 1 |
| 49 | a 5 | b5 | c 1 |
| 50 | a 6 | b5 | c 1 |
| 51 | a 7 | b5 | c 1 |
| 52 | a 8 | b5 | c 1 |
| 53 | a 9 | b5 | c 1 |
| 54 | a10 | b5 | c 1 |
| 55 | a11 | b5 | c 1 |
| 56 | a 1 | b6 | c 1 |
| 57 | a 2 | b6 | c 1 |
| 58 | a 3 | b6 | c 1 |
| 59 | a 4 | b6 | c 1 |
| 60 | a 5 | b6 | c 1 |
| 61 | a 6 | b6 | c 1 |
| 62 | a 7 | b6 | c 1 |
| 63 | a 8 | b6 | c 1 |
| 64 | a 9 | b6 | c 1 |
| 65 | a10 | b6 | c 1 |
| 66 | a11 | b6 | c 1 |
| 67 | a 1 | b7 | c 1 |
| 68 | a 2 | b7 | c 1 |
| 69 | a 3 | b7 | c 1 |
| 70 | a 4 | b7 | c 1 |
| 71 | a 5 | b7 | c 1 |
| 72 | a 6 | b7 | c 1 |
| 73 | a 7 | b7 | c 1 |
| 74 | a 8 | b7 | c 1 |
| 75 | a 9 | b7 | c 1 |
| 76 | a10 | b7 | c 1 |
| 77 | a11 | b7 | c 1 |
| 78 | a 1 | b8 | c 1 |
| 79 | a 2 | b8 | c 1 |
| 80 | a 3 | b8 | c 1 |
| 81 | a 4 | b8 | c 1 |
| 82 | a 5 | b8 | c 1 |
| 83 | a 6 | b8 | c 1 |
| 84 | a 7 | b8 | c 1 |
| 85 | a 8 | b8 | c 1 |
| 86 | a 9 | b8 | c 1 |
| 87 | a10 | b8 | c 1 |
| 88 | a11 | b8 | c 1 |
| 89 | a 1 | b9 | c 1 |
| 90 | a 2 | b9 | c 1 |
| 91 | a 3 | b9 | c 1 |
| 92 | a 4 | b9 | c 1 |
| 93 | a 5 | b9 | c 1 |
| 94 | a 6 | b9 | c 1 |
| 95 | a 7 | b9 | c 1 |
| 96 | a 8 | b9 | c 1 |
| 97 | a 9 | b9 | c 1 |
| 98 | a10 | b 9 | c 1 |
| 99 | a11 | b 9 | c 1 |
| 100 | a 1 | b10 | c 1 |
| 101 | a 2 | b10 | c 1 |
| 102 | a 3 | b10 | c 1 |
| 103 | a 4 | b10 | c 1 |
| 104 | a 5 | b10 | c 1 |
| 105 | a 6 | b10 | c 1 |
| 106 | a 7 | b10 | c 1 |
| 107 | a 8 | b10 | c 1 |
| 108 | a 9 | b10 | c 1 |
| 109 | a10 | b10 | c 1 |
| 110 | a11 | b10 | c 1 |
| 111 | a 1 | b11 | c 1 |
| 112 | a 2 | b11 | c 1 |
| 113 | a 3 | b11 | c 1 |
| 114 | a 4 | b11 | c 1 |
| 115 | a 5 | b11 | c 1 |
| 116 | a 6 | b11 | c 1 |
| 117 | a 7 | b11 | c 1 |
| 118 | a 8 | b11 | c 1 |
| 119 | a 9 | b11 | c 1 |
| 120 | a10 | b11 | c 1 |
| 121 | a11 | b11 | c 1 |
| 122 | a 1 | b12 | c 1 |
| 123 | a 2 | b12 | c 1 |
| 124 | a 3 | b12 | c 1 |
| 125 | a 4 | b12 | c 1 |
| 126 | a 5 | b12 | c 1 |
| 127 | a 6 | b12 | c 1 |
| 128 | a 7 | b12 | c 1 |
| 129 | a 8 | b12 | c 1 |
| 130 | a 9 | b12 | c 1 |
| 131 | a10 | b12 | c 1 |
| 132 | a11 | b12 | c 1 |
| 133 | a 1 | b13 | c 1 |
| 134 | a 2 | b13 | c 1 |
| 135 | a 3 | b13 | c 1 |
| 136 | a 4 | b13 | c 1 |
| 137 | a 5 | b13 | c 1 |
| 138 | a 6 | b13 | c 1 |
| 139 | a 7 | b13 | c 1 |
| 140 | a 8 | b13 | c 1 |
| 141 | a 9 | b13 | c 1 |
| 142 | a10 | b13 | c 1 |
| 143 | a11 | b13 | c 1 |
| 144 | a 1 | b14 | c 1 |
| 145 | a 2 | b14 | c 1 |
| 146 | a 3 | b14 | c 1 |
| 147 | a 4 | b14 | c 1 |
| 148 | a 5 | b14 | c 1 |
| 149 | a 6 | b14 | c 1 |
| 150 | a 7 | b14 | c 1 |
| 151 | a 8 | b14 | c 1 |
| 152 | a 9 | b14 | c 1 |
| 153 | a10 | b14 | c 1 |
| 154 | a11 | b14 | c 1 |
| 155 | a 1 | b15 | c 1 |
| 156 | a 2 | b15 | c 1 |
| 157 | a 3 | b15 | c 1 |
| 158 | a 4 | b15 | c 1 |
| 159 | a 5 | b15 | c 1 |
| 160 | a 6 | b15 | c 1 |
| 161 | a 7 | b15 | c 1 |
| 162 | a 8 | b15 | c 1 |
| 163 | a 9 | b15 | c 1 |
| 164 | a10 | b15 | c 1 |
| 165 | a11 | b15 | c 1 |
| 166 | a 1 | b 1 | c 2 |
| 167 | a 2 | b 1 | c 2 |
| 168 | a 3 | b 1 | c 2 |
| 169 | a 4 | b 1 | c 2 |
| 170 | a 5 | b 1 | c 2 |
| 171 | a 6 | b 1 | c 2 |
| 172 | a 7 | b 1 | c 2 |
| 173 | a 8 | b 1 | c 2 |
| 174 | a 9 | b 1 | c 2 |

| No. | Cp | Bridge | Flu |
|---|---|---|---|
| 175 | a10 | b1 | c 2 |
| 176 | a11 | b1 | c 2 |
| 177 | a 1 | b2 | c 2 |
| 178 | a 2 | b2 | c 2 |
| 179 | a 3 | b2 | c 2 |
| 180 | a 4 | b2 | c 2 |
| 181 | a 5 | b2 | c 2 |
| 182 | a 6 | b2 | c 2 |
| 183 | a 7 | b2 | c 2 |
| 184 | a 8 | b2 | c 2 |
| 185 | a 9 | b2 | c 2 |
| 186 | a10 | b2 | c 2 |
| 187 | a11 | b2 | c 2 |
| 188 | a 1 | b3 | c 2 |
| 189 | a 2 | b3 | c 2 |
| 190 | a 3 | b3 | c 2 |
| 191 | a 4 | b3 | c 2 |
| 192 | a 5 | b3 | c 2 |
| 193 | a 6 | b3 | c 2 |
| 194 | a 7 | b3 | c 2 |
| 195 | a 8 | b3 | c 2 |
| 196 | a 9 | b3 | c 2 |
| 197 | a10 | b3 | c 2 |
| 198 | a11 | b3 | c 2 |
| 199 | a 1 | b4 | c 2 |
| 200 | a 2 | b4 | c 2 |
| 201 | a 3 | b4 | c 2 |
| 202 | a 4 | b4 | c 2 |
| 203 | a 5 | b4 | c 2 |
| 204 | a 6 | b4 | c 2 |
| 205 | a 7 | b4 | c 2 |
| 206 | a 8 | b4 | c 2 |
| 207 | a 9 | b4 | c 2 |
| 208 | a10 | b4 | c 2 |
| 209 | a11 | b4 | c 2 |
| 210 | a 1 | b5 | c 2 |
| 211 | a 2 | b5 | c 2 |
| 212 | a 3 | b5 | c 2 |
| 213 | a 4 | b5 | c 2 |
| 214 | a 5 | b5 | c 2 |
| 215 | a 6 | b5 | c 2 |
| 216 | a 7 | b5 | c 2 |
| 217 | a 8 | b5 | c 2 |
| 218 | a 9 | b5 | c 2 |
| 219 | a10 | b5 | c 2 |
| 220 | a11 | b5 | c 2 |
| 222 | a 2 | b6 | c 2 |
| 223 | a 3 | b6 | c 2 |
| 224 | a 4 | b6 | c 2 |
| 225 | a 5 | b6 | c 2 |
| 226 | a 6 | b6 | c 2 |
| 227 | a 7 | b6 | c 2 |
| 228 | a 8 | b6 | c 2 |
| 229 | a 9 | b6 | c 2 |
| 230 | a10 | b6 | c 2 |
| 231 | a11 | b6 | c 2 |
| 232 | a 1 | b7 | c 2 |
| 233 | a 2 | b7 | c 2 |
| 234 | a 3 | b7 | c 2 |
| 235 | a 4 | b7 | c 2 |
| 236 | a 5 | b7 | c 2 |
| 237 | a 6 | b7 | c 2 |
| 238 | a 7 | b7 | c 2 |
| 239 | a 8 | b7 | c 2 |
| 240 | a 9 | b7 | c 2 |
| 241 | a10 | b7 | c 2 |
| 242 | a11 | b7 | c 2 |
| 243 | a 1 | b8 | c 2 |
| 244 | a 2 | b8 | c 2 |
| 245 | a 3 | b8 | c 2 |
| 246 | a 4 | b8 | c 2 |
| 247 | a 5 | b8 | c 2 |
| 248 | a 6 | b8 | c 2 |
| 249 | a 7 | b8 | c 2 |
| 250 | a 8 | b8 | c 2 |
| 251 | a 9 | b8 | c 2 |
| 252 | a10 | b8 | c 2 |
| 253 | a11 | b 8 | c 2 |
| 254 | a 1 | b 9 | c 2 |
| 255 | a 2 | b 9 | c 2 |
| 256 | a 3 | b 9 | c 2 |
| 257 | a 4 | b 9 | c 2 |
| 258 | a 5 | b 9 | c 2 |
| 259 | a 6 | b 9 | c 2 |
| 260 | a 7 | b 9 | c 2 |
| 261 | a 8 | b 9 | c 2 |
| 262 | a 9 | b 9 | c 2 |
| 263 | a10 | b 9 | c 2 |
| 264 | a11 | b 9 | c 2 |
| 265 | a 1 | b10 | c 2 |
| 266 | a 2 | b10 | c 2 |
| 267 | a 3 | b10 | c 2 |
| 268 | a 4 | b10 | c 2 |
| 269 | a 5 | b10 | c 2 |
| 270 | a 6 | b10 | c 2 |
| 271 | a 7 | b10 | c 2 |
| 272 | a 8 | b10 | c 2 |
| 273 | a 9 | b10 | c 2 |
| 274 | a10 | b10 | c 2 |
| 275 | a11 | b10 | c 2 |
| 276 | a 1 | b11 | c 2 |
| 277 | a 2 | b11 | c 2 |
| 278 | a 3 | b11 | c 2 |
| 279 | a 4 | b11 | c 2 |
| 280 | a 5 | b11 | c 2 |
| 281 | a 6 | b11 | c 2 |
| 282 | a 7 | b11 | c 2 |
| 283 | a 8 | b11 | c 2 |
| 284 | a 9 | b11 | c 2 |
| 285 | a10 | b11 | c 2 |
| 286 | a11 | b11 | c 2 |
| 287 | a 1 | b12 | c 2 |
| 288 | a 2 | b12 | c 2 |
| 289 | a 3 | b12 | c 2 |
| 290 | a 4 | b12 | c 2 |
| 291 | a 5 | b12 | c 2 |
| 292 | a 6 | b12 | c 2 |
| 293 | a 7 | b12 | c 2 |
| 294 | a 8 | b12 | c 2 |
| 295 | a 9 | b12 | c 2 |
| 296 | a10 | b12 | c 2 |
| 297 | a11 | b12 | c 2 |
| 298 | a 1 | b13 | c 2 |
| 299 | a 2 | b13 | c 2 |
| 300 | a 3 | b13 | c 2 |
| 301 | a 4 | b13 | c 2 |
| 302 | a 5 | b13 | c 2 |
| 303 | a 6 | b13 | c 2 |
| 304 | a 7 | b13 | c 2 |
| 305 | a 8 | b13 | c 2 |
| 306 | a 9 | b13 | c 2 |
| 307 | a10 | b13 | c 2 |
| 308 | a11 | b13 | c 2 |
| 309 | a 1 | b14 | c 2 |
| 310 | a 2 | b14 | c 2 |
| 311 | a 3 | b14 | c 2 |
| 312 | a 4 | b14 | c 2 |
| 313 | a 5 | b14 | c 2 |
| 314 | a 6 | b14 | c 2 |
| 315 | a 7 | b14 | c 2 |
| 316 | a 8 | b14 | c 2 |
| 317 | a 9 | b14 | c 2 |
| 318 | a10 | b14 | c 2 |
| 319 | a11 | b14 | c 2 |
| 320 | a 1 | b15 | c 2 |
| 321 | a 2 | b15 | c 2 |
| 322 | a 3 | b15 | c 2 |
| 323 | a 4 | b15 | c 2 |
| 324 | a 5 | b15 | c 2 |
| 325 | a 6 | b15 | c 2 |
| 326 | a 7 | b15 | c 2 |
| 327 | a 8 | b15 | c 2 |
| 328 | a 9 | b15 | c 2 |
| 329 | a10 | b15 | c 2 |

| No. | Cp | Bridge | Flu |
|---|---|---|---|
| 330 | a11 | b15 | c 2 |
| 331 | a 1 | b 1 | c 3 |
| 332 | a 2 | b 1 | c 3 |
| 333 | a 3 | b 1 | c 3 |
| 334 | a 4 | b 1 | c 3 |
| 335 | a 5 | b 1 | c 3 |
| 336 | a 6 | b 1 | c 3 |
| 337 | a 7 | b 1 | c 3 |
| 338 | a 8 | b 1 | c 3 |
| 339 | a 9 | b 1 | c 3 |
| 340 | a10 | b 1 | c 3 |
| 341 | a11 | b 1 | c 3 |
| 342 | a 1 | b 2 | c 3 |
| 343 | a 2 | b 2 | c 3 |
| 344 | a 3 | b 2 | c 3 |
| 345 | a 4 | b 2 | c 3 |
| 346 | a 5 | b 2 | c 3 |
| 347 | a 6 | b 2 | c 3 |
| 348 | a 7 | b 2 | c 3 |
| 349 | a 8 | b 2 | c 3 |
| 350 | a 9 | b 2 | c 3 |
| 351 | a10 | b 2 | c 3 |
| 352 | a11 | b 2 | c 3 |
| 353 | a 1 | b 3 | c 3 |
| 354 | a 2 | b 3 | c 3 |
| 355 | a 3 | b 3 | c 3 |
| 356 | a 4 | b 3 | c 3 |
| 357 | a 5 | b 3 | c 3 |
| 358 | a 6 | b 3 | c 3 |
| 359 | a 7 | b 3 | c 3 |
| 360 | a 8 | b 3 | c 3 |
| 361 | a 9 | b 3 | c 3 |
| 362 | a10 | b 3 | c 3 |
| 363 | a11 | b 3 | c 3 |
| 364 | a 1 | b 4 | c 3 |
| 365 | a 2 | b 4 | c 3 |
| 366 | a 3 | b 4 | c 3 |
| 367 | a 4 | b 4 | c 3 |
| 368 | a 5 | b 4 | c 3 |
| 369 | a 6 | b 4 | c 3 |
| 370 | a 7 | b 4 | c 3 |
| 371 | a 8 | b 4 | c 3 |
| 372 | a 9 | b 4 | c 3 |
| 373 | a10 | b 4 | c 3 |
| 374 | a11 | b 4 | c 3 |
| 375 | a 1 | b 5 | c 3 |
| 376 | a 2 | b 5 | c 3 |
| 377 | a 3 | b 5 | c 3 |
| 378 | a 4 | b 5 | c 3 |
| 379 | a 5 | b 5 | c 3 |
| 380 | a 6 | b 5 | c 3 |
| 381 | a 7 | b 5 | c 3 |
| 382 | a 8 | b 5 | c 3 |
| 383 | a 9 | b 5 | c 3 |
| 384 | a10 | b 5 | c 3 |
| 385 | a11 | b 5 | c 3 |
| 386 | a 1 | b 6 | c 3 |
| 387 | a 2 | b 6 | c 3 |
| 388 | a 3 | b 6 | c 3 |
| 389 | a 4 | b 6 | c 3 |
| 390 | a 5 | b 6 | c 3 |
| 391 | a 6 | b 6 | c 3 |
| 392 | a 7 | b 6 | c 3 |
| 393 | a 8 | b 6 | c 3 |
| 394 | a 9 | b 6 | c 3 |
| 395 | a10 | b 6 | c 3 |
| 396 | a11 | b 6 | c 3 |
| 397 | a 1 | b 7 | c 3 |
| 398 | a 2 | b 7 | c 3 |
| 399 | a 3 | b 7 | c 3 |
| 400 | a 4 | b 7 | c 3 |
| 401 | a 5 | b 7 | c 3 |
| 402 | a 6 | b 7 | c 3 |
| 403 | a 7 | b 7 | c 3 |
| 404 | a 8 | b 7 | c 3 |
| 405 | a 9 | b 7 | c 3 |
| 406 | a10 | b 7 | c 3 |
| 407 | a11 | b 7 | c 3 |
| 408 | a 1 | b 8 | c 3 |
| 409 | a 2 | b 8 | c 3 |
| 410 | a 3 | b 8 | c 3 |
| 411 | a 4 | b 8 | c 3 |
| 412 | a 5 | b 8 | c 3 |
| 413 | a 6 | b 8 | c 3 |
| 414 | a 7 | b 8 | c 3 |
| 415 | a 8 | b 8 | c 3 |
| 416 | a 9 | b 8 | c 3 |
| 417 | a10 | b 8 | c 3 |
| 418 | a11 | b 8 | c 3 |
| 419 | a 1 | b 9 | c 3 |
| 420 | a 2 | b 9 | c 3 |
| 421 | a 3 | b 9 | c 3 |
| 422 | a 4 | b 9 | c 3 |
| 423 | a 5 | b 9 | c 3 |
| 424 | a 6 | b 9 | c 3 |
| 425 | a 7 | b 9 | c 3 |
| 426 | a 8 | b 9 | c 3 |
| 427 | a 9 | b 9 | c 3 |
| 428 | a10 | b 9 | c 3 |
| 429 | a11 | b 9 | c 3 |
| 430 | a 1 | b10 | c 3 |
| 431 | a 2 | b10 | c 3 |
| 432 | a 3 | b10 | c 3 |
| 433 | a 4 | b10 | c 3 |
| 434 | a 5 | b10 | c 3 |
| 435 | a 6 | b10 | c 3 |
| 436 | a 7 | b10 | c 3 |
| 437 | a 8 | b10 | c 3 |
| 438 | a 9 | b10 | c 3 |
| 439 | a10 | b10 | c 3 |
| 440 | a11 | b10 | c 3 |
| 441 | a 1 | b11 | c 3 |
| 442 | a 2 | b11 | c 3 |
| 443 | a 3 | b11 | c 3 |
| 444 | a 4 | b11 | c 3 |
| 445 | a 5 | b11 | c 3 |
| 446 | a 6 | b11 | c 3 |
| 447 | a 7 | b11 | c 3 |
| 448 | a 8 | b11 | c 3 |
| 449 | a 9 | b11 | c 3 |
| 450 | a10 | b11 | c 3 |
| 451 | a11 | b11 | c 3 |
| 452 | a 1 | b12 | c 3 |
| 453 | a 2 | b12 | c 3 |
| 454 | a 3 | b12 | c 3 |
| 455 | a 4 | b12 | c 3 |
| 456 | a 5 | b12 | c 3 |
| 457 | a 6 | b12 | c 3 |
| 458 | a 7 | b12 | c 3 |
| 459 | a 8 | b12 | c 3 |
| 460 | a 9 | b12 | c 3 |
| 461 | a10 | b12 | c 3 |
| 462 | a11 | b12 | c 3 |
| 463 | a 1 | b13 | c 3 |
| 464 | a 2 | b13 | c 3 |
| 465 | a 3 | b13 | c 3 |
| 466 | a 4 | b13 | c 3 |
| 467 | a 5 | b13 | c 3 |
| 468 | a 6 | b13 | c 3 |
| 469 | a 7 | b13 | c 3 |
| 470 | a 8 | b13 | c 3 |
| 471 | a 9 | b13 | c 3 |
| 472 | a10 | b13 | c 3 |
| 473 | a11 | b13 | c 3 |
| 474 | a 1 | b14 | c 3 |
| 475 | a 2 | b14 | c 3 |
| 476 | a 3 | b14 | c 3 |
| 477 | a 4 | b14 | c 3 |
| 478 | a 5 | b14 | c 3 |
| 479 | a 6 | b14 | c 3 |
| 480 | a 7 | b14 | c 3 |
| 481 | a 8 | b14 | c 3 |
| 482 | a 9 | b14 | c 3 |
| 483 | a10 | b14 | c 3 |

| No. | Cp | Bridge | Flu |
|---|---|---|---|
| 484 | a11 | b14 | c 3 |
| 485 | a 1 | b15 | c 3 |
| 486 | a 2 | b15 | c 3 |
| 487 | a 3 | b15 | c 3 |
| 488 | a 4 | b15 | c 3 |
| 489 | a 5 | b15 | c 3 |
| 490 | a 6 | b15 | c 3 |
| 491 | a 7 | b15 | c 3 |
| 492 | a 8 | b15 | c 3 |
| 493 | a 9 | b15 | c 3 |
| 494 | a10 | b15 | c 3 |
| 495 | a11 | b15 | c 3 |
| 496 | a 1 | b 1 | c 4 |
| 498 | a 3 | b 1 | c 4 |
| 499 | a 4 | b 1 | c 4 |
| 500 | a 5 | b 1 | c 4 |
| 501 | a 6 | b 1 | c 4 |
| 502 | a 7 | b 1 | c 4 |
| 503 | a 8 | b 1 | c 4 |
| 504 | a 9 | b 1 | c 4 |
| 505 | a10 | b 1 | c 4 |
| 506 | a11 | b 1 | c 4 |
| 507 | a 1 | b 2 | c 4 |
| 508 | a 2 | b 2 | c 4 |
| 509 | a 3 | b 2 | c 4 |
| 510 | a 4 | b 2 | c 4 |
| 511 | a 5 | b 2 | c 4 |
| 512 | a 6 | b 2 | c 4 |
| 513 | a 7 | b 2 | c 4 |
| 514 | a 8 | b 2 | c 4 |
| 515 | a 9 | b 2 | c 4 |
| 516 | a10 | b 2 | c 4 |
| 517 | a11 | b 2 | c 4 |
| 518 | a 1 | b 3 | c 4 |
| 519 | a 2 | b 3 | c 4 |
| 520 | a 3 | b 3 | c 4 |
| 521 | a 4 | b 3 | c 4 |
| 522 | a 5 | b 3 | c 4 |
| 523 | a 6 | b 3 | c 4 |
| 524 | a 7 | b 3 | c 4 |
| 525 | a 8 | b 3 | c 4 |
| 526 | a 9 | b 3 | c 4 |
| 527 | a10 | b 3 | c 4 |
| 528 | a11 | b 3 | c 4 |
| 529 | a 1 | b 4 | c 4 |
| 530 | a 2 | b 4 | c 4 |
| 531 | a 3 | b 4 | c 4 |
| 532 | a 4 | b 4 | c 4 |
| 533 | a 5 | b 4 | c 4 |
| 534 | a 6 | b 4 | c 4 |
| 535 | a 7 | b 4 | c 4 |
| 536 | a 8 | b 4 | c 4 |
| 537 | a 9 | b 4 | c 4 |
| 538 | a10 | b 4 | c 4 |
| 539 | a11 | b 4 | c 4 |
| 540 | a 1 | b 5 | c 4 |
| 541 | a 2 | b 5 | c 4 |
| 542 | a 3 | b 5 | c 4 |
| 543 | a 4 | b 5 | c 4 |
| 544 | a 5 | b 5 | c 4 |
| 545 | a 6 | b 5 | c 4 |
| 546 | a 7 | b 5 | c 4 |
| 547 | a 8 | b 5 | c 4 |
| 548 | a 9 | b 5 | c 4 |
| 549 | a10 | b 5 | c 4 |
| 550 | a11 | b 5 | c 4 |
| 551 | a 1 | b 6 | c 4 |
| 552 | a 2 | b 6 | c 4 |
| 553 | a 3 | b 6 | c 4 |
| 554 | a 4 | b 6 | c 4 |
| 555 | a 5 | b 6 | c 4 |
| 556 | a 6 | b 6 | c 4 |
| 557 | a 7 | b 6 | c 4 |
| 558 | a 8 | b 6 | c 4 |
| 559 | a 9 | b 6 | c 4 |
| 560 | a10 | b 6 | c 4 |
| 561 | a11 | b 6 | c 4 |
| 562 | a 1 | b 7 | c 4 |
| 563 | a 2 | b 7 | c 4 |
| 564 | a 3 | b 7 | c 4 |
| 565 | a 4 | b 7 | c 4 |
| 566 | a 5 | b 7 | c 4 |
| 567 | a 6 | b 7 | c 4 |
| 568 | a 7 | b 7 | c 4 |
| 569 | a 8 | b 7 | c 4 |
| 570 | a 9 | b 7 | c 4 |
| 571 | a10 | b 7 | c 4 |
| 572 | a11 | b 7 | c 4 |
| 573 | a 1 | b 8 | c 4 |
| 574 | a 2 | b 8 | c 4 |
| 575 | a 3 | b 8 | c 4 |
| 576 | a 4 | b 8 | c 4 |
| 577 | a 5 | b 8 | c 4 |
| 578 | a 6 | b 8 | c 4 |
| 579 | a 7 | b 8 | c 4 |
| 580 | a 8 | b 8 | c 4 |
| 581 | a 9 | b 8 | c 4 |
| 582 | a10 | b 8 | c 4 |
| 583 | a11 | b 8 | c 4 |
| 584 | a 1 | b 9 | c 4 |
| 585 | a 2 | b 9 | c 4 |
| 586 | a 3 | b 9 | c 4 |
| 587 | a 4 | b 9 | c 4 |
| 588 | a 5 | b 9 | c 4 |
| 589 | a 6 | b 9 | c 4 |
| 590 | a 7 | b 9 | c 4 |
| 591 | a 8 | b 9 | c 4 |
| 592 | a 9 | b 9 | c 4 |
| 593 | a10 | b 9 | c 4 |
| 594 | a11 | b 9 | c 4 |
| 595 | a 1 | b10 | c 4 |
| 596 | a 2 | b10 | c 4 |
| 597 | a 3 | b10 | c 4 |
| 598 | a 4 | b10 | c 4 |
| 599 | a 5 | b10 | c 4 |
| 600 | a 6 | b10 | c 4 |
| 601 | a 7 | b10 | c 4 |
| 602 | a 8 | b10 | c 4 |
| 603 | a 9 | b10 | c 4 |
| 604 | a10 | b10 | c 4 |
| 605 | a11 | b10 | c 4 |
| 606 | a 1 | b11 | c 4 |
| 607 | a 2 | b11 | c 4 |
| 608 | a 3 | b11 | c 4 |
| 609 | a 4 | b11 | c 4 |
| 610 | a 5 | b11 | c 4 |
| 611 | a 6 | b11 | c 4 |
| 612 | a 7 | b11 | c 4 |
| 613 | a 8 | b11 | c 4 |
| 614 | a 9 | b11 | c 4 |
| 615 | a10 | b11 | c 4 |
| 616 | a11 | b11 | c 4 |
| 617 | a 1 | b12 | c 4 |
| 618 | a 2 | b12 | c 4 |
| 619 | a 3 | b12 | c 4 |
| 620 | a 4 | b12 | c 4 |
| 621 | a 5 | b12 | c 4 |
| 622 | a 6 | b12 | c 4 |
| 623 | a 7 | b12 | c 4 |
| 624 | a 8 | b12 | c 4 |
| 625 | a 9 | b12 | c 4 |
| 626 | a10 | b12 | c 4 |
| 627 | a11 | b12 | c 4 |
| 628 | a 1 | b13 | c 4 |
| 629 | a 2 | b13 | c 4 |
| 630 | a 3 | b13 | c 4 |
| 631 | a 4 | b13 | c 4 |
| 632 | a 5 | b13 | c 4 |
| 633 | a 6 | b13 | c 4 |
| 634 | a 7 | b13 | c 4 |
| 635 | a 8 | b13 | c 4 |
| 636 | a 9 | b13 | c 4 |
| 637 | a10 | b13 | c 4 |
| 638 | a11 | b13 | c 4 |

-continued

| No. | Cp | Bridge | Flu |
|---|---|---|---|
| 639 | a 1 | b14 | c 4 |
| 640 | a 2 | b14 | c 4 |
| 641 | a 3 | b14 | c 4 |
| 642 | a 4 | b14 | c 4 |
| 643 | a 5 | b14 | c 4 |
| 644 | a 6 | b14 | c 4 |
| 645 | a 7 | b14 | c 4 |
| 646 | a 8 | b14 | c 4 |
| 647 | a 9 | b14 | c 4 |
| 648 | a10 | b14 | c 4 |
| 649 | a11 | b14 | c 4 |
| 650 | a 1 | b15 | c 4 |
| 651 | a 2 | b15 | c 4 |
| 652 | a 3 | b15 | c 4 |
| 653 | a 4 | b15 | c 4 |
| 654 | a 5 | b15 | c 4 |
| 655 | a 6 | b15 | c 4 |
| 656 | a 7 | b15 | c 4 |
| 657 | a 8 | b15 | c 4 |
| 658 | a 9 | b15 | c 4 |
| 659 | a10 | b15 | c 4 |
| 660 | a11 | b15 | c 4 |
| 661 | a 1 | b 1 | c 5 |
| 662 | a 2 | b 1 | c 5 |
| 663 | a 3 | b 1 | c 5 |
| 664 | a 4 | b 1 | c 5 |
| 665 | a 5 | b 1 | c 5 |
| 666 | a 6 | b 1 | c 5 |
| 667 | a 7 | b 1 | c 5 |
| 668 | a 8 | b 1 | c 5 |
| 669 | a 9 | b 1 | c 5 |
| 670 | a10 | b 1 | c 5 |
| 671 | a11 | b 1 | c 5 |
| 672 | a 1 | b 2 | c 5 |
| 673 | a 2 | b 2 | c 5 |
| 674 | a 3 | b 2 | c 5 |
| 675 | a 4 | b 2 | c 5 |
| 676 | a 5 | b 2 | c 5 |
| 677 | a 6 | b 2 | c 5 |
| 678 | a 7 | b 2 | c 5 |
| 679 | a 8 | b 2 | c 5 |
| 680 | a 9 | b 2 | c 5 |
| 681 | a10 | b 2 | c 5 |
| 682 | a11 | b 2 | c 5 |
| 683 | a 1 | b 3 | c 5 |
| 684 | a 2 | b 3 | c 5 |
| 685 | a 3 | b 3 | c 5 |
| 686 | a 4 | b 3 | c 5 |
| 687 | a 5 | b 3 | c 5 |
| 688 | a 6 | b 3 | c 5 |
| 689 | a 7 | b 3 | c 5 |
| 690 | a 8 | b 3 | c 5 |
| 691 | a 9 | b 3 | c 5 |
| 692 | a10 | b 3 | c 5 |
| 693 | a11 | b 3 | c 5 |
| 694 | a 1 | b 4 | c 5 |
| 695 | a 2 | b 4 | c 5 |
| 696 | a 3 | b 4 | c 5 |
| 697 | a 4 | b 4 | c 5 |
| 698 | a 5 | b 4 | c 5 |
| 699 | a 6 | b 4 | c 5 |
| 700 | a 7 | b 4 | c 5 |
| 701 | a 8 | b 4 | c 5 |
| 702 | a 9 | b 4 | c 5 |
| 703 | a10 | b 4 | c 5 |
| 704 | a11 | b 4 | c 5 |
| 705 | a 1 | b 5 | c 5 |
| 706 | a 2 | b 5 | c 5 |
| 707 | a 3 | b 5 | c 5 |
| 708 | a 4 | b 5 | c 5 |
| 709 | a 5 | b 5 | c 5 |
| 710 | a 6 | b 5 | c 5 |
| 711 | a 7 | b 5 | c 5 |
| 712 | a 8 | b 5 | c 5 |
| 713 | a 9 | b 5 | c 5 |
| 714 | a10 | b 5 | c 5 |
| 715 | a11 | b 5 | c 5 |

-continued

| No. | Cp | Bridge | Flu |
|---|---|---|---|
| 716 | a 1 | b 6 | c 5 |
| 717 | a 2 | b 6 | c 5 |
| 718 | a 3 | b 6 | c 5 |
| 719 | a 4 | b 6 | c 5 |
| 720 | a 5 | b 6 | c 5 |
| 721 | a 6 | b 6 | c 5 |
| 722 | a 7 | b 6 | c 5 |
| 723 | a 8 | b 6 | c 5 |
| 724 | a 9 | b 6 | c 5 |
| 725 | a10 | b 6 | c 5 |
| 726 | a11 | b 6 | c 5 |
| 727 | a 1 | b 7 | c 5 |
| 728 | a 2 | b 7 | c 5 |
| 729 | a 3 | b 7 | c 5 |
| 730 | a 4 | b 7 | c 5 |
| 731 | a 5 | b 7 | c 5 |
| 732 | a 6 | b 7 | c 5 |
| 733 | a 7 | b 7 | c 5 |
| 734 | a 8 | b 7 | c 5 |
| 735 | a 9 | b 7 | c 5 |
| 736 | a10 | b 7 | c 5 |
| 737 | a11 | b 7 | c 5 |
| 738 | a 1 | b 8 | c 5 |
| 739 | a 2 | b 8 | c 5 |
| 740 | a 3 | b 8 | c 5 |
| 741 | a 4 | b 8 | c 5 |
| 742 | a 5 | b 8 | c 5 |
| 743 | a 6 | b 8 | c 5 |
| 744 | a 7 | b 8 | c 5 |
| 745 | a 8 | b 8 | c 5 |
| 746 | a 9 | b 8 | c 5 |
| 747 | a10 | b 8 | c 5 |
| 748 | a11 | b 8 | c 5 |
| 749 | a 1 | b 9 | c 5 |
| 750 | a 2 | b 9 | c 5 |
| 751 | a 3 | b 9 | c 5 |
| 752 | a 4 | b 9 | c 5 |
| 753 | a 5 | b 9 | c 5 |
| 754 | a 6 | b 9 | c 5 |
| 755 | a 7 | b 9 | c 5 |
| 756 | a 8 | b 9 | c 5 |
| 757 | a 9 | b 9 | c 5 |
| 758 | a10 | b 9 | c 5 |
| 759 | a11 | b 9 | c 5 |
| 760 | a 1 | b10 | c 5 |
| 761 | a 2 | b10 | c 5 |
| 762 | a 3 | b10 | c 5 |
| 763 | a 4 | b10 | c 5 |
| 764 | a 5 | b10 | c 5 |
| 765 | a 6 | b10 | c 5 |
| 766 | a 7 | b10 | c 5 |
| 767 | a 8 | b10 | c 5 |
| 768 | a 9 | b10 | c 5 |
| 769 | a10 | b10 | c 5 |
| 770 | a11 | b10 | c 5 |
| 771 | a 1 | b11 | c 5 |
| 772 | a 2 | b11 | c 5 |
| 773 | a 3 | b11 | c 5 |
| 774 | a 4 | b11 | c 5 |
| 775 | a 5 | b11 | c 5 |
| 776 | a 6 | b11 | c 5 |
| 777 | a 7 | b11 | c 5 |
| 778 | a 8 | b11 | c 5 |
| 779 | a 9 | b11 | c 5 |
| 780 | a10 | b11 | c 5 |
| 781 | a11 | b11 | c 5 |
| 782 | a 1 | b12 | c 5 |
| 783 | a 2 | b12 | c 5 |
| 784 | a 3 | b12 | c 5 |
| 785 | a 4 | b12 | c 5 |
| 786 | a 5 | b12 | c 5 |
| 787 | a 6 | b12 | c 5 |
| 788 | a 7 | b12 | c 5 |
| 789 | a 8 | b12 | c 5 |
| 790 | a 9 | b12 | c 5 |
| 791 | a10 | b12 | c 5 |
| 792 | a11 | b12 | c 5 |

| No. | Cp | Bridge | Flu |
|-----|-----|--------|-----|
| 793 | a 1 | b13 | c 5 |
| 794 | a 2 | b13 | c 5 |
| 795 | a 3 | b13 | c 5 |
| 796 | a 4 | b13 | c 5 |
| 797 | a 5 | b13 | c 5 |
| 798 | a 6 | b13 | c 5 |
| 799 | a 7 | b13 | c 5 |
| 800 | a 8 | b13 | c 5 |
| 801 | a 9 | b13 | c 5 |
| 802 | a10 | b13 | c 5 |
| 803 | a11 | b13 | c 5 |
| 804 | a 1 | b14 | c 5 |
| 805 | a 2 | b14 | c 5 |
| 806 | a 3 | b14 | c 5 |
| 807 | a 4 | b14 | c 5 |
| 808 | a 5 | b14 | c 5 |
| 809 | a 6 | b14 | c 5 |
| 810 | a 7 | b14 | c 5 |
| 811 | a 8 | b14 | c 5 |
| 812 | a 9 | b14 | c 5 |
| 813 | a10 | b14 | c 5 |
| 814 | a11 | b14 | c 5 |
| 815 | a 1 | b15 | c 5 |
| 816 | a 2 | b15 | c 5 |
| 817 | a 3 | b15 | c 5 |
| 818 | a 4 | b15 | c 5 |
| 819 | a 5 | b15 | c 5 |
| 820 | a 6 | b15 | c 5 |
| 821 | a 7 | b15 | c 5 |
| 822 | a 8 | b15 | c 5 |
| 823 | a 9 | b15 | c 5 |
| 824 | a10 | b15 | c 5 |
| 825 | a11 | b15 | c 5 |
| 826 | a 1 | b 1 | c 6 |
| 827 | a 2 | b 1 | c 6 |
| 828 | a 3 | b 1 | c 6 |
| 829 | a 4 | b 1 | c 6 |
| 830 | a 5 | b 1 | c 6 |
| 831 | a 6 | b 1 | c 6 |
| 832 | a 7 | b 1 | c 6 |
| 833 | a 8 | b 1 | c 6 |
| 834 | a 9 | b 1 | c 6 |
| 835 | a10 | b 1 | c 6 |
| 836 | a11 | b 1 | c 6 |
| 837 | a 1 | b 2 | c 6 |
| 838 | a 2 | b 2 | c 6 |
| 839 | a 3 | b 2 | c 6 |
| 840 | a 4 | b 2 | c 6 |
| 841 | a 5 | b 2 | c 6 |
| 842 | a 6 | b 2 | c 6 |
| 843 | a 7 | b 2 | c 6 |
| 844 | a 8 | b 2 | c 6 |
| 845 | a 9 | b 2 | c 6 |
| 846 | a10 | b 2 | c 6 |
| 847 | a11 | b 2 | c 6 |
| 848 | a 1 | b 3 | c 6 |
| 849 | a 2 | b 3 | c 6 |
| 850 | a 3 | b 3 | c 6 |
| 851 | a 4 | b 3 | c 6 |
| 852 | a 5 | b 3 | c 6 |
| 853 | a 6 | b 3 | c 6 |
| 854 | a 7 | b 3 | c 6 |
| 855 | a 8 | b 3 | c 6 |
| 856 | a 9 | b 3 | c 6 |
| 857 | a10 | b 3 | c 6 |
| 858 | a11 | b 3 | c 6 |
| 859 | a 1 | b 4 | c 6 |
| 860 | a 2 | b 4 | c 6 |
| 861 | a 3 | b 4 | c 6 |
| 862 | a 4 | b 4 | c 6 |
| 863 | a 5 | b 4 | c 6 |
| 864 | a 6 | b 4 | c 6 |
| 865 | a 7 | b 4 | c 6 |
| 866 | a 8 | b 4 | c 6 |
| 867 | a 9 | b 4 | c 6 |
| 868 | a10 | b 4 | c 6 |
| 869 | a11 | b 4 | c 6 |
| 870 | a 1 | b 5 | c 6 |
| 871 | a 2 | b 5 | c 6 |
| 872 | a 3 | b 5 | c 6 |
| 873 | a 4 | b 5 | c 6 |
| 874 | a 5 | b 5 | c 6 |
| 875 | a 6 | b 5 | c 6 |
| 876 | a 7 | b 5 | c 6 |
| 877 | a 8 | b 5 | c 6 |
| 878 | a 9 | b 5 | c 6 |
| 879 | a10 | b 5 | c 6 |
| 880 | a11 | b 5 | c 6 |
| 881 | a 1 | b 6 | c 6 |
| 882 | a 2 | b 6 | c 6 |
| 883 | a 3 | b 6 | c 6 |
| 884 | a 4 | b 6 | c 6 |
| 885 | a 5 | b 6 | c 6 |
| 886 | a 6 | b 6 | c 6 |
| 887 | a 7 | b 6 | c 6 |
| 888 | a 8 | b 6 | c 6 |
| 889 | a 9 | b 6 | c 6 |
| 890 | a10 | b 6 | c 6 |
| 891 | a11 | b 6 | c 6 |
| 892 | a 1 | b 7 | c 6 |
| 893 | a 2 | b 7 | c 6 |
| 894 | a 3 | b 7 | c 6 |
| 895 | a 4 | b 7 | c 6 |
| 896 | a 5 | b 7 | c 6 |
| 897 | a 6 | b 7 | c 6 |
| 898 | a 7 | b 7 | c 6 |
| 899 | a 8 | b 7 | c 6 |
| 900 | a 9 | b 7 | c 6 |
| 901 | a10 | b 7 | c 6 |
| 902 | a11 | b 7 | c 6 |
| 903 | a 1 | b 8 | c 6 |
| 904 | a 2 | b 8 | c 6 |
| 905 | a 3 | b 8 | c 6 |
| 906 | a 4 | b 8 | c 6 |
| 907 | a 5 | b 8 | c 6 |
| 908 | a 6 | b 8 | c 6 |
| 909 | a 7 | b 8 | c 6 |
| 910 | a 8 | b 8 | c 6 |
| 911 | a 9 | b 8 | c 6 |
| 912 | a10 | b 8 | c 6 |
| 913 | a11 | b 8 | c 6 |
| 914 | a 1 | b 9 | c 6 |
| 915 | a 2 | b 9 | c 6 |
| 916 | a 3 | b 9 | c 6 |
| 917 | a 4 | b 9 | c 6 |
| 918 | a 5 | b 9 | c 6 |
| 919 | a 6 | b 9 | c 6 |
| 920 | a 7 | b 9 | c 6 |
| 921 | a 8 | b 9 | c 6 |
| 922 | a 9 | b 9 | c 6 |
| 923 | a10 | b 9 | c 6 |
| 924 | a11 | b 9 | c 6 |
| 925 | a 1 | b10 | c 6 |
| 926 | a 2 | b10 | c 6 |
| 927 | a 3 | b10 | c 6 |
| 928 | a 4 | b10 | c 6 |
| 929 | a 5 | b10 | c 6 |
| 930 | a 6 | b10 | c 6 |
| 931 | a 7 | b10 | c 6 |
| 932 | a 8 | b10 | c 6 |
| 933 | a 9 | b10 | c 6 |
| 934 | a10 | b10 | c 6 |
| 935 | a11 | b10 | c 6 |
| 936 | a 1 | b11 | c 6 |
| 937 | a 2 | b11 | c 6 |
| 938 | a 3 | b11 | c 6 |
| 939 | a 4 | b11 | c 6 |
| 940 | a 5 | b11 | c 6 |
| 941 | a 6 | b11 | c 6 |
| 942 | a 7 | b11 | c 6 |
| 943 | a 8 | b11 | c 6 |
| 944 | a 9 | b11 | c 6 |
| 945 | a10 | b11 | c 6 |
| 946 | a11 | b11 | c 6 |

| No. | Cp | Bridge | Flu |
|---|---|---|---|
| 947 | a 1 | b12 | c 6 |
| 948 | a 2 | b12 | c 6 |
| 949 | a 3 | b12 | c 6 |
| 950 | a 4 | b12 | c 6 |
| 951 | a 5 | b12 | c 6 |
| 952 | a 6 | b12 | c 6 |
| 953 | a 7 | b12 | c 6 |
| 954 | a 8 | b12 | c 6 |
| 955 | a 9 | b12 | c 6 |
| 956 | a10 | b12 | c 6 |
| 957 | a11 | b12 | c 6 |
| 958 | a 1 | b13 | c 6 |
| 959 | a 2 | b13 | c 6 |
| 960 | a 3 | b13 | c 6 |
| 961 | a 4 | b13 | c 6 |
| 962 | a 5 | b13 | c 6 |
| 963 | a 6 | b13 | c 6 |
| 964 | a 7 | b13 | c 6 |
| 965 | a 8 | b13 | c 6 |
| 966 | a 9 | b13 | c 6 |
| 967 | a10 | b13 | c 6 |
| 968 | a11 | b13 | c 6 |
| 969 | a 1 | b14 | c 6 |
| 970 | a 2 | b14 | c 6 |
| 971 | a 3 | b14 | c 6 |
| 972 | a 4 | b14 | c 6 |
| 973 | a 5 | b14 | c 6 |
| 974 | a 6 | b14 | c 6 |
| 975 | a 7 | b14 | c 6 |
| 976 | a 8 | b14 | c 6 |
| 977 | a 9 | b14 | c 6 |
| 978 | a10 | b14 | c 6 |
| 979 | a11 | b14 | c 6 |
| 980 | a 1 | b15 | c 6 |
| 981 | a 2 | b15 | c 6 |
| 982 | a 3 | b15 | c 6 |
| 983 | a 4 | b15 | c 6 |
| 984 | a 5 | b15 | c 6 |
| 985 | a 6 | b15 | c 6 |
| 986 | a 7 | b15 | c 6 |
| 987 | a 8 | b15 | c 6 |
| 988 | a 9 | b15 | c 6 |
| 989 | a10 | b15 | c 6 |
| 990 | a11 | b15 | c 6 |
| 991 | a 1 | b 1 | c 7 |
| 992 | a 2 | b 1 | c 7 |
| 993 | a 3 | b 1 | c 7 |
| 994 | a 4 | b 1 | c 7 |
| 995 | a 5 | b 1 | c 7 |
| 996 | a 6 | b 1 | c 7 |
| 997 | a 7 | b 1 | c 7 |
| 998 | a 8 | b 1 | c 7 |
| 999 | a 9 | b 1 | c 7 |
| 1000 | a10 | b 1 | c 7 |
| 1001 | a11 | b 1 | c 7 |
| 1002 | a 1 | b 2 | c 7 |
| 1003 | a 2 | b 2 | c 7 |
| 1004 | a 3 | b 2 | c 7 |
| 1005 | a 4 | b 2 | c 7 |
| 1006 | a 5 | b 2 | c 7 |
| 1007 | a 6 | b 2 | c 7 |
| 1008 | a 7 | b 2 | c 7 |
| 1009 | a 8 | b 2 | c 7 |
| 1010 | a 9 | b 2 | c 7 |
| 1011 | a10 | b 2 | c 7 |
| 1012 | a11 | b 2 | c 7 |
| 1013 | a 1 | b 3 | c 7 |
| 1014 | a 2 | b 3 | c 7 |
| 1015 | a 3 | b 3 | c 7 |
| 1016 | a 4 | b 3 | c 7 |
| 1017 | a 5 | b 3 | c 7 |
| 1018 | a 6 | b 3 | c 7 |
| 1019 | a 7 | b 3 | c 7 |
| 1020 | a 8 | b 3 | c 7 |
| 1021 | a 9 | b 3 | c 7 |
| 1022 | a10 | b 3 | c 7 |
| 1023 | a11 | b 3 | c 7 |
| 1024 | a 1 | b 4 | c 7 |
| 1025 | a 2 | b 4 | c 7 |
| 1026 | a 3 | b 4 | c 7 |
| 1027 | a 4 | b 4 | c 7 |
| 1028 | a 5 | b 4 | c 7 |
| 1029 | a 6 | b 4 | c 7 |
| 1030 | a 7 | b 4 | c 7 |
| 1031 | a 8 | b 4 | c 7 |
| 1032 | a 9 | b 4 | c 7 |
| 1033 | a10 | b 4 | c 7 |
| 1034 | a11 | b 4 | c 7 |
| 1035 | a 1 | b 5 | c 7 |
| 1036 | a 2 | b 5 | c 7 |
| 1037 | a 3 | b 5 | c 7 |
| 1038 | a 4 | b 5 | c 7 |
| 1039 | a 5 | b 5 | c 7 |
| 1040 | a 6 | b 5 | c 7 |
| 1041 | a 7 | b 5 | c 7 |
| 1042 | a 8 | b 5 | c 7 |
| 1043 | a 9 | b 5 | c 7 |
| 1044 | a10 | b 5 | c 7 |
| 1045 | a11 | b 5 | c 7 |
| 1046 | a 1 | b 6 | c 7 |
| 1047 | a 2 | b 6 | c 7 |
| 1048 | a 3 | b 6 | c 7 |
| 1049 | a 4 | b 6 | c 7 |
| 1050 | a 5 | b 6 | c 7 |
| 1051 | a 6 | b 6 | c 7 |
| 1052 | a 7 | b 6 | c 7 |
| 1053 | a 8 | b 6 | c 7 |
| 1054 | a 9 | b 6 | c 7 |
| 1055 | a10 | b 6 | c 7 |
| 1056 | a11 | b 6 | c 7 |
| 1057 | a 1 | b 7 | c 7 |
| 1058 | a 2 | b 7 | c 7 |
| 1059 | a 3 | b 7 | c 7 |
| 1060 | a 4 | b 7 | c 7 |
| 1061 | a 5 | b 7 | c 7 |
| 1062 | a 6 | b 7 | c 7 |
| 1063 | a 7 | b 7 | c 7 |
| 1064 | a 8 | b 7 | c 7 |
| 1065 | a 9 | b 7 | c 7 |
| 1066 | a10 | b 7 | c 7 |
| 1067 | a11 | b 7 | c 7 |
| 1068 | a 1 | b 8 | c 7 |
| 1069 | a 2 | b 8 | c 7 |
| 1070 | a 3 | b 8 | c 7 |
| 1071 | a 4 | b 8 | c 7 |
| 1072 | a 5 | b 8 | c 7 |
| 1073 | a 6 | b 8 | c 7 |
| 1074 | a 7 | b 8 | c 7 |
| 1075 | a 8 | b 8 | c 7 |
| 1076 | a 9 | b 8 | c 7 |
| 1077 | a10 | b 8 | c 7 |
| 1078 | a11 | b 8 | c 7 |
| 1079 | a 1 | b 9 | c 7 |
| 1080 | a 2 | b 9 | c 7 |
| 1081 | a 3 | b 9 | c 7 |
| 1082 | a 4 | b 9 | c 7 |
| 1083 | a 5 | b 9 | c 7 |
| 1084 | a 6 | b 9 | c 7 |
| 1085 | a 7 | b 9 | c 7 |
| 1086 | a 8 | b 9 | c 7 |
| 1087 | a 9 | b 9 | c 7 |
| 1088 | a10 | b 9 | c 7 |
| 1089 | a11 | b 9 | c 7 |
| 1090 | a 1 | b10 | c 7 |
| 1091 | a 2 | b10 | c 7 |
| 1092 | a 3 | b10 | c 7 |
| 1093 | a 4 | b10 | c 7 |
| 1094 | a 5 | b10 | c 7 |
| 1095 | a 6 | b10 | c 7 |
| 1096 | a 7 | b10 | c 7 |
| 1097 | a 8 | b10 | c 7 |
| 1098 | a 9 | b10 | c 7 |
| 1099 | a10 | b10 | c 7 |
| 1100 | a11 | b10 | c 7 |

-continued

| No. | Cp | Bridge | Flu |
|---|---|---|---|
| 1101 | a 1 | b11 | c 7 |
| 1102 | a 2 | b11 | c 7 |
| 1103 | a 3 | b11 | c 7 |
| 1104 | a 4 | b11 | c 7 |
| 1105 | a 5 | b11 | c 7 |
| 1106 | a 6 | b11 | c 7 |
| 1107 | a 7 | b11 | c 7 |
| 1108 | a 8 | b11 | c 7 |
| 1109 | a 9 | b11 | c 7 |
| 1110 | a10 | b11 | c 7 |
| 1111 | a11 | b11 | c 7 |
| 1112 | a 1 | b12 | c 7 |
| 1113 | a 2 | b12 | c 7 |
| 1114 | a 3 | b12 | c 7 |
| 1115 | a 4 | b12 | c 7 |
| 1116 | a 5 | b12 | c 7 |
| 1117 | a 6 | b12 | c 7 |
| 1118 | a 7 | b12 | c 7 |
| 1119 | a 8 | b12 | c 7 |
| 1120 | a 9 | b12 | c 7 |
| 1121 | a10 | b12 | c 7 |
| 1122 | a11 | b12 | c 7 |
| 1123 | a 1 | b13 | c 7 |
| 1124 | a 2 | b13 | c 7 |
| 1125 | a 3 | b13 | c 7 |
| 1126 | a 4 | b13 | c 7 |
| 1127 | a 5 | b13 | c 7 |
| 1128 | a 6 | b13 | c 7 |
| 1129 | a 7 | b13 | c 7 |
| 1130 | a 8 | b13 | c 7 |
| 1131 | a 9 | b13 | c 7 |
| 1132 | a10 | b13 | c 7 |
| 1133 | a11 | b13 | c 7 |
| 1134 | a 1 | b14 | c 7 |
| 1135 | a 2 | b14 | c 7 |
| 1136 | a 3 | b14 | c 7 |
| 1137 | a 4 | b14 | c 7 |
| 1138 | a 5 | b14 | c 7 |
| 1139 | a 6 | b14 | c 7 |
| 1140 | a 7 | b14 | c 7 |
| 1141 | a 8 | b14 | c 7 |
| 1142 | a 9 | b14 | c 7 |
| 1143 | a10 | b14 | c 7 |
| 1144 | a11 | b14 | c 7 |
| 1145 | a 1 | b15 | c 7 |
| 1146 | a 2 | b15 | c 7 |
| 1147 | a 3 | b15 | c 7 |
| 1148 | a 4 | b15 | c 7 |
| 1149 | a 5 | b15 | c 7 |
| 1150 | a 6 | b15 | c 7 |
| 1151 | a 7 | b15 | c 7 |
| 1152 | a 8 | b15 | c 7 |
| 1153 | a 9 | b15 | c 7 |
| 1154 | a10 | b15 | c 7 |
| 1155 | a11 | b15 | c 7 |

According to the above table, the ligand structure of No. 331 means a combination of a1-b1-c3, so that when the metal part MQj is $ZrCl_2$, the following metallocene compound is exemplified.

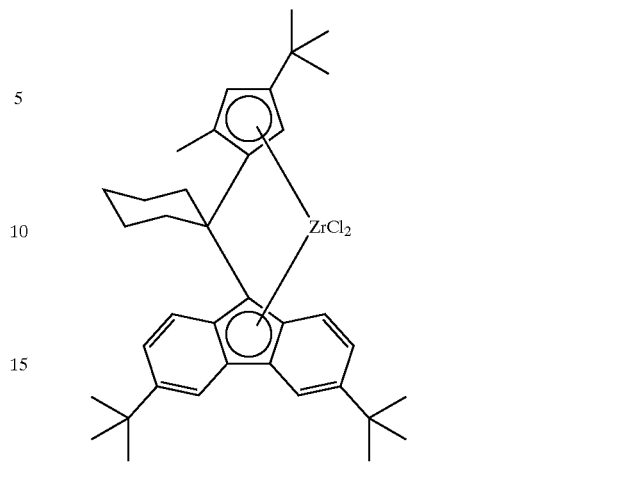

Specific examples of MQj include $ZrCl_2$, $ZrBr_2$, $ZrMe_2$, $Zr(OTs)_2$, $Zr(OMs)_2$, $Zr(OTf)_2$, $TiCl_2$, $TiBr_2$, $TiMe_2$, $Ti(OTs)_2$, $Ti(OMs)_2$, $Ti(OTf)_2$, $HfCl_2$, $HfBr_2$, $HfMe_2$, $Hf(OTs)_2$, $Hf(OMs)_2$ and $Hf(OTf)_2$.

Preferred examples of the metallocene compounds represented by the formula (1b) or (2b) according to the invention include:

a metallocene compound of the formula (1b) wherein $R^{21}$, $R^{13}$ and $R^{14}$ are each methyl, $R^{22}$ is tert butyl, $R^5$, $R^6$, $R^7$, $R^8$, $R^9$, $R^{10}$, $R^{11}$ and $R^{12}$ are each hydrogen, M is zirconium, Y is carbon, Q is chlorine, and j is 2;

a metallocene compound of the formula (1b) wherein $R^{21}$, $R^{13}$ and $R^{14}$ are each methyl, $R^{22}$ is tert-butyl, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, and j is 2;

a metallocene compound of the formula (1b) wherein $R^{21}$, $R^{13}$ and $R^{14}$ are each methyl, $R^{22}$ is tert-butyl, $R^5$, $R^7$, $R^8$, $R^9$, $R^{10}$ and $R^{12}$ are each hydrogen, $R^6$ and $R^{11}$ are each tert-butyl, M is zirconium, Y is carbon, Q is chlorine, and j is 2;

a metallocene compound of the formula (2b) wherein $R^{21}$ is methyl, $R^{22}$ is tert-butyl, $R^5$, $R^6$, $R^7$, $R^8$, $R^9$, $R^{10}$, $R^{11}$ and $R^{12}$ are each hydrogen, M is zirconium, Y is carbon, Q is chlorine, j is 2, and A is —$(CH_2)_5$—; and a metallocene compound of the formula (2b) wherein $R^{21}$ is methyl, $R^{22}$ is tert-butyl, $R^5$, $R^6$, $R^8$, $R^9$, $R^{11}$ and $R^{12}$ are each hydrogen, $R^7$ and $R^{10}$ are each tert-butyl, M is zirconium, Y is carbon, Q is chlorine, j is 2, and A is —(CH2)$_5$—.

There is no specific limitation on the process for preparing the metallocene compound represented by the formula (1b) or (2b), and the compound can be prepared by, for example, the following process.

In the process for preparing the metallocene compound according to the invention, the metallocene compound represented by the formula (1b) or (2b) is selectively prepared so as not to include an isomeric compound wherein $R^1$ and $R^2$ are adjacent to each other. To attain this purpose, it is necessary to selectively prepare the ligand precursor, etc. of the metallocene compound. Such a process is described with reference to the following example.

Process for Preparing Metallocene Compound

The ligand precursor (7) used as starting material for preparing the metallocene compound represented by the formula (1b) can be selectively prepared through the following step (H) or (I).

[H]
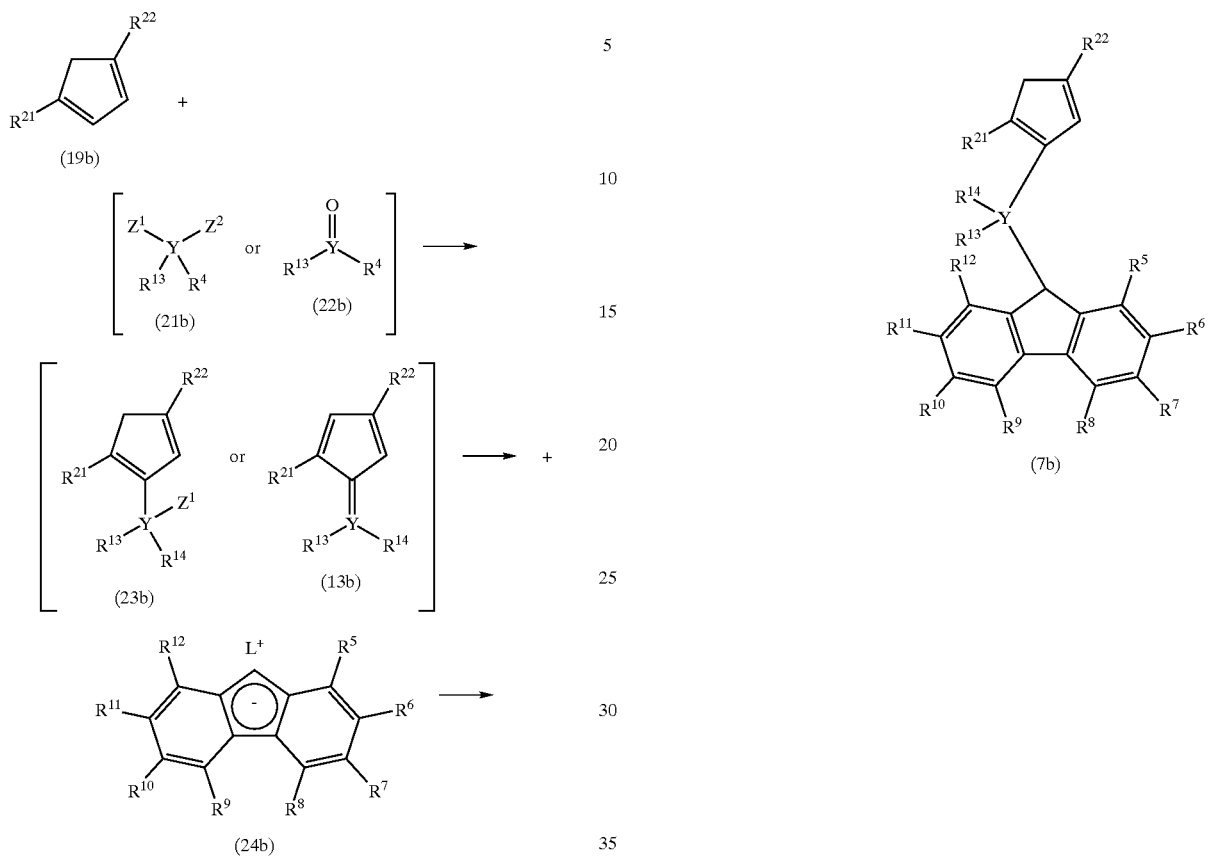
[I]
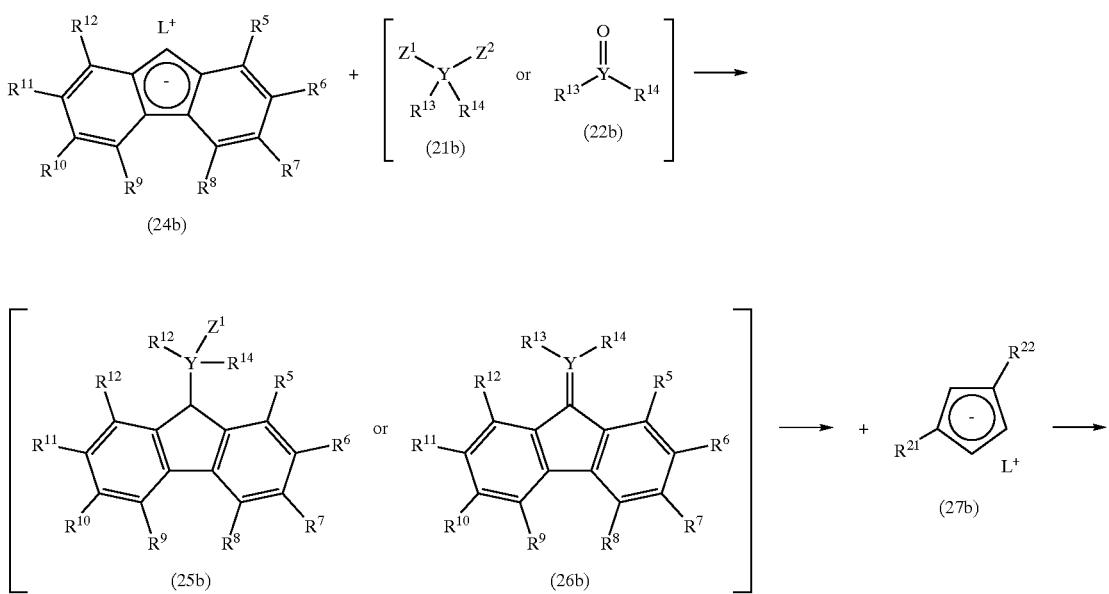

-continued

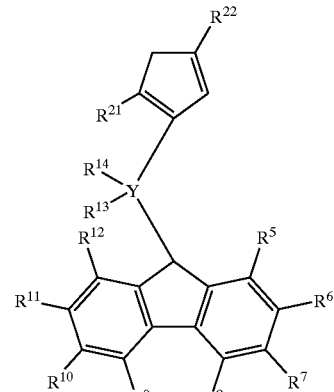

(7b)

In the compounds shown in the above steps (H) and (I), $R^5$ to $R^{14}$, $R^{21}$, $R^{22}$ and Y have the same meanings as those of $R^5$ to $R^{14}$, $R^{21}$, $R^{22}$ and Y in the formula (1b), respectively, L is an alkali metal, and $Z^1$ and $Z^2$ may be the same or different and are each a halogen or an anionic ligand.

With regard to the cyclopentadiene (19b), the precursor compound (23b) and the ligand precursor (7b), presence of isomers different in only the position of a double bond in the cyclopentadienyl ring can be thought, but only one example is shown. Each of them may be another isomer different in only the position of a double bond in the cyclopentadienyl ring or a mixture thereof.

By the preparation of a precursor compound through the step (H) or (I), the precursor compound (13b) can be prepared without producing the following isomeric compound (15b) or (16b), and the ligand precursor (7b) can be prepared without producing the following isomeric compound (9b) or (10b).

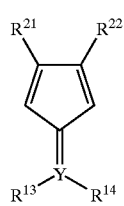

(15b)

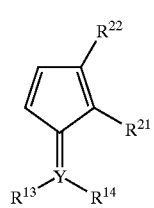

(16b)

wherein $R^{21}$, $R^{22}$, $R^{13}$, $R^{14}$ and Y have the same meanings as those of $R^{21}$, $R^{22}$, $R^{13}$, $R^{14}$ and Y in the formula (1b), respectively.

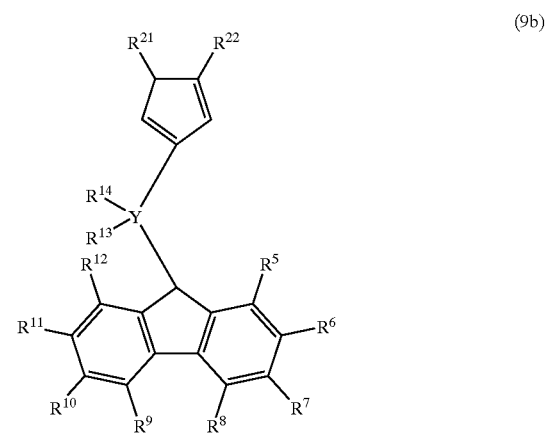

(9b)

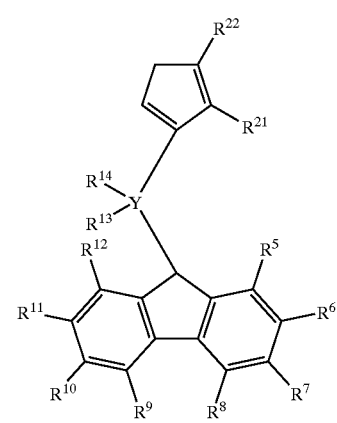

(10b)

wherein $R^{21}$, $R^{22}$, $R^{13}$, to $R^{14}$, and Y have the same meanings as those of $R^{21}$, $R^{22}$, $R^5$ to $R^{14}$, and Y in the formula (1b), respectively, and the cyclopentadienyl group may be another isomer different in only the position of a double bond in the cyclopentadienyl ring or a mixture thereof.

The ligand precursor (8b) of the metallocene compound represented by the formula (2b) can be selectively prepared through the following step (J) or (K).

[J]
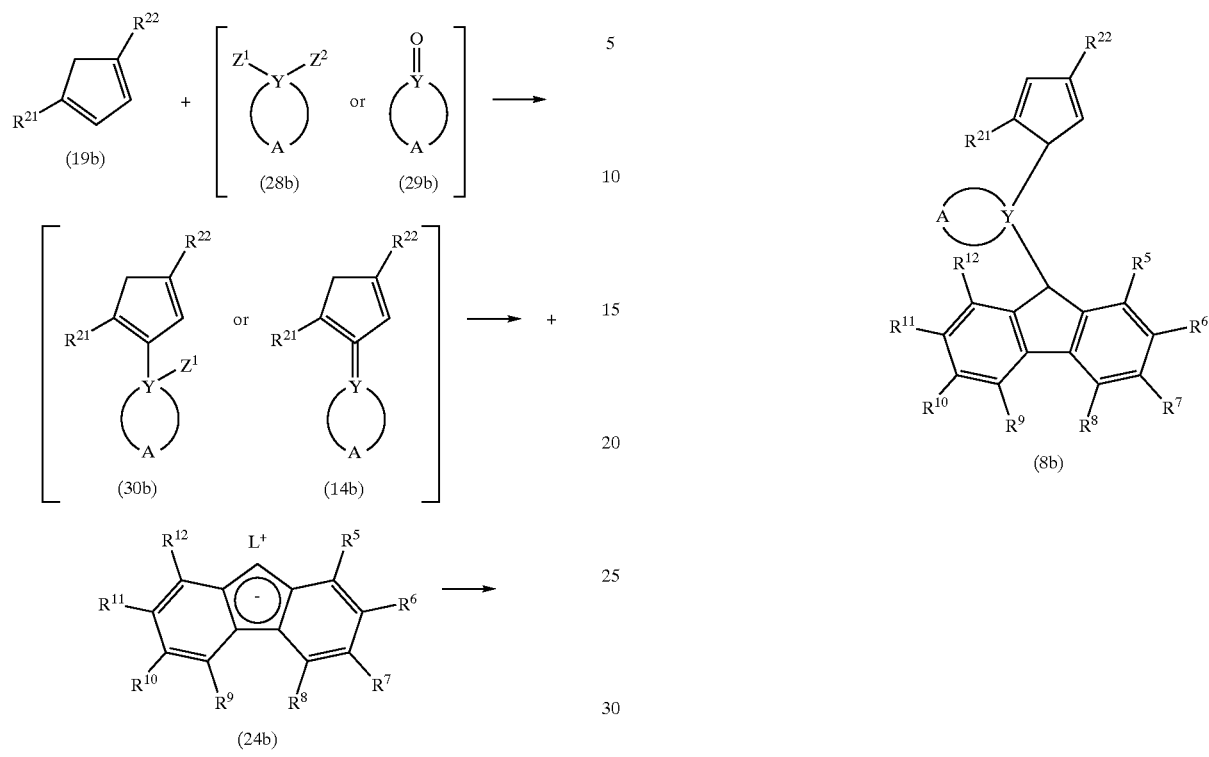
[K]
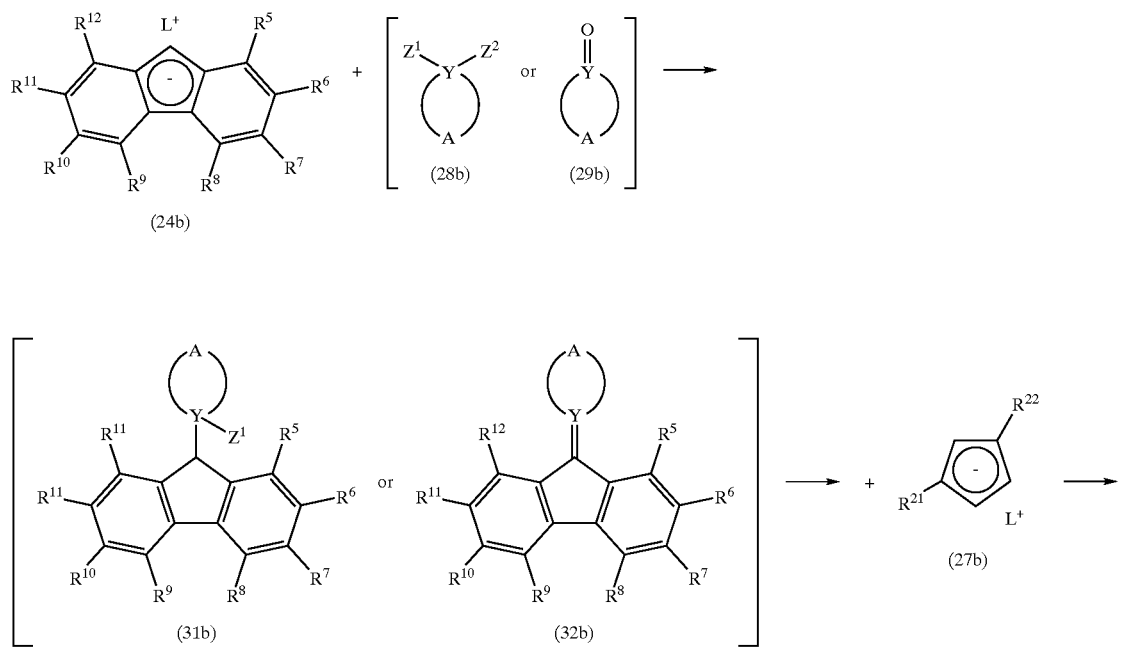

In the compounds shown in the above steps (J) and (K), $R^5$ to $R^{14}$, $R^{21}$, $R^{22}$, Y and A have the same meanings as those of $R^5$ to $R^{14}$, $R^{21}$, $R^{22}$, Y and A in the formula (2b), respectively, L is an alkali metal, and $Z^1$ and $Z^2$ may be the same or different and are each a halogen or an anionic ligand.

With regard to the cyclopentadiene (19b), the precursor compound (30b) and the ligand precursor (8b), presence of isomers different in only the position of a double bond in the cyclopentadienyl ring can be thought, but only one example is shown. Each of them may be another isomer different in only the position of a double bond in the cyclopentadienyl ring or a mixture thereof.

By the preparation of a precursor compound through the step (J) or (K), the precursor compound (14b) can be prepared without producing the following isomeric compound (17b) or (18b), and the ligand precursor (8b) can be prepared without producing the following isomeric compound (11b) or (12b).

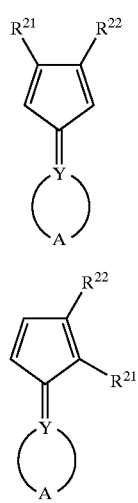

wherein $R^{21}$, $R^{22}$, Y and A have the same meanings as those of $R^{21}$, $R^{22}$, Y and A in the formula (2b), respectively.

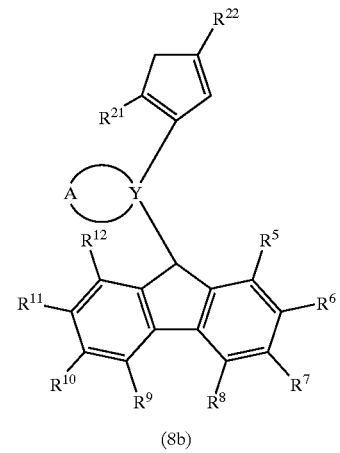

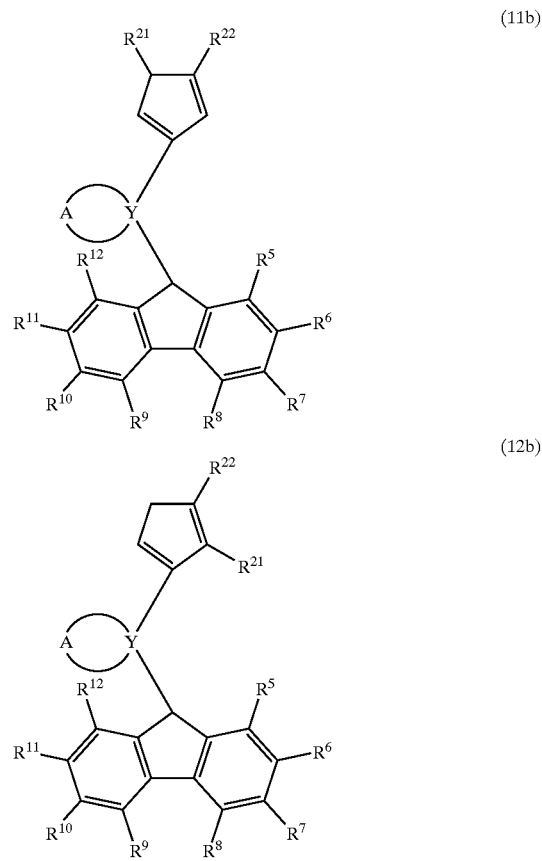

wherein $R^{21}$, $R^{22}$, $R^5$ to $R^{12}$, A and Y have the same meanings as those of $R^{21}$-$R^{22}$, $R^5$ to $R^{12}$, A and Y in the formula (2b), respectively, and the cyclopentadienyl group may be another isomer different in only the position of a double bond in the cyclopentadienyl ring or a mixture thereof.

The cyclopentadiene (19) that is a precursor common to the metallocene compounds represented by the formulas (1b) and (2b) can be selectively prepared through, for example, the following step (L).

[L]

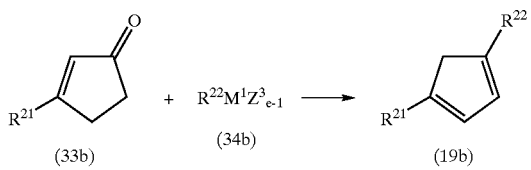

In the compounds shown in the step (L), each of $R^{21}$ and $R^{22}$ has the same meaning as described in the formula (1b) or (2b), $M^1$ is an alkali metal or an alkaline earth metal, $Z^3$ is the same as. $R^{22}$ or is a halogen or an anionic ligand, and e is a valence of $M^1$.

As another step for preparing the cyclopentadiene (19b), the following step (M) or (N) is also available. In the step (M) or (N), however, an isomer (20b) wherein $R^{21}$ and $R^{22}$ are adjacent to each other is occasionally produced as a by-product, and therefore, the step (M) or (N) is employable only when the isomer (20b) is not produced owing to combination of $R^{21}$ and $R^{22}$, reaction conditions, etc.

[M]

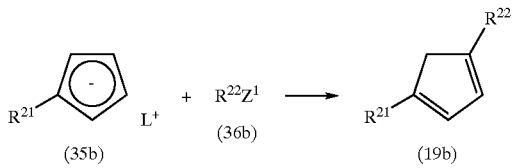

[N]

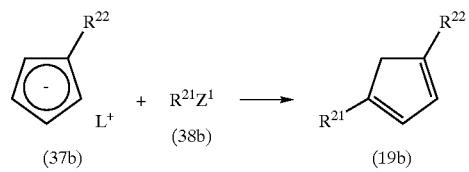

In the compounds shown in the above steps (M) and (N), $R^{21}$ and $R^{22}$ have the same meanings as those of $R^{21}$ and $R^{22}$ in the formula (1b) or (2b), respectively, L is an alkali metal, and $Z^1$ is a halogen or an anionic ligand.

When $R^{22}$ is a substituent group represented by $CR^{15}R^{16}R^{17}$, the cyclopentadiene (19b) can be prepared also through the following step (O).

[O]

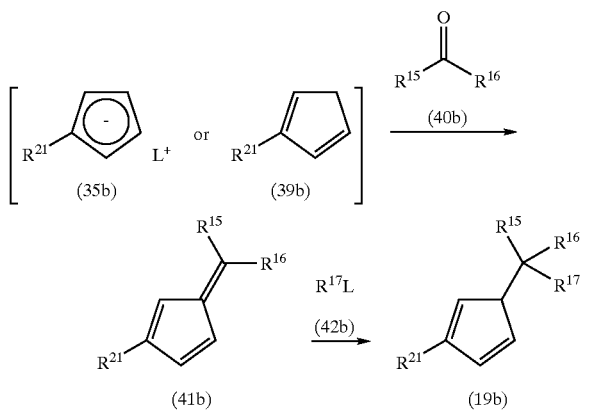

In the compounds shown in the step (O), $R^{21}$ has the same meaning as that of $R^{21}$ in the formula (1b) or (2b) $R^{13}$, $R^{14}$ and $R^{15}$ may be the same or different and are each selected from a hydrogen atom, a hydrocarbon group and a silicon-containing hydrocarbon group, and L is an alkali metal.

Also in this step, an isomer (20b) wherein $R^{21}$ and $R^{22}$ are adjacent to each other is occasionally produced as a by-product, and therefore, the step (O) is employable only when the isomer (20b) is not produced owing to combination of $R^{21}$ and $R^{22}$, reaction conditions, etc.

By the preparation of cyclopentadiene through any one of the steps (L) to (O), the cyclopentadiene (19b) can be prepared without producing the following isomeric compound (20b).

wherein $R^{21}$ and $R^{22}$ have the same meanings as those of $R^{21}$ and $R^{22}$ in the formula (1b) or (2b), respectively, and the cyclopentadienyl group may be another isomer different in only the position of a double bond in the cyclopentadienyl ring or a mixture thereof.

Examples of the alkali metals, the alkaline earth metals, the halogens and the anionic ligands used for the reactions of the steps (H) to (O) include the same ones as used for the reactions of the aforesaid steps (A) to (G).

Next, an example of the process for preparing the metallocene compound from the ligand precursor represented by the formula (7b) or (8b) is described.

In the first place, the ligand precursor represented by the formula (7b) or (8b) that is obtained by the reaction of the step (H), (I), (J) or (K) is brought into contact with an alkali metal, an alkali metal hydride or an organic alkali metal in an organic solvent at a reaction temperature of −80 to 200° C. to prepare a di-alkali metal salt.

Examples of the organic solvents used for the above reaction include the same ones as used for preparing the metallocene compound from the ligand precursor represented by the formula (5) or (6).

Examples of the alkali metals and the alkali metal hydrides used for the reaction include the same ones as used for preparing the metallocene compound from the ligand precursor represented by the formula (5) or (6).

In the next place, the di-alkali metal salt is allowed to react, in an organic solvent, with a compound represented by the following formula (43b):

wherein M is a metal selected from Group 4 of the periodic table, each Z may be the same or different and is selected from a halogen, an anionic ligand and a neutral ligand capable of coordination by a lone pair, and k is an integer of 3 to 6.

Thus, the metallocene compound represented by the formula (1b) or (2b) can be synthesized.

Preferred examples of the compounds represented by formula (43b) include trivalent or tetravalent titanium fluoride, chloride, bromide or iodide; tetravalent zirconium fluoride, chloride, bromide or iodide; tetravalent hafnium fluoride, chloride, bromide or iodide; and complexes of these compounds with ethers such as THF, diethyl ether, dioxane and 1,2-dimethoxyethane.

Examples of the organic solvents used include the same ones as previously described.

The reaction of the di-alkali metal salt with the compound represented by the formula (43b) is preferably an equimolar reaction, and can be carried out in the aforesaid organic solvent at a reaction temperature of −80 to 200° C.

The metallocene compound obtained by the reaction can be isolated and purified by, for example, extraction, recrystallization or sublimation.

The metallocene compound prepared by the process of the invention contains no unnecessary isomer, so that when it is used as, for example, an olefin polymerization catalyst, obtainable are favorable results such that an atactic polymer is hardly produced.

Olefin Polymerization Catalyst

A preferred embodiment of use of the metallocene compound of the invention as an olefin polymerization catalyst is described below.

When the metallocene compound of the invention is used as an olefin polymerization catalyst, the catalyst comprises:
(A) the metallocene compound,
(B) at least one compound selected from:
    (B-1) an organometallic compound,
    (B-2) an organoaluminum oxy-compound, and
    (B-3) a compound which reacts with the metallocene compound (A) to form an ion pair,
and optionally,
(C) a particle carrier.

The components (B) and (C) for forming the catalyst are described below.

(B-1) Organometallic Compound

Examples of the organometallic compounds (B-1) used in the preparation of the ethylene/α-olefin copolymer include the below-described organometallic compounds containing metals of Group 1, Group 2, Group 12 and Group 13 of the periodic table.

(B-1a) Organoaluminum compound represented by the following formula:

$$R^a{}_m Al(OR^b)_n H_p X_q$$

wherein Ra and Rb may be the same or different and are each a hydrocarbon group of 1 to 15 carbon atoms, preferably 1 to 4 carbon atoms; X is a halogen atom; and m, n, p and q are numbers satisfying the conditions of $0<m\leq3$, $0\leq n<3$, $0\leq p<3$, $0\leq q<3$ and $m+n+p+q=3$.

(B-1b) Alkyl complex compound comprising a metal of Group 1 of the periodic table and aluminum, which is represented by the following formula:

$$M^2 AlR^a{}_4$$

wherein $M^2$ is Li, Na or K; and Ra is a hydrocarbon group of 1 to 15 carbon atoms, preferably 1 to 4 carbon atoms.

(B-1c) Dialkyl compound containing a metal of Group 2 or Group 12 of the periodic table, which is represented by the following formula:

$$R^a R^b M^3$$

wherein $R^a$ and $R^b$ may be the same or different and are each a hydrocarbon-group of 1 to 15 carbon atoms, preferably 1 to 4 carbon atoms; and $M^3$ is Mg, Zn or Cd.

Examples of the organoaluminum compounds (B-1a) include:

an organoaluminum compound represented by the following formula:

$$R^a{}_m Al(OR^b)_{3-m}$$

wherein $R^a$ and $R^b$ may be the same or different and are each a hydrocarbon group of 1 to 15 carbon atoms, preferably 1 to 4 carbon atoms, and m is preferably a number satisfying the condition of $1.5\leq m\leq3$;

an organoaluminum compound represented by the following formula:

$$R^a{}_m AlX_{3-m}$$

wherein $R^a$ is a hydrocarbon group of 1 to 15 carbon atoms, preferably 1 to 4 carbon atoms, X is a halogen atom, and m is preferably a number satisfying the condition of $0<m<3$;

an organoaluminum compound represented by the following formula:

$$R^a{}_m AlH_{3-m}$$

wherein $R^a$ is a hydrocarbon group of 1 to 15 carbon atoms, preferably 1 to 4 carbon atoms, and m is preferably a number satisfying the condition of $2\leq m\leq3$; and an organoaluminum compound represented by the following formula:

$$R^a{}_m Al(OR^b)_n X_q$$

wherein $R^a$ and $R^b$ may be the same or different and are each a hydrocarbon group of 1 to 15 carbon atoms, preferably 1 to 4 carbon atoms, X is a halogen atom, and m, n and q are numbers satisfying the conditions of $0<m\leq3$, $0\leq n<3$, $0\leq q<3$ and $m+n+q=3$.

Specific examples of the organoaluminum compounds (B-1a) include:

tri-n-alkylaluminums, such as trimethylaluminum, triethylaluminum, tri-n-butylaluminum, tripropylaluminum, tripentylaluminum, trihexylaluminum, trioctylaluminum and tridecylaluminum;

branched-chain trialkylaluminums, such as triisopropylaluminum, triisobutylaluminum, tri-sec-butylaluminum, tri-tert-butylaluminum, tri-2-methylbutylaluminum, tri-3-methylbutylaluminum, tri-2-methylpentylaluminum, tri-3-methylpentylaluminum, tri-4-methylpentylaluminum, tri-2-methylhexylaluminum, tri-3-methylhexylaluminum and tri-2-ethylhexylaluminum;

tricycloalkylaluminums, such as tricyclohexylaluminum and tricyclooctylaluminum;

triarylaluminums, such as triphenylaluminum and tritolylaluminum;

dialkylaluminum hydrides, such as diisopropylaluminum hydride and diisobutylaluminum hydride;

alkenylaluminums represented by the formula $(i\text{-}C_4H_9)_x Al_y (C_5H_{10})_z$ (wherein x, y and z are each a positive number, and $z\geq2x$) or the like, such as isoprenylaluminum;

alkylaluminum alkoxides, such as isobutylaluminum methoxide, isobutylaluminum ethoxide and isobutylaluminum isopropoxide;

dialkylaluminum alkoxides, such as dimethylaluminum methoxide, diethylaluminum ethoxide and dibutylaluminum butoxide;

alkylaluminum sesquialkoxides, such as ethylaluminum sesquiethoxide and butylaluminum sesquibutoxide;

partially alkoxylated alkylaluminums having an average composition, which are represented by $R^a_{2.5}Al(OR^b)_{0.5}$ or the like;

alkylaluminum aryloxides, such as diethylaluminum phenoxide, diethylaluminum(2,6-di-t-butyl-4-methylphenoxide), ethylaluminumbis(2,6-di-t-butyl-4-methylphenoxide), diisobutylalumium(2,6-di-t-butyl-4-methylphenoxide) and isobutylaluminumbis(2,6-di-t-butyl-4-methylphenoxide);

dialkylaluminum halides, such as dimethylaluminum chloride, diethylaluminum chloride, dibutylaluminum chloride, diethylaluminum bromide and diisobutylaluminum chloride;

alkylaluminum sesquihalides, such as ethylaluminum sesquichloride, butylaluminum sesquichloride and ethylaluminum sesquibromide, partially halogenated alkylaluminums, e.g., alkylaluminum dihalides, such as ethylaluminum dichloride, propylaluminum dichloride and butylaluminum dibromide;

dialkylaluminum hydrides, such as diethylaluminum hydride and dibutylaluminum hydride;

partially hydrogenated alkylaluminums, e.g., alkylaluminum dihydrides, such as ethylaluminum dihydride and propylaluminum dihydride; and partially alkoxylated and halogenated alkylaluminums, such as ethylaluminum ethoxychloride, butylaluminum butoxychloride and ethylaluminum ethoxybromide.

Also employable are compounds analogous to the organoaluminum compound (B-1a). For example, there can be mentioned organoaluminum compounds wherein two or more aluminum compounds are combined through a nitrogen atom, such as $(C_2H_5)_2AlN(C_2H_5)Al(C_2H_5)_2$.

Examples of the compounds (B-1b) include $LiAl(C_2H_5)_4$ and $LiAl(C_7H_{15})_4$.

Other compounds, such as methyllithium, ethyllithium, propyllithium, butyllithium, methylmagnesium bromide, methylmagnesium chloride, ethylmagnesium bromide, ethylmagnesium chloride, propylmagnesium bromide, propylmagnesium chloride, butylmagnesium bromide, butylmagnesium chloride, dimethylmagnesium, diethymagnesium, dibutylmagnesium and butylethylmagnesium, are also employable as the organometallic compounds (B-1).

Combinations of compounds capable of forming the above-mentioned organoaluminum compounds in the polymerization system, e.g., a combination of halogenated aluminum and alkyllithium and a combination of halogenated aluminum and alkylmagnesium, are also employable.

Of the organometallic compounds (B-1), the organoaluminum compounds are preferable.

The organometallic compounds (B-1) mentioned above are used singly or in combination of two or more kinds.

(B-2) Organoaluminum Oxy-Compound

The organoaluminum oxy-compound (B-2) used in the present invention may be conventional aluminoxane or such a benzene-insoluble organoaluminum oxy-compound as exemplified in Japanese Patent Laid-Open Publication No. 78687/1990.

The conventional aluminoxane can be prepared by, for example, the following processes, and is generally obtained as a hydrocarbon solvent solution.

(1) An organoaluminum compound such as trialkylaluminum is added to a hydrocarbon medium suspension of a compound containing adsorption water or a salt containing water of crystallization, e.g., magnesium chloride hydrate, copper sulfate hydrate, aluminum sulfate hydrate, nickel sulfate hydrate or cerous chloride hydrate, to allow the organoaluminum compound to react with the adsorption water or the water of crystallization.

(2) Water, ice or water vapor is allowed to directly act on an organoaluminum compound such as trialkylaluminum in a medium such as benzene, toluene, ethyl ether or tetrahydrofuran (3) An organotin oxide such as dimethyltin oxide or dibutyltin oxide is allowed to react with an organoaluminum compound such as trialkylaluminum in a medium such as decane, benzene or toluene.

The aluminoxane may contain a small amount of an organometallic component. Further, it is possible that the solvent or the unreacted organoaluminum compound is distilled off from the recovered solution of aluminoxane and the remainder is redissolved in a solvent or suspended in a poor solvent for aluminoxane.

Examples of the organoaluminum compounds used for preparing the aluminoxane include the same organoaluminum compounds as previously exemplified with respect to the organoaluminum compound (B-1a). Of these, preferable are trialkylaluminums and tricycloalkylaluminums. Particularly preferable is trimethylaluminum.

The organoaluminum compounds are used singly or in combination of two or more kinds.

An aluminoxane prepared from the trimethylaluminum is referred as methylaluminoxane or MAO, and is the commonly used compound.

Examples of the solvents used for preparing the aluminoxane include aromatic hydrocarbons, such as benzene, toluene, xylene, cumene and cymene; aliphatic hydrocarbons, such as pentane, hexane, heptane, octane, decane, dodecane, hexadecane and octadecane; alicyclic hydrocarbons, such as cyclopentane, cyclohexane, cyclooctane and methylcyclopentane; petroleum fractions, such as gasoline, kerosine and gas oil; and halogenated products of these aromatic, aliphatic and alicyclic hydrocarbons, particularly chlorinated or brominated products thereof. Also employable are ethers such as ethyl ether and tetrahydrofuran. Of the solvents, particularly preferable are aromatic hydrocarbons and aliphatic hydrocarbons.

The benzene-insoluble organoaluminum oxy-compound used in the present invention is preferably one containing an Al component that is soluble in benzene at 60° C. in an amount of usually not more than 10% preferably not more than 5%, particularly preferably not more than 2%, in terms of Al atom. That is, the benzene-insoluble organoaluminum oxy-compound is preferably insoluble or sparingly soluble in benzene.

The organoaluminum oxy-compound used in the present invention is, for example, an organoaluminum oxy-compound containing boron, which is represented by the following formula (i):

$$R^d_2AlOB(R^c)OAlR^d_2 \qquad (i)$$

wherein $R^c$ is a hydrocarbon group of 1 to 10 carbon atoms; and each $R^d$ may be the same or different and is a hydrogen atom, a halogen atom or a hydrocarbon group of 1 to 10 carbon atoms.

The organoaluminum oxy-compound containing boron, which is represented by the formula (i), can be prepared by allowing an alkylboronic acid represented by the following formula (ii) to react with an organoaluminum compound in an inert solvent at a temperature of −80C to room temperature for 1 minute to 24 hours under an inert gas atmosphere.

$$R^cB(OH)_2 \qquad (ii)$$

wherein $R^c$ is the same group as described above.

Examples of the alkylboronic acids represented by the formula (ii) include methylboronic acid, ethylboronic acid, isopropylboronic acid, n-propylboronic acid, n-butylboronic acid, isobutylboronic acid, n-hexylboronic acid, cyclohexylboronic acid, phenylboronic acid, 3,5-difluoroboronic acid, pentafluorophenylboronic acid and 3,5-bis(trifluoromethyl) phenylboronic acid. Of these, preferable are methylboronic acid, n-butylboronic acid, isobutylboronic acid, 3,5-difluorophenylboronic acid and pentafluorophenylboronic acid.

These alkylboronic acids are used singly or in combination of two or more kinds.

Examples of the organoaluninum compounds to be reacted with the alkylboronic acid include the same organoaluminum compounds as previously exemplified with respect to the organoaluminum compound (B-1).

Of these, preferable are trialkylaluminums and tricycloalkylaluminums. Particularly preferable are trimethylaluminum, triethylaluminum and triisobutylaluminum. These organoaluminum compounds are used singly or in combination of two or more kinds.

The organoaluminum oxy-compounds (B-2) mentioned above are used singly or in combination of two or more kinds.

(B-3) Compound which Reacts with the Metallocene Compound (A) to form Ion Pair

The compound (B-3) which reacts with the metallocene compound (A) to form an ion pair (referred to as an "ionizing ionic compound" hereinafter) includes Lewis acid, an ionic compound, a borane compound and a carborane compound described in Japanese Patent Laid-Open Publications No. 501950/1989, No. 502036/1989, No. 179005/1991, No. 179006/1991, No. 207703/1991 and No. 207704/1991, U.S. Pat. No. 5,321,106, etc.

The Lewis acid includes a compound represented by $BR_3$ (R is fluorine or a phenyl group which may have a substituent group such as fluorine, methyl or trifluoromethyl). Examples of such compounds include trifluoroboron, triphenylboron, tris(4-fluorophenyl)boron, tris(3,5-difluorophenyl)boron, tris(4-fluoromethylphenyl)boron, tris (pentafluorophenyl)boron, tris(p-tolyl)boron, tris(o-tolyl) boron and tris(3,5-dimethylphenyl)boron.

The ionizing ionic compound includes, for example, a compound represented by the following formula (iii).

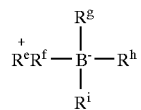

(iii)

In the above formula, $R^e$ is $H^+$, carbenium cation, oxonium cation, ammonium cation, phosphonium cation, cycloheptyltrienyl cation, ferrocenium cation having a transition metal, or the like.

$R^f$ to $R^i$ may be the same or different and are each an organic group, preferably an aryl group or a substituted aryl group.

Examples of the carbenium cations include tri-substituted carbenium cations, such as triphenylcarbenium cation, tris (methylphenyl)carbenium cation and tris(dimethylphenyl) carbenium cation.

Examples of the ammonium cations include trialkylammonium cations, such as trimethylammonium cation, triethylammonium cation, tri(n-propyl)ammonium cation, tri (isopropyl)ammonium cation, tri(n-butyl)ammonium cation and triisobutylammonium cation; N,N-dialkylanilinium cations, such as N,N-dimethylanilinium cation, N,N-diethylanilinium cation and N,N-2,4,6-pentamethylanilinium cation; and dialkylammonium cations, such as di (isopropyl) ammonium cation and dicyclohexylammonium cation.

Examples of the phosphonium cations include triarylphosphonium cations, such as triphenylphosphonium cation, tris(methylphenyl)phosphonium cation and tris (dimethylphenyl)phosphonium cation.

$R^e$ is preferably carbenium cation, ammonium cation or the like, particularly preferably triphenylcarbenium cation, N,N-dimethylanilinium cation or N,N-diethylanilinium cation.

Examples of the carbenium salts include triphenylcarbeniumtetraphenylborate, triphenylcarbeniumtetrakis(pentafluorophenyl)borate, triphenylcarbeniumtetrakis(3,5-ditrifluoromethylphenyl) borate, tris(4-methylphenyl)carbeniumtetrakis (pentafluorophenyl)borate, and tris(3,5-dimethylphenyl) carbeniumtetrakis(pentafluorophenyl)borate.

Examples of the ammonium salts include a trialkyl-substituted ammonium salt, a N,N-dialkylanilinium salt, a dialkylammonium salt or a triarylphosphonium salt.

Examples of the trialkyl-substituted ammonium salts include triethylammoniumtetraphenylborate, tripropylammoniumtetraphenylborate, tri(n-butyl) ammoniumtetraphenylborate, trimethylammoniumtetrakis (p-tolyl)borate, trimethylammoniumtetrakis(o-tolyl)borate, tri(n-butyl)ammoniumtetrakis(pentafluorophenyl)borate, triethylammoniumtetrakis(pentafluorophenyl)borate, tripropylammoniumtetrakis(pentafluorophenyl)borate, tripropylammoniumtetrakis(2,4-dimethylphenyl)borate, tri (n-butyl)ammoniumtetrakis(3,5-dimethylphenyl)borate, tri (n-butyl)ammoniumtetrakis(4-trifluoromethylphenyl) borate, tri(n-butyl)ammoniumtetrakis(3,5-ditrifluoromethylphenyl)borate and tri(n-butyl) ammoniumtetrakis(o-tolyl)borate.

Examples of the N,N-dialkylanilinium salts include N,N-dimethylaniliniumtetraphenylborate, N,N-dimethylaniliniumtetrakis(pentafluorophenyl)borate, N,N-dimethylaniliniumtetrakis(3,5-ditrifluoromethylphenyl) borate, N,N-diethylaniliniumtetraphenylborate N,N-diethylaniliniumtetrakis(pentafluorophenyl)borate, N,N-diethylaniliniumtetrakis(3,5-ditrifluoromethylphenyl) borate, N,N-2,4,6-pentamethylaniliniumtetraphenylborate and N,N-2,4,6-pentamethylaniliniumtetrakis (pentafluorophenyl)borate.

Examples of the dialkylammonium salts include di(1-propyl)ammoniumtetrakis(pentafluorophenyl)borate and dicyclohexylammoniumtetraphenylborate.

Further employable are ferroceniumtetrakis (pentafluorophenyl)borate, triphenylcarbeniumpentaphenylcyclopentadienyl complex, N,N-diethylaniliniumpentaphenylcyclopentadienyl complex or a borate compound represented by the following formula (iv) or (v).

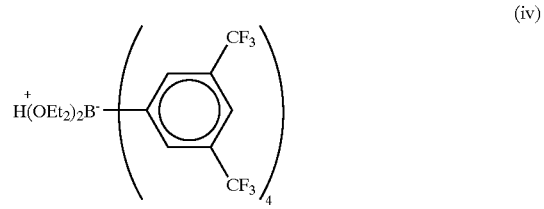

(iv)

wherein Et is an ethyl group.

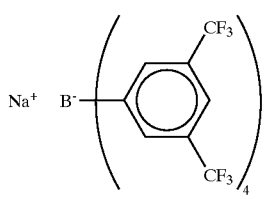
(v)

Examples of the borane compounds include:

decaborane(14);

salts of anions, such as bis(tri(n-butyl)ammonium) nonaborate, bis(tri(n-butyl)ammonium)decaborate, bis(tri(n-butyl)ammonium)undecaborate, bis(tri(n-butyl)ammonium)dodecaborate, bis(tri(n-butyl)ammonium)decachlorodecaborate and bis(tri(n-butyl)ammonium)dodecachlorododecaborate; and salts of metallic borane anions, such as tri(n-butyl)ammoniumbis(dodecahydridododecaborate)cobaltate(III) and bis(tri(n-butyl)ammonium)bis-(dodecahydridododecaborate)nickelate(III).

Examples of the carborane compounds include:

salts of anions, such as 4-carbanonaborane(14), 1,3-dicarbanonaborane(13), 6,9-dicarbadecaborane(14), dodecahydrido-1-phenyl-1,3-dicarbanonaborane, dodecahydrido-1-methyl-1,3-dicarbanonaborane, undecahydrido-1,3-dimethyl-1,3-dicarbanonaborane, 7,8-dicarbaundecaborane(13), 2,7-dicarbaundecaborane(13), undecahydrido-7,8-dimethyl-7,8-dicarbaundecaborane, dodecahydrido-11-methyl-2,7-dicarbaundecaborane, tri(n-butyl)ammonium-1-carbadecaborate, tri(n-butyl)ammonium-1-carbaundecaraborate, tri(n-butyl)ammonium-1-carbadodecaborate, tri(n-butyl)ammonium-1-trimethylsilyl-1-carbadecaborate, tri(n-butyl)ammoniumbromo-1-carbadodecaborate, tri(n-butyl)ammonium-6-carbadecaborate(14), tri(n-butyl)ammonium-6-carbadecaborate (12), tri(n-butyl)ammonium-7-carbaundecaborate(13), tri(n-butyl)ammonium-7,8-dicarbaundecaborate(12), tri(n-butyl)ammonium-2,9-dicarbaundecaborate(12), tri(n-butyl)ammoniumdodecahydrido-8-methyl-7,9-dicarbaundecaborate, tri(n-butyl)ammoniumundecahydrido-8-ethyl-7,9-dicarbaundecaborate, tri(n-butyl)ammoniumundecahydrido-8-butyl-7,9-dicarbaundecaborate, tri(n-butyl)ammoniumundecahydrido-8-allyl-7,9-dicarbaundecaborate, tri(n-butyl)ammoniumundecahydrido-9-trimethylsilyl-7,8-dicarbaundecaborate and tri(n-butyl)ammoniumundecahydrido-4,6-dibromo-7-carbaundecaborate; and salts of metallic carborane anions, such as tri(n-butyl)ammoniumbis(nonahydrido-1,3-dicarbanonaborate)cobaltate(III), tri-(n-butyl)ammoniumbis(undecahydrido 7,8-dicarbaundecaborate)ferrate(III), tri(n-butyl)ammoniumbis(undecahydrido-7,8-dicarbaundecaborate)cobaltate(III), tri(n-butyl)ammoniumbis(undecahydrido-7,8-dicarbaundecaborate)nickelate(III), tri(n-butyl)ammoniumbis(undecahydrido-7,8-dicarbaundecaborate)cuprate(III), tri(n-butyl)ammoniumbis(undecahydrido-7,8-dicarbaundecaborate)aurate(III), tri(n-butyl)ammoniumbis(nonahydrido-7,8-dimethyl-7,8-dicarbaundecaborate)ferrate(III), tri(n-butyl)ammoniumbis(nonahydrido-7,8-dimethyl-7,8-dicarbaundecaborate)chromate(III), tri(n-butyl)ammoniumbis(tribromooctahydrido-7,8-dicarbaundecaborate)cobaltate(III), tris(tri(n-butyl)ammonium)bis(undecahydrido-7-carbaundecaborate)chromate(III), bis(tri(n-butyl)ammonium)bis(undecahydrido-7-carbaundecaborate)manganate(IV), bis(tri(n-butyl)ammonium)bis(undecahydrido-7-carbaundecaborate)cobaltate(III) and bis(tri(n-butyl)ammonium)bis(undecahydrido-7-carbaundecaborate)nickelate(IV).

The ionizing ionic compounds (B-3) mentioned above are used singly or in combination of two or more kinds.

(C) Particle Carrier

The particle carrier (C) that is optionally used in the invention is an inorganic or organic compound of granular or particulate solid having a particle diameter of 5 to 300 $\mu$m, preferably 10 to 200 $\mu$m. As the inorganic compound, a porous oxide or chloride is preferable, and examples thereof include $SiO_2$, $Al_2O_3$, $MgCl_2$, MgO, ZrO, $TiO_2$, $B_2O_3$, CaO, ZnO, BaO, $ThO_2$, and mixtures containing them, such as $SiO_2$-MgO, $SiO_2$-$Al_2O_3$, $SiO_2$-$TiO_2$, $SiO_2$-$V_2O_5$, $SiO_2$-$Cr_2O_3$, $SiO_2$-$MgCl_2$, MgO-$MgCl_2$ and $SiO_2$-$TiO_2$-MgO. Of these, preferable are those containing at least one component selected from the group consisting of $SiO_2$ and $Al_2O_3$.

In the inorganic oxides, small amounts of carbonate, sulfate, nitrate and oxide components, such as $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_3$, $Na_2O$, $K_2O$ and $Li_2O$, may be contained.

As the particle carrier, an ion-exchangeable layered silicate is also employable. When the ion-exchangeable layered silicate is used, the silicate functions as a carrier, and additionally, the amount of the organoaluminum oxy-compound used such as alkylaluminoxane can be decreased by utilizing the ion-exchange properties and layered structure of the silicate. Although the ion-exchangeable layered silicate naturally occurs as a main component of a clay mineral, not only a natural one but also a synthetic one is employable. Examples of the ion-exchangeable layered silicates include kaolinite, montmorillonite, hectorite, bentonite, smectite, vermiculite, synthetic mica and synthetic hectorite.

Although the properties of the particle carrier varies depending upon the type and the preparation process, the specific surface area is desired to be in the range of 50 to 1000 m$^2$/g, preferably 100 to 800 m$^2$/g, and the pore volume is desired to be in the range of 0.3 to 3.0 cm$^3$/g. The carrier is used after calcined at 80 to 1000° C., preferably 100 to 800° C., when needed.

The particle carrier (C) employable in the invention may be an organic compound of granular or particulate solid having a particle diameter of 5 to 300 $\mu$m. Examples of the organic compounds include polymers or copolymers produced using as a main component an $\alpha$-olefin of 2 to 14 carbon atoms, such as ethylene, propylene, 1-butene or 4-methyl-1-pentene; polymers or copolymers produced using as a main component vinylcyclohexane or styrene; and polar functional group-containing polymers obtained by copolymerizing or graft polymerizing these polymers with polar monomers such as acrylic acid, acrylic ester and maleic anhydride.

In the polymerization process, the catalyst components can be used in any way and in any order. For example, the following processes are available.

(1) The metallocene compound (A) and at least one compound (B) selected from the organometallic compound (B-1), the organoaluminum oxy-compound (B-2) and the ionizing ionic compound (B-3) (referred to as a "component (B)" simply hereinafter) are fed to the polymerization reactor in an arbitrary order.

(2) A catalyst obtained by previously contacting the metallocene compound (A) with the component (B) is fed to the polymerization reactor.

(3) A catalyst component obtained by previously contacting the metallocene compound (A) with the component (B) and the component (B) are fed to the polymerization reactor in an arbitrary order. In this case, the components (B) may be the same or different.

(4) A catalyst component wherein the metallocene compound (A) is supported on the particle carrier (C), and the component (B) are fed to the polymerization reactor in an arbitrary order.

(5) A catalyst wherein the metallocene compound (A) and the component (B) are supported on the particle carrier (C) is fed to the polymerization reactor.

(6) A catalyst component wherein the metallocene compound (A) and the component (B) are supported on the particle carrier (C) and the component (B) are fed to the polymerization reactor in an arbitrary order. In this case, the components (B) may be the same or different.

(7) A catalyst component wherein the component (B) is supported on the particle carrier (C), and the metallocene compound (A) are added to the polymerization reactor in an arbitrary order.

(8) A catalyst component wherein the component (B) is supported on the particle carrier (C), the metallocene compound (A) and the component (B) are added to the polymerization reactor in an arbitrary order. In this case, the components (B) may be the same or different.

(9) A catalyst component obtained by previously contacting a catalyst wherein the metallocene compound (A) and the component (B) are supported on the particle carrier (C) with the component (B) is added to the polymerization reactor. In this case, the components (B) may be the same or different.

(10) A catalyst component obtained by previously contacting a catalyst wherein the metallocene compound (A) and the component (B) are supported on the particle carrier (C) with the component (B), and the component (B) are added to the polymerization reactor in an arbitrary order. In this case, the components (B) may be the same or different.

Onto the solid catalyst component wherein the metallocene compound (A) and the component (B) are supported on the particle carrier (C), an olefin may be prepolymerized. In the solid catalyst component thus prepolymerized, a polyolefin produced as a prepolymer is contained in an amount of usually 0.1 to 1000 g, preferably 0.3 to 500 g, particularly preferably 1 to 200 g, based on 1 g of the solid catalyst component.

For the purpose of smoothly promoting the polymerization, an antistatic agent, an antifouling agent and the like may be used in combination or may be supported on the particle carrier.

Process for Preparing Polyolefin

In the process for preparing a polyolefin using the olefin polymerization catalyst according to the invention, the polymerization can be carried out as any of liquid phase polymerization such as solution polymerization or suspension polymerization and gas phase polymerization.

Examples of inert hydrocarbon solvents used in the liquid phase polymerization include aliphatic hydrocarbons, such as propane, butane, pentane, hexane, heptane, octane, decane, dodecane and kerosine; alicyclic hydrocarbons, such as cyclopentane, cyclohexane and methylcyclopentane; aromatic hydrocarbons, such as benzene, toluene and xylene; halogenated hydrocarbons, such as ethylene chloride, chlorobenzene and dichloromethane; and mixtures thereof. The α-olefin used for the polymerization-may be per se used as a solvent.

In the polymerization, the component (A) is used in an amount of usually $10^{-8}$ to $10^{-2}$ mol, preferably $10^{-7}$ to $10^{-3}$ mol, based on 1 liter of the polymerization volume.

The component (B-1) is used in such an amount that the molar ratio ((B-1)/(M)) of the component (B-1) to the transition metal atom (M) in the component (A) becomes usually 0.01 to 5000, preferably 0.05 to 2000. The component (B-2) is used in such an amount that the molar ratio ((B-2)/(M)) of the aluminum atom in the component (B-2) to the transition metal atom (M) in the component (A) becomes usually 10 to 5000, preferably 20 to 2000. The component (B-3) is used in such an amount that the molar ratio ((B-3)/(M)) of the component (B-3) to the transition metal atom (M) in the component (A) becomes usually 1 to 10, preferably 1 to 5.

The temperature of polymerization of olefin using the olefin polymerization catalyst is in the range of usually −50 to +200° C., preferably 0 to 170° C. The polymerization pressure is in the range of usually atmospheric pressure to 10 MPa (gage-pressure), preferably atmospheric pressure to 5 MPa (gage-pressure). The polymerization reaction can be carried out by any of batchwise, semi-continuous and continuous processes. It is possible to conduct the polymerization in two or more stages under different reaction conditions.

In the polymerization, the molecular weight of the resulting polymer or polymerization activity can be regulated by adding hydrogen in amount of about 0.01 to 100 NL based on 1 kg of the olefin.

In the present invention, as olefins used in the polymerization reaction preferable are those of 2 to 20 carbon atoms, particularly α-olefins of 2 to 10 carbon atoms. Example of the olefins include ethylene, propylene, 1-butene, 1-pentene, 1-hexene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 1-octene, 1-decene, 1-dodecene, 1-tetradecene, 1-hexadecene, 1-octadecene, 1-eicosene, vinylcyclohexane and styrene.

Further examples include dienes of 4 to 20 carbon atoms such as butadiene, 1,4-pentadiene, 1,5-hexadiene and 1,4-hexadiene, cyclicolefins such as dicyclopentadiene, norbornene, methylnorbornene, tetracyclododecene and methyltetracyclododecene and silicon-containing olefins such as allyltrimethylsilane and vinyltrimethylsilane.

Of the olefin polymerization catalysts according to the invention, the catalyst containing the metallocene compound represented by the formula (1) or (2) is favorably used for copolymerization of at least 2 kinds of olefins.

At least one of the olefins used is preferably an α-olefin of 4 or less carbon atoms.

The copolymerization of two or more olefins using the olefin polymerization catalyst of the invention has advantages such as high polymerization activity and good copolymerizability and is characterized in that a copolymer of desired properties can be obtained.

An example of the copolymer obtained from two or more olefins is a copolymer comprising recurring units ($U_1$) derived from one α-olefin selected from α-olefins of 3 to 8 carbon atoms in amounts of 50 to 99.9% by mol and recurring units ($U_2$) other than the recurring units ($U_1$), said recurring units ($U_2$) being derived from at least one α-olefin selected from α-olefins of 2 to 20 carbon atoms, in amounts of 50 to 0.1% by mol.

Examples of the α-olefins of 3 to 8 carbon atoms include propylene, 1-butene, 1-pentene, 1-hexene, 0.3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene and 1-octene. Examples of the α-olefins of 2 to 20 carbon atoms include the same ones as described above.

Such a copolymer is, for example, a copolymer comprising propylene units in amounts of 50 to 99.5% by mol and units of an α-olefin of 2 to 20 carbon atoms other than propylene in amounts of 50 to 0.5% by mol.

The random copolymer comprising propylene units in amounts of 95 to 99.5% by mol and units of an α-olefin of 2 to 20 carbon atoms other than propylene in amounts of 5 to 0.5% by mol preferably has the following properties: the pentad isotacticity as determined from $^{13}$C-NMR spectrum measurement is not less than 80%, preferably not less than 85%; the proportion of 2,1-insertion and the proportion of 1,3-insertion are each not more than 0.2%, preferably not more than 0.1%; the MFR is in the range of 0.01 to 1000 g/10 min, preferably 0.01 to 500 g/10 min; the molecular weight distribution (Mw/Mn) as calculated from molecular weights (Mw: weight-average molecular weight, Mn: number-average molecular weight) measured by gel-permeation chromatography (GPC) is in the range of 1 to 3, preferably 1 to 2.5, more preferably 1 to 2.3; and the quantity of a decane-soluble component (after the polymer is treated with n-decane at 150° C. for 2 hours and cooled to room temperature, the amount (weight %) of the polymer dissolved in the n-decane is measured) is not more than 2% by weight, preferably not more than 1% by weight.

Of the olefin polymerization catalysts according to the invention, the catalyst containing the metallocene compound represented by the formula (1a) or (2a) is favorably used for homopolymerization of an olefin.

The homopolymerization of an α-olefin of 3 or more carbon atoms using the olefin polymerization catalyst of the invention is characterized in that an olefin polymer having high stereoregularity can be obtained and the polymer usually has high isotacticity.

The homopolymer of an α-olefin of 3 or more carbon atoms, particularly polypropylene, preferably has the following properties: the pentad isotacticity as determined from $^{13}$C-NMR spectrum measurement is not less than 85%, preferably not less than 90%, more preferably not less than 95%; the proportion of 2,1-insertion and the proportion of 1,3-insertion are each not more than 0.2%, preferably not more than 0.1%, more preferably not more than 0.05%; the melting point (Tm) as measured by differential scanning calorimetry (DSC) is not lower than 140° C., preferably not lower than 150° C., more preferably not lower than 153° C.; the MFR is in the range of 0.01 to 1000 g/10 min, preferably 0.01 to 500 g/10 min; the molecular weight distribution (Mw/Mn) as calculated from molecular weights measured by GPC is in the range of 1 to 3, preferably 1 to 2.5, more preferably 1 to 2.3; and the quantity of a decane-soluble component is not more than 2% by weight, preferably not more than 1% by weight, more preferably not more than 0.5% by weight.

Of the olefin polymerization catalysts according to the invention, the catalyst containing the metallocene compound represented by the formula (1b) or (2b) is favorably used for homopolymerization of an olefin or copolymerization of at least two kinds of olefins.

Of the polymers obtained by the use of such a catalyst, a homopolymer of an α-olefin of 3 to 8 carbon atoms, particularly polypropylene, preferably has the following properties: the pentad isotacticity as determined from $^{13}$C-NMR spectrum measurement is not less than 85%, preferably not less than 90%, more preferably not less than 95%; the proportion of 2,1-insertion and the proportion of 1,3-insertion are each not more than 0.2%, preferably not more than 0.1%, more preferably not more than 0.05%; the melting point (Tm) as measured by DSC is not lower than 140° C., preferably not lower than 150° C., more preferably not lower than 153° C.; the MFR is in the range of 0.01 to 1000 g/10 min, preferably 0.01 to 500 g/10 min; the molecular weight distribution (Mw/Mn) as calculated from molecular weights measured by GPC is in the range of 1 to 3, preferably 1 to 2.5, more preferably 1 to 2.3; and the quantity of a decane-soluble component is not more than 2% by weight, preferably not more than by weight, more preferably not more than 0.5% by weight.

An example of the copolymer obtained from two or more olefins using the catalyst containing the metallocene compound represented by the formula (1b) or (2b) is a copolymer comprising recurring units ($U_1$) derived from one α-olefin selected from α-olefins of 3 to 8 carbon atoms in amounts of 50 to 99.9% by mol and recurring units ($U_2$) other than the recurring units ($U_1$), said recurring units ($U_2$) being derived from at least one α-olefin selected from α-olefins of 2 to 20 carbon atoms, in amounts of 50 to 0.1% by mol.

Such a copolymer is, for example, a copolymer comprising propylene units in amounts of 50 to 99.5% by mol and units of an α-olefin other than propylene in amounts of 50 to 0.5% by mol.

The copolymer comprising propylene units in amounts of 95 to 99.5% by mol and units of an α-olefin of 2 to 20 carbon atoms other than propylene in amounts of 5 to 0.5% by mol preferably has the following properties: the pentad isotacticity as determined from $^{13}$C-NMR spectrum measurement is not less than 80%, preferably not less than 85%; the proportion of 2,1-insertion and the proportion of 1,3-insertion are each not more than 0.2%, preferably not more than 0.1%; the MFR is in the range of 0.01 to 1000 g/10 min, preferably 0.01 to 500 g/10 min; the molecular weight distribution (Mw/Mn) as calculated from molecular weights measured by GPC is in the range of 1 to 3, preferably 1 to 2.5, more preferably 1 to 2.3; and the quantity of a decane-soluble component is not more than 2% by weight, preferably not more than 1% by weight.

Polyolefin

The polyolefin according to the invention is a polyolefin comprising recurring units ($U_1$) derived from one α-olefin selected from α-olefins of 3 to 8 carbon atoms in amounts of 50 to 100% by mol, preferably 65 to 100% by mol, more preferably 80 to 100% by mol, and recurring units ($U_2$) other than the recurring units ($U_1$), said recurring units ($U_2$) being derived from at least one olefin selected from α-olefins of 2 to 20 carbon atoms, in amounts of 50 to 0% by mol, preferably 35 to 0% by mol, more preferably 20 to 0% by mol.

Examples of the α-olefins of 3 to 8 carbon atoms and the α-olefins of 2 to 20 carbon atoms include the same ones as previously described.

This polyolefin satisfies the following requisites (i) to (iii):

(i) the proportion of 2,1-insertion and the proportion of 1,3-insertion are each not more than 0.2%, preferably not more than 0.1%, (ii) the molecular weight distribution (Mw/Mn) as determined by (GPC) is in the range of 1 to 3, preferably 1 to 2.5, more preferably 1 to 2.3, and (iii) the quantity of a decane-soluble component is not more than 2% by weight, preferably not more than 1% by weight.

The polyolefin preferably comprises recurring units derived from propylene in amounts of 50 to 99.5% by mol, preferably 65 to 99.5% by mol, more preferably 80 to 99.5% by mol, and recurring units derived from at least one olefin selected from α-olefins of 2 to 20 carbon atoms other than propylene in amounts of 50 to 0.5% by mol, preferably 35 to 0.5% by mol, more preferably 20 to 0.5% by mol.

Such a polyolefin of the invention has excellent elastic modulus, impact resistance and transparency.

Another embodiment of the polyolefin of the invention is a homopolymer of one α-olefin selected from α-olefins of 3 to 8 carbon atoms.

Examples of the α-olefins of 3 to 8 carbon atoms include the same ones as previously described.

This polyolefin satisfies the following requisites (i) to (vi):

(i) the pentad isotacticity as determined from $^{13}$C-NMR spectrum measurement is not less than 85%, preferably not less than 90%, more preferably not less than 95%, (ii) the proportion of 2,1-insertion and the proportion of 1,3-insertion are each not more than 0.2%, preferably not more than 0.1%, more preferably not more than 0.05%, (iii) the MFR is in the range of 0.01 to 1000 g/10 min, preferably 0.01 to 500 g/10 min, more preferably 0.02 to 400 g/10 min, (iv) the molecular weight distribution (Mw/Mn) as determined by GPC is in the range of 1 to 3, preferably 1 to 2.5, more preferably 1 to 2.3, (v) the quantity of a decane-soluble component is not more than 2% by weight, preferably not more than 1% by weight, more preferably not more than 0.5% by weight, and (vi) the melting point (Tm) as measured by DSC is not lower than 140° C., preferably not lower than 150° C., more preferably not lower than 153° C.

The polyolefin is preferably a homopolymer of propylene.

Such a polyolefin of the invention has excellent elastic modulus, impact resistance and transparency.

A further embodiment of the polyolefin of the invention is a polyolefin comprising recurring units ($U_1$) derived from one α-olefin selected from α-olefins of 3 to 8 carbon atoms in amounts of 95 to 99.5% by mol, preferably 95 to 99% by mol, more preferably 95 to 98% by mol, and recurring units ($U_2$) other than the recurring units ($U_1$), said recurring units ($U_2$) being derived from at least one olefin selected from α-olefins of 2 to 20 carbon atoms, in amounts of 5 to 0.05% by mol, preferably 5 to 1% by mol, more preferably 5 to 2% by mol.

Examples of the α-olefins of 3 to 8 carbon atoms and the α-olefins of 2 to 20 carbon atoms include the same ones as previously described.

This polyolefin satisfies the following requisites (i) to (vi):

(i) the pentad isotacticity as determined from $^{13}$C-NMR spectrum measurement is not less than 80%, preferably not less than 85%, (ii) the proportion of 2,1-insertion and the proportion of 1,3-insertion are each not more than 0.2%, preferably not more than 0.1%, (iii) the MFR is in the range of 0.01 to 1000 g/10 min, preferably 0.01 to 500 g/10 min, more preferably 0.02 to 400 g/10 min, (iv) the molecular weight distribution (Mw/Mn) as determined by GPC is in the range of 1 to 3, preferably 1 to 2.5, more preferably 1 to 2.3, (v) the quantity of a decane-soluble component is not more than 2% by weight, preferably not more than 1% by weight, more preferably not more than 0.5% by weight, and (vi) the melting point (Tm) as measured by a differential scanning calorimeter is not higher than 145° C., preferably not higher than 140° C.

The polyolefin preferably comprises recurring units derived from propylene in amounts of 95 to 99.5% by mol, preferably 95 to 99% by mol, more preferably 95 to 98% by mol, and recurring units derived from at least one olefin selected from α-olefins of 2 to 20 carbon atoms other than propylene in amounts of 5 to 0.5% by mol, preferably 5 to 1% by mol, more preferably 5 to 2% by mol.

Such a polyolefin of the invention has excellent elastic modulus, impact resistance and transparency.

The polyolefin of the invention mentioned above can be prepared by polymerizing or copolymerizing the corresponding olefin under the above-mentioned conditions using the olefin polymerization catalyst containing the metallocene compound represented by the formula (1), (2), (1a), (2a), (1b) or (2b).

Effect of the Invention

The metallocene compound represented by the formula (1) or (2) according to the invention and the olefin polymerization catalyst containing this metallocene compound have excellent olefin polymerization activity and are of industrially great value. The olefin copolymer obtained by the use of the catalyst, particularly a propylene random copolymer, has excellent elastic modulus, impact resistance and transparency.

The metallocene compound represented by the formula (1a) or (2a) according to the invention and the olefin polymerization catalyst containing this metallocene compound have excellent olefin polymerization activity and are of industrially great value. The poly-α-olefin obtained by the use of the catalyst, particularly polypropylene, has excellent elastic modulus, impact resistance and transparency.

The metallocene compound represented by the formula (1b) or (2b) according to the invention and the olefin polymerization catalyst containing this metallocene compound have excellent olefin polymerization activity and are of industrially great value. The poly-α-olefin obtained by the use of the catalyst, particularly polypropylene, has excellent elastic modulus, impact resistance and transparency. The olefin copolymer obtained by the use of the catalyst, particularly a propylene random copolymer, has excellent elastic modulus, impact resistance and transparency.

The process for preparing a metallocene compound according to the invention is excellent as a process for selectively preparing a metallocene compound having a desirable specific structure, and is of industrially great value.

The polyolefin according to the invention has excellent elastic modulus, impact resistance and transparency.

The polyolefin according to the invention can be favorably used for nonwoven fabrics, films, sealants, industrial materials, transparent injection, block polymers, alloys, modifiers, etc., and can be broadly used specifically for hygienic materials, civil engineering materials, automobile parts, electrical appliances, food containers, packaging materials, miscellaneous goods, etc.

EXAMPLE

The present invention is further described with reference to the following examples, but it should be construed that the invention is in no way limited to those examples.

In the present invention, the melting point (Tm) of a polymer was determined as follows. Through differential scanning calorimetry (DSC) a polymer sample kept at 240° C. for 10 minutes was cooled to 30° C., kept for 5 minutes and then heated at a rate of 10° C./min to obtain a crystal melting peak, from which the melting point was calculated.

The molecular weight (Mw, Mn) was measured by GPC (gel permeation chromatography).

The quantity of a decane-soluble component was determined as follows. A polymer was treated with n-decene at 150° C. for 2 hours and then cooled to room temperature, and the quantity of the polymer (% by weight) dissolved in n-decane was measured.

The stereoregularity (pentad isotacticity (mmmm), 2,1-insertion, 1,3-insertion) of a polymer was determined from $^{13}$C-NMR spectrum measurement.

The intrinsic viscosity (η) was measured in decalin at 135° C.

The MFR was measured after heating of a polymer at 230° C. for 6 minutes.

Example 1

Synthesis of dimethylmethylene(3-tert-butyl-5-methylcyclopentadienyl)fluorenylzirconium Dichloride (1) Synthesis of 1-tert-butyl-3-methylcyclopentadiene To a solution obtained by adding 350 ml of dehydrated diethyl ether to 450 ml (0.90 mol) of a tert-butylmagnesium chloride/diethyl ether solution (concentration: 2.0 mol/liter), a solution of 43.7 g (0.45 mmol) of 3-methylcyclopentenone in 150 ml of dehydrated diethyl ether was dropwise added in a nitrogen atmosphere at 0° C. with ice cooling, followed by stirring at room temperature for 15 hours. To the reaction solution, a solution of 80.0 g (1.50 mol) of ammonium chloride in 350 ml of water was dropwise added at 0° C. with ice cooling. To the resulting solution, 2500 ml of water was added, followed by stirring. Then, the organic phase was separated and washed with water. To the organic phase, 82 ml of a 10% hydrochloric acid aqueous solution was added at 0° C. with ice cooling, followed by stirring at room temperature for 6 hours. The organic phase was separated from the reaction solution, washed with water, a saturated sodium hydrogencarbonate aqueous solution, water and a saturated saline solution, and then dried over anhydrous magnesium sulfate. The drying agent was filtered, and from the filtrate the solvent was distilled off to obtain a liquid. The liquid was subjected to vacuum distillation (45–47° C./10 mmHg) to obtain 14.6 g of a light yellow liquid. The analyzed values are given below.

$^1$H-NMR (270 MHz, in CDCl$_3$, based on TMS): δ6.31+ 6.13+5.94+5.87 (s+s+t+d, 2H), 3.04+2.95 (s+s, 2H), 2.17+ 2.09 (s+s, 3H), 1.27 (d, 9H)

(2) Synthesis of 3-tert-butyl-1,6,6-trimethylfulvene

To a solution of 13.0 g (95.6 mmol) of 1-tert-butyl-3-methylcyclopentadiene in 130 ml of dehydrated methanol, 55.2 g (950.4 mmol) of dehydrated acetone was dropwise added in a nitrogen atmosphere at 0° C. with ice cooling, and 68.0 g (956.1 mmol) of pyrrolidine was further dropwise added, followed by stirring at room temperature for 4 days. After the reaction solution was diluted with 400 ml of diethyl ether, 400 ml of water was added. The organic phase was separated, washed with a 0.5N hydrochloric acid aqueous solution (150 ml×4), water (200 ml×3) and a saturated saline solution (150 ml), and then dried over anhydrous magnesium sulfate. The drying agent was filtered, and from the filtrate the solvent was distilled off to obtain a liquid. The liquid was subjected to vacuum distillation (70–80° C./0.1 mmHg) to obtain 10.5 g of a yellow liquid. The analyzed values are given below.

$^1$H-NMR (270 MHz, in CDCl$_3$, based on TMS): δ6.23 (s, 1H), 6.05 (d, 1H), 2.23 (s, 3H), 2.17 (d, 6H), 1.17 (s, 9H)

(3) Synthesis of 2-(3-tert-butyl-5-methylcyclopentadienyl)-2-fluorenylpropane

To a solution of 10.1 g (60.8 mmol) of fluorene in 300 ml of THF, 40 ml (61.6 mmol) of a hexane solution of n-butyllithium was dropwise added in a nitrogen atmosphere with ice cooling, followed by stirring at room temperature for 5 hours (dark brown solution). The solution was ice cooled again, and a solution of 11.7 g (66.5 mmol) of 3-tert-butyl-1,6,6-trimethylfulvene in 300 ml of THF was dropwise added in a nitrogen atmosphere. After stirring at room temperature for 14 hours, the resulting brown solution was ice cooled, and 200 ml of water was added. The organic phase extracted with diethyl ether and separated was dried over magnesium sulfate and then filtered. From the filtrate, the solvent was removed under reduced pressure to obtain an orangy brown oil. The oil was purified by silica gel column chromatography (developing solvent: hexane) to obtain 3.8 g of a yellow oil. The analyzed values are given below.

$^1$H-NMR (270 MHz, in CDCl$_3$, Based on TMS): δ7.70 (d, 4H), 7.34–7.26 (m, 6H), 7.18–7.11 (m, 6H), 6.17 (s, 1H), 6.01 (s, 1H), 4.42 (s, 1H), 4.27 (s, 1H), 3.01 (s, 2H), 2.87 (s, 2H), 2.17 (s, 3H), 1.99 (s, 3H), 2.10 (s, 9H), 1.99 (s, 9H), 1.10 (s, 6H), 1.07 (s, 6H)

(4) Synthesis of dimethylmethylene(3-tert-butyl-5-methylcyclopentadienyl)fluorenylzirconium Dichloride To a solution of 1.14 g (3.3 mmol) of 2-(3-tert-butyl-5-methylcyclopentadienyl)-2-fluorenylpropane in 25 ml of diethyl ether, 5.0 ml (7.7 mmol) of a hexane solution of n-butyllithium was dropwise added in a nitrogen atmosphere with ice cooling, and the mixture was stirred at room temperature for 14 hours to obtain a pink slurry. To the slurry, 0.77 g (3.3 mmol) of zirconium tetrachloride was added at −78° C., and the mixture was stirred at −78° C. for several hours, followed by further stirring at room temperature for 65 hours. The resulting dark brown slurry was filtered. The substance remaining on the filter was washed with 10 ml of diethyl ether and extracted with dichloroethane to obtain a red solution. From the solution, the solvent was vacuum distilled off to obtain 0.53 g of a reddish orange solid. The analyzed values are given below.

$^1$H-NMR (270 MHz, in CDCl$_3$, Based on TMS): δ8.11– 8.02 (m, 3H), 7.82 (d, 1H), 7.56–7.45 (m, 2H), 7,23–7.17 (m, 2H), 6.08 (d, 1H), 5.72 (d, 1H), 2.59 (s, 3H), 2.41 (s, 3H), 2.30 (s, 3H), 1.08 (s, 9H) FD-MS: m/z=500, 502, 504 (M$^+$)

Example 2

Synthesis of cyclohexylidene(3-tert-butyl-5-methylcyclopentadienyl)fluorenylzirconium Dichloride (1) Synthesis of 3-tert-butyl-5-methyl-6,6-pentamethylenefulvene To 50 ml of dehydrated methanol, 0.5 g (3.68 mmol) of 1-tert-butyl-3-methylcyclopentadiene and 3.81 ml (36.8 mmol) of cyclohexanone were added, then 3.07 ml (36.8 mmol) of pyrrolidine was dropwise added at 0° C., and the mixture was reacted at room temperature for 7 days. Then, 20 ml of water was added at 0° C. After extraction with ether, the organic phase was washed with water and successively dried over anhydrous magnesium sulfate. Then, the solvent was distilled off to obtain 1.3 g of a light yellow solid. The analyzed values are given below.

$^1$H-NMR (270 MHz, in CDCl$_3$, Based on TMS): δ6.26 (s, 1H), 6.10 (s, 1H), 2.71 (dd, 2H), 2.61 (dd, 2H), 2.27 (d, 3H), 1.80–1.61 (m, 6H), 1.17 (s, 9H)

(2) Synthesis of 1-(3-tert-butyl-5-methylcyclopentadienyl)-1-fluorenylcyclohexane To a solution of 0.8 g (4.5 mmol) of fluorene in 40 ml of THF, 2.9 ml (4.6 mmol) of a hexane solution of n-butyllithium was dropwise added in a nitrogen atmosphere with ice cooling, followed by stirring at room temperature for 6 hours. To the resulting red solution, a solution of 1.0 g (4.8 mmol) of 3-tert-butyl-5-methyl-6,6-pentamethylenefulvene in 15 ml of THE was dropwise added in a nitrogen atmosphere with ice cooling. After stirring at room temperature for 16 hours, 30 ml of water was added. The organic phase extracted with diethyl ether and separated was dried over magnesium sulfate and then filtered. From the filtrate, the solvent was removed under reduced pressure to obtain a light yellow liquid. The liquid was passed through a silica gel column using hexane as an eluent. From the resulting hexane solution, the solvent was removed under reduced pressure to obtain 1.3 g of a light yellow solid. The analyzed values are given below.

$^1$H-NMR (270 MHz, in CDCl$_3$, Based on TMS): δ7.64 (d, 2H), 7.34–7.24 (m, 4H), 7.16–7.10 (m, 2H), 5.79 (s, 1H), 4.02 (s, 1H), 2.87–2.77 (s+s, 3H), 2.26–2.00 (m, 2H), 1.75–1.60 (s+s, 3H), 1.55–1.23 (m, 8H), 1.12 (d, 9H)

(3) Synthesis of cyclohexylidene(3-tert-butyl-5-methylcyclopentadienyl)fluorenylzirconium Dichloride To a solution of 1.3 g (3.3 mmol) of 1-(3-tert-butyl-5-methylcyclopentadienyl)-1-fluorenylcyclohexane in 40 ml of THF, 4.8 ml (6.8 mmol) of a hexane solution of n-butyllithium was dropwise added in a nitrogen atmosphere with ice cooling, followed by stirring at room temperature for 16 hours. From the reaction mixture, the solvent was removed under reduced pressure to obtain a reddish orange solid. To the solid, 150 ml of dichloromethane was added at −78° C., and they were stirred to give a solution. Then, the solution was added to 10 ml of a dichloromethane suspension of 1.1 g (2.9 mmol) of zirconium tetrachloride (THF) 2-complex having been cooled to −78° C., and the mixture was stirred at −78° C. for 6 hours, followed by further stirring at room temperature for one day and night. From the reaction solution, the solvent was removed under reduced pressure to obtain a vermilion solid. The solid was extracted with diethyl ether and subjected to sellaite filtration. The filtrate was concentrated to precipitate 18 mg of a reddish brown solid, and the solid was separated from the mother liquor. The analyzed values are given below.

$^1$H-NMR (270 MHz, in CDCl$_3$, Based on TMS); δ8.10 (m, 2H), 7.90 (d, 1H), 7.76 (d, 1H), 7.56–7.46 (m, 2H), 7.28–7.18 (m, 2H), 6.07 (d, 1H), 5.72 (d, 1H), 3.73 (br, 1H), 3.34 (br, 1H), 2.55–2.33 (m, 2H), 2.27 (s, 3H), 2.05–1.64 (m, 6H), 1.08 (s, 9H)

FD-MS: m/z=540, 542, 544 (M$^+$)

Reference Example

Synthesis of 3,6-di-tert-butylfluorene

(1) Synthesis of 4,4'-di-t-butyldiphenylmethane

A 300 ml two-necked flask was thoroughly purged with nitrogen. In the flask, 38.4 g (289 mmol) of AlCl$_3$ was placed, and 80 ml of CH$_3$NO$_2$ was added to give a solution (1). Separately, a 500 ml three-necked flask equipped with a dropping funnel and a magnetic stirrer was thoroughly purged with nitrogen. In the flask, 25.6 g (152 mmol) of dipheylmethane and 43.8 g (199 mmol) of 2,6-di-t-butyl-4-methylphenol were placed, and 80 ml of CH$_3$NO$_2$ was added to give a solution. With stirring, this solution was cooled with an ice bath. To the solution was dropwise added the solution (1) over a period of 35 minutes, and the reaction solution was stirred at 12° C. for 1 hour. The reaction solution was poured into 500 ml of ice water and extracted with 800 ml of hexane. The organic phase was washed with 600 ml of a 5% NaOH aqueous solution and dried over MgSO$_4$. Then, the MgSO$_4$ was filtered off, and the solvent was evaporated to obtain an oil. The oil was cooled to −78° C. to precipitate a solid. The solid was recovered by filtration, washed with 300 ml of EtOH and dried under reduced pressure to obtain 4,4'-di-t-butyldiphenylmethane (yield: 18.9 g).

(2) Synthesis of 2,2'-diiodo-4,4'-di-t-butyldiphenylmethane

In a 200 ml flask equipped with a magnetic stirrer, 1.95 g (6.96 mmol) of 4,4'-di-t-butyldiphenylmethane, 0.78 g (3.48 mmol) of HIO$_4$, 1.55 g (6.12 mmol) of I$_2$ and 0.48 ml of concentrated H$_2$SO$_4$ were placed. Then, 17.5 ml of acetic acid and 3.75 ml of water were added, and the mixture was heated to 90° C. with stirring and reacted for 5 hours. The reaction solution was poured into 50 ml of ice water and extracted with Et$_2$O. The organic phase was washed with 100 ml of a saturated NaHSO$_4$ aqueous solution, and then Na$_2$CO$_3$ was added. After stirring, the Na$_2$CO$_3$ was filtered off. The organic phase was washed with 800 ml of water, and Mg$_2$SO$_4$ was added to dry the organic phase. After the Mg$_2$SO$_4$ was filtered off, the solvent was distilled off to obtain a yellow oil. The oil was purified by column chromatography to obtain 2,2'-diiodo-4,4'-di-t-butyldiphenylmethane (yield: 3.21 g).

(3) Synthesis of 3,6-di-t-butylfluorene

In a 50 ml two-necked flask, 3.21 g (6.03 mmol) of 2,2'-diiodo-4,4'-di-t-butyldiphenylmethane was placed, and 2.89 g (47.0 mmol) of a copper powder was added. The mixture was heated to 230° C. and reacted for 5 hours with stirring. After extraction with acetone, the solvent was distilled off to obtain a reddish brown oil. The oil was subjected to column chromatography to obtain a light yellow oil. The fractions containing the unreacted material was subjected to column chromatography again to recover the desired product only. The obtained product was recrystallized from methanol to obtain a white solid (yield: 1.08 g).

Example 3

Synthesis of dimethylmethylene(3-tert-butyl-5-methylcyclopentadienyl)(3,6-di-tert-butylfluorenyl) zirconium Dichloride

(1) Synthesis of 2-(3-tert-butyl-5-methylcyclopentadienyl)-2-(3,6-di-tert-butylfluorenyl)propane To a solution of 0.9 g (3.4 mmol) of 3,6-di-tert-butylfluorene in 30 ml of THF, 2.1 ml (3.4 mmol) of a hexane solution of n-butyllithium was dropwise added in a nitrogen atmosphere with ice cooling, followed by stirring at room temperature for 6 hours. To the resulting red solution, a solution of 0.6 g (3.5 mmol) of 3-tert-butyl-5,6,6-trimethylfulvene in 15 ml of THF was dropwise added in a nitrogen atmosphere with ice cooling, followed by stirring at room temperature for 12 hours. Then, 30 ml of water was added. The organic phase extracted with diethyl ether and separated was dried over magnesium sulfate and then filtered. From the filtrate, the solvent was removed under reduced pressure to obtain a solid. The solid was recrystallized from hot methanol to obtain 1.2 g of a light yellow solid. The analyzed values are given below.

$^1$H-NMR (270 MHz, in CDCl$_3$, Based on TMS): δ7.72 (d, 2H), 7.18–7.05 (m, 4H), 6.18–5.99 (s+s, 1H), 4.32–4.18 (s+s, 1H), 3.00–2.90 (s+s, 2H), 2.13–1.98 (t+s, 3H), 1.38 (s, 18H), 1.19 (s, 9H), 1.10 (d, 6H)

(2) Synthesis of dimethylmethylene(3-tert-butyl-5-methylcyclopentadienyl)(3,6-di-tert-butylfluorenyl) zirconium Dichloride To a solution of 1.3 g (2.8 mmol) of 2-(3-tert-butyl-5-methylcyclopentadienyl)-2-(3,6-di-tert-butylfluorenyl) propane in 40 ml of diethyl ether, 3.6 ml (5.8 mmol) of a hexane solution of n-butyllithium was dropwise added in a nitrogen atmosphere with ice cooling, followed by stirring at room temperature for 16 hours. From the reaction mixture, the solvent was removed under reduced pressure to obtain a reddish orange solid. To the solid, 150 ml of dichloromethane was added at −78° C., and they were stirred to give a solution. Then, the solution was added to a suspension of 1.0 g (2.7 mmol) of zirconium tetrachloride (THF) 2-complex in 10 ml of dichloromethane having been cooled to −78° C., and the mixture was stirred at −78° C. for 6 hours, followed by further stirring at room temperature for one day and night. From the reaction solution, the solvent was removed under reduced pressure to obtain an orange solid. The solid was extracted with toluene and subjected to sellaite filtration. From the filtrate, the solvent was removed under reduced pressure, and the residue was recrystallized from diethyl ether to obtain 0.18 g of an orange solid. The analyzed values are given below.

$^1$H-NMR (270 MHz, in CDCl$_3$, Based on TMS): δ7.98 (dd, 2H), 7.90 (d, 1H), 7.69 (d, 1H), 7.32–7.25 (m, 2H), 6.01 (d, 1H), 5.66 (d, 1H), 2.54 (s, 3H), 2.36 (s, 3H), 2.28 (s, 1H), 1.43 (d, 18H), 1.08 (s, 9H)

FD-MS: m/z=612, 614, 616 (M$^+$)

Example 4

Synthesis of cyclohexylidene(3-tert-butyl-5-methylcyclopentadienyl)(3,6-di-tert-butylfluorenyl) zirconium Dichloride (1) Synthesis of 1-(3-tert-butyl-5-methylcyclopentadienyl)-1-(3,6-di-tert-butylfluorenyl)cyclohexane To a solution of 0.81 g (2.91 mmol) of 3,6-di-tert-butylfluorene in 40 ml of THF, 1.91 ml (3.06 mmol) of a hexane solution of n-butyllithium was dropwise added in a nitrogen atmosphere at 0° C., followed by stirring at room temperature for 16 hours. To the resulting solution, a solution of 0.69 g (3.20 mmol) of 3-tert-butyl-5-methyl-6,6-pentamethylenefulvene in 30 ml of THF was dropwise added in a nitrogen atmosphere at 0° C., followed by stirring at room temperature for 16 hours, to perform reaction. After the reaction, 30 ml of water was added. The organic phase was extracted with ether and dried over anhydrous magnesium sulfate. From the resulting solution, the solvent was distilled off under reduced pressure to obtain 1.26 g of a yellow solid. The analyzed values are given below.

$^1$H-NMR (270 MHz, in CDCl$_3$, Based on TMS): δ7.64 (d, 2H), 7.22 (d, 2H), 7.15 (d,d, 2H)), 6.10, 5.76 (1H), 3.89 (s, 1H), 2.82–2.58 (2H), 1.70 (s, 3H), 1.38 (s, 18H), 1.09 (s, 9H), 2.26–1.25 (10H)

(2) Synthesis of cyclohexylidene(3-tert-butyl-5-methylcyclopentadienyl)(3,6-di-tert-butylfluorenyl) zirconium Dichloride To a solution of 1.22 g (2.47 mmol) of 1-(3-tert-butyl-5-methylcyclopentadienyl)-1-(3,6-di-tert-butylfluorenyl) cyclohexane in 50 ml of THF, 3.39 ml (5.43 mmol) of a hexane solution of n-butyllithium was dropwise added in a nitrogen atmosphere with ice cooling, followed by stirring at room temperature for 16 hours. From the reaction mixture, the solvent was removed under reduced pressure to obtain a reddish orange solid. To the solid, a solution of 0.93 g (2.47 mmol) of zirconium tetrachloride (THF) 2-complex in 100 ml of dichloromethane having been cooled to −78° C. was added. The mixture was stirred and reacted while the temperature of the mixture was allowed to naturally rise to room temperature. The resulting red suspension was subjected to sellaite filtration to remove lithium chloride. Then, to the orange filtrate was added 10 ml of toluene, and the mixture was concentrated until a solid was precipitated, followed by cooling to −20° C. The precipitated solid was recovered and then recrystallized from toluene to obtain 27 mg of a red solid. The analyzed values are given below.

$^1$H-NMR (270 MHz, in CDCl$_3$, Based on TMS): δ8.02 (d, 1H), 7.97 (d, 1H), 7.76 (d, 1H), 7.62 (d, 1H), 7.33–7.29 (d,d, 2H), 6.01 (d, 1H), 5.66 (d, 1H), 3.69 (br,d, 1H), 3.29 (br,d, 1H), 2.25 (s, 3H), 2.54–1.53 (m, 8H), 1.44 (s, 9H), 1.43 (s, 9H), 1.07 (s, 9H)

FD-MS: m/z=652, 654, 656 (M$^+$)

Example 5

Synthesis of dimethylmethylene(3-tert-butyl-5-methylcyclopentadienyl)-(2, 7-di-tert butylfluorenyl)zirconium Dichloride (1) Synthesis of 2-(3-tert-butyl-5-methylcyclopentadienyl)-2-(2,7-di-tert-butylfluorenyl)propane To a solution of 0.9 g (3.4 mmol) of 2,7-di-tert-butylfluorene in 30 ml of THF, 2.1 ml (3.4 mmol) of a hexane solution of n-butyllithium was dropwise added in a nitrogen atmosphere with ice cooling, followed by stirring at room temperature for 6 hours. To the resulting red solution, a solution of 0.6 g (3.5 mmol) of 3-tert-butyl-5,6,6-trimethylfulvene in 15 ml of THF was dropwise added in a nitrogen atmosphere with ice cooling, followed by stirring at room temperature for 12 hours. Then, 30 ml of water was added. The organic phase extracted with diethyl ether and separated was dried over magnesium sulfate and then filtered. From the filtrate, the solvent was removed under reduced pressure to obtain 1.1 g of a crude product. The crude product was per se used for the next reaction without being purified.

(2) Synthesis of dimethylmethylene(3-tert-butyl-5-methylcyclopentadienyl)(2,7-di-tert-butylfluorenyl) zirconium Dichloride To a solution of 0.87 g (1.92 mmol) of 2-(3-tert-butyl-5-methylcyclopentadienyl)-2-(2,7 di-tert butylfluorenyl)

propane in 50 ml of THF, 2.88 ml (4.60 mmol) of a hexane solution of n-butyllithium was dropwise added in a nitrogen atmosphere with ice cooling, followed by stirring at room temperature for 16 hours. From the reaction mixture, the solvent was removed under reduced pressure to obtain a reddish orange solid. To the solid, a solution of 0.72 g (1.92 mmol) of zirconium tetrachloride (THF) 2-complex in 100 ml of dichloromethane having been cooled to −78° C. was added. The mixture was stirred and reacted while the temperature of the mixture was allowed to naturally rise to room temperature. The resulting red suspension was subjected to sellaite filtration to remove lithium chloride. Then, to the orange filtrate was added 10 ml of toluene, and the mixture was concentrated until a solid was precipitated, followed by cooling to −20° C. The precipitated solid was recovered and then recrystallized from toluene to obtain 17 mg of a red solid. The analyzed values are given below.

$^1$H-NMR (270 MHz, in CDCl$_3$, Based on TMS): δ7.96 (d, 1H), δ7.94 (s, 1H), δ7.93 (d, 1H), 7.69 (s, 1H), 7.59 (d, 1H), 7.53 (d, 1H), 6.03 (d, 1H), 5.68 (d, 1H), 2.60 (s, 1H), 2.41 (s, 1H), 2.31 (s, 1H), 1.32 (s, 18H), 1.08 (s, 9H)

FD-MS: m/z=612, 614, 616 (M$^+$)

Example 6

Synthesis of dimethylmethylene(3-tert-butylcyclopentadienyl)(3,6-di-tert-butylfluorenyl) zirconium Dichloride (1) Synthesis of 3-tert-butyl-6,6-dimethylfulvene To a solution of 1.53 g (13 mmol) of tert-butylcyclopentadiene in 30 ml of THF, 9.0 ml (14 mmol) of a hexane solution of n-butyllithium was dropwise added in a nitrogen atmosphere with ice cooling, followed by stirring at room temperature for one night. Then, 1.7 ml (16 mmol) of acetone was further added at −78° C., followed by stirring at room temperature for 2 days. To the reaction solution, water was added. After extraction with ether, the solvent was distilled off, and the residue was subjected to column chromatography (silica gel, developing solvent: hexane) to obtain 2.00 g of a yellow liquid (yield: 95%). The analyzed values are given below.

$^1$H-NMR (270 MHz, in CDCl$_3$, Based on TMS): δ6.53 (d, 2H), 6.14 (t, 1H), 2.16 (s, 3H), 2.14 (s, 3H), 1.20 (s, 9H)

The 3-tert-6,6-dimethylfulvene could be synthesized also by the following process.

To a mixed solution of 1.40 g (11 mmol) of tert-butylcyclopentadiene, 8.4 ml (114 mmol) of acetone and 20 ml of methanol, 9.5 ml (114 mmol) of pyrrolidine was added with ice cooling, followed by stirring at room temperature for one night. To the reaction solution, 50 ml of water, 100 ml of ether and 3 ml of acetic acid were added with ice cooling. The separated organic phase was washed with water and dried over anhydrous sodium sulfate. After the solvent was distilled off, the residue was subjected to column chromatography (silica gel, developing solvent: hexane) to obtain 1.62 g of a yellow liquid (yield: 88%).

(2) Synthesis of 2-(3-tert-butylcyclopentadienyl)-2-(3,6-di-tert-butylfluorenyl)propane To a solution of 1.98 g (7.1 mmol) of 3,6-di-tert-butylfluorene in 40 ml of ether, 4.6 ml (7.5 mmol) of a hexane solution of n-butyllithium was dropwise added in a nitrogen atmosphere with ice cooling, followed by stirring at room temperature for one night. To the resulting red solution, a solution of 1.56 g (9.6 mmol) of 3-tert-butyl-6,6-dimethylfulvene in 20 ml of ether was further dropwise added in a nitrogen atmosphere with ice cooling, followed by stirring at room temperature for one night. Then, 60 ml of water was added. The separated organic phase was dried over magnesium sulfate and then filtered. From the filtrate, the solvent was removed under reduced pressure to obtain a solid. The solid was purified by column chromatography (silica gel, developing solvent: hexane) to obtain 1.35 g of a light yellow solid (yield: 43%). The analyzed values are given below.

$^1$H-NMR (270 MHz, in CDCl$_3$, Based on TMS): δ7.71 (t, 2H), 7.20–6.97 (m, 4H), 6.48–5.70 (m, 2H), 4.04–3.98 (m, 1H), 3.10 (d, 2H), 1.38 (s, 18H), 1.24–1.20 (m, 9H), 1.05 (s, 6H)

(3) Synthesis of dimethylmethylene(3-tert-butylcyclopentadienyl)(3,6-di-tert-butylfluorenyl) zirconium Dichloride To a solution of 1.01 g (2.3 mmol) of 2-(3-tert-butylcyclopentadienyl)-2-(3,6-di-tert-butylfluorenyl)propane in 50 ml of ether, 2.9 ml (4.7 mmol) of a hexane solution of n-butyllithium was dropwise added in a nitrogen atmosphere with ice cooling, followed by stirring at room temperature for 20 hours. To the resulting reddish orange reaction mixture having been cooled to −78° C., 0.85 g (2.3 mmol) of zirconium tetrachloride (THF) 2-complex was added, followed by stirring at room temperature for one day and night. The resulting reaction mixture was subjected to sellaite filtration. From the filtrate, the solvent was removed under reduced pressure, and the residue was recrystallized from diethyl ether to obtain 0.91 g of an orange solid (yield: 67%). The analyzed values are given below.

$^1$H-NMR (270 MHz, in CDCl$_3$, Based on TMS): δ8.02 (d, 2H), 7.74–7.65 (d+d, 2H), 7.33 (d+d, 2H), 6.11 (t, 1H), 5.73 (t, 1H), 5.53 (t, 1H), 2.32 (s, 6H), 1.44 (s, 18H), 1.16 (s, 9H)

FD-MS: m/z=598, 600, 602 (M$^+$)

Example 7

Synthesis of dimethylmethylene(3-(1-methyl-1-cyclohexyl)cyclopentadienyl)(3,6-di-tert-butylfluorenyl)zirconium Dichloride (1) Synthesis of (1-methyl-1-cyclohexyl) cyclopentadiene To a solution of 6.50 g (44.5 mmol) of cyclohexylfulvene in 60 ml of THF, 44.8 ml (51.1 mmol) of an ether solution of methyllithium was dropwise added in a nitrogen atmosphere with ice cooling, followed by stirring at room temperature for one night. After the reaction solution was diluted with 100 ml of ether, 30 ml of water was added. The separated organic phase was washed with water and a saturated saline solution, then dried over magnesium sulfate and filtered. From the filtrate, the solvent was removed under reduced pressure to obtain a liquid. The liquid was isolated and purified by column chromatography (silica gel, developing solvent: hexane) to obtain 2.72 g (16.76 mmol) of a colorless transparent liquid (yield: 38%). The analyzed values are given below.

$^1$H-NMR (270 MHz, in CDCl$_3$, Based on TMS): 66.58+6.42+6.28+6.18+6.00 (m+m+m+m+m, 3H), 2.95+2.86 (s+m, 2H), 1.90–0.80 (m, 10H), 1.10 (s, 3H)

(2) Synthesis of 3-(1-methyl-1-cyclohexyl)-6,6-dimethylfulvene

To a solution of 2.71 g (16.7 mmol) of (1-methyl-1-cyclohexyl)cyclopentadiene in 30 ml of methanol, 25 ml (340.5 mmol) of acetone and 2.8 ml (33.5 mmol) of pyrrolidine were added with ice cooling, followed by stirring at room temperature for 3 days. After the reaction solution was diluted with 100 ml of ether, 50 ml of water was added. The organic phase was separated, washed with water and a saturated saline solution, then dried over anhydrous magnesium sulfate and filtered. From the filtrate, the solvent was removed under reduced pressure to obtain a liquid. The liquid was isolated and purified by column chromatography (silica gel, developing solvent: hexane) to obtain 2.95 g (14.58 mmol) of a yellow liquid (yield: 87%). The analyzed values are given below.

$^1$H-NMR (270 MHz, in CDCl$_3$, Based on TMS): δ7.80–6.16 (m, 3H), 2.18 (d, 6H), 2.25–0.80 (m, 14H), 1.23 (s, 3H)

(3) Synthesis of 2-(3-(1-methyl-1-cyclohexyl)cyclopentadienyl)-2-(3,6-di-tert-butylfluorenyl)propane To a solution of 2.64 g (9.5 mmol) of 3,6-di-tert-butylfluorene in 45 ml of THF, 6.4 ml (10.4 mmol) of a hexane solution of n-butyllithium was dropwise added in a nitrogen atmosphere with ice cooling, followed by stirring at room temperature for one night. To the resulting red solution, a solution of 2.00 g (9.9 mmol) of 3-(1-methyl-1-cyclohexyl)-6,6-dimethylfulvene in 30 ml of THF was further dropwise added in a nitrogen atmosphere with ice cooling, followed by stirring at room temperature for 3 days. After the reaction solution was diluted with 100 ml of ether, 50 ml of water was added. The separated organic phase was washed with water and a saturated saline solution, then dried over magnesium sulfate and filtered. From the filtrate, the solvent was removed under reduced pressure to obtain a liquid. The liquid was isolated and purified by column chromatography (silica gel, developing solvent: hexane) to obtain 1.96 g (4.08 mmol) of a white solid (yield: 43%). The analyzed values are given below.

$^1$H-NMR (270 MHz, in CDCl$_3$, Based on TMS): 87.73+7.25–6.95 (d+m, 6H), 6.51+6.11+5.98+5.73 (s+s+s+s, 2H), 4.08+3.98 (d+s, 1H), 3.17+3.08+2.98 (s+s+s, 2H), 1.95–0.85 (m, 10H+3H+6H), 1.38 (s, 18H)

(4) Synthesis of dimethylmethylene(3-(1-methyl-1-cyclohexyl)cyclopentadienyl)(3,6-di-tert-butylfluorenyl)zirconium Dichloride To a solution of 0.70 g (1.5 mmol) of 2-(3-(1-methyl-1-cyclohexyl)cyclopentadienyl)-2-(3,6-di-tert-butylfluorenyl)propane in 30 ml of diethyl ether, 1.9 ml (3.0 mmol) of a hexane solution of n-butyllithium was dropwise added in a nitrogen atmosphere with ice cooling, followed by stirring at room temperature for one night. The solution was cooled to –78° C., and 0.53 g (1.4 mmol) of zirconium tetrachloride (THF) 2-complex was added, followed by stirring at room temperature for 3 days. The reaction solution was subjected to sellaite filtration in a nitrogen atmosphere. From the resulting liquid, the solvent was removed under reduced pressure to obtain 0.80 g (1.25 mmol) of an orange solid (yield: 85%). The analyzed values are given below.

$^1$H-NMR (270 MHz, in CDCl$_3$, Based on TMS): δ8.10–7.10 (m, 6H), 6.16+5.75+5.58 (m+m+m, 3H), 2.44–1.14 (m, 10H+3H+6H), 1.46 (s, 18H)

FD-MS: m/z=638, 640, 642 (M$^+$)

Example 8

Synthesis of dimethylmethylene(3-tert-butylcyclopentadienyl)(1,1,4,4,7,7,10,10-octamethyl-1,2,3,4,7,8,9,10-octahydrodibenzo(b,h)-fluorenyl)zirconium Dichloride

(1) Synthesis of 1,1,4,4,7,7,10,10-octamethyl-1,2,3,4,7,8,9,10-octahydrodibenzo(b,h)-fluorene In a 500 ml three-necked flask purged with nitrogen, 9.72 g (58.6 mmol, 1 eq) of fluorene and 19.61 g (134 mmol, 2.3 eq) of 2,5-dimethyl-2,5-hexanediol were placed at room temperature. Then, 85 ml of dehydrated dichloromethane was added. After stirring by a magnetic stirrer, the mixture was cooled to –8° C. with an ice bath (light brown slurry). To the slurry, 38.9 g (292 mmol, 5.0 eq) of pulverized anhydrous aluminum chloride was added over a period of 70 minutes, followed by stirring at 0° C. for 2 hours. The ice bath was removed, and the solution was stirred at room temperature for 19 hours (dark brown solution). After disappearance of fluorene was confirmed by gas chromatography, the dark brown solution was poured into 150 ml of ice water to perform quenching (yellowish brown slurry). After the soluble component was extracted with 500 ml of diethyl ether, the organic phase was neutralized with a saturated sodium hydrogencarbonate aqueous solution and washed with water. The dispensed organic phase was dried over MgSO$_4$, then the MgSO$_4$ was filtered off, and from the filtrate the solvent was vacuum distilled off by a rotary evaporator. The residue was transferred onto a Kiriyama funnel, washed 6 times with 10 ml of hexane and vacuum dried to obtain a white powder (12.0 g, yield: 53%)

(2) Synthesis of 2-(3-tert-butylcyclopentadienyl)-2-(1,1,4,4,7,7,10,10-octamethyl-1,2,3,4,7,8,9,10-octahydrodibenzo(b,h)-fluorenyl)propane To a solution of 1.55 g (4.0 mmol) of 1,1,4,4,7,7,10,10-octamethyl-1,2,3,4,7,8,9,10-octahydrodibenzo(b,h)-fluorene in 50 ml of THF, 2.6 ml (~4.2 mmol) of a hexane solution of n-butyllithium was dropwise added in a nitrogen atmosphere with ice cooling, followed by stirring at room temperature for one night. To the resulting red solution, a solution of 0.97 g (6.0 mmol) of 3-tert-butyl-6,6-dimethylfulvene in 25 ml of THF was further dropwise added in a nitrogen atmosphere with ice cooling, followed by stirring at room temperature for one night. Then, 60 ml of water was added. The organic phase extracted with ether and separated was dried over magnesium sulfate and then filtered. From the filtrate, the solvent was removed under reduced pressure to obtain a solid. The solid was purified by column chromatography (silica gel, developing solvent: hexane) to obtain 0.95 g of a light yellow solid (yield: 43%). The analyzed values are given below.

$^1$H-NMR (270 MHz, in CDCl$_3$, Based on TMS): δ7.54 (d, 2H), 7.10 (d, 2H), 6.55–5.68 (d+d, 2H), 4.06–4.02 (s+s, 1H), 3.19–3.06 (s+s, 2H), 1.67 (s, 8H), 1.36–1.20 (m, 33H), 1.00 (s, 6H)

(3) Synthesis of dimethylmethylene(3-tert-butylcyclopentadienyl)(1,1,4,4,7,7,10,10-octamethyl-1,2,3,4,7,8,9,10-octahydrodibenzo(b,h)-fluorenyl)zirconium Dichloride To a solution of 0.91 g (1.7 mmol) of 2-(3-tert-butylcyclopentadienyl)-2-(1,1,4,4,7,7,10,10-octamethyl-1,2,3,4,7,8,9,10-octahydrodibenzo(b,h)-fluorenyl)propane in 50 ml of ether, 2.1 ml (3.4 mmol) of a hexane solution of n-butyllithium was dropwise added in a nitrogen atmosphere with ice cooling, followed by stirring at room temperature for 5 days. To the resulting reddish orange reaction mixture having been cooled to –78° C., 0.64 g (1.7 mmol) of zirconium tetrachloride (THF) 2-complex was added, followed by stirring at room temperature for 5 days. The resulting reaction mixture was subjected to sellaite filtration. From the filtrate, the solvent was removed under reduced pressure, and the residue was recrystallized from hexane to obtain 0.35 g of an orange solid (yield: 30%). The analyzed values are given below.

¹H-NMR (270 MHz, in CDCl₃, Based on TMS): δ7.99 (s, 2H), 7.59 (d, 2H), 6.09 (t, 1H), 5.53 (t, 1H), 5.43 (t, 1H), 2.30 (s, 6H), 1.72 (s, 8H), 1.52–1.14 (m, 33H)

FD-MS: m/z=706, 708, 710 (M⁺)

Example 9

Synthesis of dimethylmethylene(3-trimethylsilylcyclopentadienyl) (1,1,4,4,7,7,10,10-octamethyl-1,2,3,4,7,8,9,10-octahydrodibenzo(b,h)-fuluorenyl)zirconium Dichloride (1) Synthesis of 2-(cyclopentadienyl)-2-(1,1,4,4,7,7,10,10-octamethyl-1,2,3,4,7,8,9,10-octahydrodibenzo(b,h)-fluorenyl)propane In a 200 ml three-necked flask purged with nitrogen, 3.11 g (8.04 mmol, 1 eq) of 1,1,4,4,7,7,10,10-octamethyl-1,2,3,4,7,8,9,10-octahydrodibenzo(b,h)-fluorene was placed at room temperature. Then, 40 ml of dehydrated THF was added, and the mixture was stirred by a magnetic stirrer to give a solution. The solution was cooled to 2° C. with an ice bath (light yellow solution) To the solution, 5.2 ml (8.48 mmol, 1.05 eq) of n-BuLi (hexane solution) was dropwise added over a period of 10 minutes, and 10 ml of dehydrated THF was further added. The ice bath was removed, and the mixture was stirred at room temperature for 22 hours (dark red slurry). After the slurry was cooled to 0° C. with an ice bath, a solution of 1.05 ml (8.54 mmol, 1.06 eq) of 6,6-dimethylfulvene in 10 ml of dehydrated THF was dropwise added over a period of 15 minutes (dark red solution). The ice bath was removed, and the solution was stirred at room temperature for 23 hours. The resulting dark red brown solution was poured into 100 ml of a diluted hydrochloride acid solution to perform quenching. After the organic phase was washed with 100 ml of a saturated saline solution, the soluble component was extracted from the aqueous layer with 50 ml of diethyl ether. The soluble component and the dispensed organic phase were together dried over MgSO₄, then the MgSO₄ was filtered off, and from the filtrate the solvent was vacuum distilled off by a rotary evaporator to obtain a yellowish orange solid. The solid was purified by silica gel column chromatography (developing solvent: hexane) to obtain a white powder (2.70 g, yield: 68%).

¹H-NMR (270 MHz, in CDCl₃, Based on TMS): δ1.02, 1.04 (s, H, —CH3 of Bridge), 1,18–1.36 (m, 24H, —CH3 of OMOHDBFlu), 1.63–1.72 (m, 8H, —CH₂ of OMOHDBFlu), 3.08, 3.09, 3.19 (s, 2H, —CH2— of Cp), 3.97, 4.02 (s, 1H, 9-H of OMOHDBFlu), 5.90–6.97 (m, 2H, —CH— of Cp), 6.95, 7.07, 7.54 (s, 4H, Ph-H of OMOHDBFlu); OMOHDBFlu 1,1,4,4,7,7,10,10-octamethyl-1,2,3,4,7,8,9,10-octahydrodibenzo(b,h)-fluorenyl (2) Synthesis of 2-(3-trimethylsilylcyclopentadienyl)-2-(1,1,4,4,7,7,10,10-octamethyl-1,2,3,4,7,8,9,10-octahydrodibenzo(b,h)-fluorenyl)propane In a 30 ml Schlenk flask purged with nitrogen, 0.66 g (1.34 mmol, 1 eq) of 2-(cyclopentadienyl)-2-(1,1,4,4,7,7,10,10-octamethyl-1,2,3,4,7,8,9,10-octahydrodibenzo(b,h)-fluorenyl)propane was placed at room temperature. Then, 10 ml of dehydrated THF was added, and the mixture was stirred by a magnetic stirrer to give a solution. The solution was cooled with an ice bath (light brown solution). To the solution, 0.88 ml (1.43 mmol, 1.07 eq) of n-BuLi (hexane solution) was dropwise added over a period of 1 to 2 minutes. The ice bath was removed, and the solution was stirred at room temperature for 66 hours (dark violet solution). After the solution was cooled with an ice bath, 0.8 ml (6.31 mmol, 4.71 eq) of chlorotrimethylsilane was dropwise added by a syringe (reddish brown solution). The ice bath was removed, and the solution was stirred at room temperature for 2.5 hours. The resulting light yellow solution was poured into 50 ml of a diluted hydrochloric acid solution to perform quenching. After the soluble component was extracted with 30 ml of diethyl ether, the organic phase was washed with a saturated saline solution. The organic phase was dried over MgSO₄, then the MgSO₄ was filtered off, and from the filtrate the solvent was vacuum distilled off by a rotary evaporator to obtain a slightly yellow amorphous product. The amorphous product was purified by silica gel column chromatography (developing solvent: hexane) to obtain 0.71 g of a white solid (yield: 93%).

¹H-NMR (270 MHz, in CDCl₃, Based on TMS): δ-0.02 (s, 9H, —Si(CH3)₃), 1.06, 1.08 (s, 6H, —CH₃ of Bridge), 1.26–1.47 (m, 24H, —CH₃ of CMOHDBFlu), 1.60–1.71 (m, 8H, —CH2— of OMOHDBFlu), 3.33 (s, 1H, 1-H of Cp), 4.08 (s, 1H, 9-H of OMOHDBFlu), 5.97–6.91 (m, 2H, —CH— of fCp), 6.68, 7.46, 7.50, 7.56 (s, 4H, Ph-H of OMOHDBFlu)

(3) Synthesis of dimethylmethylene(3-trimethylsilylcyclopentadienyl)(1,1,4,4,7,7,10,10-octamethyl-1,2,3,4,7,8,9,10-octahydrodibenzo(b,h)-fluorenyl)zirconium Dichloride In a 50 ml Schlenk flask purged with nitrogen, 0.70 g (1.24 mmol, 1 eq) of 2-(3-trimethylsilylcyclopentadienyl)-2-(1,1,4,4,7,7,10,10-octamethyl-1,2,3,4,7,8,9,10-octahydrodibenzo(b,h)-fluorenyl)propane was placed at room temperature. Then, 23 ml of dehydrated diethyl ether was added, and the mixture was stirred by a magnetic stirrer to give a solution. The solution was cooled with an ice bath (slightly yellow solution). To the solution, 1.58 ml (2.58 mmol, 2.08 eq) of n-BuLi (hexane solution) was dropwise added by a syringe. The ice bath was removed, and the solution was stirred at room temperature for 20 hours (orangy red solution). From the solution, the solvent was vacuum distilled off, then 15 ml of dehydrated diethyl ether was added again, and the mixture was stirred by a magnetic stirrer to give a solution. The solution was cooled with an ice bath (orangy red solution). To the solution, 0.38 ml (0.62 mmol, 0.50 eq) of n-BuLi (hexane solution) was dropwise added by a syringe. The ice bath was removed, and the solution was stirred at room temperature for 20 hours (red solution). The solution was cooled with a dry ice/methanol bath, and to the solution was added 0.43 g (1.14 mmol, 0.92 eq) of zirconium tetrachloride 0 (THF) 2-complex. The mixture was stirred for 23 hours while allowing the dry ice to naturally disappear and the temperature of the mixture to naturally rise. From the resulting red slurry, the volatile component was vacuum distilled off. To the residue, 30 ml of dehydrated hexane was added, and the insoluble component was filtered. The solvent of the resulting red solution was vacuum concentrated, and the obtained solution was stored in a refrigerator to obtain 0.28 g of a red plate solid (yield: 33%).

¹H-NMR (270 MHz, in CDCl₃, Based on TMS): δ0.11 (s, 9H, —Si(CH₃)₃), 1.23–1.51 (m, 24H, —CH3 of OMOHDBFlu), 1.73–1.75 (m, 8H, —CH2— of OMOHDBFlu), 2.33 (s, 6H, —CH3 of Bridge), 5.49, 5.79, 6.30-(t, 3H, —CH of Cp), 7.60, 7.98 (s, 4H, Ph-H of OMOHDBFlu)

FD-MS: m/z 722, 724, 726 (M⁺)

Example 10

Synthesis of dimethylmethylene(3-(1,1-dimethylpropyl)cyclopentadienyl)(3,6-di-tert-butylfluorenyl)zirconium Dichloride

(1) Synthesis of 6-methyl-6-ethylfulvene

To a solution of 10.00 g (151.3 mmol) of cyclopentadiene in 30 ml of methanol, 13.6 ml (151.8 mmol) of methyl ethyl ketone and 12.8 ml (153.3 mmol) of pyrrolidine were added with ice cooling, followed by stirring at room temperature for one night. After the reaction solution was diluted with 200 ml of ether, 100 ml of water was added. The organic phase was separated, washed with water and a saturated saline solution, then dried over anhydrous magnesium sulfate and filtered. From the filtrate, the solvent was removed under reduced pressure to obtain a liquid. The liquid was subjected to vacuum distillation (75–82° C./20 mmHg) to obtain 9.20 g (76.55 mmol) of a yellow liquid (yield: 51%). The analyzed values are given below.

$^1$H-NMR (270 MHz, in CDCl$_3$, Based on TMS): δ6.50 (m, 4H), 2.55 (f, 2H), 2.20 (s, 3H), 1.18 (t, 3H)

(2) Synthesis of (1,1-dimethylpropyl)cyclopentadiene

To a solution of 8.00 g (66.6 mmol) of 6-methyl-6-ethylfulvene in 40 ml of ether, 66.0 ml (75.2 mmol) of an ether solution of methyllithium was dropwise added in an nitrogen atmosphere with ice cooling, followed by stirring at room temperature for one night. Then, 30 ml of water was added. The separated organic phase was washed with water and a saturated saline solution, then dried over magnesium sulfate and filtered. From the filtrate, the solvent was removed under reduced pressure to obtain a liquid. The liquid was subjected to vacuum distillation (165° C./270 mmHg) to obtain 8.40 g (61.66 mmol) of a light yellow liquid (yield: 93%). The analyzed values are given below.

$^1$H-NMR (270 MHz, in CDCl$_3$, Based on TMS): δ6.55+6.41+6.26+6.14+5.96 (m+m+m+m+m, 3H), 2.94+2.88 (m+m, 2H), 1.48 (m, 2H), 1.12 (s, 6H), 0.72 (m, 3H)

(3) Synthesis of 3-(1,1-dimethylpropyl)-6,6-dimethylfulvene

To a solution of 3.00 g (22.0 mmol) of (1,1-dimethylpropyl)cyclopentadiene in 30 ml of methanol, 16.2 ml (220.4 mmol) of acetone and 3.7 ml (44.0 mmol) of pyrrolidine were added with ice cooling, followed by stirring at room temperature for one night. After the reaction solution was diluted with 100 ml of ether, 50 ml of water was added. The organic phase was separated, washed with water and a saturated saline solution, then dried over anhydrous magnesium sulfate and filtered. From the filtrate, the solvent was removed under reduced pressure to obtain a liquid. The liquid was subjected to vacuum distillation (100° C./1 mmHg) to obtain 1.85 g (10.49 mmol) of a yellow liquid (yield: 48%). The analyzed values are given below.

$^1$H-NMR (270 MHz, in CDCl$_3$, Based on TMS): δ6.52 (m, 2H), 6.13 (m, 1H), 2.18 (d, 6H), 1.52 (f, 2H), 1.18 (s, 6H), 0.80 (t, 3H)

(4) Synthesis of 2-(3-(1,1-dimethylpropyl)cyclopentadienyl)-2-(3,6-di-tert-butylfluorenyl)propane To a solution of 2.14 g (7.7 mmol) of 3,6-di-tert-butylfluorene in 40 ml of THF, 5.0 ml (8.1 mmol) of a hexane solution of n-butyllithium was dropwise added in a nitrogen atmosphere with ice cooling, followed by stirring at room temperature for one night. To the resulting red solution, a solution of 1.81 g (10.3 mmol) of 3-(1,1-dimethylpropyl)-6,6-dimethylfulvene in 30 ml of THF was dropwise added in a nitrogen atmosphere with ice cooling, followed by stirring at room temperature for 3 days. After the reaction solution was diluted with 100 ml of ether, 5 ml of water was added. The separated organic phase was washed with water and a saturated saline solution, then dried over magnesium sulfate and filtered. From the filtrate, the solvent was removed under reduced pressure to obtain a liquid. The liquid was isolated and purified by column chromatography (silica gel, developing solvent: hexane) to obtain 2.06 g (4.53 mmol) of a white solid (yield: 59%). The analyzed values are given below.

$^1$H-NMR (270 MHz, in CDCl$_3$, Based on TMS): δ7.72+7.20–6.95 (s+m, 6H), 6.42+6.08+5.92+5.72 (s+s+s+s, 2H), 4.05 (d, 1H), 3.13+2.98+2.88 (s+s+s, 2H), 1.52 (m, 2H), 1.38 (s, 18H), 1.19+1.13 (d+s, 6H), 1.08 (d, 6H), 0.82 (m, 3H)

(5) Synthesis of dimethylmethylene(3-(1,1-dimethylpropyl)cyclopentadienyl)(3,6-di-tert-butylfluorenyl)zirconium Dichloride To a solution of 0.82 g (1.8 mmol) of 2-(3-(1,1-dimethylpropyl)cyclopentadienyl)-2-(3,6-di-tert-butylfluorenyl)propane in 30 ml of diethyl ether, 2.3 ml (3.8 mmol) of a hexane solution of n-butyllithium was dropwise added in a nitrogen atmosphere with ice cooling, followed by stirring at room temperature for one night. The solution was cooled to −78° C., and 0.66 g (1.8 mmol) of zirconium tetrachloride (THF) 2 complex was added, followed by stirring at room temperature for one night. The reaction solution was subjected to sellaite filtration in a nitrogen atmosphere. From the resulting liquid, the solvent was removed under reduced pressure. To the reside, 10 ml of hexane was added, and the mixture was cooled to perform crystallization and thereby obtain 0.38 g (0.62 mmol) of a red solid (yield: 34%). The analyzed values are given below.

$^1$H-NMR (270 MHz, in CDCl$_3$, Based on TMS): δ8.02+7.70, 7.30 (t+m+m, 6H), 6.10+5.75+5.52 (t+t+t, 3H), 2.32 (d, 6H), 1.46 (s, 18H), 1.40 (f, 2H), 1.20+1.10 (s+s, 6H), 0.65 (t, 3H)

FD-MS: m/z=612, 614, 616 (M$^+$)

Example 11

Synthesis of dimethylmethylene(3-(1-ethyl-1-methylpropyl)cyclopentadienyl)(3,6-di-tert-butylfluorenyl)zirconium Dichloride

(1) Synthesis of 6,6-diethylfulvene

To a solution of 22.00 g (332.8 mmol) of cyclopentadiene in 35 ml of methanol, 36.0 ml (665.1 mmol) of diethyl ketone and 28.0 ml (335.5 mmol) of pyrrolidine were added with ice cooling, followed by stirring at room temperature for one night. After the reaction solution was diluted with 200 ml of ether, 100 ml of water was added. The organic phase was separated, washed with water and a saturated saline solution, then dried over anhydrous magnesium sulfate and filtered. From the filtrate, the solvent was removed under reduced pressure to obtain a liquid. The liquid was subjected to vacuum distillation (78–83° C./4 mmHg) to obtain 36.50 g (271.94 mmol) of a yellow liquid (yield: 82%). The analyzed values are given below.

¹H-NMR (270 MHz, in CDCl₃, Based on TMS): δ6.50 (m, 4H), 2.55 (f, 4H), 1.18 (t, 6H)

(2) Synthesis of (1-ethyl-1-methylpropyl) cyclopentadiene

To a solution of 8.00 g (59.6 mmol) of 6,6-diethylfulvene in 35 ml of ether, 60.0 ml (68.4 mmol) of an ether solution of methyllithium was dropwise added in a nitrogen atmosphere with ice cooling, followed by stirring at room temperature for one night. Then, 30 ml of water was added. The separated organic phase was washed with water and a saturated saline solution, then dried over magnesium sulfate and filtered. From the filtrate, the solvent was removed under reduced pressure to obtain a liquid. The liquid was subjected to vacuum distillation (92° C./40 mmHg) to obtain 5.50 g (36.6 mmol) of a light yellow liquid (yield: 61%). The analyzed values are given below.

¹H-NMR (270 MHz, in CDCl₃, Based on TMS): δ6.60–5.90 (m, 3H), 2.94+2.88 (f+f, 2H), 1.48 (m, 4H), 1.08 (s, 3H), 0.72 (m, 6H)

(3) Synthesis of 3-(1-ethyl-1-methylpropyl)-6,6-dimethylfulvene

To a solution of 2.50 g (16.6 mmol) of (1-ethyl-1-methylpropyl)cyclopentadiene in 20 ml of methanol, 8.4 ml (114.4 mmol) of acetone and 2.8 ml (33.5 mmol) of pyrrolidine were added with ice cooling, followed by stirring at room temperature for one night. After the reaction solution was diluted with 100 ml of ether, 50 ml of water was added. The organic phase was separated, washed with water and a saturated saline solution, then dried over anhydrous magnesium sulfate and filtered. From the filtrate, the solvent was removed under reduced pressure to obtain a liquid. The liquid was isolated and purified by column chromatography (silica gel, developing solvent: hexane) to obtain 2.90 g (15.24 mmol) of a yellow liquid (yield: 92%). The analyzed values are given below.

¹H-NMR (270 MHz, in CDCl₃, Based n TMS): δ6.50 (m, 2H), 6.11 (m, 1H), 2.13 (d, 6H), 1.50 (f, 4H), 1.09 (d, 3H), 0.78 (m, 6H)

(4) Synthesis of 2-(3-(1-ethyl-1-methylpropyl) cyclopentadienyl)-2-(3,6-di-tert-butylfluorenyl) propane To a solution of 1.93 g (6.9 mmol) of 3,6-di-tert-butylfluorene in 30 ml of THF, 4.7 ml (7.6 mmol) of a hexane solution of n-butyllithium was dropwise added in a nitrogen atmosphere with ice cooling, followed by stirring at room temperature for one night. To the resulting red solution, a solution of 1.70 g (8.9 mmol) of 3-(1-ethyl-1-methylpropyl)-6,6-dimethylfulvene in 10 ml of THF was dropwise added in a nitrogen atmosphere with ice cooling, followed by stirring at room temperature for 5 days. After the reaction solution was diluted with 100 ml of ether, 50 ml of water was added. The separated organic phase was washed with water and a saturated saline solution, then dried over magnesium sulfate and filtered. From the filtrate, the solvent was removed under reduced pressure to obtain a liquid. The liquid was isolated and purified by column chromatography (silica gel, developing solvent: hexane) to obtain 1.20 g (2.56 mmol) of a white solid (yield: 37%). The analyzed values are given below.

¹H-NMR (270 MHz, in CDCl₃, Based on TMS): δ7.72+7.20–6.95 (s+m, 6H), 6.42+6.08+5.92+5.72 (s+s+s+s, 2H), 4.05 (d, 1H), 3.13+2.98+2.88 (s+s+s, 2H), 1.52 (m, 4H), 1.38 (s, 18H), 1.09, 1.06 (m,m, 9H), 0.80 (m, 6H)

(5) Synthesis of dimethylmethylene(3-(1-ethyl-1-methylpropyl)cyclopentadienyl)(3,6-di-tert-butylfluorenyl)zirconium Dichloride To a solution of 0.70 g (1.5 mmol) of 2-(3-(1-ethyl-1-methylpropyl)cyclopentadienyl)-2-(3,6-di-tert-butylfluorenyl)propane in 35 ml of diethyl ether, 1.9 ml (3.1 mmol) of a hexane solution of n-butyllithium was dropwise added in a nitrogen atmosphere with ice cooling, followed by stirring at room temperature for one night. The solution was cooled to −78° C., and 0.55 g (1.5 mmol) of zirconium tetrachloride (THF) 2-complex was added, followed by stirring at room temperature for one night. The reaction solution was subjected to sellaite filtration in a nitrogen atmosphere. From the resulting liquid, the solvent was removed under reduced pressure. To the residue, 5 ml of hexane was added, and the mixture was cooled to perform crystallization and thereby obtain 0.33 g (0.52 mmol) of a red solid (yield: 35%). The analyzed values are given below.

¹H-NMR (270 MHz, in CDCl₃, Based on TMS): δ8.00+7.70, 7.30 (t+m+m, 6H), 6.09+5.74+5.52 (t+t+t, 3H), 2.31 (m, 6H), 1.46 (s, 18H), 1.27 (m, 4H), 1.10 (m, 3H), 0.64 (m, 6H)

FD-MS: m/z=626, 628, 630 (M⁺)

Example 12

Synthesis of dimethylmethylene (3-(1,1,3-trimethylbutyl)cyclopentadienyl) 3,6-di-tert-butylfluorenyl)zirconium dichloride

(1) Synthesis of 6-methyl-6-isobutylfulvene

To a solution of 10.00 g (151.3 mmol) of cyclopentadiene in 30 ml of methanol, 18.9 ml (151.1 mmol) of methyl isobutyl ketone and 12.8 ml (153.3 mmol) of pyrrolidine were added with ice cooling, followed by stirring at room temperature for one night. After the reaction solution was diluted with 100 ml of ether, 50 ml of water was added. The organic phase was separated, washed with water and a saturated saline solution, then dried over anhydrous magnesium sulfate and filtered. From the filtrate, the solvent was removed under reduced pressure to obtain a liquid. The liquid was subjected to vacuum distillation (83–88° C./10 mmHg) to obtain 15.80 g (106.58 mmol) of a yellow liquid (yield: 71%). The analyzed values are given below.

¹H-NMR (270 MHz, in CDCl₃, Based on TMS): δ6.50 (m, 4H), 2.42 (d, 2H), 2.19 (s, 3H), 1.96 (m, 1H), 0.93 (d, 6H)

(2) Synthesis of (1,1,3-trimethylbutyl) cyclopentadiene

To a solution of 8.00 g (54.0 mmol) of 6-methyl-6-isobutylfulvene in 30 ml of ether, 54.0 ml (61.6 mmol) of an ether solution of methyllithium was dropwise added in a nitrogen atmosphere with ice cooling, followed by stirring at room temperature for 4 days. Then, 30 ml of water was added. The separated organic phase was washed with water and a saturated saline solution, then dried over magnesium sulfate and filtered. From the filtrate, the solvent was removed under reduced pressure to obtain a liquid. The liquid was subjected to vacuum distillation (120° C./25 mmHg) to obtain 7.10 g (43.2 mmol) of a light yellow liquid (yield: 80%)

(3) Synthesis of 3-(1,1,3-trimethylbutyl)-6,6-dimethylfulvene

To a solution of 3.00 g (18.3 mmol) of (1,1,3-trimethylbutyl)cyclopentadiene in 30 ml of methanol, 13.4 ml (182.5 mmol) of acetone and 3.1 ml (36.6 mmol) of pyrrolidine were added with ice cooling, followed by stirring at room temperature for one night. After the reaction solution was diluted with % 100 ml of ether, 50 ml of water was added. The organic phase was separated, washed with water and a saturated saline solution, then dried over anhydrous magnesium sulfate and filtered. From the filtrate, the solvent was removed under reduced pressure to obtain a liquid. The liquid was subjected to vacuum distillation (130° C./1 mmHg) to obtain 3.50 g (17.1 mmol) of a yellow liquid (yield: 94%). The analyzed values are given below.

$^1$H-NMR (270 MHz, in CDCl$_3$, Based on TMS): δ6.50 (m, 2H), 6.11 (m, 1H), 2.15 (d, 6H), 1.52 (m, 1H), 1.42 (d, 2H), 1.17 (s, 6H), 0.81 (d, 6H)

(4) Synthesis of 2-(3-(1,1,3-trimethylbutyl)cyclopentadienyl)-2-(3,6-di-tert-butylfluorenyl)propane To a solution of 2.16 g (7.8 mmol) of 3,6-di-tert-butylfluorene in 35 ml of THF, 5.0 ml (8.2 mmol) of a hexane solution of n-butyllithium was dropwise added in a nitrogen atmosphere with ice cooling, followed by stirring at room temperature for one night. To the resulting red solution, a solution of 2.16 g (10.6 mmol) of 3-(1,1,3-trimethylbutyl)-6,6-dimethylfulvene in 10 ml of THF was dropwise added in a nitrogen atmosphere with ice cooling, followed by stirring at room temperature for 5 days. After the reaction solution was diluted with 100 ml of ether, 50 ml of water was added. The separated organic phase was washed with water and a saturated saline solution, then dried over magnesium sulfate and filtered. From the filtrate, the solvent was removed under reduced pressure to obtain a liquid. The liquid was isolated and purified by column chromatography (silica gel, developing solvent: hexane) to obtain 2.80 g (5.80 mmol) of a white solid (yield: 74%). The analyzed values are given below.

$^1$H-NMR (270 MHz, in CDCl$_3$, Based on TMS): δ7.71+ 7.14–6.95 (s+m, 6H), 6.42+6.08+5.92+5.72 (s+s+s+s, 2H), 4.05 (d, 1H), 3.13+2.98+2.88 (s+s+s, 2H), 1.62 (m, 1H), 1.45 (m, 2H), 1.38 (s, 18H), 1.22+1.18+1.06 (s+s+m, 12H), 0.80 (m, 6H)

(5) Synthesis of dimethylmethylene(3-(1,1,3-trimethylbutyl)cyclopentadienyl) (3,6-di-tert-butylfluorenyl)zirconium Dichloride To a solution of 0.87 g (1.8 mmol) of 2-(3-(1,1,3-trimethylbutyl)cyclopentadienyl)-2-(3,6-di-tert-butylfluorenyl)propane in 35 ml of diethyl ether, 2-0.3 ml (3.7 mmol) of a hexane solution of n-butyllithium was dropwise added in a nitrogen atmosphere with ice cooling, followed by stirring at room temperature for one night. The solution was cooled to −78° C., and 0.67 g (1.8 mmol) of zirconium tetrachloride (THF) 2-complex was added, followed by stirring at room temperature for 2 days. The reaction solution was subjected to sellaite filtration in a nitrogen atmosphere. From the resulting liquid, the solvent was removed under reduced pressure to obtain 0.6 g (0.93 mmol) of a red solid (yield: 52%). The analyzed values are given below.

$^1$H-NMR (270 MHz, in CDCl$_3$, Based on TMS): 88.00+ 7.70, 7.30 (t+m+m, 6H), 6.06+5.69+5.49 (t+t+t, 3H), 2.28 (m, 6H), 1.41 (s, 18H), 1.42–0.64 (m, 9H), 0.59 (m, 6H)

FD-MS: m/z=640, 642, 644 (M+)

Example 13

Synthesis of dimethylmethylene(3-trimethylsilylcyclopentadienyl)(3,6-di-tert-butylfluorenyl)zirconium Dichloride (1) Synthesis of 2-(cyclopentadienyl)-2-(3,6-di-tert-butylfluorenyl)propane To a solution of 3.0 g(10.8 mmol) of 3,6-di-tert-butylfluorene in 40 ml of THF, 7.0 ml (11.3 mmol) of a hexane solution of n-butyllithium was dropwise added in a nitrogen atmosphere with ice cooling, followed by stirring at room temperature for 6 hours. From the reaction mixture, the solvent was removed under reduced pressure, and the residue was washed with pentane and dried to obtain a white solid. To a solution of the solid in 30 ml of THF, a solution of 1.4 g (13.2 mmol) of 6,6-dimethylfulvene in 30 ml of THF was dropwise added in a nitrogen atmosphere with ice cooling, followed by stirring for 5 hours. Then, 30 ml of water was added. The organic phase extracted with diethyl ether and separated was dried over magnesium sulfate and filtered. From the filtrate, the solvent was removed under reduced pressure to obtain a solid. The solid was recrystallized from methanol to obtain 2.9 g of a slightly yellow solid. The analyzed values are given below.

$^1$H-NMR (270 MHz, in CDCl$_3$, Based on TMS): δ7.73 (s, 2H), 7.20–6.98 (m, 4H), 6.95–5.93 (m, 3H), 4.06 (d, 1H), 3.13 (d, 2H), 1.39 (s, 18H), 1.07 (d, 6H)

(2) Synthesis of 2-(3-trimethylsilylcyclopentadienyl)-2-(3,6-di-tert-butylfluorenyl)propane In a 50 ml Schlenk flask purged with nitrogen, 1.44 g (3.74 mmol, 1 eq) of 2 (cyclopentadienyl)-2-(3,6-di-tert-butylfluorenyl)propane was placed at room temperature. Then, 20 ml of dehydrated THF was added, and the mixture was stirred by a magnetic stirrer to give a solution. The solution was cooled with an ice bath (light yellowish orange solution). To the solution, 2.5 ml (1.63 mmol, 1.09 eq) of n-BuLi (hexane solution) was dropwise added. The ice bath was removed, and the solution was stirred at room temperature for 19 hours (dark red solution). The solution was cooled with an ice bath, and to the solution, 2.7 ml (21.3 mmol, 5.70 eq) of chlorotrimethylsilane was dropwise added by a syringe. The ice bath was removed, and the solution was stirred at room temperature for 3 hours. The resulting yellow solution was poured into 80 ml of a diluted hydrochloric acid solution to perform quenching. After the soluble component was extracted with 100 ml of diethyl ether, the organic phase was washed with 50 ml of a saturated saline solution. The organic phase was dried over MgSO$_4$, then the MgSO$_4$ was filtered off, and from the filtrate the solvent was vacuum distilled off by a rotary evaporator to obtain a light yellow solid. The solid was washed with 50 ml of methanol and vacuum dried to obtain 1.44 g a light creamy powder (yield: 84%).

$^1$H-NMR (270 MHz, in CDCl$_3$, Based on TMS): δ−0.01 (s, 9H, —Si(CH$_3$)$_3$), 1.35, 1.39 (s, 18H, tBu of 3, 6-tBu$_2$Flu), 1.37, 1.41 (s, 6H, —CH$_3$ of Bridge), 3.34 (s, 1H, 1-H of Cp), 4.14 (s, 1H, 9-H of 3,6-tBu$_2$Flu), 6.01, 6.58, 6.87 (m, 3H, —CH— of Cp), 6.71–7.72 (m, 6H, Ph-H of 3, 6-tBu$_2$Flu)

(3) Synthesis of dimethylmethylene(3-trimethylsilylcyclopentadienyl)(3,6-di-tert-butylfluorenyl)zirconium Dichloride In a 50 ml Schlenk flask purged with nitrogen, 1.32 g (2.89 mmol, 1 eq) of 2-(3-trimethylsilylcyclopentadienyl)-2-(3,6-di-tert-butylfluorenyl)propane was placed at room temperature. Then, 30 ml of dehydrated diethyl ether was added, and the mixture was stirred by a magnetic stirrer to give a solution. The solution was cooled with an ice bath (creamy solution). To the solution, 3.9 ml (6.36 mmol, 2.20 eq) of n-BuLi (hexane solution) was dropwise added by a syringe. The ice bath was removed, and the mixture was stirred at room temperature for 27 hours (yellowish orange slurry). The slurry was cooled with a dry ice/methanol bath, and thereto was added 1.09 g (2.89 mmol, 1.00 eq) of zirconium tetrachloride (THF) 2-complex. The mixture was stirred for 22 hours while allowing the dry ice to naturally disappear and the temperature of the mixture to naturally rise to room temperature. From the resulting reddish orange slurry, the volatile component was vacuum distilled off. To the residue, 50 ml of dehydrated hexane was added, and then the insoluble component was filtered through a filter. To the orange powder remaining on the filter, 10 ml of dehydrated dichloromethane was added to filter the soluble component. From the resulting red solution., the solvent was vacuum distilled off to obtain an orange solid (0.74 g, yield: 42%).

$^1$H-NMR (270 MHz, in CDCl$_3$, Based on TMS): δ0.12 (s, 9H, —Si(CH$_3$)$_3$), 1.44 (s, 18H, tBu of 3, 6-tBu$_2$Flu), 2.35 (s, 6H, —CH$_3$ of Bridge), 5.61, 5.96, 6.33 (t, 3H, —CH— of Cp), 7.32, 7.33 (d, 2H, 1, 8-H of 3, 6-tBu$_2$Flu), 7.70 (m, 2H, 2, 7-H of 3, 6-tBu$_2$Flu), 8.01 (s, 2H, 4, 5-H of 3, 6-tBu$_2$Flu)

FD-MS: m/z 614, 616, 618 (M$^+$)

Example 14

Synthesis of dimethylmethylene(3-(1,1-dimethylbutyl)cyclopentadienyl)(3,6-di-tert-butylfluorenyl)zirconium Dichloride (1) Synthesis of 6-methyl-6-propylfulvene To a solution of 10.00 g (151.3 mmol) of cyclo pentadiene in 40 ml of methanol, 18.6 ml (174.2 mmol) of methyl propyl ketone and 4.5 ml (54.7 mmol) of pyrrolidine were added with ice cooling, followed by stirring at room temperature for one night. After the reaction solution was diluted with 100 ml of ether, 50 ml of water was added. The organic phase was separated, washed with water and a saturated saline solution, then dried over anhydrous magnesium sulfate and filtered. From the filtrate, the solvent was removed under reduced pressure to obtain a liquid. The liquid was subjected to vacuum distillation (70° C./1 mmHg) to obtain 12.30 g (91.64 mmol) of a yellow liquid (yield: 61%). The analyzed values are given below.

$^1$H-NMR (270 MHz, in CDCl$_3$, Based on TMS): δ6.55 (m, 4H), 2.56 (m, 2H), 2.23 (t, 3H), 1.67 (m, 2H), 1.00 (m, 3H)

(2) Synthesis of (1,1-dimethylbutyl)cyclopentadiene

To a solution of 7.00 g (52.2 mmol) of 6-methyl-6-propylfulvene in 40 ml of THF, 50.3 ml (57.3 mmol) of an ether solution of methyllithium was dropwise added in a nitrogen atmosphere with ice cooling, followed by stirring at room temperature for one night. After the reaction solution was diluted with 100 ml of ether, 30 ml of water was added. The separated organic phase was washed with water and a saturated saline solution, then dried over magnesium sulfate and filtered. From the filtrate, the solvent was removed under reduced pressure to obtain a liquid. The liquid was subjected to vacuum distillation (75° C./5–7 mmHg) to obtain 6.40 g (42.6 mmol) of a light yellow liquid (yield: 82%). The analyzed values are given below.

$^1$H-NMR (270 MHz, in CDCl$_3$, Based on TMS): δ6.55+ 6.41+6.26+6.14+5.96 (m+m+m+m+m, 3H), 2.94+2.88 (m+m, 2H), 1.48 (m, 2H), 1.12 (s, 6H), 1.00–0.80 (m, 5H)

(3) Synthesis of 3-(1,1-dimethylbutyl)-6,6-dimethylfulvene

To a solution of 3.00 g (20.0 mmol) of (1,1-dimethylbutyl)cyclopentadiene in 30 ml of methanol, 14.6 ml (198.8 mmol) of acetone and 2.5 ml (29.9 mmol) of pyrrolidine were added with ice cooling, followed by stirring at room temperature for 3 days. After the reaction solution was diluted with 100 ml of ether, 50 ml of water was added. The organic phase was separated, washed with water and a saturated saline solution, then dried over anhydrous magnesium sulfate and filtered. From the filtrate, the solvent was removed under reduced pressure to obtain a liquid. The liquid was isolated and purified by column chromatography (silica gel, developing solvent: hexane) to obtain 2.70 g (14.19 mmol) of a yellow liquid (yield: 71%). The analyzed values are given below.

$^1$H-NMR (270 MHz, in CDCl$_3$, Based on TMS): δ6.51 (m, 2H), 6.11 (m, 1H), 2.15 (d, 6H), 1.44 (m, 2H), 1.26–1.10 (m, 2H), 1.15 (s, 6H), 0.85 (t, 3H)

(4) Synthesis of 2-(3-(1,1-dimethylbutyl) cyclopentadienyl)-2-(3,6-di-tert-butylfluorenyl) propane To a solution of 1.70 g (6.1 mmol) of 3,6-di-tert-butylfluorene in 40 ml of THF, 3.9 ml (6.4 mmol) of a hexane solution of n-butyllithium was dropwise added in a nitrogen atmosphere with ice cooling, followed by stirring at room temperature for one night. To the resulting red solution, a solution of 1.22 g (6.4 mmol) of 3-(1,1-dimethylbutyl)-6,6-dimethylfulvene in 35 ml of THF was dropwise added in a nitrogen atmosphere with ice cooling, followed by stirring at room temperature for one night. After the reaction solution was diluted with 100 ml of ether, 50 ml of water was added. The separated organic phase was washed with water and a saturated saline solution, then dried over magnesium sulfate and filtered. From the filtrate, the solvent was removed under reduced pressure to obtain a liquid. The liquid was isolated and purified by column chromatography. (silica gel, developing solvent: hexane) to obtain 1.73 g (3.69 mmol) of an oily liquid (yield: 61%). The analyzed values are given below.

$^1$H-NMR (270 MHz, in CDCl$_3$, Based on TMS): δ7.71+ 7.16–6.95 (s+m, 6H), 6.42–5.70 (m, 2H), 4.03 (d, 1H), 3.12+3.03+2.94 (s+s+s, 2H), 1.38 (s, 18H), 1.27+1.18 (m+d, 10H), 1.06 (s, 6H), 0.92 (m, 3H)

(5) Synthesis of dimethylmethylene(3-(1,1-dimethylbutyl)cyclopentadienyl)(3,6-di-tert-butylfluorenyl)zirconium Dichloride To a solution of 0.60 g (1.3 mmol) of 2-(3-(1,1-dimethylbutyl)cyclopentadienyl)-2-(3,6-di-tert-butylfluorenyl)propane in 50 ml of diethyl ether, 1.6 ml (2.6 mmol) of a hexane solution of n-butyllithium was dropwise added in a nitrogen atmosphere with ice cooling, followed by stirring at room temperature for 3 days. The solution was cooled to −78° C., and 0.46 g (1.2 mmol) of zirconium tetrachloride (THF) 2-complex was added, followed by stirring at room temperature for 4 days. The reaction solution was subjected to sellaite filtration in a nitrogen atmosphere. From the resulting liquid, the solvent was removed under reduced pressure. To the residue, 15 ml of hexane was added, and the mixture was cooled to perform crystallization and thereby obtain 0.33 g (0.53 mmol) of a red solid (yield: 43%) The analyzed values are given below.

$^1$H-NMR (270 MHz, in CDCl$_3$, Based on TMS): δ8.01+ 7.70, 7.30 (t+m+m, 6H), 6.07+5.72+5.50 (t+t+t, 3H), 2.31 (d, 6H), 1.44 (s, 18H), 1.42–0.80 (m, 10H), 0.76 (t, 3H)

FD-MS: m/z=626, 628, 630 (M+)

Example 15

Synthesis of dimethylmethylene(3-tert-butylcyclopentadienyl)(2,7-di-tert-butylfluorenyl) zirconium Dichloride (1) Synthesis of 2-(3-tert-butyl-5-methylcyclopentadienyl)-2-(2,7-di-tert-butylfluorenyl)propane To a solution of 2.45 g (8.80 mmol) of 2,7-di-tert-butylfluorene in 50 ml of THF, 5.67 ml (9.24 mmol) of a hexane solution of n-butyllithium was dropwise added in a nitrogen atmosphere at 0° C., followed by stirring at room temperature overnight. To the resulting solution, a solution of 2.85 g (17.6 mmol) of 3-tert-butyl-6,6-dimethylfulvene in 30 ml of THF was successively dropwise added in a nitrogen atmosphere at 0° C., followed by stirring at room temperature overnight to perform reaction. After the reaction, 30 ml of water was added. The organic phase was extracted with ether and dried over anhydrous magnesium sulfate. From the resulting solution, the solvent was distilled off to obtain a crude yellow solid. The solid was washed with methanol to obtain 2.77 g of a powdery white solid (yield: 71.5%). The analyzed values are given below.

$^1$H-NMR (270 MHz, in CDCl$_3$, Based on TMS): δ7.56 (d, 2H), 7.33–7.12 (4H), 6.59–5.68 (2H), 4.14–4.05 (1H), 3.21+3.04 (2H), 1.29 (s, 18H), 1.01 (s, 6H)

(2) Synthesis of dimethylmethylene(3-tert-butylcyclopentadienyl)(2,7-di-tert-butylfluorenyl) zirconium Dichloride To a solution of 1.0 g (2.27 mmol) of 2-(3-tert-butylcyclopentadienyl)-2-(2,7-di-tert-butylfluorenyl)propane in 50 ml of diethyl ether, 2.9 ml (4.65 mmol) of a hexane solution of n-butyllithium was dropwise added in a nitrogen atmosphere at –78° C. With stirring, the temperature of the mixture was allowed to naturally rise to room temperature, and the reaction was performed overnight to obtain a red solution. The solution was cooled to –78° C. again, and 0.86 g (2.27 mmol) of zirconium tetrachloride (THF) 2-complex was added in a nitrogen atmosphere. The mixture was stirred and reacted while the temperature of the mixture was allowed to naturally rise to room temperature. The resulting red suspension was subjected to sellaite filtration to remove a white solid. Then, the orange filtrate was concentrated and dried to obtain a crude red solid. The solid was recrystallized from 5 ml of toluene to obtain 113 mg of a red solid. The analyzed values are given below.

$^1$H-NMR (270 MHz, in CDCl$_3$, Based on TMS): δ8.00–7.95 (2H), 7.72–7.58 (4H), 6.12 (t, 1H), 5.60 (t, 1H), 5.56 (t, 1H), 2.36 (s, 6H), 1.34 (s, 18H), 1.14 (s, 9H)

FD-MS: m/z=598, 600, 602 (M$^+$)

Example 16

Synthesis of diphenylmethylene(3-trimethylsilylcyclopentadienyl)(3,6-di-tert-butylfluorenyl)zirconium Dichloride (1) Synthesis of 1-(cyclopentadienyl)-1-(3,6-di-tert-butylfluorenyl)diphenylmethane To a solution of 2.5 g (9.0 mmol) of 3,6-di-tert-butylfluorene in 40 ml of THF, 6.1 ml (9.8 mmol) of a hexane solution of n-butyllithium was dropwise added in a nitrogen atmosphere with ice cooling, followed by stirring at room temperature for 4 hours. The resulting solution was ice cooled again, and thereto was dropwise added a solution of 2.5 g (10.8 mmol) of 6,6-diphenylfulvene in 30 ml of THF in a nitrogen atmosphere, followed by stirring at room temperature for 5 hours. Then, 50 ml of water was added. The organic phase extracted with diethyl ether and separated was dried over magnesium sulfate and then filtered. From the filtrate, the solvent was removed under reduced pressure to obtain a solid. The solid was recrystallized from methanol to obtain 3.4 g of a slightly yellow solid. The analyzed values are given below. $^1$H-NMR (270 MHz, in CDCl$_3$, Based on TMS): δ7.47 (s, 2H), 7.28 (br, 4H), 7.07–7.01 (br, 10H), 6.51–6.18 (m, 3H), 5.46+5.41 (s+s, 1H), 2.94+2.86 (s+s, 2H), 1.30 (s, 18H)

(2) Synthesis of 1-(3-trimethylsilylcyclopentadienyl)-1-(3,6-di-tert-butylfluorenyl)diphenylmethane To a solution of 0.45 g (0.88 mmol) of 1-(cyclopentadienyl)-1-(3,6-di-tert-butylfluorenyl)diphenylmethane in 30 ml of THF, 0.54 ml (0.97 mmol) of a hexane solution of n butyllithium was dropwise added in a nitrogen atmosphere with ice cooling, followed by stirring at room temperature for 16 hours. After the resulting solution was cooled to –78° C., a solution of 0.22 ml (1.76 mmol) of chlorotrimethylsilane in 10 ml of THF was slowly added, followed by stirring at room temperature for 6 hours. To the reaction solution, 20 ml of water was added to terminate the reaction. The resulting solution was subjected to extraction with diethyl ether, then dried over anhydrous magnesium sulfate and vacuum evaporated to dryness to obtain a yellow solid. The solid was washed with a small amount of methanol and dried under reduced pressure to obtain 0.42 g of an opaque white solid (yield: 81.8%). The analyzed values are given below.

$^1$H-NMR (270 MHz, in CDCl$_3$, Based on TMS): δ7.80 (t, 2H), 7.63 (dd, 2H), 7.31 (ddd, 2H), 6.99 (dd, 1H), 6.50 (t, 1H), 6.44 (dd, 1H), 1.80 (d, 6H), 1.41 (d, 18H), (1.12 (s, 9H)

(3) Synthesis of diphenylmethylene(3-trimethylsilylcyclopentadienyl)(3,6-di-tert-butylfluorenyl)zirconium Dichloride To a solution of 0.58 g (1.14 mmol) of 1-(3-trimethylsilylcyclopentadienyl)-1-(3,6-di-tert-butylfluorenyl)diphenylmethane in 40 ml of THF, 1.47 ml (2.40 mmol) of a hexane solution of n-butyllithium was dropwise added in a nitrogen atmosphere with ice cooling, followed by stirring at room temperature for 8 hours. From the reaction mixture, the solvent was removed under reduced pressure to obtain an reddish orange solid. To the solid, 100 ml of dichloromethane was added at –78° C., and they were stirred to give a solution. Then, the solution was added to a suspension of 0.44 g (1.02 mmol) of zirconium tetrachloride (THF) 2-complex in 5 ml of dichloromethane having been cooled to –78° C., followed by stirring at –78° C. for 4 hours. The solution was slowly heated and stirred at room temperature for one day and night. From the reaction solution, the solvent was removed under reduced pressure to obtain a yellowish brown solid. The solid was extracted with hexane and subjected to sellaite filtration. The filtrate was concentrated under reduced pressure and kept at –25° C. to obtain an orange solid. The solid was washed with a small amount of diethyl ether to obtain 0.19 g of a reddish orange solid. The analyzed values are given below.

$^1$H-NMR (270 MHz, in CDCl$_3$, Based on TMS): δ7.80 (t, 2H), 7.63 (dd, 2H), 7.31 (ddd, 2H), 6.99 (dd, 1H), 6.50 (t, 1H), 6.44 (dd, 1H), 1.80 (d, 6H), 1.41 (d, H), 1.12 (s, 9H)

FD-MS: m/z 738, 740, 742 (M$^+$)

Example 17

Synthesis of diphenylmethylene(3-phenylcyclopentadienyl)(1,1,4,4,7,7,10,10-octamethyl-1,2,3,4,7,8,9,10-octahydrodibenzo(b,h)-fluorenyl)zirconium Dichloride

(1) Synthesis of Phenylcyclopentadiene

To 160 ml (120 mmol) of a THF solution of phenylmagnesium chloride, a solution of 8.38 ml (100 mmol) of 2-cyclopentenone in 70 ml of THF was dropwise added with ice cooling. The mixture was stirred at 0° C. for 1 hour and then further stirred at room temperature for 1 hour. Then, 200 ml of an ammonium chloride saturated aqueous solution was added. To the reaction solution, diethyl ether was added to perform extraction. The resulting ether solution was dried over magnesium sulfate, and the solvent was distilled off to obtain of a crude product of phenylcyclopentenol as a gold liquid (17.5 g). In a glass tube oven, 6 g of the crude product was placed, and the product was heated at 180 to 190° C. for 1 hour at atmospheric pressure, then cooled to room temperature and slowly heated (finally) to 195° C. under reduced pressure (1 to 4 mmHg) As a result, 2.5 g of a white crystal was sublimed (51.3%).

$^1$H-NMR (270 MHz, in CDCl$_3$, Based on TMS): δ{7.58 (dd), 7.50 (dd), 7.47–7.10 (m), 5H}, {6.94 (dt), 6.89 (p), 6.65 (p), 7.58 (m), 6.43 (m), 3.38 (t), 3.19 (t), 5H)}

(2) Synthesis of 3,6,6-triphenylfulvene

A solution of 2.5 g (17.6 mmol) of phenylcyclopentadiene in 30 ml of toluene was ice cooled, and thereto was dropwise added 13.0 ml (21.1 mmol) of a hexane solution of n-butyllithium. The resulting white slurry was stirred at room temperature for one night. From the slurry, the solvent was filtered off to give a THF solution (brown solution). To the solution, a solution of 3.2 g (17.6 mmol) of benzophenone in 10 ml of THF was added, followed by stirring at room temperature for one night. After addition of water, the mixture was subjected to extraction with diethyl ether and dried over magnesium sulfate. Then, the ether was distilled off to obtain a red viscous liquid. The liquid was purified by a silica gel column to obtain a red solid.

$^1$H-NMR (270 MHz, in CDCl$_3$, Based on TMS): δ{7.81 (d), 7.61 (d), 7.56–7.24 (m), 15H}, 7.04 (dd, 1H), 6.59 (t, 1H), 6.46 (dd, 1H)

(3) Synthesis of 1-(3-phenylcyclopentadienyl)-1-(1,1,4,4,7,7,10,10-octamethyl-1,2,3,4,7,8,9,10-octahydrodibenzo(b,h)-fluorenyl)diphenylmethane To a solution of 1.0 g (2.59 mmol) of 1,1,4,4,7,7,10,10-octamethyl-1,2,3,4,7,8,9,10-octahydrodibenzo(b,h)-fluorene in 30 ml of THF, 1.75 ml (2.85 mmol) of a hexane solution of n-butyllithium was dropwise added in a nitrogen atmosphere with ice cooling, followed by stirring at room temperature for 4 hours. Then, a solution of 0.92 g (3.11 mmol) of 3,6,6-triphenylfulvene in 10 ml of THF was slowly added at room temperature, followed by stirring for 15 hours. To the reaction solution, 20 ml of water was added to terminate the reaction. The resulting solution was subjected to extraction with diethyl ether, then dried over anhydrous magnesium sulfate and vacuum evaporated to dryness to obtain a yellow solid. The solid was washed twice with a small amount of methanol and dried under reduced pressure to obtain 1.24 g of an opaque white solid (yield: 69.1%).

(4) Synthesis of diphenylmethylene(3-phenylcyclopentadienyl)(1,1,4,4,7,7,10,10-octamethyl-1,2,3,4,7,8,9,10-octahydrodibenzo(b,h)-fluorenyl)zirconium Dichloride To a solution of 1.20 g (1.73 mmol) of 1-(3-phenylcyclopentadienyl)-1-(1,1,4,4,7,7,10,10-octamethyl-1,2,3,4,7,8,9,10-octahydrodibenzo(b,h)-fluorenyl)diphenylmethane in 30 ml of THF, 2.23 ml (3.63 mmol) of a hexane solution of n-butyllithium was dropwise added in a nitrogen atmosphere with ice cooling, followed by stirring at room temperature for 8 hours. From the reaction mixture, the solvent was removed under reduced pressure to obtain a reddish orange solid. To the solid, 100 ml of dichloromethane was added at −78° C., and they were stirred to give a solution. Then, the solution was added to a suspension of 0.59 g (1.56 mmol) of titanium tetrachloride (THF) 2-complex in 5 ml of dichloromethane having been cooled to −78° C., followed by stirring at −78° C. for 4 hours. The resulting solution was slowly heated and stirred at room temperature for one day and night. From the reaction solution, the solvent was removed under reduced pressure to obtain a yellowish brown solid. The solid was extracted with hexane and subjected to sellaite filtration. The filtrate was concentrated under reduced pressure, and a small amount of diethyl ether was added to produce an orange precipitate. The mother liquor was removed, and the pressure was reduced to obtain 3 mg of a reddish orange solid (yield: 2.3%). The analyzed values are given below.

$^1$H-NMR (270 MHz, in CDCl$_3$, Based on TMS): δ8.07 (d, 2H), 8.01 (d, 2H), 7.89 (d, 2H), 7.48 (tt, 2H), 7.33 (p, 5H), 7.26 (s, 3H), 7.18 (m, 2H), 6.49 (m, 1H), 6.24 (d, 2H), 5.74 (t, 1H), 5.66 (t, 1H), 1.73–1.52 (m, 6H), 1.47 (s, 3H), 1.42 (s, 3H), 1.39 (s, 6H), 1.24 (d, 3H), 0.97 (d, 6H), 0.84 (d, 6H)

FD-MS: m/z=850, 852, 854 (M+)

Example 18

Synthesis of diphenylmethylene(3-trimethylsilylcyclopentadienyl)(1,1,4,4,7,7,10,10-octamethyl-1,2,3,4,7,8,9,10-octahydrodibenzo(b,h)-fluorenyl)zirconium Dichloride

(1) Synthesis of 1-(cyclopentadienyl)-1(1,1,4,4,7,7,10,10-octamethyl-1,2,3,4,7,8,9,10-octahydrodibenzo(b,h)-fluorenyl)diphenylmethane In a 200 ml three-necked flask purged with nitrogen, 2.64 g (6.83 mmol, 1 eq) of 1,1,4,4,7,7,10,10-octamethyl-1,2,3,4,7,8,9,10-octahydrodibenzo(b,h)-fluorene was placed at room temperature. Then, 40 ml of dehydrated THF was added, and the mixture was stirred by a magnetic stirrer to give a solution. The solution was cooled with an ice bath (light yellow solution). To the solution, 4.6 ml (7.50 mmol, 1.10 eq) of a hexane solution of n-BuLi was dropwise added over a period of 10 minutes. Then, the ice bath was removed, and the solution was stirred at room temperature for 23 hours (dark red solution). The solution was cooled to 1° C. with an ice bath, and to the solution, a solution of 2.06 (8.94 mmol, 1.31 eq) of 6,6-diphenylfulvene in 20 ml of dehydrated THF was dropwise added over a period of 20 minutes (dark red slurry). The ice bath was removed, and the solution was stirred at room temperature for 65 hours. The resulting dark reddish brown solution was poured into 100 ml of a diluted hydrochloric acid solution to perform quenching. From the aqueous layer, the soluble component was extracted with diethyl ether, and the organic phase was washed with 100 ml of a saturated saline solution. The dispensed organic phase was dried over MgSO$_4$, then the MgSO$_4$ was filtered off, and from the filtrate the solvent was vacuum distilled off by a rotary evaporator to obtain an orangy yellow amorphous product. The amorphous product was washed with methanol, then filtered and dried in a vacuum disiccator to obtain 3.31 g of a slightly yellow powder (yield: 79%).

$^1$H-NMR (270 MHz, in CDCl$_3$, Based on TMS): δ0.86–1.40 (m, 24H, —CH$_3$ of OMOHDBFlu), 1.60–1.62 (m, 8H, —CH$_2$— of OMOHDBFlu), 2.8–3.1 (br, 2H, —CH$_2$— of Cp), 5.37, 5.42 (s, 1H, 0.9-H of OMOHDBFlu), 6.0–6.6 (br, 3H, —CH— of Cp), 6.9–7.5 (br, 14H, Ph-H of OMCHDBFlu, Ph-H of Bridge)

(2) Synthesis of 1-(3-trimethylsilylcyclopentadienyl)-1-(1,1,4,4,7,7,10,10-octamethyl-1,2,3,4,7,8,9,10-octahydrodibenzo(b,h)-fluorenyl)diphenylmethane In a 30 ml Schlenk flask purged with nitrogen, 0.92 g (1.48 mmol, 1 eq) of 1-(cyclopentadienyl)-1-(1,1,4,4,7,7,10,10-octamethyl-1,2,3,4,7,8,9,10-octahydrodibenzo(b,h)-fluorenyl)diphenylmethane was placed at room temperature. Then, 20 ml of dehydrated THF was added, and the mixture was stirred by a magnetic stirrer to give a solution. The solution was cooled with an ice bath (light orangy brown solution). To the solution, 1.0 ml (1.63 mmol, 1.10 eq) of a hexane solution of n-BuLi was dropwise added. Then, the ice bath was removed, and the solution was stirred at room temperature for 18 hours (dark red solution). The solution was cooled with an ice bath, and to the solution, 1.05 ml (8.28 mmol, 5.59 eq) of chlorotrimethylsilane was dropwise added by a syringe (dark brown solution). The ice bath was removed, and the solution was stirred at room temperature for 3 hours. The resulting dark brown solution was poured into 50 ml of a diluted hydrochloric acid solution to perform quenching. After the soluble component was extracted with 30 ml of diethyl ether, the organic phase was washed with 50 ml of a saturated saline solution. The organic phase was dried over MgSO$_4$, then the MgSO$_4$ was filtered off, and from the filtrate the solvent was vacuum distilled off by a rotary evaporator to obtain a yellowish brown amorphous product. The amorphous product was purified by silica gel column chromatography (developing solvent: hexane:dichloromethane=19:1) to obtain 0.62 g a light yellow amorphous product (yield: 61%).

$^1$H-NMR (270 MHz, in CDCl$_3$, Based on TMS): δ−0.22 (s, 9H, —Si(CH$_3$)$_3$), 0.86–1.31 (m, 24H, —CH$_3$ of OMOHDBFlu), 1.60–1.62 (m, 8H, —CH$_2$— of OMOHDBFlu), 3.20 (br, 1H, 1-H of Cp), 5.52 (s, 1H, 9-H of OMOHDBFlu), 6.3 (br, 2H, —CH— of Cp), 6.8–7.7 (br, 14H, Ph-H of OMOHDBFlu, Ph-H of Bridge)

(3) Synthesis of diphenylmethylene(3-trimethylsilylcyclopentadienyl)(1,1,4,4,7,7,10,10-octamethyl-1,2,3,4,7,8,9,10-octahydrodibenzo(b,h)-fluorenyl)zirconium Dichloride In a 50 ml Schlenk flask purged with nitrogen; 0.62 g (0.90 mmol, 1 eq) of 1-(3-trimethylsilylcyclopentadienyl)-1-(1,1,4,4,7,7,10,10-octamethyl-1,2,3,4,7,8,9,10-octahydrodibenzo(b,h)-fluorenyl)diphenylmethane was placed at room temperature. Then, 15 ml of dehydrated diethyl ether was added, and the mixture was stirred by a magnetic stirrer to give a solution. The solution was cooled with an ice bath (yellow solution). To the solution, 1.25 ml (2.04 mmol, 2.27 eq) of n-BuLi (hexane solution) was dropwise added by a syringe. Then, the ice bath was removed, and the solution was stirred at room temperature for 22 hours (orange slurry). The slurry was cooled with a dry ice/methanol bath, and thereto was added 20.32 g (0.86 mmol, 0.95 eq) of zirconium tetrachloride (THF) 2-complex. The mixture was stirred for 24 hours while allowing the dry ice to naturally disappear and the temperature of the mixture to naturally rise to room temperature. From the resulting dark brown slurry, the volatile component was vacuum distilled off. To the residue, 50 ml of dehydrated hexane was added, and then the insoluble component was filtered through a filter. The solvent of the resulting orangy brown solution was vacuum concentrated, and the obtained solution was stored in a refrigerator to obtain 0.20 g of a pink powder (yield: 28%).

$^1$H-NMR (270 MHz, in CDCl$_3$, Based on TMS): δ0.12 (s, H, —Si(CH$_3$)$_3$), 0.82–1.49 (m, 24H, —CH$_3$ of OMOHDBFlu), 1.58–1.70 (m, 8H, —CH2— of OMOHDBFlu), 5.49, 5.77, 6.34 (t, H, —CH— of Cp), 6.16, 6.18, 8.04 (s, 4H, Ph-H of OMOHDBFlu), 7.27–8.01 (m, 10H, Ph-H of Bridge)

FD-MS: m/z=846, 848, 850 (M$^+$)

Example 19

Synthesis of methylphenylmethylene(3-tert-butylcyclopentadienyl)(3,6-di-tert-butylfluorenyl)zirconium Dichloride (1) Synthesis of 3-tert-butyl-6,6-methylphenylfulvene To a solution of 3.78 g (30.9 mmol) of tert-butylcyclopentadiene in 35 ml of THF, 20.0 ml (32.6 mmol) of a hexane solution of n-butyllithium was dropwise added in a nitrogen atmosphere with ice cooling, followed by stirring at room temperature for 8 hours. To the resulting solution, a solution of 3.73 g (31.0 mmol) of acetophenone in 10 ml of THF was dropwise added in a nitrogen atmosphere with ice cooling, followed by stirring at room temperature for one night. After the reaction solution was diluted with 100 ml of ether, 50 ml of water was added. The separated organic phase was washed with water and a saturated saline solution, then dried over magnesium sulfate and filtered. From the filtrate, the solvent was removed under reduced pressure to obtain a liquid. The liquid was isolated and purified by column chromatography (silica gel, developing solvent: hexane) to obtain 1.70 g (7.58 mmol) of a red liquid (yield: 25%). The analyzed values are given below.

$^1$H-NMR (270 MHz, in CDCl$_3$, Based on TMS): δ7.39 (m, 5H), 6.63+6.53+6.23+6.16+5.81 (m+m+m+m+m, 3H), 2.50 (d, 3H), 1.23+1.15 (s+s, 9H)

(2) Synthesis of 1-phenyl-1-(3-tert-butylcyclopentadienyl)-1-(3,6-di-tert-butylfluorenyl)ethane To a solution of 1.92 g (6.9 mmol) of 3,6-di-tert-butylfluorene in 30 ml of THF, 4.4 ml (7.2 mmol) of a hexane solution of n-butyllithium was dropwise added in a nitrogen atmosphere with ice cooling, followed by stirring at room temperature for one night. To the resulting red solution, a solution of 1.70 g (7.6 mmol) of 3-tert-butyl-6,6-methylphenylfulvene in 40 ml of THF was dropwise added in a nitrogen atmosphere with ice cooling, followed by stirring at room temperature for one night. After the reaction solution was diluted with 100 ml of ether, 50 ml of water was added. The separated organic phase was washed with water and a saturated saline solution, then dried over magnesium sulfate and filtered. From the filtrate, the solvent was removed under reduced pressure to obtain a solid. The solid was reslurried with 50 ml of methanol, and the resulting slurry was filtered to obtain 1.0 g (1.99 mmol) of a white solid (yield: 29%). The analyzed values are given below.

$^1$H-NMR (270 MHz, in CDCl$_3$, Based on TMS): δ7.71+7.63 (d+d, 5H), 7.40+7.28+7.10+6.90+6.69+6.46+5.94 (t+t+m+d+d+s+m, 8H), 4.86 (s, 1H), 3.13+3.05+2.96+2.88 (s+s+s+s, 2H), 1.35 (d, 18H), 1.20 (d, 9H), 1.00 (s, 3H)

(3) Synthesis of methylphenylmethylene(3-tert-butylcyclopentadienyl)(3,6-di-tert-butylfluorenyl) zirconium Dichloride To absolution of 0.53 g (1.1 mmol) of 1-phenyl-1-(3-tert-butylcyclopentadienyl)-1-(3,6-di-tert-butylfluorenyl)ethane in 50 ml of ether, 1.4 ml (2.3 mmol) of a hexane solution of n-butyllithium was dropwise added in a nitrogen atmosphere with ice cooling, followed by stirring at room temperature for 2 days. To the resulting reddish orange reaction mixture having been cooled to −78° C., 0.41 g (1.1 mmol) of zirconium tetrachloride (THF) 2-complex was added, and the mixture, was stirred at room temperature for 3 days. The resulting reaction mixture was subjected to sellaite filtration. From the filtrate, the solvent was removed under reduced pressure, and the residue was recrystallized from diethyl ether to obtain 0.20 g of an orange solid (yield: 28%). The analyzed values are given below.

$^1$H-NMR (270 MHz, in CDCl$_3$, Based on TMS): δ8.03 (dd, 2H), 7.89–7.38 (m, 7H), 6.96 (dd, 1H), 6.09 (t, 1H), 6.07 (d, 1H), 5.68 (t, 1H), 5.65 (t, 1H), 2.46 (s, 3H), 1.47 (s, 9H), 1.37 (s, 9H), 1.22 (s, 9H) FD-MS: m/z=660, 662, 664 (M$^+$)

Example 20

Synthesis of diethylmethylene(3-tert-butylcyclopentadienyl)(3,6-di-tert-butylfluorenyl) zirconium Dichloride (1) Synthesis of 3-tert-butyl-6,6-diethylfulvene To a THF solution of 1.53 g (13 mmol) of tert-butylcyclopentadiene, 9.0 ml (14 mmol) of a hexane solution of n-butyllithium was dropwise added in a nitrogen atmosphere with ice cooling, followed by stirring at room temperature for one night. Then, 1.7 ml (16 mmol) of 3-pentanone was further added at −78° C., followed by stirring at room temperature for 2 days. To the reaction solution, water was added. The mixture was subjected to extraction with ether, then the solvent was distilled off, and the residue was subjected to column chromatography (silica gel, developing solvent: hexane) to obtain 1.50 g of a yellow liquid (Yield: 63%). The analyzed values are given below.

$^1$H-NMR (270 MHz, in CDCl$_3$, Based on TMS): δ6.52 (qd, 2H), 6.11 (t, 1H), 2.53 (qd, 4H), 1.20 (s, 9H), 1.17–1.12 (m, 6H)

(2) Synthesis of 2-(3-tert-butylcyclopentadienyl)-3-(3,6-di-tert-butylfluorenyl)pentane To a solution of 1.99 g (7.1 mmol) of 3,6-di-tert-butylfluorene in 30 ml of THF, 4.6 ml (7.5 mmol) of a hexane solution of n-butyllithium was dropwise added in a nitrogen atmosphere with ice cooling, followed by stirring at room temperature for one night. To the resulting red solution, a solution of 1.50 g (7.9 mmol) of 3-tert-butyl-6,6-diethylfulvene in 30 ml of THF was dropwise added in a nitrogen atmosphere with ice cooling, followed by stirring at room temperature for one night. After the reaction solution was diluted with 100 ml of ether, 50 ml of water was added. The separated organic phase was washed with water and a saturated saline solution, then dried over magnesium sulfate and filtered. From the filtrate, the solvent was removed under reduced pressure to obtain a liquid. The liquid was isolated and purified by column chromatography (silica gel, developing solvent: hexane) to obtain 2.34 g (4.99 mmol) of a white solid (yield: 70%). The analyzed values are given below.

$^1$H-NMR (270 MHz, in CDCl$_3$, Based on TMS): 67.65+7.26–7.12 (d+m, 6H), 6.12–5.60 (m, 2H), 4.06 (d, 1H), 2.80 (s, 2H), 1.80 (m, 4H), 1.38 (s, 18H), 1.08 (s, 9H), 0.66 (m, 6H)

(3) Synthesis of diethylmethylene(3-tert-butylcyclopentadienyl)(3,6-di-tert-butylfluorenyl) zirconium Dichloride To a solution of 0.74 g (1.7 mmol) of 3-(3-tert-butyl-cyclopentadienyl)-3-(3,6-di-tert-butylfluorenyl)pentane in 50 ml of ether, 2.2 ml (3.6 mmol) of a hexane solution of n-butyllithium was dropwise added in a nitrogen atmosphere with ice cooling, followed by stirring at room temperature for 2 days. To the resulting reddish orange reaction mixture having been cooled to −78° C., 0.66 g (1.7 mmol) of zirconium tetrachloride (THF) 2-complex was added, followed by stirring at room temperature for one day and night. The resulting reaction mixture was subjected to sellaite filtration. From the filtrate, the solvent was removed under reduced pressure, and the residue was recrystallized from hexane to obtain 0.44 g of an orange solid (yield: 40%). The analyzed values are given below.

$^1$H-NMR (270 MHz, in CDCl$_3$, Based on TMS): δ8.00 (s, 2H), 7.70 (d, 1H), 7.64 (d, 1H), 7.32 (d, 1H), 7.31 (d, 1H), 6.10 (t, 1H), 5.71 (t, 1H), 5.50 (t, 1H), 2.76 (q, 4H), 1.43 (s, 18H), 1.26 (t, 6H), 1.14 (s, 9H)

FD-MS: m/z=626, 628, 630 (M$^+$)

Example 21

Synthesis of cyclohexylidene(3-trimethylsilylcyclopentadienyl)(3,6-di-tert-butylfluorenyl)zirconium Dichloride (1) Synthesis of 1-(cyclopentadienyl)-1-(3,6-di-tert-butylfluorenyl)cyclohexane In a 200 ml two-necked flask purged with nitrogen, 1.96 g (7.04 mmol, 1 eq) of 3,6-di-tert-butylfluorene was placed at room temperature. Then, 40 ml of dehydrated THF was added, and the mixture was stirred by a magnetic stirrer to give a solution. The solution was cooled with an ice bath (colorless transparent solution). To the solution, 5.0 ml (8.15 mmol, 1.16 eq) of a hexane solution of n-BuLi was dropwise added over a period of 5 minutes. Then, the ice bath was removed, and the solution was stirred at room temperature for 21 hours (red solution). After the olution was cooled with an ice bath, a solution of 1.37 g (9.37 mmol, 1.33 eq) of 6-cyclohexylfulvene in 5 ml of dehydrated THF was dropwise added over a period of 10 minutes. The ice bath was removed, and the solution was stirred at room temperature for 42 hours. The resulting brownish red solution was poured into 50 ml of a diluted hydrochloric acid solution to perform quenching. The soluble component was extracted from the aqueous layer with 100 ml of diethyl ether, and the organic phase was washed with 80 ml of a saturated saline solution. The dispensed organic phase was dried over MgSO$_4$, then the MgSO$_4$ was filtered off, and from the filtrate the solvent was vacuum distilled off by a rotary evaporator to obtain a brownish yellow solid. The solid was purified by silica gel column chromatography (developing solvent: hexane) to obtain 1.31 g of a white solid (yield: 44%).

$^1$H-NMR (270 MHz, in CDCl$_3$, Based on TMS): δ1.23-1.87 (br, 10H, —CH$_2$— of Bridge), 1.38 (s, 18H, tBu of 3, 6-tBu$_2$Flu), 2.81, 3.02 (m, 2H, —CH$_2$— of Cp), 3.83, 3.85 (s, 1H, 9-H of 3, 6-tBu$_2$Flu), 5.91, 5.96, 6.30, 6.43, 6.56 (m, 4H, —CH— of Cp), 7.08 (s, 2H, 1, 8-H of 3, 6-tBu$_2$Flu), 7.13–7.19 (m, 2H, 2, 7-H of 3, 6-tBu$_2$Flu), 7.66 (s, 2H, 4, 5-H of 3, 6-tBu$_2$Flu)

(2) Synthesis of 1-(3-trimethylsilylcyclopentadienyl)-1-(3,6-di-tert-butylfluorenyl)cyclohexane In a 30 ml Schlenk flask purged with nitrogen, 0.86 g (2.02 mmol, 1 eq) of 1-(cyclopentadienyl)-1-(3,6-di-tert-butylfluorenyl)cyclohexane was placed at room temperature. Then, 12 ml of dehydrated THF was added, and the mixture was stirred by a magnetic stirrer to give a solution. The solution was cooled with an ice bath (colorless transparent solution). To the solution, 1.4 ml (2.28 mmol, 1.13 eq) of n-BuLi (hexane solution) was dropwise added. Then, the ice bath was removed, and the solution was stirred at room temperature for 19 hours. The solution was cooled with an ice bath, and to the solution, 1.6 ml (12.6 mmol, 6.24 eq) of chlorotrimethylsilane was dropwise added by a syringe. The ice bath was removed, and the solution was stirred at room temperature for 4 hours. The resulting yellow solution was poured into 50 ml of a diluted hydrochloric acid solution to perform quenching. After the soluble component was extracted with 70 ml of diethyl ether, the organic phase was washed with 50 ml of a saturated saline solution. The organic phase was dried over MgSO$_4$ then the MgSO$_4$ was filtered off, and from the filtrate the solvent was vacuum distilled off by a rotary evaporator to obtain a yellow amorphous product. The amorphous product was purified by silica gel column chromatography (developing solution: hexane) to obtain 0.46 g a white amorphous product (yield: 46%).

$^1$H-NMR (270 MHz, in CDCl$_3$, Based on TMS): δ−0.03 (s, 9H, —Si(CH3)$_3$), 1.11–2.20 (br, 10H, —CH$_2$— of Bridge), 1.36, 1.38, 1.40 (s, 18H, tBu of 3, 6-tBu$_2$Flu), 3.20 (s, 1H, 1-H of Cp), 3.85, 3.87 (s, 1H, 9-H of 3, 6-tBu$_2$Flu), 5.94–6.52 (m, 3H, —CH— of Cp), 6.68–7.67 (m, 6H, Ph-H of 3, 6-tBu$_2$Flu)

(3) Synthesis of cyclohexylidene(3-trimethylsilylcyclopentadienyl)(3,6-di-tert-butylfluorenyl)zirconium Dichloride In a 30 ml Schlenk flask purged with nitrogen, 0.46 g (0.93 mmol, 1 eq) of 1-(3-trimethylsilylcyclopentadienyl)-1-(3,6-di-tert-butylfluorenyl)cyclohexane was placed at room temperature. Then, 10 ml of dehydrated diethyl ether was added, and the mixture was stirred by a magnetic stirrer to give a solution. The solution was cooled with an ice bath (colorless transparent solution). To the solution, 1.25 ml (2.04 mmol, 2.19 eq) of a hexane solution of n-BuLi was dropwise added by a syringe. Then, the ice bath was removed, and the solution was stirred at room temperature for 22 hours (reddish brown solution). The slurry was cooled with a dry ice/methanol bath, and thereto was added 0.35 g (0.92 mmol, 0.99 eq) of zirconium tetrachloride (THF) 2-complex. The mixture was stirred for 24 hours while allowing the dry ice to naturally disappear and the temperature of the mixture to naturally rise to room temperature. From the resulting dark orange slurry, the volatile component was vacuum distilled off. To the residue, 40 ml of dehydrated hexane was added, and then the insoluble component was filtered through a filter. To the orangy brown powder remaining on the filter, 5 ml of dehydrated dichloromethane was added to filter the soluble component. From the resulting red solution, the solvent was vacuum distilled off to obtain 0.34 g of an orange solid (yield: 57%).

$^1$H-NMR (270 MHz, in CDCl$_3$, Based on TMS): δ0.12 (s, 9H, —Si(CH3)$_3$), 1.44, 1.45 (s, 18H, tBu of 3, 6-tBu$_2$Flu), 1.68–3.32 (br, 10H, —CH2— of Bridge), 5.62, 5.96, 6.33 (t, 3H, —CH— of Cp), 7.34, 7.34 (d, 2H, 1, 8-H of 3, 6-tBu$_2$Flu), 7.61, 7.65 (d, 2H, 2, 7-H of 3, 6-tBu$_2$Flu), 8.02 (s, 2H, 4, 5-H of 3, 6-tBu$_2$Flu)

FD-MS: m/z=654, 656, 658 (M$^+$)

Example 22

Synthesis of cyclopentylidene(3-tert-butylcyclopentadienyl)(3,6-di-tert-butylfluorenyl) zirconium Dichloride (1) Synthesis of 3-tert-butyl-6,6-cyclopentylfulvene To a THF solution of 1.53 g (13 mmol) of tert-butylcyclopentadiene, 9.0 ml (14 mmol) of a hexane solution of n-butyllithium was dropwise added in a nitrogen atmosphere with ice cooling, followed by stirring at room temperature for one night. Then, 1.4 ml (16 mmol) of cyclopentanone was added at −78° C., followed by stirring at room temperature for 2 days. To the reaction solution, water was added. The mixture was subjected to extraction with ether, then the solvent was distilled off, and the residue was subjected to column chromatography (silica gel, developing solvent: hexane) to obtain 1.18 g of a yellow liquid (yield: 50%). The analyzed values are given below.

$^1$H-NMR (270 MHz, in CDCl$_3$, Based on TMS): δ6.48 (dd, 1H), 6.38 (dd, 1H), 6.00 (t, 1H), 2.78–2.73 (m, 4H), 1.80–1.75 (m, 4H), 1.19 (s, 9H)

(2) Synthesis of 1-(3-tert-butylcyclopentadienyl)-1-(3,6-di-tert-butylfluorenyl)cyclopentane To a solution of 1.59 g (5.7 mmol) of 3,6-di-tert-butylfluorene in 30 ml of THF, 3.7 ml (6.0 mmol) of a hexane solution of n-butyllithium was dropwise added in a nitrogen atmosphere with ice cooling, followed by stirring at room temperature for one night. To the resulting red solution, a solution of 1.18 g (6.3 mmol) of 3-tert-butyl-6,6-cyclopentylfulvene in 30 ml of THF was dropwise added in a nitrogen atmosphere with ice cooling, followed by stirring at room temperature for one night. After the reaction solution was diluted with 100 ml of ether, 50 ml of water was added. The separated organic phase was washed with water and a saturated saline solution, then dried over magnesium sulfate and filtered. From the filtrate, the solvent was removed under reduced pressure to obtain a liquid. The liquid was isolated and purified by column chromatography (silica gel, developing solvent: hexane) to obtain 1.52 g (3.26 mmol) of a white solid (yield: 57%). The analyzed values are given below.

$^1$H-NMR (270 MHz, in CDCl$_3$, Based on TMS): 57.60+ 7.37–7.08 (s+m, 6H), 5.77–5.45 (m, 2H), 4.02 (m, 1H), 2.65–2.33 (m, 2H), 1.38 (s, 18H), 2.20–0.80 (m, 17H)

(3) Synthesis of cyclopentylidene(3-tert-butylcyclopentadienyl)(3,6-di-tert-butylfluorenyl) zirconium Dichloride To a solution of 0.58 g (1.3 mmol) of 1-(3-tert-butylcyclopentadienyl)-1-(3,6-di-tert-butylfluorenyl)

cyclopentane in 50 ml of ether, 2.2 ml (3.6 mmol) of a hexane solution of n-butyllithium was dropwise added in a nitrogen atmosphere with ice cooling, followed by stirring at room temperature for 2 days. After the reaction suspension was filtered, 0.40 g (0.9 mmol) of the resulting solid was suspended in. 50 ml of ether. The suspension was cooled to −78° C., and to the suspension, 0.33 g (0.9 mmol) of zirconium tetrachloride (THF) 2-complex was added, followed by stirring at room temperature for 5 days. The resulting reaction mixture was subjected to sellaite filtration. From the filtrate, the solvent was removed under reduced pressure, and the residue was recrystallized from ether to obtain 0.12 g of an orange solid (yield: 15%). The analyzed values are given below.

$^1$H-NMR (270 MHz, in $CDCl_3$, Based on TMS): δ8.01 (d, 2H), 7.56 (d+d, 2H), 7.32 (d+d, 2H), 6.08 (t, 1H), 5.66 (t, 1H), 5.47 (t, 1H), 3.20–3.10 (m, 2H), 2.80–2.60 (m, 2H), 2.10-2.00 (m, 4H), 1.44 (s, 18H), 1.14 (s, 9H)

FD-MS: m/z=624, 626, 628 ($M^+$)

Example 23

Synthesis of cyclohexylidene(3-(1,1-dimethylpropyl)cyclopentadienyl)(3,6-di-tert-butylfluorenyl)zirconium Dichloride (1) Synthesis of 3-(1,1-dimethylpropyl)-6,6-cyclohexylfulvene To a solution of 3.00 g (29.4 mmol) of (1,1-dimethylpropyl)cyclopentadiene in 30 ml of methanol, 6.1 ml (58.9 mmol) of cyclohexanone and 4.9 ml (58.7 mmol) of pyrrolidine were added with ice cooling, followed by stirring at room temperature for one night. After the reaction solution was diluted with 100 ml of ether, 50 ml of water was added. The organic phase was separated, washed with water and a saturated saline solution, then dried over anhydrous magnesium sulfate and filtered. From the filtrate, the solvent was removed under reduced pressure to obtain a liquid. The liquid was isolated and purified by column chromatography (silica gel, developing solvent: hexane) to obtain 2.00 g (9.24 mmol) of a yellow liquid (yield: 31%). The analyzed values are given below.

$^1$H-NMR (270 MHz, in $CDCl_3$, Based on TMS): δ6.54 (m, 2H), 6.16 (m, 1H), 2.61+1.72 (m+m, 10H), 1.50 (f, 2H), 1.15 (s, 6H), 0.77 (t, 3H)

(2) Synthesis of 1-(3-(1,1-dimethylpropyl)cyclopentadienyl)-1-(3,6-di-tert-butylfluorenyl)cyclohexane To a solution of 2.38 g (8.5 mmol) of 3,6-di-tert-butylfluorene in 40 ml of THF, 5.7 ml (9.2 mmol) of a hexane solution of n-butyllithium was dropwise added in a nitrogen atmosphere with ice cooling, followed by stirring at room temperature for one night. To the resulting red solution, a solution of 2.00 g (9.2 mmol) of 3-(1,1-dimethylpropyl)-6,6-dimethylfulvene in 30 ml of THF was dropwise added in a nitrogen atmosphere with ice cooling, followed by stirring at room temperature for one night. After the reaction solution was diluted with 100 ml of ether, 50 ml of water was added. The separated organic phase was washed with water and a saturated saline solution, then dried over magnesium sulfate and filtered. From the filtrate, the solvent was removed under reduced pressure to obtain a liquid. The liquid was isolated and purified by column chromatography (silica gel, developing solvent: hexane) to obtain 1.88 g (3.80 mmol) of a white solid (yield: 45%). The analyzed values are given below.

$^1$H-NMR (270 MHz, in $CDCl_3$, Based on TMS): δ7.62+ 7.20–7.10 (s+m, 6H), 6.85–6.55 (m, 2H), 3.83 (m, 1H), 2.75+2.65 (s+s, 2H), 2.15–1.00 (m, 12H), 1.38 (s, 18H), 1.08 (d, 6H), 0.75 (m, 3H)

(3) Synthesis of cyclohexylidene(3-(1,1-dimethylpropyl)cyclopentadienyl)(3,6-di-tert-butylfluorenyl)zirconium Dichloride To a solution of 0.70 g (1.4 mmol) of 1-(3-(1,1-dimethylpropyl)cyclopentadienyl)-1-(3,6-di-tert-butylfluorenyl)cyclohexane in 35 ml of diethyl ether, 1.8 ml (2.9 mmol) of a hexane solution of n-butyllithium was dropwise added in a nitrogen atmosphere with ice cooling, followed by stirring at room temperature for one night. The resulting solution was cooled to −78° C., and 0.52 g (1.4 mmol) of zirconium tetrachloride (THF) 2-complex was added, followed by stirring at room temperature for one night. The reaction solution was subjected to sellaite filtration in a nitrogen atmosphere. From the resulting liquid, the solvent was removed under reduced pressure. To the residue, 10 ml of hexane was added, and the mixture was cooled. The resulting reaction solution was subjected to sellaite filtration, and the filtrate was concentrated to obtain 0.45 g (0.70 mmol) of a reddish brown solid (yield: 48%) The analyzed values are given below.

$^1$H-NMR (270 MHz, in $CDCl_3$, Based on TMS): δ8.02– 7.10 (m, 6H), 6.10–4.40 (m, 3H), 1.46 (s, 18H), 2.90–0.70 (m, 12H), 0.65 (t, 3H)

FD-MS: m/z 652, 654, 656 ($M^+$)

Example 24

Synthesis of cyclopentylidene(3-tert-butylcyclopentadienyl)(1,1,4,4,7,7,10,10-octamethyl-1,2,3,4,7,8,9,10-octahydrodibenzo(b,h)-fluorenyl)zirconium Dichloride (1) Synthesis of 3-tert-butyl-6,6-tetramethylenefulvene To 50 ml of dehydrated methanol, 3.0 g (24.4 mmol) of 3-tert-butylcyclopentadiene and 3.24 ml (36.6 mmol) of cyclopentanone were added at 0° C., and 3.06 ml (36.6 mmol) of pyrrolidine was dropwise added at 0° C., followed by stirring at room temperature for 3 days. Then, 20 ml of water was added at 0° C., and the mixture was subjected to extraction with ether. The organic phase was washed with water and dried over anhydrous magnesium sulfate. Then, the solvent was distilled off to obtain a crude orange liquid.

The liquid was purified by column chromatography (silica, hexane) to obtain 1.6 g of a desired yellow product (yield: 35.7%). The analyzed values are given below.

$^1$H-NMR (270 MHz, in $CDCl_3$, Based on TMS): δ6.50– 6.01 (3H), 2.77 (m, 4H), 1.78 (m, 4H), 1.20 (s, 9H)

(2) Synthesis of 1-(3-tert-butylcyclopentadienyl)-1-(1,1,4,4,7,7,10,10-octamethyl-1,2,3,4,7,8,9,10-octahydrodibenzo(b,h)-fluorenyl)cyclopentane To a solution of 2.32 g (6.02 mmol) of 1,1,4,4,7,7,10,10-octamethyl-1,2,3,4,7,8,9,10-octahydrodibenzo(b,h)-fluorene in 40 ml of THF, 10.1 ml (6.32 mmol) of a hexane solution of n-butyllithium was dropwise added in a nitrogen atmosphere at 0° C., followed by stirring at room temperature overnight. To the resulting solution, a solution of 1.64 g (8.71 mmol) of 3-tert-butyl-6,6-tetramethylenefulvene in 30 ml of THF was dropwise added in a nitrogen atmosphere at 0° C., followed by stirring at room temperature overnight to perform reaction. After the reaction, 30 ml of water was added, and the mixture was subjected to extraction with ether. The organic phase was dried over anhydrous magnesium sulfate. From the resulting solution, the solvent was distilled off under reduced pressure to obtain a crude yellow solid.

The solid was recrystallized from hexane to obtain 2.72 g of a desired product (yield: 78.7%). The analyzed values are given below.

$^1$H-NMR (270 MHz, in CDCl$_3$, Based on TMS): δ7.47–7.25 (4H), 5.88–5.46 (2H), 4.03–3.98 (1H), 2.70–0.94 (44H)

(3) Synthesis of cyclopentylidene(3-tert-butylcyclopentadienyl)(1,1,4,4,7,7,10,10-octamethyl-1,2,3,4,7,8,9,10-octahydrodibenzo(b,h)-fluorenyl)zirconium Dichloride To a solution of 0.95 g (1.66 mmol) of 1-(3-tert-butylcyclopentadienyl)-1-(1,1,4,4,7,7,10,10-octamethyl-1,2,3,4,7,8,9,10-octahydrodibenzo(b,h)-fluorenyl)cyclopentane in 15 ml of THF, 2.12 ml (3.39 mmol) of a hexane solution of n-butyllithium was dropwise added in a nitrogen atmosphere with ice cooling. The mixture was reacted overnight while allowing the temperature of the mixture to naturally rise to room temperature, to obtain a red solution. The solution was cooled to −78° C. again, and 0.60 g (1.60 mmol) of zirconium tetrachloride (THF) 2-complex was added in a nitrogen atmosphere. The mixture was reacted overnight while allowing the temperature of the mixture to naturally rise to room temperature similarly to the above. The resulting red suspension was subjected to sellaite filtration to remove a white solid. Then, the red filtrate was concentrated and dried to obtain a crude red solid. The solid was recrystallized from 5 ml of diethyl ether to obtain 116 mg of a red solid. The analyzed values are given below.

$^1$H-NMR (270 MHz, in CDCl$_3$, Based on TMS): δ7.98 (2H), 7.45 (d, 2H), 6.05 (t, 1H), 5.48 (t, 1H), 5.37 (t, 1H), 3.48 (m, 4H), 2.68 (m, 4H), 2.06–0.99 (36H)

FD-MS: m/z=732, 734, 736 (M$^+$)

Example 25

Bulk Copolymerization of Propylene and Ethylene using dimethylmethylene(3-tert-butyl-5-methylcyclopentadienyl)fluorenylzirconium Dichloride In a 50 ml two-necked flask thoroughly purged with nitrogen, 0.72 mmol (in terms of aluminum) of silica-supported methylaluminoxane was suspended in 20 ml of heptane. To the suspension, a toluene solution of 0.65 mg (1.3 μmol) of the reddish orange solid obtained in Example 1 was added, then triisobutylaluminum (0.33 mmol) and triethylaluminum (1.0 mmol) were added as alkylaluminum, and they were stirred for 30 minutes to give a catalyst suspension.

A 2000 ml autoclave thoroughly purged with nitrogen was charged with 400 g of propylene and 2NL of an ethylene gas, and the catalyst suspension was added to perform polymerization at 60° C. for 60 minutes under a pressure of 3.0 to 3.5 MPa. Thereafter, methanol was added to terminate the polymerization, and propylene was purged of, to obtain a polymer. The polymer was dried under vacuum at 80° C. for 6 hours. The quantity of the polymer obtained was 127 g. This polymer had Tm of 128° C., MFR of 5.5 g/10 min and a decane-soluble component quantity of 0.2% by weight.

Example 26

Bulk Copolymerization of Propylene and Ethylene using dimethylmethylene(3-tert-butyl-5-methylcyclopentadienyl)fluorenylzirconium Dichloride Copolymerization of propylene and ethylene was carried out in the same manner as in Example 25, except that the charge of ethylene was changed to 3 NL. The quantity of the polymer obtained was 146 g. This polymer had Tm of 124° C., MFR of 5.5 g/10 min and a decane-soluble component quantity of 0.3% by weight.

Example 27

Bulk Copolymerization of Propylene and Ethylene using dimethylmethylene(3-tert-butyl-5-methylcyclopentadienyl)fluorenylzirconium Dichloride Polymerization was carried out in the same manner as in Example 25, except that the silica-supported methylaluminoxane was used in an amount of 0.52 mmol in terms of aluminum, and only the triethylaluminum (1.3 mmol) was used as alkylaluminum. The quantity of the polymer obtained was 79 g. This polymer had Tm of 124° C., MFR of 7.5 g/10 min and a decane-soluble component quantity of 0.2% by weight.

Example 28

Bulk Copolymerization of Propylene and Ethylene using dimethylmethylene(3-tert-butyl-5-methylcyclopentadienyl)fluorenylzirconium Dichloride Copolymerization of propylene and ethylene was carried out in the same manner as in Example 25, except that 0.5 NL of hydrogen was added. The quantity of the polymer obtained was 49 g. This polymer had Tm of 120° C., MFR of 65 g/10 min and a decane-soluble component quantity of 0.2% by weight.

Example 29

Bulk Copolymerization of Propylene and Ethylene using dimethylmethylene(3-tert-butyl-5-methylcyclopentadienyl)(2,7-di-tert-butylfluorenyl)zirconium Dichloride Copolymerization of propylene and ethylene was carried out in the same manner as in Example 25, except that 0.8 mg of the orange solid obtained in Example 5 was used. The quantity of the polymer obtained was 97 g. This polymer had Tm of 126° C., MFR of 2.0 g/10 min and a decane-soluble component quantity of 0.2% by weight.

Example 30

Bulk Copolymerization of Propylene and Ethylene using dimethylmethylene(3-tert-butyl-5-methylcyclopentadienyl)(2,7-di-tert-butylfluorenyl)zirconium Dichloride Copolymerization of propylene and ethylene was carried out in the same manner as in Example 29, except that the charge of ethylene was changed to 4 NL. The quantity of the polymer obtained was 142 g. This polymer had Tm of 116° C., MFR of 4.1 g/10 min and a decane-soluble component quantity of 0.3% by weight.

Example 31

Bulk Copolymerization of Propylene and Ethylene using cyclohexylidene(3-tert-butyl-5-methylcyclopentadienyl)fluorenylzirconium Dichloride Copolymerization of propylene and ethylene was carried out in the same manner as in Example 25, except that 0.7 mg of the reddish brown solid obtained in Example 2 was used. The quantity of the polymer obtained was 89 g. This polymer had Tm of 126° C., MFR of 13.0 g/10 min and a decane-soluble component quantity of 0.2% by weight.

Example 32

Bulk Copolymerization of Propylene and Ethylene using cyclohexylidene(3-tert-butyl-5-methylcyclopentadienyl)fluorenylzirconium Dichloride Copolymerization of propylene and ethylene was carried out in the same manner as in Example 31, except that the charge of ethylene was changed to 3 NL. The quantity of the polymer obtained was 107 g. This polymer had Tm of 122° C., MFR of 18.0 g/10 min and a decane-soluble component quantity of 0.5% by weight.

Example 33

Bulk Copolymerization of Propylene and Ethylene using cyclohexylidene(3-tert-butyl-5-methylcyclopentadienyl)(3,6-di-tert-butylfluorenyl)zirconium Dichloride Copolymerization of propylene and ethylene was carried out in the same manner as in Example 25, except that 1.3 mg of the reddish brown solid obtained in Example 4 was used, and the charge of ethylene was changed to 4 NL. The quantity of the polymer obtained was 297 g. This polymer had Tm of 141° C., MFR of 58 g/10 min and a decane-soluble component quantity of 0.3% by weight.

Example 34

Bulk Copolymerization of Propylene and Ethylene using cyclohexylidene(3-tert-butyl-5-methylcyclopentadienyl)(3,6-di-tert-butylfluorenyl)zirconium Dichloride Copolymerization of propylene and ethylene was carried out in the same manner as in Example 33, except that the charge of ethylene was changed to 5 NL. The quantity of the polymer obtained was 284 g. This polymer had Tm of 137° C., MFR of 97 g/10 min and a decane-soluble component quantity of 0.6% by weight.

Example 35

Bulk Copolymerization of Propylene and Ethylene using cyclohexylidene(3-tert-butyl-5-methylcyclopentadienyl)(3,6-di-tert-butylfluorenyl)zirconium Dichloride Copolymerization of propylene and ethylene was carried out in the same manner as in Example 33, except that the charge of ethylene was changed to 5 NL, and the polymerization temperature was changed to 50° C. The quantity of the polymer obtained was 262 g. This polymer had Tm of 137° C., MFR of 115 g/10 min, Mw of 112000, Mn of 62000, Mw/Mn of 1.8 and a decane-soluble component quantity of 0.8% by weight. As the stereoregularity of the polymer, the mmmm was 95.7%, proportion of 2,1-insertion was 0.02%, and the proportion of 1,3-insertion was 0.18%.

Example 36

Bulk Copolymerization of Propylene and Ethylene using cyclohexylidene(3-tert-butyl-5-methylcyclopentadienyl)(3,6-di-tert-butylfluorenyl)zirconium Dichloride Copolymerization of propylene and ethylene was carried out in the same manner as in Example 33, except that the charge of ethylene was changed to 5 NL, and 0.5 NL of hydrogen was added. The quantity of the polymer obtained was 205 g. This polymer had Tm of 131° C., MFR of 310 g/10 and a decane-soluble component quantity of 1.0% by weight. As the stereoregularity of the polymer, the mmmm was 95.0%, the proportion of 2,1-insertion was 0.03%, and the proportion of 1,3-insertion was 0.20%.

Example 37

Pressure Solution Polymerization of Propylene and 1-butene using dimethylmethylene(3-tert-butyl-5-methylcyclopentadienyl)fluorenylzirconium Dichloride A 2000 ml polymerization apparatus thoroughly purged with nitrogen was charged with 900 ml of dry hexane and 30 g of 1-butene at ordinary temperature. Then, the internal temperature of the polymerization apparatus was raised to 70° C., and the apparatus was pressurized to 0.7 MPa with propylene. To the polymerization apparatus, a catalyst solution obtained by adding 0.9 mmol (in terms of aluminum) of methylaluminoxane (available from Albemarle Co.) to a toluene solution of 1.0 mg (2 μmol) of the reddish orange solid obtained in Example 1 and triisobutylaluminum (1.0 mmol) were added, and polymerization was conducted for 30 minutes with maintaining the internal temperature at 70° C. and the propylene pressure at 0.7 MPa. Thereafter, methanol was added to terminate the polymerization. After the pressure was released, a polymer was precipitated from the polymer solution with methanol and dried under vacuum at 130° C. for 12 hours. The quantity of the polymer obtained was 9.95 g. This polymer had Tm of 102.7° C. and an intrinsic viscosity (η) of 0.89 dl/g.

Example 38

Polymerization was carried out in the same manner as in Example 37, except that the charge of 1-butene was changed to 60 g. The quantity of the polymer obtained was 7.31 g. This polymer had Tm of 73.6° C. and an intrinsic viscosity (η) of 0.94 dl/g.

Example 39

A 2000 ml polymerization apparatus thoroughly purged with nitrogen was charged with 750 ml of dry hexane and 40 g of 1-butene at ordinary temperature. Then, the internal temperature of the polymerization apparatus was raised to 50° C., and the apparatus was pressurized to 0.7 MPa with propylene. To the polymerization apparatus, a catalyst solution obtained by adding 1.35 mmol (in terms of aluminum) of methylaluminoxane (available from Albemarle Co.) to a toluene solution of 1.5 mg (3 μmol) of the reddish orange solid obtained in Example 1 and triisobutylaluminum (1.0 mmol) were added, and polymerization was conducted for 30 minutes with maintaining the internal temperature at 50° C. and the propylene pressure at 0.7 MPa. Thereafter, methanol was added to terminate the polymerization. After the pressure was released, a polymer was precipitated from the polymer solution with methanol and dried under vacuum at 130° C. for 12 hours. The quantity of the polymer obtained was 30.0 g. This polymer had Tm of 108.1° C. and an intrinsic viscosity (η) of 2.13 dl/g.

Example 40

Polymerization was carried out in the same manner as in Example 39, except that the charge of dry hexane was changed to 700 ml, and the charge of 1-butene was changed to 60 g. The quantity of the polymer obtained was 39.0 g. This polymer had Tm of 80.0° C. and an intrinsic viscosity (η) of 1.83 dl/g.

Example 41

A 1000 ml polymerization apparatus thoroughly purged with nitrogen was charged with 830 ml of dry hexane and 70 ml of 1-butene at ordinary temperature. Then, the internal temperature of the polymerization apparatus was raised to 40° C., and the apparatus was pressurized to 0.5 MPa with propylene. To the polymerization apparatus, a catalyst solution obtained by adding 1.35 mmol (in terms of aluminum) of methylaluminoxane (available from Albemarle Co.) to a toluene solution of 1.5 mg (3 μmol) of the reddish orange solid obtained in Example 1 and triisobutylaluminum (1.0 mmol) were added, and polymerization was conducted for 40 minutes with maintaining the internal temperature at 40° C. and the propylene pressure at 0.5 MPa. Thereafter, methanol was added to terminate the polymerization. After the pressure was released, a polymer was precipitated from the polymer solution with methanol and dried under vacuum at 130° C. for 12 hours. The quantity of the polymer obtained was 25.5 g. This polymer had Tm of 100.7° C. and an intrinsic viscosity (η) of 3.41 dl/g.

Example 42

Polymerization was carried out in the same manner as in Example 41, except that the charge of dry hexane was changed to 810 ml, and the charge of 1-butene was changed to 90 ml. The quantity of the polymer obtained was 23.8 g. This polymer had Tm of 90.6° C. and an intrinsic viscosity (η) of 3.56 dl/g.

Examples 43–46

Films were prepared from the sample polymers obtained in Examples 39 to 42, and properties of the films were measured.

Preparation of Film and Properties thereof

On a press plate, an aluminum sheet of 0.1 mm thickness, a polyethylene terephthalate (PET) sheet and an aluminum sheet of 0.1 mm thickness from the center of which a square of 15 cm×15 cm had been cut away were superposed in this order, and on the center (cut portion) of the aluminum sheet, 3.3 g of a sample polymer was placed. Then, a PET sheet, an aluminum plate and a press plate were further superposed in this order.

The sample polymer interposed between the press plates was placed in a hot press at 200° C. and preheated for about 7 minutes. In order to remove bubbles from the sample polymer, an operation of pressure-application (50 kg/cm$^2$-G)/pressure-release was repeated several times. Then, the pressure was finally increased to 100 kg/cm$^2$-G, and the sample polymer was heated for 2 minutes under pressure. After the pressure was released, the press plates were taken out of the pressing machine, then transferred into a different pressing machine wherein the pressing zone was maintained at 0° C., and cooled under a pressure of 100 kg/cm$^2$-G for 4 minutes. After the pressure was released, the sample polymer was taken out. Thus, a film having a uniform thickness of about 0.15 to 0.17 mm was obtained. The properties of the film are set forth in Table 1.

The properties of the film were measured in the following manner.

1. Heat Sealing Temperature (° C.)

Films were heat sealed by a heat sealer at a given temperature for 1 second under a load of 2 kg/cm$^2$ to obtain a specimen having a width of 15 mm. The specimen was peeled at a peel rate of 20 mm/min and a peel angle of 180° C. The temperature wherein the peel resistance was 300 g, was taken as a heat sealing temperature.

2. Anti-Blocking Properties (mN/cm)

Two films superposed upon each other were allowed to adhere under the following conditions, and the anti-blocking properties were measured in accordance with ASTM-D1893.

The measurement was made after the films were allowed to stand for 24 hours under the adhesion conditions of 50° C. and a load of 10 kg.

3. ΔHaze (%)

Using a specimen of 1 mm thickness, the haze was measured by a digital haze meter DH-20D manufactured by Nippon Denshoku Kogyo K. K.

After a heat treatment of the specimen at 80° C. for 3 days, the haze was further measured in the same manner as described above. The difference in haze before and after the heat treatment was taken as ΔHaze.

4. Static Friction Coefficient

The static friction coefficient was measured in accordance with ASTM-D1894.

5. Film impact strength (KJ/m)

The film impact strength was measured at 23° C. in accordance with ASTM-D3420.

TABLE 1

| Sample polymer | Ex. 43 Polymer obtained in Ex. 39 | Ex. 44 Polymer obtained in Ex. 40 | Ex. 45 Polymer obtained in Ex. 41 | Ex. 46 Polymer obtained in Ex. 42 |
|---|---|---|---|---|
| Heat sealing starting temperature (° C.) | 110 | 83 | 100 | 90 |
| Anti-blocking properties (mN/cm) | 3 | 18 | 1 | 15 |
| ΔHaze (%) | 0.5 | 0.2 | 0.4 | 0.2 |
| Static friction coefficient | 0.9 | 1.4 | 1 | 1.2 |
| Film impact strength (KJ/m) | 10.1 | 5.7 | 8.7 | 8.5 |

Comparative Example 1

Bulk Copolymerization of Propylene and Ethylene using dimethylsilylenebis(2-methyl-4,5-benzoindenyl)zirconium Dichloride Copolymerization of propylene and ethylene was carried out in the same manner as in Example 27, except that 0.8 mg of dimethylsilylenebis(0.2-methyl-4,5-benzoindenyl) zirconium dichloride was used as metallocene, and the charge of ethylene was changed to 4 NL. The quantity of the polymer obtained was 112 g. This polymer had Tm of 132° C., MFR of 7 g/10 min, Mw/Mn of 2.9 and a decane-soluble component quantity of 0.7% by weight. As the stereoregularity of the polymer, the mmmm was 90.4%, the proportion of 2,1-insertion was 0.79%, and the proportion of 1,3-insertion was 0.11%, so that the proportion of 2,1-insertion was high.

Comparative Example 2

Bulk Copolymerization of Propylene and Ethylene using dimethylsilylenebis(2-methyl-4,5-benzoindenyl)zirconium Dichloride Copolymerization of propylene and ethylene was carried out in the same manner as in Example 27, except that 0.8 mg of dimethylsilylenebis(2-methyl-4,5-benzoindenyl) zirconium dichloride was used as metallocene, and the charge of ethylene was changed to 8 NL. The quantity of the polymer obtained was 145 g. This polymer had Tm of 120° C., MFR of 14 g/10 min, Mw/Mn of 3.4 and a decane-soluble component quantity of 1.1% by weight. As the stereoregularity of the polymer, the mmmm was 88.8%, the proportion of 2,1-insertion was 0.69%, and the proportion of 1,3-insertion was 0.31%, so that the proportion of 2,1-insertion was high.

Comparative Example 3

Properties of Random PP prepared using Ziegler-Natta Catalyst

Properties of commercially available random PP (trade name: F637, available from Grand Polymer Co.) obtained by the use of a magnesium chloride-supported titanium catalyst are as follows. This polymer had Tm of 142° C., MFR of 6 g/10 min, Mw/Mn of 6.0 and a decane-soluble component quantity of 8.0% by weight, and the value of Mw/Mn was large. As the stereoregularity of the polymer, the mmmm was 91.1%, and none of the 2,1-insertion and the 1,3-insertion were detected.

Comparative Example 4

Properties of Thermally Decomposed Product of Random PP prepared using Ziegler-Natta Catalyst Commercially available random PP (trade name: F637, available from Grand Polymer Co.) obtained by the use of a magnesium chloride-supported titanium catalyst was thermally decomposed under the conditions of 400° C. and 100 minutes. Properties of the thus thermally decomposed polymer are as follows. This polymer had Tm of 140° C., MFR of 1000 g/10 min, Mw/Mn of 2.3 and a decane-soluble component quantity of 22% by weight, and the decane-soluble component quantity was large. As the stereoregularity of the polymer, the mmmm was 92.0%, and none of the 2,1-insertion and the 1,3-insertion were detected.

Example 47

Normal Pressure Polymerization of Propylene using dimethylmethylene(3-tert-butyl-5-methylcyclopentadienyl)(2,7-di-tert-butylfluorenyl) zirconium Dichloride A 500 ml glass polymerization apparatus thoroughly purged with nitrogen was charged with 250 ml of dry toluene, and then propylene was bubbled to saturate the apparatus. Thereafter, a catalyst solution obtained by adding 5 mmol (in terms of aluminum) of methylaluminoxane (available from Albemarle Co.) to a toluene solution of 2.35 mg (3.8 µmol) of the red solid obtained in Example 5 was added. With stirring, polymerization was conducted at 25° C. for 60 minutes while propylene was bubbled. Thereafter, methanol and a small amount of hydrochloric acid were added to terminate the polymerization. The resulting polymer was filtered, washed with methanol and dried under vacuum at 80° C. for 6 hours. The quantity of the polymer obtained was 0.50 g. This polymer had Tm of 140° C.

Example 48

Normal Pressure Polymerization of Propylene using dimethylmethylene(3-tert-butyl-5-methylcyclopentadienyl)(2,7-di-tert-butylfluorenyl) zirconium Dichloride Polymerization was carried out in the same manner as in Example 47, except that 10.3 mg (16.75 µmol) of the red solid obtained in Example 5 was used, and the polymerization temperature was changed to 50° C. The quantity of the polymer obtained was 6.2 g. This polymer had Tm of 138° C.

Example 49

Normal Pressure Polymerization of Propylene using cyclohexylidene(3-tert-butyl-5-methylcyclopentadienyl)(3,6-di-tert-butylfluorenyl) zirconium Dichloride A 500 ml glass polymerization apparatus thoroughly purged with nitrogen was charged with 250 ml of dry toluene, and then propylene was bubbled to saturate the apparatus. Thereafter, a catalyst solution obtained by adding 5 mmol (in terms of aluminum) of methylaluminoxane (available from Albemarle Co.) to a toluene solution of 3.27 mg (5.0 µmol) of the red solid obtained in Example 4 was added. With stirring, polymerization was conducted at 25° C. for 30 minutes while propylene was bubbled. Thereafter, methanol and a small amount of hydrochloric acid were added to terminate the polymerization. The resulting polymer was filtered, washed with methanol and dried under vacuum at 80° C. for 6 hours. The quantity of the polymer obtained was 0.9 g. This polymer had Tm of 155° C.

Example 50

Normal Pressure Polymerization of Propylene using cyclohexylidene(3-tert-butyl-5-methylcyclopentadienyl)(3,6-di-tert-butylfluorenyl) zirconium Dichloride Polymerization was carried out in the same manner as in Example 49, except that the polymerization temperature was changed to 50° C. The quantity of the polymer obtained was 4.9 g. This polymer had Tm of 144° C.

Example 51

Normal Pressure Polymerization of Propylene using cyclohexylidene(3-tert-butyl-5-methylcyclopentadienyl)fluorenylzirconium Dichloride A 500 ml glass polymerization apparatus thoroughly purged with nitrogen was charged with 250 ml of dry toluene, and then propylene was bubbled to saturate the apparatus. Thereafter, a catalyst solution obtained by adding 5 mmol (in terms of aluminum) of methylaluminoxane (available from Albemarle Co.) to a toluene solution of 2.71 mg (5.0 µmol) of the reddish brown solid obtained in Example 2 was added. With stirring, polymerization was conducted at 25° C. for 15 minutes while propylene was bubbled. Thereafter, methanol and a small amount of hydrochloric acid were added to terminate the polymerization. The resulting polymer was filtered, washed with methanol and dried under vacuum at 80° C. for 6 hours. The quantity of the polymer obtained was 1.3 g. This polymer had Tm of 145° C.

Example 52

Normal Pressure Polymerization of Propylene using cyclohexylidene(3-tert-butyl-5-methylcyclopentadienyl) fluorenylzirconium Dichloride Polymerization was carried out in the same manner as in Example 51, except that the polymerization temperature was changed to 50° C. The quantity of the polymer obtained was 3.8 g. This polymer had Tm of 139° C.

Example 53

Normal Pressure Polymerization of Propylene using dimethylmethylene(3-(1-methyl-1-cyclohexyl)cyclopentadienyl)(3,6-di-tert-butylfluorenyl)zirconium Dichloride Polymerization of propylene was carried out in the same manner as in Example 47, except that 9.61 mg (5 mmol) of the orange solid obtained in Example 7 was used. The quantity of the polymer obtained was 0.3 g. This polymer had Tm of 147° C.

Example 54

Normal Pressure Polymerization of Propylene using dimethylmethylene(3-(1-methyl-1-cyclohexyl)cyclopentadienyl)(3,6-di-tert-butylfluorenyl)zirconium Dichloride Polymerization was carried out in the same manner as in Example 53, except that the polymerization temperature was changed to 50° C. The quantity of the polymer obtained was 0.2 g. This polymer had Tm of 134° C.

Example 55

Normal Pressure Polymerization of Propylene using dimethylmethylene(3-tert-butylcyclopentadienyl)(1,1,4,4,7,7,10,10-octamethyl-1,2,3,4,7,8,9,10-octahydrodibenzo(b,h)-fluorenyl)zirconium Dichloride Polymerization of propylene was carried out in the same manner as in Example 47, except that 1.7 mg (2.5 µmol) of the orange solid obtained in Example 8 was used. The quantity of the polymer obtained was 0.3 g. This polymer had Tm of 143° C.

Example 56

Normal Pressure Polymerization of Propylene using dimethylmethylene(3-tert-butylcyclopentadienyl)(1,1,4,4,7,7,10,10-octamethyl-1,2,3,4,7,8,9,10-octahydrodibenzo(b,h)-fluorenyl)zirconium Dichloride Polymerization was carried out in the same manner as in Example 55, except that the polymerization temperature was changed to 50° C. The quantity of the polymer obtained was 0.4 g. This polymer had Tm of 140° C.

Example 57

Normal Pressure Polymerization of Propylene using dimethylmethylene(3-trimethylsilylcyclopentadienyl)(1,1,4,4,7,7,10,10-octamethyl-1,2,3,4,7,8,9,10-octahydrodibenzo(b,h)-fluorenyl)zirconium Dichloride Polymerization of propylene was carried out in the same manner as in Example 47, except that 3.7 mg (5 µmol) of the red plate solid obtained in Example 9 was used. The quantity of the polymer obtained was 0.5 g. This polymer had Tm of 137° C.

Example 58

Normal Pressure Polymerization of Propylene using dimethylmethylene(3-trimethylsilylcyclopentadienyl)(1,1,4,4,7,7,10,10-octamethyl-1,2,3,4,7,8,9,10-octahydrodibenzo(b,h)-fluorenyl)zirconium Dichloride Polymerization was carried out in the same manner as in Example 57, except that the polymerization temperature was changed to 50° C. The quantity of the polymer obtained was 1.1 g. This polymer had Tm of 142° C.

Example 59

Normal Pressure Polymerization of Propylene using dimethylmethylene(3-(1,1-dimethylpropyl)cyclopentadienyl)(3,6-di-tert-butylfluorenyl)zirconium Dichloride Polymerization of propylene was carried out in the same manner as in Example 47, except that 3.07 mg (5 µmol) of the red solid obtained in Example 10 was used, and the polymerization time was changed to 45 minutes. The quantity of the polymer obtained was 1.1 g. This polymer had Tm of 150° C.

Example 60

Normal Pressure Polymerization of Propylene using dimethylmethylene(3-(1,1-dimethylpropyl)cyclopentadienyl)(3,6-di-tert-butylfluorenyl)zirconium Dichloride Polymerization was carried out in the same manner as in Example 59, except that the polymerization temperature was changed to 50° C. The quantity of the polymer obtained was 0.74 g. This polymer had Tm of 138° C.

Example 61

Normal Pressure Polymerization of Propylene using dimethylmethylene(3-(1-ethyl-1-methylpropyl)cyclopentadienyl)(3,6-di-tert-butylfluorenyl)zirconium Dichloride Polymerization of propylene was carried out in the same manner as in Example 47, except that 3.15 mg (5 mmol) of the orange solid obtained in Example 11 was used. The quantity of the polymer obtained was 0.13 g. This polymer had Tm of 142° C.

Example 62

Normal Pressure Polymerization of Propylene using dimethylmethylene(3-(1-ethyl-1-methylpropyl)cyclopentadienyl)(3,6-di-tert-butylfluorenyl)zirconium Dichloride Polymerization was carried out in the same manner as in Example 61, except that the polymerization temperature was changed to 50° C. The quantity of the polymer obtained was 0.02 g. This polymer had Tm of 123° C.

Example 63

Normal Pressure Polymerization of Propylene using dimethylmethylene(3-(1,1,3-trimethylbutyl)cyclopentadienyl)(3,6-di-tert-butylfluorenyl)zirconium Dichloride Polymerization of propylene was carried out in the same manner as in Example 47, except that 3.22 mg (5 µmol) of the reddish brown solid obtained in Example 12 was used. The quantity of the polymer obtained was 0.62 g. This polymer had Tm of 146° C.

Example 64

Normal Pressure Polymerization of Propylene using dimethylmethylene(3-(1,1,3-trimethylbutyl)cyclopentadienyl)(3,6-di-tert-butylfluorenyl)zirconium Dichloride Polymerization was carried out in the same manner as in Example 63, except that the polymerization temperature was changed to 50° C. The quantity of the polymer obtained was 1.2 g. This polymer had Tm of 136° C.

Example 65

Normal Pressure Polymerization of Propylene using dimethylmethylene(3-(1,1-dimethylbutyl)cyclopentadienyl)(3,6-di-tert-butylfluorenyl)zirconium Dichloride Polymerization of propylene was carried out in the same manner as in Example 47, except that 3.14 mg (5 µmol) of the red solid obtained in Example 14 was used. The quantity of the polymer obtained was 1.67 g. This polymer had Tm of 149° C.

Example 66

Normal Pressure Polymerization of Propylene using dimethylmethylene(3-(1,1-dimethylbutyl)cyclopentadiethyl)(3,6-di-tert-butyl-fluorenyl)zirconium Dichloride Polymerization was carried out in the same manner as in Example 65, except that the polymerization temperature was changed to 50° C. The quantity of the polymer obtained was 1.2 g. This polymer had Tm of 137° C.

Example 67

Normal Pressure Polymerization of Propylene using dimethylmethylene(3-tert-butylcyclopentadienyl)(2,7-di-tert-butylfluorenyl)zirconium Dichloride Polymerization of propylene was carried out in the same manner as in Example 47, except that 3.0 mg (5 mmol) of the red solid obtained in Example 15 was used. The quantity of the polymer obtained was 1.27 g. This polymer had Tm of 140° C.

Example 68

Normal Pressure Polymerization of Propylene using dimethylmethylene(3-tert-butylcyclopentadienyl)(2,7-di-tert-butylfluorenyl)zirconium Dichloride Polymerization was carried out in the same manner as in Example 67, except that the polymerization temperature was changed to 50° C. The quantity of the polymer obtained was 5.11 g. This polymer had Tm of 137° C.

Example 69

Normal Pressure Polymerization of Propylene using diphenylmethylene(3-phenylcyclopentadienyl)(1,1,4,4,7,7,10,10-octamethyl-1,2,3,4,7,8,9,10-octahydrodibenzo(b,h)-fluorenyl)zirconium Dichloride Polymerization of propylene was carried out in the same manner as in Example 47, except that 4.27 mg (5 µmol) of the reddish orange solid obtained in Example 17 was used. The quantity of the polymer obtained was 0.08 g. This polymer had Tm of 105° C.

Example 70

Normal Pressure Polymerization of Propylene using diphenylmethylene(3-trimethylsilylcyclopentadienyl)(1,1,4,4,7,7,10,10-octamethyl-1,2,3,4,7,8,9,10-octahydrodibenzo(b,h)-fluorenyl)zirconium Dichloride Polymerization of propylene was carried out in the same manner as in Example 47, except that 4.05 mg (5 µmol) of the pink powder obtained in Example 18 was used. The quantity of the polymer obtained was 0.18 g. This polymer had Tm of 139° C.

Example 71

Normal Pressure Polymerization of Propylene using diphenylmethylene(3-trimethylsilylcyclopentadienyl)(1,1,4,4,7,7,10,10-octamethyl-1,2,3,4,7,8,9,10-octahydrodibenzo(b,h)-fluorenyl)zirconium Dichloride Polymerization was carried out in the sane manner as in Example 70, except that the polymerization temperature was changed to 50° C. The quantity of the polymer obtained was 0.64 g. This polymer had Tm of 139° C.

Example 72

Normal Pressure Polymerization of Propylene using methylphenylmethylene(3-tert-butylcyclopentadienyl)(3,6-di-tert-butylfluorenyl)zirconium Dichloride Polymerization of propylene was carried out in the same manner as in Example 47, except that 3.32 mg (5 µmol) of the orange solid obtained in Example 19 was used, and the polymerization time was changed to 45 minutes. The quantity of the polymer obtained was 1.16 g. This polymer had Tm of 144° C.

Example 73

Normal Pressure Polymerization of Propylene using methylphenylmethylene (3-tert-butylcyclopentadienyl) (3,6-di-tert-butylfluorenyl)zirconium Dichloride Polymerization was carried out in the same manner as in Example 72, except that the polymerization temperature was changed to 50° C. The quantity of the polymer obtained was 8.65 g. This polymer had Tm of 144° C.

Example 74

Normal Pressure Polymerization of Propylene using diethylmethylene (3-tert-butylcyclopentadienyl) (3,6-di-tert-butylfluorenyl)zirconium Dichloride Polymerization of propylene was carried out in the same manner as in Example 47, except that 3.14 mg (5 µmol) of the orange solid obtained in Example 20 was used. The quantity of the polymer obtained was 0.83 g. This polymer had Tm of 150° C.

Example 75

Normal Pressure Polymerization of Propylene using diethylmethylene(3-tert-butylcyclopentadienyl)(3,6-di-tert-butylfluorenyl)zirconium Dichloride Polymerization was carried out in the same manner as in Example 74, except that the polymerization temperature was changed to 50° C. The quantity of the polymer obtained was 3.15 g. This polymer had Tm of 143° C.

Example 76

Normal Pressure Polymerization of Propylene using cyclohexylidene(3-trimethylsilylcyclopentadienyl)(3,6-di-tert-butylfluorenyl)zirconium Dichloride Polymerization of propylene was carried out in the same manner as in Example 47, except that 3.3 mg (5 μmol) of the orange solid obtained in Example 21 was used. The quantity of the polymer obtained was 0.58 g. This polymer had Tm of 141° C.

Example 77

Normal Pressure Polymerization of Propylene using cyclohexylidene(3-trimethylsilylcyclopentadienyl)(3,6-di-tert-butylfluorenyl)zirconium Dichloride Polymerization was carried out in the same manner as in Example 76, except that the polymerization temperature was changed to 50° C. The quantity of the polymer obtained was 0.8 g. This polymer had Tm of 139° C.

Example 78

Normal Pressure Polymerization of Propylene using cyclopentylidene(3-tert-butylcyclopentadienyl)(3,6-di-tert-butylfluorenyl)zirconium Dichloride Polymerization of propylene was carried out in the same manner as in Example 47, except that 3.13 mg (5 mmol) of the orange solid obtained in Example 22 was used. The quantity of the polymer obtained was 0.3 g. This polymer had Tm of 146° C.

Example 79

Normal Pressure Polymerization of Propylene using cyclopentylidene(3-tert-butylcyclopentadienyl)(3,6-di-tert-butylfluorenyl)zirconium Dichloride Polymerization was carried out in the same manner as in Example 78, except that the polymerization temperature was changed to 50° C. The quantity of the polymer obtained was 3.1 g. This polymer had Tm of 143° C.

Example 80

Normal Pressure Polymerization of Propylene using cyclohexylidene(3-(1,1-dimethylpropyl)cyclopentadienyl)(3,6-di-tert-butylfluorenyl)zirconium Dichloride Polymerization of propylene was carried out in the same manner as in Example 47, except that 3.28 mg (5 μmol) of the reddish brown solid obtained in Example 23 was used. The quantity of the polymer obtained was 0.37 g. This polymer had Tm of 143° C.

Example 81

Normal Pressure Polymerization of Propylene using cyclohexylidene(3-(1,1-dimethylpropyl)cyclopentadienyl)(3,6-di-tert-butylfluorenyl)zirconium Dichloride Polymerization was carried out in the same manner as in Example 80, except that the polymerization temperature was changed to 50° C. The quantity of the polymer obtained was 0.19 g. This polymer had Tm of 129° C.

Example 82

Normal Pressure Polymerization of Propylene using cyclopentylidene(3-tert-butylcyclopentadienyl)(1,1,4,4,7,7,10,10-octamethyl-1,2,3,4,7,8,9,10-octahydrodibenzo(b,h)-fluorenyl)zirconium Dichloride Polymerization of propylene was carried out in the same manner as in Example 47, except that 3.67 mg (5 μmol) of the red solid obtained in Example 24 was used. The quantity of the polymer obtained was 0.33 g.

Example 83

Normal Pressure Polymerization of Propylene using cyclopentylidene(3-tert-butylcyclopentadienyl)(1,1,4,4,7,7,10,10-octamethyl-1,2,3,4,7,8,9,10-octahydrodibenzo(b,h)-fluorenyl)zirconium Dichloride Polymerization was carried out in the same manner as in Example 82, except that the polymerization temperature was changed to 50° C. The quantity of the polymer obtained was 0.37 g.

Example 84

Bulk Polymerization of Propylene using cyclohexylidene(3-tert-butyl-5-methylcyclopentadienyl)fluorenylzirconium Dichloride In a 50 ml two-necked flask thoroughly purged with nitrogen, 2.0 mmol (in terms of aluminum) of silica-supported methylaluminoxane was suspended in 20 ml of heptane. To the suspension, a toluene solution of 1.1 mg (2 μmol) of the reddish brown solid obtained in Example 2 was added, then triisobutylaluminum (1 mmol) was added, and they were stirred for 30 minutes to give a catalyst suspension.

A 2000 ml autoclave thoroughly purged with nitrogen was charged with 500 g of propylene, and the catalyst suspension was added to perform polymerization at 70° C. for 40 minutes under a pressure of 3.0 to 3.5 MPa. Thereafter, methanol was added to terminate the polymerization, and propylene was purged of, to obtain a polymer. The polymer was dried under vacuum at 80° C. for 6 hours. The quantity of the polymer obtained was 103 g. This polymer had Tm of 139° C., MFR of −1.2 g/10 min, Mw of 348000, Mn of 184000, Mw/Mn of 1.9 and a decane-soluble component quantity of 0.5% by weight.

Example 85

Bulk Polymerization of Propylene using cyclohexylidene(3-tert-butyl-5-methylcyclopentadienyl)fluorenylzirconium Dichloride Polymerization of propylene-was carried out in the same manner as in Example 84, except that 2 NL of hydrogen was added. The quantity of the polymer obtained was 55 g. This polymer had Tm of 141° C., MFR of 1000 g/10 min, Mw of 69000, Mn of 30000, Nw/Mn of 2.3 and a decane-soluble component quantity of 0.8% by weight. As the stereoregularity of the polymer, the mmmm was 85.8%, the proportion of 2,1-insertion was 0.08%, and the proportion of 1,3-insertion was 0.02%.

Example 86

Bulk Polymerization of Propylene using cyclohexylidene(3-tert-butyl-5-methylcyclopentadienyl)(3,6-di-tert-butylfluorenyl) zirconium Dichloride Polymerization of propylene was carried out in the same manner as in Example 84, except that 1.3 mg (2 μmol) of the red solid obtained in Example 4 was used. The quantity of the polymer obtained was 49 g. This polymer had Tm of 155° C., MFR of 1.6 g/10 min, Mw of 357000, Mn of 193000, Mw/Mn of 1.8 and a decane-soluble component quantity of 0.3% by weight.

Example 87

Bulk Polymerization of Propylene using cyclohexylidene(3-tert-butyl-5-methylcyclopentadienyl)(3,6-di-tert-butylfluorenyl) zirconium Dichloride Polymerization of propylene was carried out in the same manner as in Example 86, except that 1 NL of hydrogen was added. The quantity of the polymer obtained was 328 g. This polymer had Tm of 156° C., MFR of 150 g/10 min, Mw of 117000, Mn of 52000, Mw/Mn of 2.3 and a decane-soluble component quantity of 0.1% by weight. As the stereoregularity of the polymer, the mmmm was 95.6%, and none of the 2,1-insertion and the 1,3-insertion were detected.

Example 88

10 Bulk Polymerization of Propylene using cyclohexylidene(3-tert-butyl-5-methylcyclopentadienyl)(3,6-di-tert-butylfluorenyl)zirconium Dichloride Polymerization of propylene was carried out in the same manner as in Example 86, except that 1 NL of hydrogen was added, and the polymerization temperature was changed to 60° C. The quantity of the polymer obtained was 252 g. This polymer had Tm of 158° C., MFR of 210 g/10 min, Mw of 97000, Mn of 45000, Mw/Mn of 2.1 and a decane-soluble component quantity of 0.1% by weight. As the stereoregularity of the polymer, the mmmm was 97.0%, and none of the 2,1-insertion and the 1,3-insertion were detected.

Example 89

Bulk Polymerization of Propylene using cyclohexylidene(3-tert-butyl-5-methylcyclopentadienyl)(3,6-di-tert-butylfluorenyl) zirconium Dichloride Polymerization of propylene was carried out in the same manner as in Example 86, except that 0.5 NL of hydrogen was added, and triethylaluminum (1 mmol) was used instead of triisobutylaluminum (1 mmol). The quantity of the polymer obtained was 295 g. This polymer had Tm of 157° C., MFR of 42 g/10 min, Mw of 147000, Mn of 71000, Mw/Mn of 2.1 and a decane-soluble component quantity of 0.1% by weight.

Example 90

Bulk Polymerization of Propylene using dimethylmethylene(3-tert-butyl-5-methylcyclopentadienyl)(2,7-di-tert-butylfluorenyl) zirconium Dichloride Polymerization of propylene was carried out in the same manner as in Example 84, except that 1.2 mg (2 μmol) of the red solid obtained in Example 5 was used. The quantity of the polymer obtained was 41 g. This polymer had Tm of 141° C., MFR of 0.05 g/10 min, Mw of 524000, Mn of 274000, Mw/Mn of 1.9 and a decane-soluble component quantity of 0.1% by weight. As the stereoregularity of the polymer, the mmmm was 88.4%, the proportion of 2,1-insertion was 0.04%, and the proportion of 1,3-insertion was 0.07%.

Example 91

Bulk Polymerization of Propylene using dimethylmethylene(3-(1-methyl-1-cyclohexyl) cyclopentadienyl)(3,6-di-tert-butylfluorenyl) zirconium Dichloride Polymerization of propylene was carried out in the same manner as in Example 84, except that 4.5 mg (7 pmol) of the orange solid obtained in Example 7 was used. The quantity of the polymer obtained was 33 g. This polymer had Tm of 146° C., MFR of 60 g/10 min, Mw of 115000, Mn of 67000, Mw/Mn of 1.7 and a decane-soluble component quantity of 0.7% by weight.

Example 92

Bulk Polymerization of Propylene using dimethylmethylene(3-(1-methyl-1-cyclohexyl) cyclopentadienyl)(3,6-di-tert-butylfluorenyl) zirconium Dichloride Polymerization of propylene was carried out in the same manner as in Example 91, except that 1 NL of hydrogen was added. The quantity of the polymer obtained was 24 g. This polymer had Tm of 153° C., MFR of 400 g/10 min, Mw of 59000, Mn of 30000, Mw/Mn of 2.0 and a decane-soluble component quantity of 1.0% by weight.

Example 93

Bulk Polymerization of Propylene using dimethylmethylene(3-tert-butylcyclopentadienyl)(1,1,4,4,7,7,10,10-octamethyl-1,2,3,4,7,8,9,10-octahydrodibenzo(b,h)-fluorenyl)zirconium Dichloride Polymerization of propylene was carried out in the same manner as in Example 84, except that 1.0 mg (1.4 pmol) of the orange solid obtained in Example 8 was used. The quantity of the polymer obtained was 30 g. This polymer had Tm of 149° C. and MFR of 190 g/10 min.

Example 94

Bulk Polymerization of Propylene using dimethylmethylene(3-tert-butylcyclopentadienyl)(1,1,4,4,7,7,10,10-octamethyl-1,2,3,4,7,8,9,10-octahydrodibenzo(b,h)-fluorenyl)zirconium Dichloride Polymerization of propylene was carried out in the same manner as in Example 93, except that 0.3 NL of hydrogen was added. The quantity of the polymer obtained was 183 g. This polymer had Tm of 153° C. and MFR of 1000 g/10 min.

Example 95

Bulk Polymerization of Propylene using dimethylmethylene(3-trimethylsilylcyclopentadienyl)(1,1,4,4,7,7,10,10-octamethyl-1,2,3,4,7,8,9,10-octahydrodibenzo(b,h)-fluorenyl)zirconium Dichloride Polymerization of propylene was carried out in the same manner as in Example 84, except that 10.68 mg (0.94 μmol)

of the red plate solid obtained in Example 9 was used. The quantity of the polymer obtained was 4 g. This polymer had Tm of 136° C.

Example 96

Bulk Polymerization of Propylene using dimethylmethylene(3-trimethylsilylcyclopentadienyl)(1,1,4,4,7,7,10,10-octamethyl-1,2,3,4,7,8,9,10-octahydrodibenzo(b,h)-fluorenyl)zirconium Dichloride Polymerization of propylene was carried out in the same manner as in Example 95, except that 0.3 NL of hydrogen was added. The quantity of the polymer obtained was 64 g. This polymer had Tm of 143° C.

Example 97

Bulk Polymerization of Propylene using dimethylmethylene(3-(1,1-dimethylpropyl)cyclopentadienyl)(3,6-di-tert-butylfluorenyl)zirconium Dichloride Polymerization of propylene was carried out in the same manner as in Example 84, except that 0.68 mg (1.1 µmol) of the red solid obtained in Example 10 was used. The quantity of the polymer obtained was 54 g. This polymer had Tm of 151° C.

Example 98

Bulk Polymerization of Propylene using dimethylmethylene(3-(1,1-dimethylpropyl)cyclopentadienyl)(3,6-di-tert-butylfluorenyl)zirconium Dichloride Polymerization of propylene was carried out in the same manner as in Example 97, except that 0.3 NL of hydrogen was added. The quantity of the polymer obtained was 91 g. This polymer had Tm of 151° C.

Example 99

Bulk Polymerization of Propylene using dimethylmethylene(3-(1-ethyl-1-methylpropyl)cyclopentadienyl)(3,6-di-tert-butylfluorenyl)zirconium Dichloride Polymerization of propylene was carried out in the same manner as in Example 84, except that 0.68 mg (1.1 mmol) of the red solid obtained in Example 11 was used. The quantity of the polymer obtained was 12 g. This polymer had Tm of 147° C.

Example 100

Bulk Polymerization of Propylene using dimethylmethylene(3-(1-ethyl-1-methylpropyl)cyclopentadienyl)(3,6-di-tert-butyl-fluorenyl)zirconium Dichloride Polymerization of propylene was carried out in the same manner as in Example 99, except that 0.3 NL of hydrogen was added. The quantity of the polymer obtained was 34 g. This polymer had Tm of 152° C.

Example 101

Bulk Polymerization of Propylene using dimethylmethylene(3-(1,1-dimethylbutyl)cyclopentadienyl) (3,6-di-tert-butylfluorenyl)zirconium Dichloride Polymerization of propylene was carried out in the same manner as in Example 84, except that 0.68 mg (1.1 µmol) of the red solid obtained in Example 14 was used. The quantity of the polymer obtained was 29 g. This polymer had Tm of 147° C. and MFR of 350 g/10 min.

Example 102

Bulk Polymerization of Propylene using dimethylmethylene(3-(1,1-dimethylbutyl)cyclopentadienyl)(3,6-di-tert-butylfluorenyl)zirconium Dichloride Polymerization of propylene was carried out in the same manner as in Example 101, except that 0.3 NL of hydrogen was added. The quantity of the polymer obtained was 43 g. This polymer had Tm of 150° C. and MFR of 1000 g/10 min.

Example 103

Bulk Polymerization of Propylene using dimethylmethylene(3-tert-butylcyclopentadienyl)(2,7-di-tert-butylfluorenyl)zirconium Dichloride Polymerization of propylene was carried out in the same manner as in Example 84, except that 1.3 mg (2 µmol) of the red solid obtained in Example 15 was used.

The quantity of the polymer obtained was 42 g. This polymer had Tm of 137° C. and MFR of 1000 g/10 min.

Example 104

Bulk Polymerization of Propylene using dimethylmethylene(3-tert-butylcyclopentadienyl)(2,7-di-tert-butylfluorenyl)zirconium Dichloride Polymerization of propylene was carried out in the same manner as in Example 103, except that 0.3 NL of hydrogen was added. The quantity of the polymer obtained was 84 g. This polymer had Tm of 138° C. and MFR of 1000 g/10 min.

Example 105

Bulk Polymerization of Propylene using diphenylmethylene(3-trimethylsilylcyclopentadienyl)(1,1,4,4,7,7,10,10-octamethyl-1,2,3,4,7,8,9,10-octahydrodibenzo(b,h)-fluorenyl)zirconium Dichloride Polymerization of propylene was carried out in the same manner as in Example 84, except that 0.68 mg (0.8 mmol) of the pink powder obtained in Example 18 was used. The quantity of the polymer obtained was 6 g. This polymer had Tm of 141° C.

Example 106

Bulk Polymerization of Propylene using diphenylmethylene(3-trimethylsilylcyclopentadienyl)(1,1,4,4,7,7,10,10-octamethyl-1,2,3,4,7,8,9,10-octahydrodibenzo(b,h)-fluorenyl)zirconium Dichloride Polymerization of propylene was carried out in the same manner as in Example 105, except that 0.3 NL of hydrogen was added. The quantity of the polymer obtained was 49 g. This polymer had Tm of 146° C.

Example 107

Bulk Polymerization of Propylene using methylphenylmethylene(3-tert-butylcyclopentadienyl)(3,6-di-tert-butylfluorenyl)zirconium Dichloride Polymerization of propylene was carried out in the same manner as in Example 84, except that 0.68 mg (2 µmol) of the orange solid obtained in Example 19 was used. The quantity of the polymer obtained was 87 g. This polymer had Tm of 144° C.

Example 108

Bulk Polymerization of Propylene using methylphenylmethylene(3-tert-butylcyclopentadienyl)(3,6-di-tert-butylfluorenyl)zirconium Dichloride Polymerization of propylene was carried out in the same manner as in Example 107, except that 0.3 NL of hydrogen was added. The quantity of the polymer obtained was 148 g. This polymer had Tm of 146° C.

Example 109

Bulk Polymerization of Propylene using diethylmethylene(3-tert-butylcyclopentadienyl)(3,6-di-tert-butylfluorenyl)zirconium Dichloride Polymerization of propylene was carried out in the same manner as in Example 84, except that 0.68 mg (1.1 mmol) of the orange solid obtained in Example 20 was used. The quantity of the polymer obtained was 50 g. This polymer had Tm of 149° C.

Example 110

Bulk Polymerization of Propylene using diethylmethylene(3-tert-butylcyclopentadienyl)(3,6-di-tert-butylfluorenyl)zirconium Dichloride Polymerization of propylene was carried out in the same manner as in Example 109, except that 0.3 NL of hydrogen was added. The quantity of the polymer obtained was 89 g. This polymer had Tm of 152° C.

Example 111

Bulk Polymerization of Propylene using cyclohexylidene(3-trimethylsilylcyclopentadienyl)(3,6-di-tert-butylfluorenyl)zirconium Dichloride Polymerization of propylene was carried out in the same manner as in Example 84, except that 0.68 mg (1 mmol) of the orange solid obtained in Example 21 was used. The quantity of the polymer obtained was 20 g. This polymer had Tm of 139° C.

Example 112

Bulk Polymerization of Propylene using cyclohexylidene(3-trimethylsilylcyclopentadienyl)(3,6-di-tert-butylfluorenyl)zirconium Dichloride Polymerization of propylene was carried out in the same manner as in Example 111, except that 0.3 NL of hydrogen was added. The quantity of the polymer obtained was 43 g. This polymer had Tm of 141° C., MFR of 1000 g/10 min and a decane-soluble component quantity of 0.5% by weight.

Example 113

Bulk Polymerization of Propylene using cyclopentylidene(3-tert-butylcyclopentadienyl)(3,6-di-tert-butylfluorenyl)zirconium Dichloride Polymerization of propylene was carried out in the same manner as in Example 84, except that 0.68 mg (1.1 μmol) of the orange solid obtained in Example 17 was used. The quantity of the polymer obtained was 49 g. This polymer had Tm of 149° C. and MFR of 190 g/10 min.

Example 114

Bulk Polymerization of Propylene using cyclopentylidene(3-tert-butylcyclopentadienyl)(3,6-di-tert-butylfluorenyl)zirconium Dichloride Polymerization of propylene was carried out in the same manner as in Example 113, except that 0.3 NL of hydrogen was added. The quantity of the polymer obtained was 118 g. This polymer had Tm of 151° C. and MFR of 1000 g/10 min.

Example 115

Bulk Polymerization of Propylene using cyclohexylidene(3-(1,1-dimethylpropyl)cyclopentadienyl)(3,6-di-tert-butylfluorenyl)zirconium Dichloride Polymerization of propylene was carried out in the same manner as in Example 84, except that 0.68 mg (1 mmol) of the reddish brown solid obtained in Example 23 was used. The quantity of the polymer obtained was 3 g. This polymer had Tm of 141° C.

Example 116

Bulk Polymerization of Propylene using cyclohexylidene(3-(1,1-dimethylpropyl)cyclopentadienyl)(3,6-di-tert-butylfluorenyl)zirconium Dichloride Polymerization of propylene was carried out in the same manner as in Example 115, except that 0.3 NL of hydrogen was added. The quantity of the polymer obtained was 47 g. This polymer had Tm of 150° C.

Example 117

Bulk Polymerization of Propylene using cyclopentylidene (3-tert-butylcyclopentadienyl) (1,1,4,4,7,7,10,10-octamethyl-1,2,3,4,7,8,9,10-octahydrodibenzo (b,h) -fluorenyl)zirconium Dichloride Polymerization of propylene was carried out in the same manner as in Example 84, except that 0.68 mg (0.9 μmol) of the red solid obtained in Example 24 was used. The quantity of the polymer obtained was 3 g. This polymer had Tm of 143° C.

Example 118

Bulk Polymerization of Propylene using cyclopentylidene(3-tert-butylcyclopentadienyl)(1,1,4,4,7,7,10,10-octamethyl-1,2,3,4,7,8,9,10-octahydrodibenzo(b,h)-fluorenyl)zirconium Dichloride Polymerization of propylene was carried out in the same manner as in Example 117, except that 0.3 NL of hydrogen was added. The quantity of the polymer obtained was 87 g. This polymer had Tm of 152° C.

Comparative Example 5

Bulk Polymerization of Propylene using dimethylsilylenebis(2-methyl-4,5-benzoindenyl)zirconium Dichloride Polymerization of propylene was carried out in the same manner as in Example 84, except that 0.8 mg of dimethylsilylenebis(2-methyl-4,5-benzoindenyl)zirconium dichloride was used as metallocene. The quantity of the polymer obtained was 150 g. This polymer had Tm of 145° C., MFR of 16 g/10 min, Mw/Mn of 2.1 and a decane-soluble component quantity of 0.4% by weight. As the stereoregularity of the polymer, the mmmm was 93.0%, the proportion of 2,1-insertion was 0.75%, the proportion of 1,3-insertion was 0.06%, and the proportion of the 2,1-insertion was high.

Comparative Example 6

Bulk Polymerization of Propylene using dimethylsilylenebis(2-methyl-4-phenylindenyl) zirconium Dichloride Polymerization of propylene was carried out in the same manner as in Example 84, except that 0.7 mg of dimethylsilylenebis(2-methyl-4-phenylindenyl)zirconium dichloride was used as metallocene. The quantity of the polymer obtained was 163 g. This polymer had Tm of 150° C., MFR of 1 g/10 min, Mw/Mn of 2.5 and a decane-soluble component quantity of 0.6% by weight. As the stereoregularity of the polymer, the mmmm was 95.9%, the proportion of 2,1-insertion was 0.80%, the proportion of 1,3-insertion was 0.05%, and the proportion of the 2,1-insertion was high.

Comparative Example 7

Properties of Homo-PP prepared using Ziegler-Natta Catalyst

Properties of commercially available homo-PP (trade name: J700, available from Grand Polymer Co.) obtained by the use of a magnesium chloride-supported titanium catalyst are as follows. This polymer had Tm of 161° C., MFR of 11 g/10 min, Mw/Mn of 5.2 and a decane-soluble component quantity of 2.0% by weight, and the value of Mw/Mn was large. As the stereoregularity of the polymer, the mmmm was 95.0%, and none of the 2,1-insertion and the 1,3-insertion were detected.

Comparative Example 8

Properties of Thermally Decomposed product of Homo-PP prepared using Ziegler-Natta Catalyst Commercially available homo-PP (trade name: J700, available from Grand Polymer Co.) obtained by the use of a magnesium chloride-supported titanium catalyst was thermally decomposed under the conditions of 400° C. and 100 minutes. Properties of the thus thermally decomposed polymer are as follows. This polymer had Tm of 160° C., MFR of 1000 g/10 min, Mw/Mn of 2.3 and a decane-soluble component quantity of 15% by weight, and the decane-soluble component quantity was large. As the stereoregularity of the polymer, the mmmm was 94.9%, and none of the 2,1-insertion and the 1,3-insertion were detected.

Example 119

Normal Pressure Polymerization of Propylene using dimethylmethylene(3-tert-butyl-5-methylcyclopentadienyl)(3,6-di-tert-butylfluorenyl) zirconium Dichloride A 500 ml glass polymerization apparatus thoroughly purged with nitrogen was charged with 250 ml of dry toluene, and then the apparatus was purged with propylene. Then, a catalyst solution obtained by adding 5 mmol (in terms of aluminum) of methylaluminoxane (available from Albemarle Co.) to a toluene solution of 3.1 mg (5 mmol) of the orange solid obtained in Example 3 was added. With stirring, polymerization was conducted at 25° C. for 30 minutes while propylene was bubbled. Thereafter, methanol and a small amount of hydrochloric acid were added to terminate the polymerization. The resulting polymer was filtered, washed with methanol and dried under vacuum at 80° C. for 6 hours. The quantity of the polymer obtained was 0.7 g. This polymer had Tm of 155° C.

Example 120

Normal Pressure Polymerization of Propylene using dimethylmethylene(3-tert-butyl-5-methylcyclopentadienyl)(3,6-di-tert-butylfluorenyl) zirconium Dichloride Polymerization was carried out in the same manner as in Example 119, except that the polymerization temperature was changed to 50° C. The quantity of the polymer obtained was 1.6 g. This polymer had Tm of 144° C.

Example 121

Normal Pressure Polymerization of Propylene using dimethylmethylene(3-tert-butyl-5-methylcyclopentadienyl)fluorenylzirconium Dichloride A 500 ml glass polymerization apparatus thoroughly purged with nitrogen was charged with 250 ml of dry toluene, and then propylene was bubbled to saturate the apparatus. Thereafter, a catalyst solution obtained by adding 5 mmol (in terms of aluminum) of methylaluminoxane (available from Albemarle Co.) to a toluene solution of 2.51 mg (5.0 µmol) of the reddish orange solid obtained in Example 1 was added. With stirring, polymerization was conducted at 25° C. for 10 minutes while propylene was bubbled. Thereafter, methanol and a small amount of hydrochloric acid were added to terminate the polymerization. The resulting polymer was filtered, washed with methanol and dried under vacuum at 80° C. for 6 hours. The quantity of the polymer obtained was 0.9 g. This polymer had Tm of 146° C.

Example 122

Normal Pressure Polymerization of Propylene using dimethylmethylene(3-tert-butyl-5-methylcyclopentadienyl)fluorenylzirconium Dichloride Polymerization was carried out in the same manner as in Example 121, except that the polymerization temperature was changed to 50° C. The quantity of the polymer obtained was 0.9 g. This polymer had Tm of 134° C.

Example 123

Bulk Polymerization of Propylene using dimethylmethylene(3-tert-butyl-5-methylcyclopentadienyl)fluorenylzirconium Dichloride In a 50 ml two-necked flask thoroughly purged with nitrogen, 2.0 mmol (in terms of aluminum) of silica-supported methylaluminoxane was suspended in 20 ml of heptane. To the suspension, a toluene solution of 1.0 mg (2 µmol) of the reddish orange solid obtained in Example 1 was added, then triisobutylaluminum (1 mmol) was added, and they were stirred for 30 minutes to give a catalyst suspension.

A 2000 ml autoclave thoroughly purged with nitrogen was charged with 500 g of propylene, and the catalyst suspension was added to perform polymerization at 70° C. for 40 minutes under a pressure of 3.0 to 3.5 MPa. Thereafter, methanol was added to terminate the polymerization, and propylene was purged of, to obtain a polymer. The polymer was dried under vacuum at 80° C. for 6 hours. The quantity of the polymer obtained was 102 g. This polymer had Tm of 139° C., MFR of 0.7 g/10 min. Mw of 406000, Mn of 197000, Mw/Mn of 2.1 and a decane-soluble component quantity of 0.1% by weight.

Example 124

Bulk Polymerization of Propylene using dimethylmethylene(3-tert-butyl-5-methylcyclopentadienyl)fluorenylzirconium Dichloride Polymerization of propylene was carried out in the same manner as in Example 123, except that 1 NL of hydrogen was added. The quantity of the polymer obtained was 69 g. This polymer had Tm of 142° C., MFR of 22 g/10 min, Mw of 185000, Mn of 80000, Mw/Mn of 2.3 and a decane-soluble component quantity of 0.4% by weight. As the stereoregularity of the polymer, the mmmm was 86.9%, the proportion of 2,1-insertion was 0.02%, and the proportion of 1,3-insertion was 0.05%.

Example 125

Bulk Polymerization of Propylene using dimethylmethylene(3-tert-butyl-5-methylcyclopentadienyl)(3,6-di-tert-butylfluorenyl) zirconium Dichloride Polymerization of propylene was carried out in the same manner as in Example 123, except that 1.1 mg (1.8 μmol) of the orange solid obtained in Example 3 was used. The quantity of the polymer obtained was 90 g. This polymer had Tm of 154° C., MFR of 1.8 g/10 min, Mw of 321000, Mn of 154000, Mw/Mn of 2.3 and a decane-soluble component quantity of 0.1% by weight.

Example 126

Bulk Polymerization of Propylene using dimethylmethylene(3-tert-butyl-5-methylcyclopentadienyl)(3,6-di-tert-butylfluorenyl) zirconium Dichloride Polymerization of propylene was carried out in the same manner as in Example 125, except that 1 NL of hydrogen was added. The quantity of the polymer obtained was 135 g. This polymer had Tm of 156° C., MFR of 350 g/10 min, Mw of 82000, Mn of 37000, Mw/Mn of 2.2 and a decane-soluble component quantity of 0.2% by weight. As the stereoregularity of the polymer, the mmmm was 94.8%, and none of the 2,1-insertion and the 1,3-insertion were detected.

Comparative Example 9

Synthesis of dimethylmethylene(3-tert-butyl-5-methylcyclopentadienyl)fluorenylzirconium Dichloride containing Isomer (1) Synthesis of 2,6,6-trimethylfulvene To 130 ml of dehydrated methanol, 22.6 g (283 mmol) of methylcyclopentadiene and 8.50 ml (116 mmol) of acetone were added, then 14.5 ml (174 mmol) of pyrrolidine was dropwise added at 0° C., and the mixture was reacted at room temperature for one night. Then, 10 ml (180 mmol) of acetic acid was added at 0° C. The mixture was diluted with ether and water and then subjected to extraction. Then, the organic phase was separated, washed with water and dried over anhydrous magnesium sulfate to obtain 12.9 g of a brown liquid. The analyzed values are given below.

$^1$H-NMR (270 MHz, in CDCl$_3$, Based on TMS, main peak): δ6.49 (d, 1H), 6.32 (d, 1H), 6.17 (s, 1H), 2.14 (s, 3H), 2.13 (s, 3H), 2.06 (s, 3H)

(2) Synthesis of 1-tert-butyl-3-methylcyclpentadiene

In a 300 ml flask purged with nitrogen, 2.86 g (23.8 mmol) of trimethylfulvene synthesized in the above step (1) and 80 ml of dry ether were placed. Then, 17 ml (23.8 mmol) of a methyllithium/ether solution (concentration: 1.4 mol/liter) was dropwise added at –78° C., and the mixture was reacted at room temperature for 2 days. Then, 20 ml of an ammonium chloride saturated aqueous solution was added, and the organic phase was separated, washed with water, washed with a sodium chloride saturated aqueous solution and dried over anhydrous magnesium sulfate. Thereafter, the solvent was distilled off, and the residue was purified by column chromatography (silica gel, developing solvent: hexane) to obtain 2.04 g of a brown liquid. The analyzed values are given below.

$^1$H-NMR (270 MHz, in CDCl$_3$, Based on TMS, main peak): δ6.31+6.13+5.94+5.87 (s+s+t+d, 2H), 3.04+2.95 (s+s, 2H), 2.17+2.09 (s+s, 3H), 1.27 (d, 9H)

Peaks derived from proton of an isomer were observed in the vicinity of 85.5 and 5.1. From the integral value of proton, the ratio of the presence between the main product and the by-product proved to be about 8:1.

(3) Synthesis of dimethylmethylene(3-tert-butyl-5-methylcyclopentadienyl)fluorenylzirconium Dichloride Dimethylmethylene(3-tert-butyl-5-methylcyclopentadienyl)fluorenylzirconium dichloride was synthesized in the same manner as in the steps (3) and (4) of Example 1, except that 1-tert-butyl-3-methylcyclopentadiene containing an isomer obtained in the step (2) was used.

Peaks derived from proton of an isomer were observed in the vicinity of 87.4 and 6.1. From the integral value of proton, the ratio of the presence between the main product and the by-product proved to be about 8:1.

Comparative Example 10

Bulk Polymerization of Propylene using dimethylmethylene(3-tert-butyl-5-methylcyclopentadienyl)fluorenylzirconium Dichloride containing Isomer Polymerization of propylene was carried out in the same manner as in Example 84, except that dimethylmethylene (3-tert-butyl-5-methylcyclopentadienyl)fluorenylzirconium dichloride containing an isomer obtained in Comparative Example 9 was used. The quantity of the polymer obtained was 89 g. This polymer had Tm of 138° C., Mw of 394000 and Mn of 197000. The decane-soluble component quantity was 2.5% by weight and was large.

Comparative Example 11

Bulk Polymerization of Propylene using dimethylmethylene(3-tert-butyl-5-methylcyclopentadienyl)fluorenylzirconium Dichloride containing Isomer Polymerization of propylene was carried out in the same manner as in Comparative Example 10, except that 2 NL of hydrogen was added. The quantity of the polymer obtained was 54 g. This polymer had Tm of 140° C., MFR of 130 g/10 min, Mw of 135000 and Mn of 34000. The decane-soluble component quantity was 4.5% by weight and was large.

What is claimed is:

1. A metallocene compound represented by the following formula (1b) or (2b):

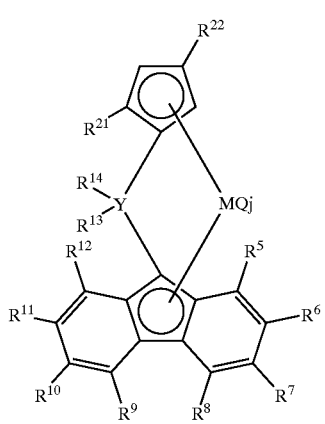

(1b)

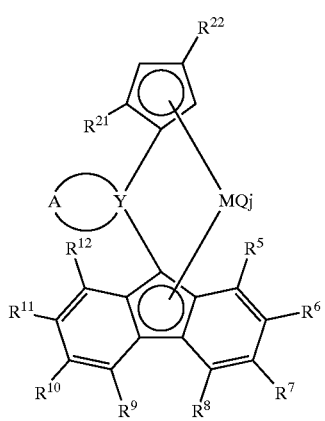

(2b)

wherein $R^{21}$ and $R^{22}$ may be the same or different and are each selected from a hydrocarbon group or a silicon-containing hydrocarbon group; $R^5$, $R^6$, $R^7$, $R^8$, $R^9$, $R^{10}$, $R^{11}$, $R^{12}$, $R^{13}$ and $R^{14}$ may be the same or different and are each selected from a hydrogen atom, a hydrocarbon group or a silicon-containing hydrocarbon group; of the groups indicated by $R^5$ to $R^{12}$, neighboring groups may be bonded to form a ring; and when $R^{22}$ is tert-butyl and $R^{13}$ and $R^{14}$ are methyl, $R^6$, $R^7$, $R^{10}$ and $R^{11}$ are not all hydrogen; when all of $R^5$ to $R^{12}$ are hydrogen, $R^{22}$ is a hydrocarbon other than phenyl, and when $R^7$ and $R^{10}$ are both tert-butyl and $R^5$, $R^6$, $R^8$, $R^9$, $R^{11}$ and $R^{12}$ are all hydrogen, $R^{22}$ is not methyl, tert-butyl or trimethylsilyl; A is a divalent hydrocarbon group of 2 to 20 carbon atoms which may contain an unsaturated bond and/or an aromatic ring; A may contain two or more cyclic structures including a ring formed by A in cooperation with Y; M is a metal selected from Group 4 of the periodic table; Y is a carbon atom or a silicon atom; j is an integer of 1 to 4; Q is selected from the group consisting of a halogen atom, a hydrocarbon group, an anionic ligand and a neutral ligand capable of coordination by a lone pair; and when j is 2 or greater, each Q may be the same or different.

2. An olefin polymerization catalyst comprising the metallocene compound of claim 1.

3. An olefin polymerization catalyst comprising:
   (A) the metallocene compound of claim 1, and
   (B) at least one compound selected from:
      (B1) an organometallic compound,
      (B-2) an organoaluminum oxy-compound, and
      (B-3) a compound which reacts with the metallocene compound (A) to form an ion pair.

4. An olefin polymerization catalyst of claim 3 and (C) a particle carrier.

5. A process for preparing a polyolefin comprising polymerizing or copolymerizing an olefin in the presence of the olefin polymerization catalyst of claim 2.

6. The process for preparing a polyolefin as claimed in claim 5, wherein the metallocene compound is the metallocene compound represented by the formula (1b) or (2b), and at least 2 kinds of olefins are copolymerized.

7. The process for preparing a polyolefin as claimed in claim 5, wherein the metallocene compound is the metallocene compound represented by the formula (1b) or (2b), and a single olefin is polymerized.

8. A process for preparing a polyolefin comprising polymerizing or copolymerizing an olefin in the presence of the olefin polymerization catalyst of claim 3.

9. The process for preparing a polyolefin as claimed in claim 8, wherein the metallocene compound (A) is the metallocene compound represented by the formula (1b) or (2b), and at least 2 kinds of olefins are copolymerized.

10. The process for preparing a polyolefin as claimed in claim 8, wherein the metallocene (A) compound is the metallocene compound represented by the formula (1b) or (2b), and a single olefin is polymerized.

11. A process for preparing a polyolefin comprising polymerizing or copolymerizing an olefin in the presence of the olefin polymerization catalyst of claim 4.

12. The process for preparing a polyolefin as claimed in claim 11 wherein the metallocene (A) compound is the metallocene compound represented by the formula (1b) or (2b), and at least 2 kinds of olefins are copolymerized.

13. The process for preparing a polyolefin as claimed in claim 11, wherein the metallocene (A) compound is the metallocene compound represented by the formula (1b) or (2b), and a single olefin is polymerized.

14. A process for preparing a metallocene compound, comprising selectively preparing a metallocene compound represented by the following formula (1b) or (2b) from a cyclopentadiene represented by the following formula (19b) as a starting material which is free of isomer represented by formula (20b), said process comprising the steps of:
   converting the cyclopentadiene of formula (19b) to a precursor compound represented by the following formula (13b) or (14b),
   converting the precursor compound of formula (13b) or (14b) to a ligand precursor represented by the formula (7b) or (8b), and
   forming the metallocene compound represented by the following formula (1b) or (2b) from the ligand precursor represented by the formula (7b) or (8b);

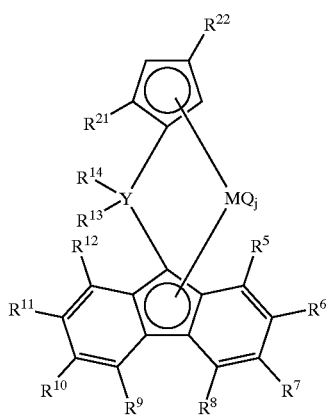
(1b)

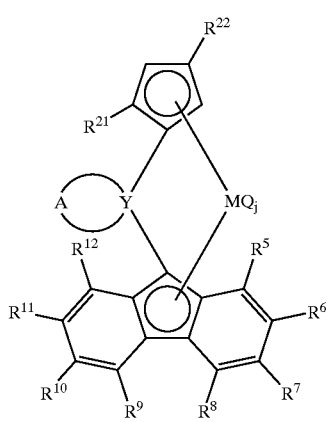
(2b)

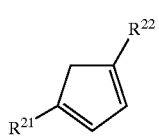
(19b)

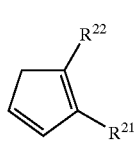
(20b)

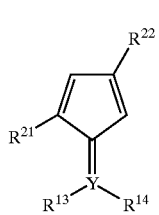
(13b)

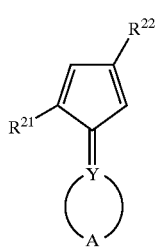
(14b)

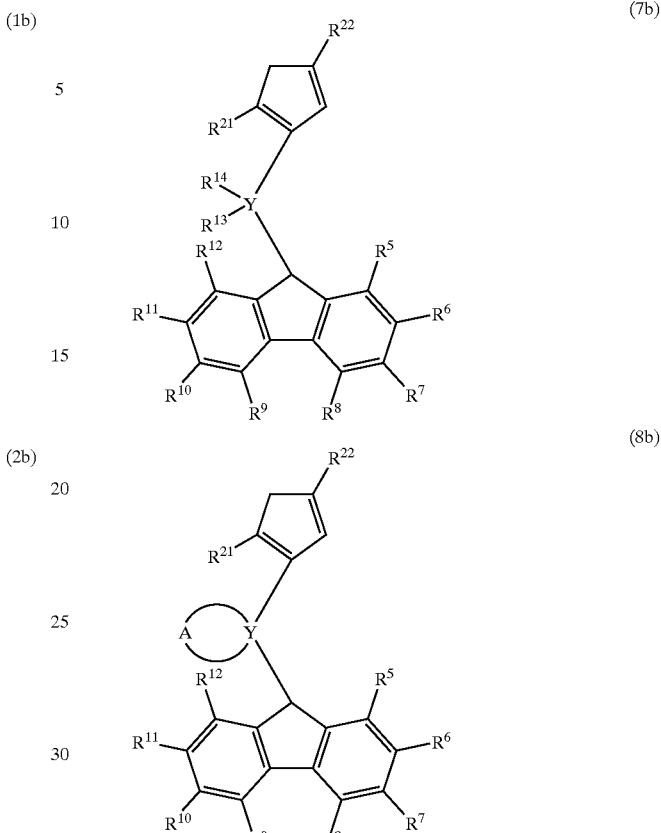

wherein $R^{21}$ and $R^{22}$ may be the same or different and are each selected from a hydrocarbon group or a silicon-containing hydrocarbon group; $R^5$, $R^6$, $R^7$, $R^8$, $R^9$, $R^{10}$, $R^{11}$, $R^{12}$, $R^{13}$ and $R^{14}$ may be the same or different and are each selected from a hydrogen atom, a hydrocarbon group and a silicon-containing hydrocarbon group; of the groups indicated by $R^5$ to $R^{12}$, neighboring groups may be bonded to from a ring; and when $R^{22}$ is tert-butyl and $R^{13}$ and $R^{14}$ are methyl, $R^6$, $R^7$, $R^{10}$ and $R^{11}$ are not all hydrogen;

when all of $R^5$ to $R^{12}$ are hydrogen, $R^{22}$ is a hydrocarbon other than phenyl, when $R^7$ and $R^{10}$ are both tert-butyl, and $R^5$, $R^6$, $R^8$, $R^9$, $R^{11}$ and $R^{12}$ are all hydrogen, $R^{22}$ is not methyl, tert-butyl or trimethylsilyl;

A is a divalent hydrocarbon group of 2 to 20 carbon atoms which may contain an unsaturated bond and/or an aromatic ring; A may contain two or more cyclic structures including a ring formed by A in cooperation with Y; M is a metal selected from Group 4 of the periodic table; Y is a carbon atom or a silicon atom; j is an integer of 1 to 4; Q is selected from the group consisting of a halogen atom, a hydrocarbon group, an anionic ligand and a neutral ligand capable of coordination by a lone pair; and when j is 2 or greater, each Q may be the same or different.

\* \* \* \* \*